（12）United States Patent　　　(10) Patent No.: US 7,576,063 B2
Fujikura et al.　　　　　　　　　　(45) Date of Patent: Aug. 18, 2009

(54) PYRAZOLE DERIVATIVE, MEDICINAL COMPOSITION CONTAINING THE SAME, MEDICINAL USE THEREOF AND INTERMEDIATE IN PRODUCING THE SAME

(75) Inventors: Hideki Fujikura, Nagano (JP); Norihiko Kikuchi, Nagano (JP); Shigeki Tazawa, Nagano (JP); Tokuhisa Yamato, Nagano (JP); Masayuki Isaji, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 468 days.

(21) Appl. No.: 10/529,895

(22) PCT Filed: Sep. 30, 2003

(86) PCT No.: PCT/JP03/12477

§ 371 (c)(1),
(2), (4) Date: Sep. 19, 2005

(87) PCT Pub. No.: WO2004/031203

PCT Pub. Date: Apr. 15, 2004

(65) Prior Publication Data

US 2006/0128635 A1　　Jun. 15, 2006

(30) Foreign Application Priority Data

Oct. 4, 2002　(JP)　............................ 2002-293090
Nov. 14, 2002　(JP)　............................ 2002-330694
Dec. 27, 2002　(JP)　............................ 2002-378959

(51) Int. Cl.
*A01N 43/04*　　(2006.01)
*A61K 31/70*　　(2006.01)
*C07H 17/00*　　(2006.01)

(52) U.S. Cl. ........................... 514/27; 514/25; 514/866; 536/4.1; 536/18.1

(58) Field of Classification Search ........................ None
See application file for complete search history.

(56) References Cited

U.S. PATENT DOCUMENTS 4,410,525 A　　10/1983　Jarreau et al.

(Continued)

FOREIGN PATENT DOCUMENTS

EP　　0 076 756 A1　　4/1983

(Continued)

OTHER PUBLICATIONS

Yamanouchi, T. et al., Common reabsorption system of 1, 5-anhydro-D-glucitol, fructose, and mannose in rat renaltubule., Biochim. Biophys.Acta., 1996, 1291, pp. 89 to 95.

(Continued)

*Primary Examiner*—Traviss C McIntosh, III
(74) *Attorney, Agent, or Firm*—Sughrue Mion, PLLC

(57) ABSTRACT

The present invention provides pyrazole derivatives represented by the general formula:

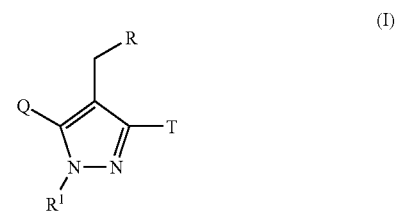

wherein $R^1$ represents H, an optionally substituted $C_{1-6}$ alkyl group etc.; one of Q and T represents a group selected from the following groups:

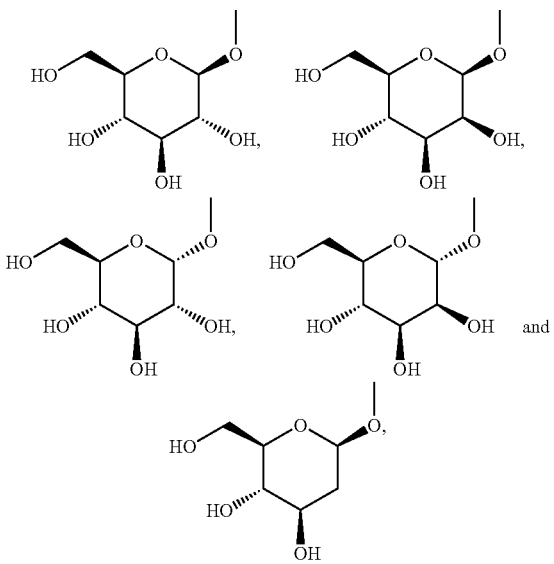

and the other represents —$(CH_2)_n$—Ar wherein Ar represents an optionally substituted $C_{6-10}$ aryl group or an optionally substituted $C_{1-9}$ heteroaryl group; and n represents an integral number from 0 to 2, an optionally substituted $C_{1-6}$ alkoxyl group, an optionally substituted amino group, an optionally substituted $C_{2-9}$ heterocycloalkyl group or an optionally substituted heterocycle-fused phenyl group; R represents an optionally substituted $C_{3-8}$ cycloalkyl group, an optionally substituted $C_{6-10}$ aryl group etc., pharmaceutically acceptable salts thereof or prodrugs thereof, which exhibit an excellent inhibitory activity in human 1,5-anhydroglucitol/fructose/mannose transporter and are useful as agents for the prevention, inhibition of progression or treatment of a disease associated with the excess uptake of at least a kind of carbohydrates selected from glucose, fructose and mannose or a disease associated with hyperglycemia (e.g., diabetic complications, diabetes, etc.), and pharmaceutical compositions comprising the same, pharmaceutical uses thereof, and intermediates for production thereof.

23 Claims, 1 Drawing Sheet

U.S. PATENT DOCUMENTS

| | | | |
|---|---|---|---|
| 4,526,895 A | | 7/1985 | Jarreau et al. |
| 6,414,126 B1 | | 7/2002 | Ellsworth et al. |
| 6,455,525 B1 | | 9/2002 | Singh et al. |
| 6,515,117 B2 | | 2/2003 | Ellsworth et al. |
| 6,815,428 B2 | * | 11/2004 | Ohsumi et al. ............... 514/25 |
| 6,972,283 B2 | * | 12/2005 | Fujikura et al. ............... 514/27 |
| 7,084,123 B2 | * | 8/2006 | Fujikura et al. ............... 514/27 |
| 7,087,579 B2 | * | 8/2006 | Nishimura et al. ............ 514/27 |
| 7,294,618 B2 | * | 11/2007 | Fushimi et al. ............... 514/25 |
| 2003/0087843 A1 | | 5/2003 | Washburn |
| 2003/0137903 A1 | | 7/2003 | Hiranuma et al. |
| 2003/0162775 A1 | | 8/2003 | Singh et al. |
| 2004/0053397 A1 | | 3/2004 | Iwamoto et al. |
| 2004/0110936 A1 | | 6/2004 | Ohsumi et al. |
| 2004/0116357 A1 | | 6/2004 | Fushimi et al. |
| 2004/0132669 A1 | | 7/2004 | Nishimura et al. |
| 2004/0176308 A1 | | 9/2004 | Shiohara et al. |

FOREIGN PATENT DOCUMENTS

| | | |
|---|---|---|
| EP | 0 099 815 A1 | 2/1984 |
| EP | 1213296 A1 | 6/2002 |
| EP | 1338603 A1 | 8/2003 |
| EP | 1354888 A1 | 10/2003 |
| FR | 2529786 A1 | 1/1984 |
| JP | 2003-012686 A | 1/2003 |
| WO | WO 01/16147 A1 | 3/2001 |
| WO | WO 01/27128 A1 | 4/2001 |
| WO | 01/32653 A1 | 5/2001 |
| WO | WO 02/36602 A1 | 5/2002 |
| WO | WO 02/053573 A1 | 7/2002 |
| WO | WO 02/053738 A1 | 7/2002 |
| WO | WO 02/068439 A1 | 9/2002 |
| WO | WO 02/068440 A1 | 9/2002 |
| WO | WO 02/088157 A1 | 11/2002 |
| WO | WO 02/098893 A1 | 12/2002 |
| WO | WO 03/020737 A1 | 3/2003 |

OTHER PUBLICATIONS

Kees, Kenneth L. et al., Studies on New Acidic Azoles as Glucose-Lowering Agents in Obese, Diabetic db/db Mice, Journal of Medicinal Chemistry, vol. 38, No. 4, pp. 617-628 (1995).

Ila Sircar, et al.; Cardiotonic Agents. 6. Synthesis and Inotropic Activity of 2,4-Dihydro-5-[4-(1H-imidazol-l-yl)phenyl]-3H-pyrazol-3-ones: Ring-Contracted Analogues of Imazodan (CI-914), Journal of Medicinal Chemistry, vol. 30, No. 10, pp. 1724-1728 (1987).

Sakakibara H. et al., Reactions of 2,3-Dimethylindole and Tetrahydrocarbozole with N-Bromosuccimide, Tetrahedron, vol. 22, No. 8, pp. 2475-2479 (1966).

Leemann H. G. et al.L"20. Uber die Ermittlung der Struktur eines bei der Herstellung von 1-[N-Methylpiperidyl-(4')]-4-benzyl-5-phenyl-pyrazol-3-on" Helvetica Chimica Acta, vol. 45, pp. 177-179 (1962).

Veibel, Stig et al., Pyrazole Studies, VIII Oxidation of 4-Alkylsubstituted Pyrazol-5-ones with Tertiary Butylhydroperoxide, Acta Chimica Scandinavica, vol. 8, pp. 1383-1388 (1954).

Gagnon, Paul E. et al., Study of 4-Mono- and 4,4-Disubstituted-3-Imino-2-Benzoly-5-Pyrazolones, Canadian Journal of Chemistry, vol. 30, pp. 52-61 (1952).

Gagnon, Paul E. et al., Synthesis and Ultraviolet Absorption of Some Pyrazolones, Canadian Journal of Chemistry, vol. 29, pp. 843-847 (1951).

Gagnon, Paul E. et al, Contribution to the Study of 4-Monosubstituted-3-Amino-5-Pyrazolones, Canadian Journal of Chemistry, vol. 29, pp. 328-332 (1951).

Gagnon, Paul E. et al., The Synthesis and Ultraviolet Spectra of Some Pyrazolones, Canadian Journal of Chemistry, vol. 29, pp. 182-191 (1951).

* cited by examiner

PYRAZOLE DERIVATIVE, MEDICINAL COMPOSITION CONTAINING THE SAME, MEDICINAL USE THEREOF AND INTERMEDIATE IN PRODUCING THE SAME

TECHNICAL FIELD

The present invention relates to pyrazole derivatives, pharmaceutically acceptable salts thereof or prodrugs thereof which are useful as medicaments, pharmaceutical compositions comprising the same, pharmaceutical uses thereof and intermediates for production thereof.

More particularly, the present invention relates to pyrazole derivatives having an inhibitory activity to a cotransporter of glucose, 1,5-anhydroglucitol, fructose and mannose coupled with sodium (hereinafter referred to as 1,5-anhydroglucitol/fructose/mannose transporter), pharmaceutically acceptable salts thereof or prodrugs thereof which are useful as agents for the prevention, inhibition of progression or treatment of diseases associated with the excess uptake of at least a kind of carbohydrates selected from glucose, fructose and mannose such as diabetic complications and diabetes, pharmaceutical compositions comprising the same, pharmaceutical uses thereof and intermediates for production thereof.

BACKGROUND ART

Glucose, one of the most important energy sources for body, is taken up into a cell across cell membrane to be made available in the body. A membrane protein called glucose transporter is involved in this uptake at cell membrane. Glucose transporter is classified into two main categories of facilitated glucose transporter which uptakes glucose depending on intracellular and extracellular glucose concentration difference, and sodium/glucose cotransporter (SGLT) which uptakes glucose by using intracellular and extracellular ion concentration difference (for example, see the following Reference 1). Regarding SGLT, it has been known that SGLT1, sodium/glucose cotransporter having a high affinity, mainly exists in the small intestine, and SGLT2, sodium/glucose cotransporter having a low affinity, mainly exists in renal tubule (for example, see the following References 2 and 3). In addition, SGLT3, a human homologue of pig sodium/glucose cotransporter with a low affinity, pSAAT (for example, see the following Reference 4) was reported (for example, see the following Reference 5). Thus, SGLTs are involved in glucose absorption in the small intestine and glucose reabsorption in the kidney (for example, see the following Reference 6). Therefore, a SGLT inhibitor is expected to lower blood glucose level by suppressing the intestinal glucose absorption and accelerating glucose excretion into urine. Actually, as a result of a study using phlorizin known as a SGLT inhibitor, it was confirmed that by inhibiting SGLT urinary glucose excretion increased, blood glucose level lowered and insulin resistance was improved (for example, see the following References 7 and 8). In these years, various SGLT inhibitors has been found and are currently under development as treatment agents for diseases associated with glucose, lipid and energy metabolism including diabetes (for example, see the following References 9-12).

In these years, a gene that codes for a protein having a sodium/glucose cotransporting activity was newly reported (see the following Reference 13) and applied for a patent (Japan Patent Application no.2002-88318). The protein of the Japan patent application no.2002-88318 (hereinafter referred to as SMINT) has 7 amino-acid residues (Met Ser Lys Glu Leu Ala Ala; SEQ ID NO: 1) at N-terminal extended from a protein described in the Reference 13 (hereinafter referred to as SGLTh). The both proteins share high DNA and amino-acid sequence homology with SGLT1 and SGLT2, and mammalian cells being expressed these genes show an activity of the sodium-dependent sugar uptake. Therefore, the both are considered as a member of SGLT family.

Among these SGLTs, SGLT1 is known to transport galactose in addition to glucose (for example, see the following Reference 14), while SGLT2 and SGLT3 have low abilities transporting sugars other than glucose (for example, see the following References 4 and 15). However, the characteristics of SMINT and SGLTh in transporting sugars have not been understood at all.

It has been known that blood mannose level increases in diabetes (for example, see the following Reference 16). In addition, it is known that blood mannose level has a positive correlation with blood glucose level and triglyceride level and a negative correlation with HDL cholesterol in metabolic syndrome (for example, see the following Reference 17). On the other hand, it is known that fructose consumes a lot of ATP through the intracellular metabolic pathway and forms lactose, and that causes a so-called fructose toxicity (for example, see the following Reference 18). Mannose and fructose are known to accumulate in renal glomerulus in diabetic rats, and their relations with diabetic nephropathy have been pointed out (for example, see the following Reference 19). Moreover, it has been reported that mannose and fructose have a protein glycation ability more than 5-times as glucose in glycation reaction with proteins considered as a cause of diabetic complications (for example, see the following Reference 20). Furthermore, it was reported that 1,5-anhydroglucitol/fructose/mannose transporter exists functionally in the kidney, etc. (for example, see the following References 21 and 22). Therefore, as the inhibitory effects on the excess consumption of fructose and mannose as well as glucose in the body are expected to be desirable for the prevention, inhibition of progression or the like of diabetic complications, especially including diabetic nephropathy, it has been desired to early develop an agent having such an inhibitory effect.

Although various compounds having a pyrazole structure like the present invention are known, these compounds are SGLT1 or SGLT2 inhibitors, or SGLT inhibitors which have excreting effects of urinary glucose. Therefore, it has not been known that pyrazole derivatives of the present invention have an inhibitory effect on 1,5-anhydroglucitol/fructose/mannose transporter activity, exert an inhibitory effect on uptake of carbohydrates such as glucose, fructose and mannose, and are useful for the prevention, inhibition of progression or treatment of diseases associated with excess uptake of at least a kind of carbohydrates selected from glucose, fructose and mannose (for example, see the following References 23-31).

Reference 1: Graeme I. Bell and 7 persons, Diabetes Care, March 1990, Vol. 13, No. 3, pp. 198-208;

Reference 2: Matthias A. Hediger and 2 persons, Proc. Natl. Acad. Sci. USA, August 1989, Vol. 86, pp. 5748-5752;

Reference 3: Rebecca G. Wells and 5 persons, Am. J. Physiol., September 1992, Vol. 263, pp. F459-465;

Reference 4: Bryan Mackenzie and 4 persons, J. Biol. Chem., September 1994, Vol. 269, No. 36, pp. 22488-22491;

Reference 5: GenBank Data Bank, online, search held on Mar. 11, 2002, Accession No. AJ133127;

Reference 6: Bernard Thorens, Am. J. Physiol., April 1996, Vol. 270, pp. G541-G553;

Reference 7: Luciano Rossetti and 4 persons, J. Clin. Invest., May 1987, Vol. 79, pp. 1510-1515;

Reference 8: Barbara B. Kahn and 4 persons, J. Clin. Invest., February 1991, Vol. 87, pp. 561-570;

Reference 9: International Publication no.WO01/27128;

Reference 10: Kenji Arakawa and 7 persons, Br. J. Pharmacol., January 2001, Vol. 132, No. 2, pp. 578-586;

Reference 11: Masayuki Isaji and 8 persons, FASEB J., March 2001, Vol. 15, No. 4, p.A214;

Reference 12: Kenji Katsuno and 7 persons, FASEB J., March 2001, Vol. 15, No. 4, p.A214;

Reference 13: International Publication no.WO02/053738;

Reference 14: E. Turk and 4 persons, Nature, March 1991, Vol. 350, No. 6316, pp. 354-356;

Reference 15: Yoshikatsu Kanai and 4 persons, J. Clin. Invest., January 1994, Vol. 93, pp. 397-404;

Reference 16: Elja Pitkanen, Clin. Chim. Acta, July 1996, Vol. 251, No. 1, pp. 91-103;

Reference 17: 0. M. Pitkanen and 2 persons, Scand J. Clin. Lab. Invest., December 1999, Vol. 59, No. 8, pp. 607-612;

Reference 18: R. Gitzelmann and 2 persons, The Metabolic and Molecular Bases of Inherited Disease, McGraw-Hill in the US, 1995, pp. 905-934;

Reference 19: Li Ning Wang and 3 persons, The Japanese Journal of Nephrology, 1990, Vol. 32, No. 4, pp. 401-408;

Reference 20: H. Franklin Bunn and 1 person, Science, July 1981, Vol. 213, pp. 222-224;

Reference 21: Toshikazu Yamanouchi and 5 persons, Biochim. Biophys. Acta., August 1996, Vol. 1291, No. 1, pp. 89-95;

Reference 22: T. Blasco and 5 persons, J. Membr. Biol., November 2000, Vol. 178, No. 2, pp. 127-135;

Reference 23: International Publication no.WO01/16147;

Reference 24: International Publication no.WO02/05373;

Reference 25: International Publication no.WO02/068439;

Reference 26: International Publication no.WO02/068440;

Reference 27: International Publication no.WO03/098893;

Reference 28: International Publication no.WO03/020737;

Reference 29: International Publication no.WO02/36602;

Reference 30: International Publication no.WO02/088157;

Reference 31: Japan Patent Publication no.JP2003-12686.

DISCLOSURE OF THE INVENTION

The present inventors have studied earnestly on human SMINT. As a result, it was found that the human SMINT of the Japanese patent application no.2002-88318 exists highly in the kidney and small intestine and characteristically transports 1,5-anhydroglucitol, fructose and mannose besides glucose, and human SMINT functions as a 1,5-anhydroglucitol/fructose/mannose transporter. That is, it was found that the excess uptake of glucose, fructose and mannose can be inhibited by inhibiting 1,5-anhydroglucitol/fructose/mannose transporter, and an inhibitor of 1,5-anhydroglucitol/fructose/mannose transporter is useful for the prevention, inhibition of progression or treatment of diabetes, diabetic complications including diabetic nephropathy and the like. Therefore, the present inventors have studied earnestly to find a compound which exerts an inhibitory effect on 1,5-anhydroglucitol/fructose/mannose transporter. As a result, it was found that certain pyrazole derivatives represented by the following general formula (I) show an excellent inhibitory activity on 1,5-anhydroglucitol/fructose/mannose transporter as shown below, thereby forming the basis of the present invention.

The present invention is to provide novel compounds which is useful for the prevention, inhibition of progression or treatment of a diseases associated with excess uptake of at least a kind of carbohydrates selected from glucose, fructose and mannose such as diabetic complications and diabetes, by inhibiting uptake, in particular, absorption in the small intestine, sugar reabsorption in the kidney, uptake into a cell and the like, of carbohydrates, glucose, fructose and mannose, and the like.

Specifically, the present invention relates to

[1] a pyrazole derivative represented by the following general formula (Iα):

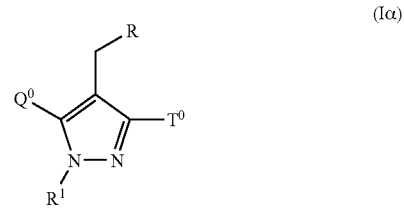

wherein $R^1$ represents a hydrogen atom, a $C_{1-6}$ alkyl group which may have the same or different 1 to 3 groups selected from the following substituent group (A), a $C_{2-6}$ alkenyl group which may have the same or different 1 to 3 groups selected from the following substituent group (A), a $C_{2-6}$ alkynyl group which may have the same or different 1 to 3 groups selected from the following substituent group (A), a $C_{3-8}$ cycloalkyl group which may have the same or different 1 to 3 groups selected from the following substituent group (A), a $C_{6-10}$ aryl group which may have the same or different 1 to 3 groups selected from the following substituent group (B), a $C_{2-9}$ heterocycloalkyl group which may have the same or different 1 to 3 groups selected from the following substituent group (A), or a $C_{1-9}$ heteroaryl group which may have the same or different 1 to 3 groups selected from the following substituent group (B);

one of $Q^0$ and $T^0$ represents a group selected from

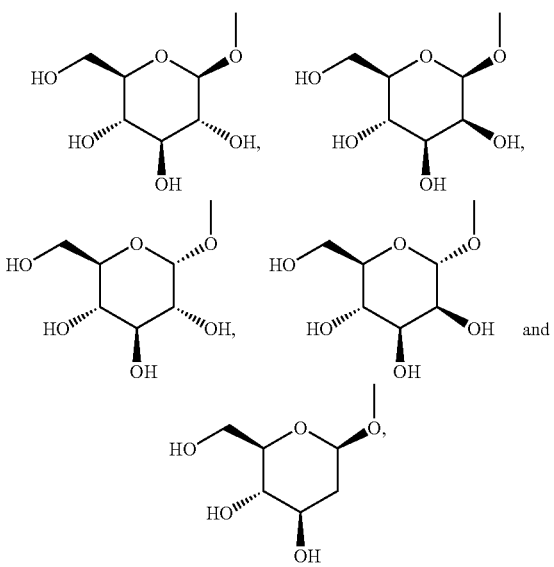

and the other represents a group represented by the formula: —(CH$_2$)$_n$—Ar wherein Ar represents a C$_{6-10}$ aryl group which may have the same or different 1 to 3 groups selected from the following substituent group (B) or a C$_{1-9}$ heteroaryl group which may have the same or different 1 to 3 groups selected from the following substituent group (B); and n represents an integral number from 0 to 2, a C$_{1-6}$ alkoxy group which may have the same or different 1 to 3 groups selected from the following substituent group (A), an optionally mono or di(C$_{1-6}$ alkyl)-substituted amino group wherein the C$_{1-6}$ alkyl group may have the same or different 1 to 3 groups selected from the following substituent group (A), a C$_{2-9}$ heterocycloalkyl group which may have the same or different 1 to 3 groups selected from the following substituent group (A), or a heterocycle-fused phenyl group which may have the same or different 1 to 3 groups selected from the following substituent group (B);

R represents a C$_{3-8}$ cycloalkyl group which may have the same or different 1 to 3 groups selected from the following substituent group (A), a C$_{6-10}$ aryl group which may have the same or different 1 to 3 groups selected from the following substituent group (B), a C$_{2-9}$ heterocycloalkyl group which may have the same or different 1 to 3 groups selected from the following substituent group (A), or a C$_{1-9}$ heteroaryl group which may have the same or different 1 to 3 groups selected from the following substituent group (B);

[Substituent Group (A)]:
a halogen atom, a nitro group, a cyano group, an oxo group, -G$^1$, —OG$^2$, —SG$^2$, —N(G$^2$)$_2$, —C(=O)G$^2$, —C(=O)OG$^2$, —C(=O)N(G$^2$)$_2$, —S(=O)$_2$G$^2$, S(=O)$_2$N(G$^2$)$_2$, —S(=O)G$^1$, —OC(=O)G$^1$, —OC(=O)N(G$^2$)$_2$, —NHC(=O)G$^2$, —OS(=O)$_2$G$^1$, —NHS(=O)$_2$G$^1$ and —C(=O)NHS(=O)$_2$G$^1$;

[Substituent Group (B)]:
a halogen atom, a nitro group, a cyano group, -G$^1$, —OG$^2$, —SG$^2$, —N(G$^2$)$_2$, -G$^3$OG$^4$, -G$^3$N(G$^4$)$_2$, —C(=O)G$^2$, —C(=O)OG$^2$, —C(=O)N(G$^2$)$_2$, —S(=O)$_2$G$^2$, —S(=O)$_2$OG$^2$, —S(=O)$_2$N(G$^2$)$_2$, —S(=O)G$^1$, —OC(=O)G$^1$, —OC(=O)N(G$^2$)$_2$, —NHC(=O)G$^2$, —OS(=O)$_2$G$^1$, —NHS(=O)$_2$G$^1$ and —C(=O)NHS(=O)$_2$G$^1$;

in the above substituent group (A) and/or (B),

G$^1$ represents a C$_{1-6}$ alkyl group which may have the same or different 1 to 3 groups selected from the following substituent group (C), a C$_{2-6}$ alkenyl group which may have the same or different 1 to 3 groups selected from the following substituent group (C), a C$_{2-6}$ alkynyl group which may have the same or different 1 to 3 groups selected from the following substituent group (C), a C$_{3-8}$ cycloalkyl group which may have the same or different 1 to 3 groups selected from the following substituent group (C), a C$_{6-10}$ aryl group which may have the same or different 1 to 3 groups selected from the following substituent group (D), a C$_{2-9}$ heterocycloalkyl group which may have the same or different 1 to 3 groups selected from the following substituent group (C), or a C$_{1-9}$ heteroaryl group which may have the same or different 1 to 3 groups selected from the following substituent group (D);

G$^2$ represents a hydrogen atom, a C$_{1-6}$ alkyl group which may have the same or different 1 to 3 groups selected from the following substituent group (C), a C$_{2-6}$ alkenyl group which may have the same or different 1 to 3 groups selected from the following substituent group (C), a C$_{2-6}$ alkynyl group which may have the same or different 1 to 3 groups selected from the following substituent group (C), a C$_{3-8}$ cycloalkyl group which may have the same or different 1 to 3 groups selected from the following substituent group (C), a C$_{6-10}$ aryl group which may have the same or different 1 to 3 groups selected from the following substituent group (D), a C$_{2-9}$ heterocycloalkyl group which may have the same or different 1 to 3 groups selected from the following substituent group (C), or a C$_{1-9}$ heteroaryl group which may have the same or different 1 to 3 groups selected from the following substituent group (D), and with the proviso that G$^2$ may be the same or different when there are 2 or more G$^2$ in the substituents;

G$^3$ represents a C$_{1-6}$ alkyl group;

G$^4$ represents a C$_{1-6}$ alkyl group which may have the same or different 1 to 3 groups selected from the following substituent group (C), and with the proviso that G$^4$ may be the same or different when there are 2 or more G$^4$ in the substituents;

[Substituent Group (C)]:
a halogen atom, a nitro group, a cyano group, an oxo group, -G$^5$, —OG$^6$, —SG$^6$, —N(G$^6$)$_2$, —C(=O)G$^6$, —C(=O)OG$^6$, —C(=O)N(G$^6$)$_2$, —S(=O)$_2$G$^6$, —S(=O)$_2$OG$^6$, —S(=O)$_2$N(G$^6$)$_2$, —S(=O)G$^5$, —OC(=O)G$^5$, —OC(=O)N(G$^6$)$_2$, —NHC(=O)G$^6$, —OS(=O)$_2$G$^5$, —NHS(=O)$_2$G$^5$ and —C(=O)NHS(=O)$_2$G$^5$; and

[Substituent Group (D)]:
a halogen atom, a nitro group, a cyano group, -G$^5$, —OG$^6$, —SG$^6$, —N(G$^6$)$_2$, —C(=O)G$^6$, —C(=O)OG$^6$, —C(=O)N(G$^6$)$_2$, —S(=O)$_2$G$^6$, —S(=O)$_2$OG$^6$, —S(=O)$_2$N(G$^6$)$_2$, —S(=O)G$^5$, —OC(=O)G$^5$, —OC(=O)N(G$^6$)$_2$, —NHC(=O)G$^6$, —OS(=O)$_2$G$^5$, —NHS(=O)$_2$G$^5$ and —C(=O)NHS(=O)$_2$G$^5$; in the substituent group (C) and/or (D), G$^5$ represents a C$_{1-6}$ alkyl group, a C$_{2-6}$ alkenyl group, a C$_{2-6}$ alkynyl, a C$_{3-8}$ cycloalkyl group, a C$_{6-10}$ aryl group, a C$_{2-9}$ heterocycloalkyl group or a C$_{1-9}$ heteroaryl group; and G$^6$ represents a hydrogen atom, a C$_{1-6}$ alkyl group, a C$_{2-6}$ alkenyl group, a C$_{2-6}$ alkynyl, a C$_{3-8}$ cycloalkyl group, a C$_{6-10}$ aryl group, a C$_{2-9}$ heterocycloalkyl group or a C$_{1-9}$ heteroaryl group, and with the proviso that G$^6$ may be the same or different when there are 2 or more G$^6$ in the substituents, or a pharmaceutically acceptable salt thereof or a prodrug thereof;

[2] a pyrazole derivative described in the above [1], wherein R$^1$ represents a hydrogen atom, a C$_{1-6}$ alkyl group which may have the same or different 1 to 3 groups selected from the substituent group (A), a C$_{3-8}$ cycloalkyl group which may have the same or different 1 to 3 groups selected from the substituent group (A), or a C$_{6-10}$ aryl group which may have the same or different 1 to 3 groups selected from the substituent group (B); Q$^0$ represents a C$_{6-10}$ aryl group which may have the same or different 1 to 3 groups selected from the substituent group (B); T$^0$ represents a group:

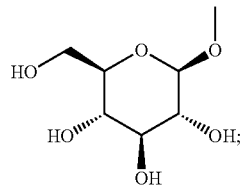

R represents a C$_{6-10}$ aryl group which may have the same or different 1 to 3 groups selected from the substituent group (B); substituent group (A) consists of a halogen atom, —OG$^2$, —SG$^2$, —N(G$^2$)$_2$, —C(=O)OG$^2$, —C(=O)N(G$^2$)$_2$, —S(=O)$_2$OG$^2$ and —S(=O)$_2$N(G$^2$)$_2$ in which G$^2$ represents a hydrogen atom, a C$_{1-6}$ alkyl group which may have the same or different 1 to 3 groups selected from the substituent group (C); or a C$_{6-10}$ aryl group which may have the same or different 1 to 3 groups selected from the substituent group (D); and substituent group (B) consists of a halogen atom, a nitro group, a cyano group, -$G^1$, —$OG^2$, —$SG^2$, —C(═O)$OG^2$ in which $G^1$ represents a $C_{1-6}$ alkyl group which may have the same or different 1 to 3 groups selected from the substituent group (C) or a $C_{6-10}$ aryl group which may have the same or different 1 to 3 groups selected from the substituent group (D); and $G^2$ has the same meaning as defined above, or a pharmaceutically acceptable salt thereof or a prodrug thereof;

[3] a pyrazole derivative described in the above [1], wherein one of $Q^0$ and $T^0$ represents a group selected from

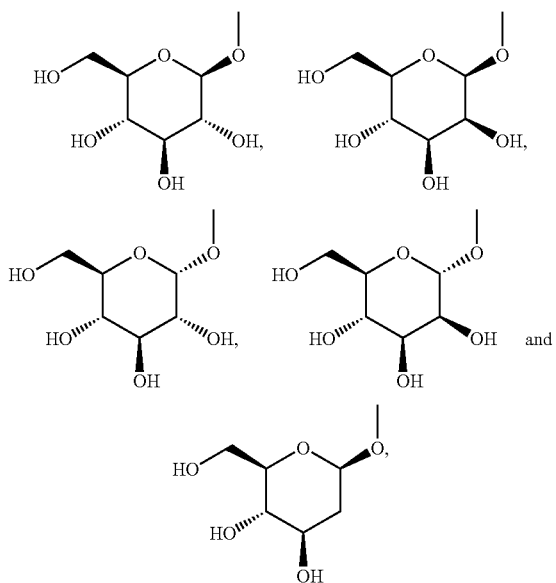

and the other represents a group represented by the formula: —(CH$_2$)$_n$—Ar, or a pharmaceutically acceptable salt thereof or a prodrug thereof;

[4] a pyrazole derivative described in the above [3], wherein wherein $Q^0$ represents a $C_{6-10}$ aryl group which may have the same or different 1 to 3 groups selected from the substituent group (B); $T^0$ represents a group selected from

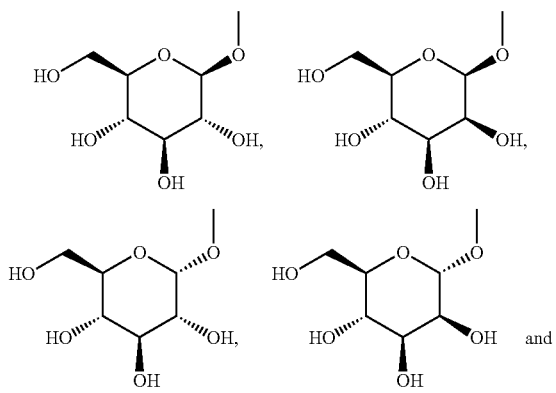

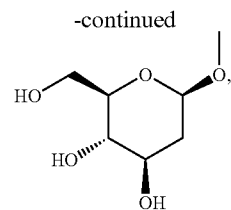

and R represents a $C_{6-10}$ aryl group which may have the same or different 1 to 3 groups selected from the substituent group (B), or a pharmaceutically acceptable salt thereof or a prodrug thereof;

[5] a pyrazole derivative described in the above [4], wherein $T^0$ represents a group:

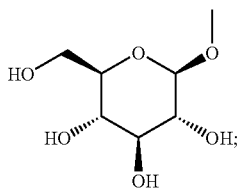

and substituent group (B) consists of a halogen atom, a nitro group, a cyano group, -$G^1$, —$OG^2$, —$SG^2$ and —C(═O)$OG^2$ in which G represents a $C_{1-6}$ alkyl group which may have the same or different 1 to 3 groups selected from the substituent group (C) or a $C_{6-10}$ aryl group which may have the same or different 1 to 3 groups selected from the substituent group (D); and $G^2$ represents a hydrogen atom, a $C_{1-6}$ alkyl group which may have the same or different 1 to 3 groups selected from the substituent group (C) or a $C_{6-10}$ aryl group which may have the same or different 1 to 3 groups selected from the substituent group (D), or a pharmaceutically acceptable salt thereof or a prodrug thereof;

[6] a pyrazole derivative described in the above [1], wherein one of $Q^0$ and $T^0$ represents a group selected from

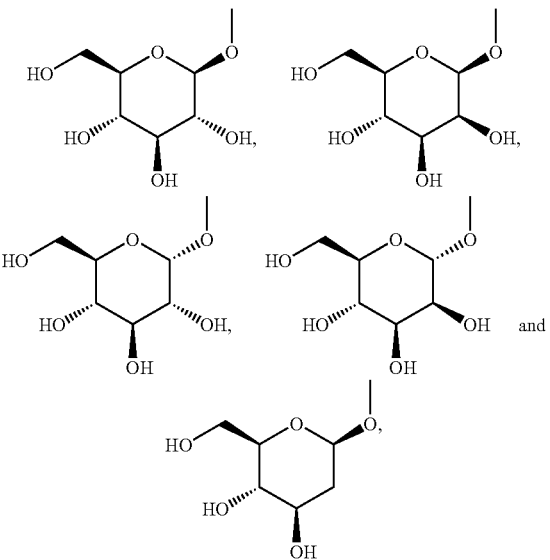

and the other represents a $C_{1-6}$ alkoxy group which may have the same or different 1 to 3 groups selected from the substituent group (A), an optionally mono or di($C_{1-6}$ alkyl)-substituted amino group in which the $C_{1-6}$ alkyl group may have the same or different 1 to 3 groups selected from the substituent group (A), or a $C_{2-9}$ heterocycloalkyl group which may have the same or different 1 to 3 groups selected from the substituent group (A), or a pharmaceutically acceptable salt thereof or a prodrug thereof;

[7] a pyrazole derivative described in the above [6], wherein $Q^0$ represents an optionally mono or di($C_{1-6}$ alkyl)-substituted amino group in which the $C_{1-6}$ alkyl group may have the same or different 1 to 3 groups selected from the substituent group (A), or a $C_{2-9}$ heterocycloalkyl group which may have the same or different 1 to 3 groups selected from the substituent group (A); and $T^0$ represents a group selected from

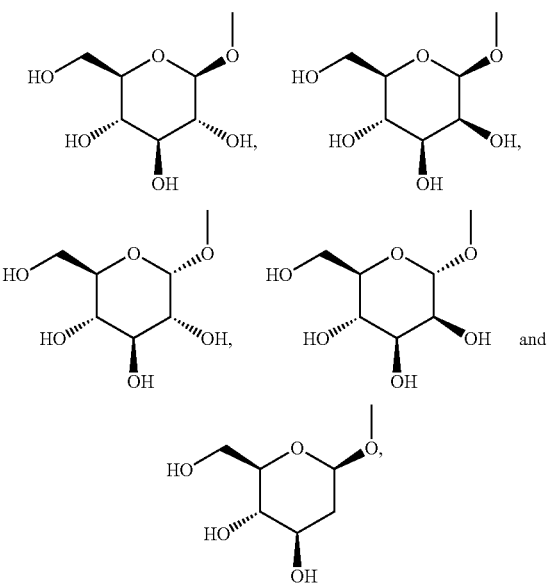

or a pharmaceutically acceptable salt thereof or a prodrug thereof;

[8] a pyrazole derivative described in the above [1], wherein one of $Q^0$ and $T^0$ represents a group selected from

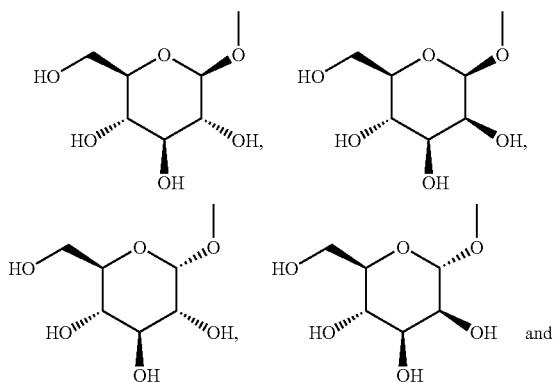

-continued

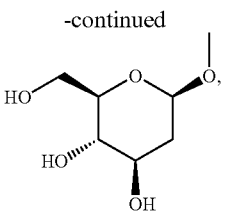

and the other represents a heterocycle-fused phenyl group which may have the same or different 1 to 3 groups selected from the substituent group (B), or a pharmaceutically acceptable salt thereof or a prodrug thereof;

[9] a pyrazole derivative described in the above [8], wherein $Q^0$ represents a heterocycle-fused phenyl group which may have the same or different 1 to 3 groups selected from the substituent group (B); and $T^0$ represents a group selected from

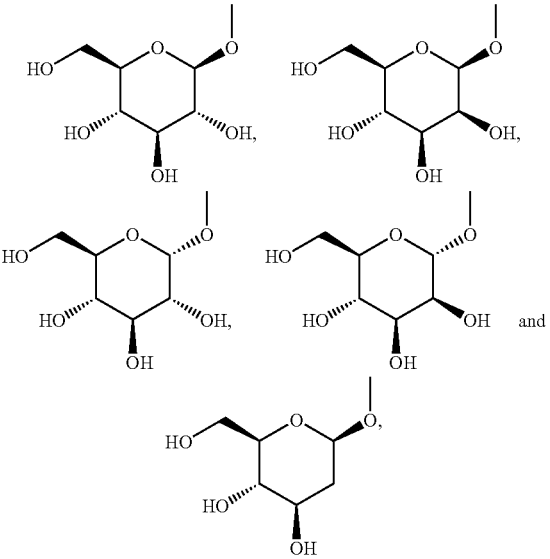

or a pharmaceutically acceptable salt thereof or a prodrug thereof;

[10] a pharmaceutical composition comprising as an active ingredient a pyrazole derivative described in any one of the above [1]-[9], or a pharmaceutically acceptable salt thereof or a prodrug thereof;

[11] an inhibitor of 1,5-anhydroglucitol/fructose/mannose transporter comprising as an active ingredient a pyrazole derivative represented by the following general formula (I):

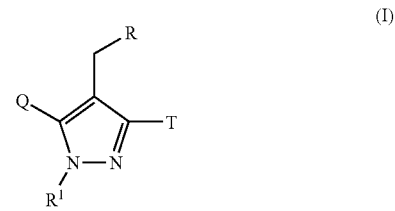

(I)

wherein $R^1$ represents a hydrogen atom, a $C_{1-6}$ alkyl group which may have the same or different 1 to 3 groups selected from the following substituent group (A), a $C_{2-6}$ alkenyl group which may have the same or different 1 to 3 groups selected from the following substituent group (A), a $C_{2-6}$ alkynyl group which may have the same or different 1 to 3 groups selected from the following substituent group (A), a $C_{3-8}$ cycloalkyl group which may have the same or different 1 to 3 groups selected from the following substituent group (A), a $C_{6-10}$ aryl group which may have the same or different 1 to 3 groups selected from the following substituent group (B), a $C_{2-9}$ heterocycloalkyl group which may have the same or different 1 to 3 groups selected from the following substituent group (A), or a $C_{1-9}$ heteroaryl group which may have the same or different 1 to 3 groups selected from the following substituent group (B);

one of Q and T represents a group selected from

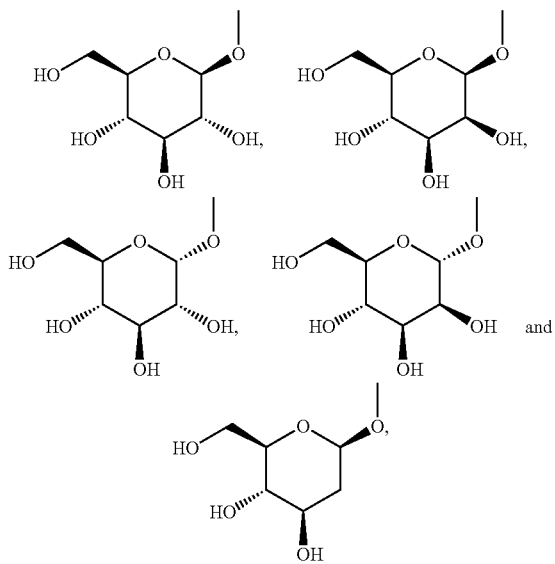

and the other represents a group represented by the formula: —$(CH_2)_n$—Ar wherein Ar represents a $C_{6-10}$ aryl group which may have the same or different 1 to 3 groups selected from the following substituent group (B) or a $C_{1-9}$ heteroaryl group which may have the same or different 1 to 3 groups selected from the following substituent group (B); and n represents an integral number from 0 to 2, a $C_{1-6}$ alkyl group which may have the same or different 1 to 3 groups selected from the following substituent group (A), a $C_{1-6}$ alkoxy group which may have the same or different 1 to 3 groups selected from the following substituent group (A), an optionally mono or di($C_{1-6}$ alkyl)-substituted amino group wherein the $C_{1-6}$ alkyl group may have the same or different 1 to 3 groups selected from the following substituent group (A), a $C_{3-8}$ cycloalkyl group which may have the same or different 1 to 3 groups selected from the following substituent group (A), a $C_{2-9}$ heterocycloalkyl group which may have the same or different 1 to 3 groups selected from the following substituent group (A), or a heterocycle-fused phenyl group which may have the same or different 1 to 3 groups selected from the following substituent group (B);

R represents a $C_{3-8}$ cycloalkyl group which may have the same or different 1 to 3 groups selected from the following substituent group (A), a $C_{6-10}$ aryl group which may have the same or different 1 to 3 groups selected from the following substituent group (B), a $C_{2-9}$ heterocycloalkyl group which may have the same or different 1 to 3 groups selected from the following substituent group (A), or a $C_{1-9}$ heteroaryl group which may have the same or different 1 to 3 groups selected from the following substituent group (B);

[substituent group (A)]:

a halogen atom, a nitro group, a cyano group, an oxo group, -$G^1$, —$OG^2$, —$SG^2$, —$N(G^2)_2$, —$C(=O)G^2$, —$C(=O)OG^2$, —$C(=O)N(G^2)_2$, —$S(=O)_2G^2$, —$S(=O)_2OG^2$, —$S(=O)_2N(G^2)_2$, —$S(=O)G^1$, —$OC(=O)G^1$, —$OC(=O)N(G^2)_2$, —$NHC(=O)G^2$, —$OS(=O)_2G^1$, —$NHS(=O)_2G^1$ and —$C(=O)NHS(=O)_2G^1$;

[substituent group (B)]:

a halogen atom, a nitro group, a cyano group, -$G^1$, —$OG^2$, —$SG^2$, —$N(G^2)_2$, —$G^3OG^4$, —$G^3N(G^4)_2$, —$C(=O)G^2$, —$C(=O)OG^2$, —$C(=O)N(G^2)_2$, —$S(=O)_2G^2$, —$S(=O)_2OG^2$, —$S(=O)_2N(G^2)_2$, —$S(=O)G^1$, —$OC(=O)G^1$, —$OC(=O)N(G^2)_2$, —$NHC(=O)G^2$, —$OS(=O)_2G^1$, —$NHS(=O)_2G^1$ and —$C(=O)NHS(=O)_2G^1$;

in the above substituent group (A) and/or (B), $G^1$ represents a $C_{1-6}$ alkyl group which may have the same or different 1 to 3 groups selected from the following substituent group (C), a $C_{2-6}$ alkenyl group which may have the same or different 1 to 3 groups selected from the following substituent group (C), a $C_{2-6}$ alkynyl group which may have the same or different 1 to 3 groups selected from the following substituent group (C), a $C_{3-8}$ cycloalkyl group which may have the same or different 1 to 3 groups selected from the following substituent group (C), a $C_{6-10}$ aryl group which may have the same or different 1 to 3 groups selected from the following substituent group (D), a $C_{2-9}$ heterocycloalkyl group which may have the same or different 1 to 3 groups selected from the following substituent group (C), or a $C_{1-9}$ heteroaryl group which may have the same or different 1 to 3 groups selected from the following substituent group (D);

$G^2$ represents a hydrogen atom, a $C_{1-6}$ alkyl group which may have the same or different 1 to 3 groups selected from the following substituent group (C), a $C_{2-6}$ alkenyl group which may have the same or different 1 to 3 groups selected from the following substituent group (C), a $C_{2-6}$ alkynyl group which may have the same or different 1 to 3 groups selected from the following substituent group (C), a $C_{3-8}$ cycloalkyl group which may have the same or different 1 to 3 groups selected from the following substituent group (C), a $C_{6-10}$ aryl group which may have the same or different 1 to 3 groups selected from the following substituent group (D), a $C_{2-9}$ heterocycloalkyl group which may have the same or different 1 to 3 groups selected from the following substituent group (C), or a $C_{1-9}$ heteroaryl group which may have the same or different 1 to 3 groups selected from the following substituent group (D), and with the proviso that $G^2$ may be the same or different when there are 2 or more $G^2$ in the substituents;

$G^3$ represents a $C_{1-6}$ alkyl group;

$G^4$ represents a $C_{1-6}$ alkyl group which may have the same or different 1 to 3 groups selected from the following substituent group (C), and with the proviso that $G^4$ may be the same or different when there are 2 or more $G^4$ in the substituents;

[Substituent Group (C)]:

a halogen atom, a nitro group, a cyano group, an oxo group, -$G^5$, —$OG^6$, —$SG^6$, —$N(G^6)_2$, —$C(=O)G^6$, —$C(=O)OG^6$, -$C(=O)N(G^6)_2$, —$S(=O)_2G^6$, —$S(=O)_2OG^6$, —$S(=O)_2$ $N(G^6)_2$, $-S(=O)G^5$, $-OC(=O)G^5$, $-OC(=O)N(G^6)_2$, $-NHC(=O)G^6$, $-OS(=O)_2G^5$, $-NHS(=O)_2G^5$ and $-C(=O)NHS(=O)_2G^5$; and

[Substituent Group (D)]:
a halogen atom, a nitro group, a cyano group, $-G^5$, $-OG^6$, $-SG^6$, $-N(G^6)_2$, $-C(=O)G^6$, $-C(=O)OG^6$, $-C(=O)N(G^6)_2$, $-S(=O)G^6$, $-S(=O)_2OG^6$, $-S(=O)_2N(G^6)_2$, $-S(=O)G^5$, $-OC(=O)G^5$, $-OC(=O)N(G^6)_2$, $-NHC(=O)G^6$, $-OS(=O)_2G^5$, $-NHS(=O)_2G^5$ and $-C(=O)NHS(=O)_2G^5$; in the substituent group (C) and/or (D), $G^5$ represents a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group; and $G^6$ represents a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group, and with the proviso that $G^6$ may be the same or different when there are 2 or more $G^6$ in the substituents, or a pharmaceutically acceptable salt thereof or a prodrug thereof;

[12] an inhibitor of 1,5-anhydroglucitol/fructose/mannose transporter comprising as an active ingredient a pyrazole derivative described in any one of the above [1]-[9], or a pharmaceutically acceptable salt thereof or a prodrug thereof;

[13] an agent described in the above [11], which is an agent for the prevention, inhibition of progression or treatment of a disease associated with the excess uptake of at least a kind of carbohydrates selected from glucose, fructose and mannose;

[14] an agent for the prevention, inhibition of progression or treatment of a disease associated with the excess uptake of at least a kind of carbohydrates selected from glucose, fructose and mannose comprising as an active ingredient a pyrazole derivative described in any one of the above [1]-[9], or a pharmaceutically acceptable salt thereof or a prodrug thereof;

[15] an agent described in the above [13], wherein the disease associated with the excess uptake of at least a kind of carbohydrates selected from glucose, fructose and mannose is diabetic complications;

[16] an agent described in the above [14], wherein the disease associated with the excess uptake of at least a kind of carbohydrates selected from glucose, fructose and mannose is diabetic complications;

[17] an agent described in the above [15], wherein the diabetic complications is diabetic nephropathy;

[18] an agent described in the above [16], wherein the diabetic complications is diabetic nephropathy;

[19] an agent described in the above [13], wherein the disease associated with the excess uptake of at least a kind of carbohydrates selected from glucose, fructose and mannose is diabetes;

[20] an agent described in the above [14], wherein the disease associated with the excess uptake of at least a kind of carbohydrates selected from glucose, fructose and mannose is diabetes;

[21] a pharmaceutical combination which comprises (component a) a pyrazole derivative described in any one of the above [1]-[9], or a pharmaceutically acceptable salt thereof or a prodrug thereof, and (component b) at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethylglutaryl coenzyme A reductase inhibitor, a fibric acid derivative, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and aurinary alkalinizer;

[22] a pyrazole derivative represented by the following general formula (IIα):

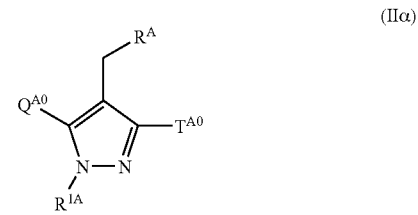

(IIα)

wherein $R^{1A}$ represents a hydrogen atom, a $C_{1-6}$ alkyl group which may have the same or different 1 to 3 groups selected from the following substituent group (A1), a $C_{2-6}$ alkenyl group which may have the same or different 1 to 3 groups selected from the following substituent group (A1), a $C_{2-6}$ alkynyl group which may have the same or different 1 to 3 groups selected from the following substituent group (A1), a $C_{3-8}$ cycloalkyl group which may have the same or different 1 to 3 groups selected from the following substituent group (A1), a $C_{6-10}$ aryl group which may have the same or different 1 to 3 groups selected from the following substituent group (B1), a $C_{2-9}$ heterocycloalkyl group which may have the same or different 1 to 3 groups selected from the following substituent group (A1), or a $C_{1-9}$ heteroaryl group which may have the same or different 1 to 3 groups selected from the following substituent group (B1);

one of $Q^{4O}$ and $T^{4O}$ represents a group selected from

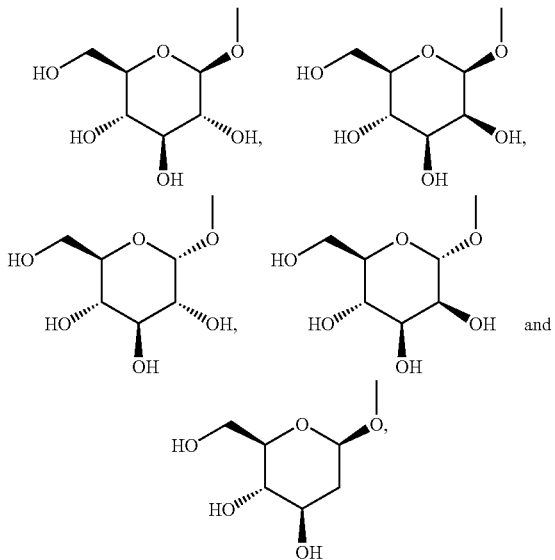

having protective group(s), and the other represents a group represented by the formula: —$(CH_2)_n$—Ar wherein $Ar^A$ represents a $C_{6-10}$ aryl group which may have the same or different 1 to 3 groups selected from the following substituent group (B1) or a $C_{1-9}$ heteroaryl group which may have the same or different 1 to 3 groups selected from the following substituent group (B1); and n represents an integral number from 0 to 2, a $C_{1-6}$ alkoxy group which may have the same or different 1 to 3 groups selected from the following substituent group (A1), an optionally mono or di($C_{1-6}$ alkyl)-substituted amino group wherein the $C_{1-6}$ alkyl group may have the same or different 1 to 3 groups selected from the following substituent group (A1), a $C_{2-9}$ heterocycloalkyl group which may have the same or different 1 to 3 groups selected from the following substituent group (A1), or a heterocycle-fused phenyl group which may have the same or different 1 to 3 groups selected from the following substituent group (B1);

$R^A$ represents a $C_{3-8}$ cycloalkyl group which may have the same or different 1 to 3 groups selected from the following substituent group (A1), a $C_{6-10}$ aryl group which may have the same or different 1 to 3 groups selected from the following substituent group (B1), a $C_{2-9}$ heterocycloalkyl group which may have the same or different 1 to 3 groups selected from the following substituent group (A1), or a $C_{1-9}$ heteroaryl group which may have the same or different 1 to 3 groups selected from the following substituent group (B1);

[Substituent Group (A1)]:

a halogen atom, a nitro group, a cyano group, an oxo group, -$G^{1A}$, —$OG^{2B}$, —$SG^{2B}$, —$N(G^{2B})_2$, —$C(=O)G^{2A}$, —$C(=O)OG^{2B}$, —$C(=O)N(G^{2B})_2$, —$S(=O)_2G^{2A}$, —$S(=O)_2OG^{2A}$, —$S(=O)_2N(G^{2B})_2$, —$S(=O)G^{1A}$, —$OC(=O)G^{1A}$, —$OC(=O)N(G^{2B})_2$, —$NHC(=O)G^{2A}$, —$OS(=O)_2G^{1A}$, —$NHS(=O)_2G^{1A}$ and —$C(=O)NHS(=O)_2G^{1A}$;

[Substituent Group (B1)]:

a halogen atom, a nitro group, a cyano group, -$G^{1A}$, —$OG^{2B}$, —$SG^{2B}$, —$N(G^{2B})_2$, —$G^3OG^{4A}$, —$G^3N(G^{4A})_2$, —$C(=O)G^{2A}$, —$C(=O)OG^{2B}$, —$C(=O)N(G^{2B})_2$, —$S(=O)_2G^{2A}$, —$S(=O)_2OG^{2A}$, —$S(=O)_2N(G^{2B})_2$, —$S(=O)G^{1A}$, —$OC(=O)G^{1A}$, —$OC(=O)N(G^{2B})_2$, —$NHC(=O)G^{2A}$, —$OS(=O)_2G^{1A}$, —$NHS(=O)_2G^{1A}$ and —$C(=O)NHS(=O)_2G^{1A}$;

in the above substituent group (A1) and/or (B1), $G^{1A}$ represents a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1);

$G^{2A}$ represents a hydrogen atom, a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1);

$G^{2B}$ represents a protective group, a hydrogen atom, a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1), and with the proviso that $G^{2B}$ may be the same or different when there are 2 or more $G^{2B}$ in the substituents;

$G^3$ represents a $C_{1-6}$ alkyl group;

$G^{4A}$ represents a $C_{1-6}$ alkyl group which may have the same or different 1 to 3 groups selected from the following substituent group (C1), and with the proviso that $G^{4A}$ may be the same or different when there are 2 or more $G^{4A}$ in the substituents;

[Substituent Group (C1)]:

a halogen atom, a nitro group, a cyano group, -$G^5$, —$OG^{6A}$, —$SG^{6A}$, —$N(G^{6A})_2$, —$C(=O)G^6$, —$C(=O)OG^{6A}$, —$C(=O)N(G^{6A})_2$, —$S(=O)_2G^6$, —$S(O)_2OG^6$, —$S(=O)_2N(G^{6A})_2$, —$S(=O)G^5$, —$OC(=O)G^5$, —$OC(=O)N(G^{6A})_2$, —$NHC(=O)G^6$, —$OS(=O)_2G^5$, —$NHS(=O)_2G^5$ and —$C(=O)NHS(=O)_2G^5$; and

[Substituent Group (D1)]:

a halogen atom, a nitro group, a cyano group, $-G^5$, $-OG^{6A}$, $-SG^{6A}$, $-N(G^{6A})_2$, $-C(=O)G^6$, $-C(=O)OG^{6A}$, $-C(=O)N(G^{6A})_2$, $-S(=O)_2G^6$, $-S(=O)_2OG^6$, $-S(=O)_2N(G^{6A})_2$, $-S(=O)G^5$, $-OC(=O)G^5$, $-OC(=O)N(G^{6A})_2$, $-NHC(=O)G^6$, $-OS(=O)_2G^5$, $-NHS(=O)_2G^5$ and $-C(=O)NHS(=O)_2G^5$; in the substituent group (C1) and/or (D1), $G^5$ represents a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group;

$G^6$ represents a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group; and $G^{6A}$ represents a protective group, a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group, and with the proviso that $G^{6A}$ may be the same or different when there are 2 or more $G^{6A}$ in the substituents, or a pharmaceutically acceptable salt thereof;

[23] a pyrazole derivative represented by the following general formula (IIIα):

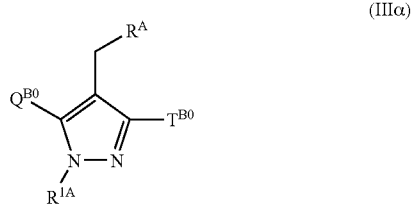

wherein $R^{1A}$ represents a hydrogen atom, a $C_{1-6}$ alkyl group which may have the same or different 1 to 3 groups selected from the following substituent group (A1), a $C_{2-6}$ alkenyl group which may have the same or different 1 to 3 groups selected from the following substituent group (A1), a $C_{2-6}$ alkynyl group which may have the same or different 1 to 3 groups selected from the following substituent group (A1), a $C_{3-8}$ cycloalkyl group which may have the same or different 1 to 3 groups selected from the following substituent group (A1), a $C_{6-10}$ aryl group which may have the same or different 1 to 3 groups selected from the following substituent group (B1), a $C_{2-9}$ heterocycloalkyl group which may have the same or different 1 to 3 groups selected from the following substituent group (A1), or a $C_{1-9}$ heteroaryl group which may have the same or different 1 to 3 groups selected from the following substituent group (B1);

one of $Q^{B0}$ and $T^{B0}$ represents a hydroxy group, and the other represents a group represented by the formula: $-(CH_2)_n-Ar^A$ wherein $Ar^A$ represents a $C_{6-10}$ aryl group which may have the same or different 1 to 3 groups selected from the following substituent group (B1) or a $C_{1-9}$ heteroaryl group which may have the same or different 1 to 3 groups selected from the following substituent group (B1); and n represents an integral number from 0 to 2, a $C_{1-6}$ alkoxy group which may have the same or different 1 to 3 groups selected from the following substituent group (A1), an optionally mono or di($C_{1-6}$ alkyl)-substituted amino group wherein the $C_{1-6}$ alkyl group may have the same or different 1 to 3 groups selected from the following substituent group (A1), a $C_{2-9}$ heterocycloalkyl group which may have the same or different 1 to 3 groups selected from the following substituent group (A1), or a heterocycle-fused phenyl group which may have the same or different 1 to 3 groups selected from the following substituent group (B1);

$R^A$ represents a $C_{3-8}$ cycloalkyl group which may have the same or different 1 to 3 groups selected from the following substituent group (A1), a $C_{6-10}$ aryl group which may have the same or different 1 to 3 groups selected from the following substituent group (B1), a $C_{2-9}$ heterocycloalkyl group which may have the same or different 1 to 3 groups selected from the following substituent group (A1), or a $C_{1-9}$ heteroaryl group which may have the same or different 1 to 3 groups selected from the following substituent group (B1);

[Substituent Group (A1)]:

a halogen atom, a nitro group, a cyano group, an oxo group, $-G^{1A}$, $-OG^{2B}$, $-SG^{2B}$, $-N(G^{2B})_2$, $-C(=O)G^{2A}$, $-C(=O)OG^{2B}$, $-C(=O)N(G^{2B})_2$, $-S(=O)_2G^{2A}$, $-S(=O)_2OG^{2A}$, $-S(=O)_2N(G^{2B})_2$, $-S(=O)G^{1A}$, $-OC(=O)G^{1A}$, $-OC(=O)N(G^{2B})_2$, $-NHC(=O)G^{2A}$, $-OS(=O)_2G^{1A}$, $-NHS(=O)_2G^{1A}$ and $-C(=O)NHS(=O)_2G^{1A}$;

[Substituent Group (B1)]:

a halogen atom, a nitro group, a cyano group, $-G^{1A}$, $-OG^{2B}$, $-SG^{2B}$, $-N(G^{2B})_2$, $-G^3OG^{4A}$, $-G^3N(G^{4A})_2$, $-C(=O)G^{2A}$, $-C(=O)OG^{2B}$, $-C(=O)N(G^{2B})_2$, $-S(=O)_2G^{2A}$, $-S(=O)_2OG^{2A}$, $-S(=O)_2N(G^{2B})_2$, $-S(=O)G^{1A}$, $-OC(=O)G^{1A}$, $-OC(=O)N(G^{2B})_2$, $-NHC(=O)G^{2A}$, $-OS(=O)_2G^{1A}$, $-NHS(=O)_2G^{1A}$ and $-C(=O)NHS(=O)_2G^{1A}$;

in the above substituent group (A1) and/or (B1), $G^{1A}$ represents a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1);

$G^{2A}$ represents a hydrogen atom, a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1);

$G^{2B}$ represents a protective group, a hydrogen atom, a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1), and with the proviso that $G^{2B}$ may be the same or different when there are 2 or more $G^{2B}$ in the substituents;

$G^3$ represents a $C_{1-6}$ alkyl group;

$G^{4A}$ represents a $C_{1-6}$ alkyl group which may have the same or different 1 to 3 groups selected from the following substituent group (C1), and with the proviso that $G^{4A}$ may be the same or different when there are 2 or more $G^{4A}$ in the substituents;

[Substituent Group (C1)]:

a halogen atom, a nitro group, a cyano group, an oxo group, -$G^5$, —$OG^{6A}$, —$SG^{6A}$, —$N(G^{6A})_2$, —$C(=O)G^6$, —$C(=O)OG^{6A}$, —$C(=O)N(G^{6A})_2$, —$S(=O)_2G^6$, —$S(=O)_2OG^6$, —$S(=O)_2N(G^{6A})_2$, —$S(=O)G^5$, —$OC(=O)G^5$, —$OC(=O)N(G^{6A})_2$, —$NHC(=O)G^6$, —$OS(=O)_2G^5$, —$NHS(=O)_2G^5$ and —$C(=O)NHS(=O)_2G^5$; and

[Substituent Group (D1)]:

a halogen atom, a nitro group, a cyano group, -$G^5$, —$OG^{6A}$, —$SG^{6A}$, —$N(G^{6A})_2$, —$C(=O)G^6$, —$C(=O)OG^{6A}$, —$C(=O)N(G^{6A})_2$, —$S(=O)_2G^6$, —$S(=O)_2OG^6$, —$S(=O)_2N(G^{6A})_2$, —$S(=O)G^5$, —$OC(=O)G^5$, —$OC(=O)N(G^{6A})_2$, —$NHC(=O)G^6$, —$OS(=O)_2G^5$, —$NHS(=O)_2G^5$ and —$C(=O)NHS(=O)_2G^5$;

in the substituent group (C1) and/or (D1), $G^5$ represents a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group;

$G^6$ represents a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group; and $G^{6A}$ represents a protective group, a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group, and with the proviso that $G^{6A}$ may be the same or different when there are 2 or more $G^{6A}$ in the substituents, or a pharmaceutically acceptable salt thereof; and the like.

In the present invention, the term "$C_{1-6}$ alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "$C_{2-6}$ alkenyl group" means a straight-chained or branched alkenyl group having 2 to 6 carbon atoms such as a vinyl group, an allyl group, a 1-propenyl group, an isopropenyl group, a 1-butenyl group, a 2-butenyl group, a 2-methylallyl group or the like; the term "$C_{2-6}$ alkynyl group" means a straight-chained or branched alkynyl group having 2 to 6 carbon atoms such as an ethynyl group, a 2-propynyl group or the like; the term "$C_{1-6}$ alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; the term "optionally mono or di($C_{1-6}$ alkyl)-substituted amino group" means an amino group optionally mono-substituted by the above $C_{1-6}$ alkyl group or di-substituted by the same or different $C_{1-6}$ alkyl groups as defined above; the term "$C_{3-8}$ cycloalkyl group" means a cyclopropyl group, a cyclobutyl group, a cyclopentyl group, a cyclohexyl group, a cycloheptyl group or a cyclooctyl group; the term "$C_{6-10}$ aryl group" means a phenyl group or a naphthyl group; the term "$C_{2-9}$ heterocycloalkyl group" means a 3 to 8-membered heterocycloalkyl group containing the same or different 1 or 2 hetero atoms other than the binding position selected from an oxygen atom, a sulfur atom and a nitrogen atom in the ring, which is derived from morpholine, thiomorpholine, tetrahydrofuran, tetrahydropyran, aziridine, azetidine, pyrrolidine, imidazolidine, oxazoline, piperidine, piperazine, pyrazolidine or the like, or a 5 or 6-membered heterocycloalkyl group as defined above fused with an aliphatic or aromatic carbocycle or heterocycle such as a cyclohexane ring, a benzene ring, a pyridine ring or the like; the term "$C_{1-9}$ heteroaryl group" means a 5 or 6-membered heteroaryl group containing the same or different 1 to 4 hetero atoms other than the binding position selected from an oxygen atom, a sulfur atom and a nitrogen atom in the ring, which is derived from thiazole, oxazole, isothiazole, isoxazole, pyridine, pyrimidine, pyrazine, pyridazine, pyrrole, thiophene, imidazole, pyrazole, oxadiazole, thiodiazole, tetrazole, furazan or the like, or the above heteroaryl group fused with a 5 or 6-membered aromatic carbocycle or heterocycle such as a benzene ring, a pyrazole ring, a pyridine ring or the like; the term "heterocycle-fused phenyl group" means a phenyl group fused with a 3 to 8-membered heterocycloalkene containing the same or different 1 or 2 hetero atoms selected from an oxygen atom, a sulfur atom and a nitrogen atom in the ring, which is derived from dioxane, dioxolan, morpholine, thiomorpholine, tetrahydrofuran, tetrahydropyran, azetidine, pyrrolidine, imidazolidine, oxazolidine, piperidine, piperazine, pyrazolidine or the like, or a phenyl group fused with a 5 or 6-membered aromatic heterocycle containing the same or different 1 to 3 hetero atoms selected from an oxygen atom, a sulfur atom and a nitrogen atom in the ring such as thiazole, oxazole, isothiazole, isoxazole, pyridine, pyrimidine, pyrazine, pyridazine, pyrrole, thiophene, imidazole, pyrazole or the like; the term "halogen atom" means a fluorine atom, a chlorine atom, a bromine atom or an iodine atom; the term "hydroxy-protective group" means a hydroxy-protective group used in general organic syntheses such as a benzyl group, a p-methoxybenzyl group, a p-nitrobenzyl group, a methoxymethyl group, an acetyl group, a tert-butyldimethylsilyl group, a triisopropylsilyl group, an allyl group, a benzoyl group, a pivaloyl group, a benzyloxycarbonyl group or the like; the term "thiol-protective group" means a thiol-protective group used in general organic syntheses such as a benzyl group, a p-methoxybenzyl group, a p-nitrobenzyl group, a triphenylmethyl group, a methoxymethyl group, an acetyl group, a benzoyl group, a pivaloyl group, a benzyloxycarbonyl group, an ethylaminocarbonyl group or the like; the term "amino-protective group" means an amino-protective group used in general organic syntheses such as a benzyloxycarbonyl group, a tert-butoxy-carbonyl group, a benzyl group, a trifluoroacetyl group or the like; the term "carboxy-protective group" means a carboxy-protective group used in general organic syntheses such as a benzyl group, a tert-butyldimethylsilyl group, an allyl group, a methyl group, an ethyl group or the like; and the term "amide-protective group" means an amide-protective group used in general organic syntheses such as a tosyl group, a methoxymethyl group, a benzyloxymethyl group, an allyl group, a triusopropylsilyl group, a benzyl group, a methoxycarbonyl group or the like.

For example, the compounds represented by the above general formula (I) of the present invention can be prepared according to the following procedure:

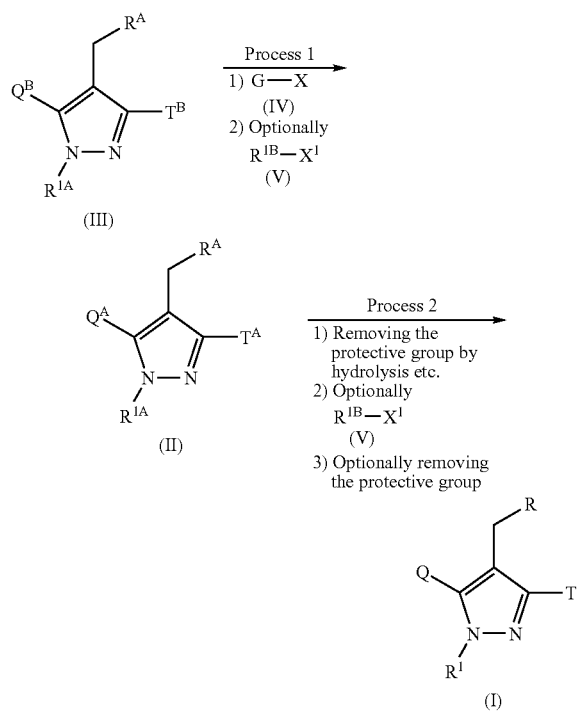

wherein

G represents a group selected from a β-D-glucopyranosyloxy group, a β-D-mannopyranosyloxy group, an α-D-glucopyranosyloxy, an α-D-mannopyranosyloxy group, β-D-2-deoxyglucopyranosyloxy group and an α-D-2-deoxyglucopyranosyloxy group, which has a hydroxy-protective group at a hydroxy group;

X represents a leaving group such as a bromine atom;

$X^1$ represents a leaving group such as a halogen atom, a mesyloxy group, a tosyloxy group;

$R^{1B}$ represents a $C_{1-6}$ alkyl group which may have the same or different 1 to 3 groups selected from the above substituent group (A1), a $C_{2-6}$ alkenyl group which may have the same or different 1 to 3 groups selected from the above substituent group (A1), a $C_{2-6}$ alkynyl group which may have the same or different 1 to 3 groups selected from the above substituent group (A1), a $C_{3-8}$ cycloalkyl group which may have the same or different 1 to 3 groups selected from the above substituent group (A1), a $C_{6-10}$ aryl group which may have the same or different 1 to 3 groups selected from the above substituent group (B1), a $C_{2-9}$ heterocycloalkyl group which may have the same or different 1 to 3 groups selected from the above substituent group (A1), or a $C_{1-9}$ heteroaryl group which may have the same or different 1 to 3 groups selected from the above substituent group (B1);

one of $Q^A$ and $T^A$ represents a group selected from

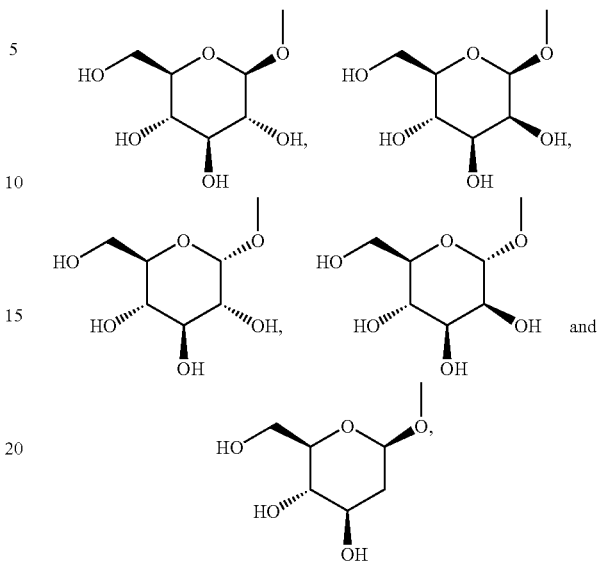

and the other represents a group represented by the formula: $-(CH_2)_n-Ar^4$ wherein $Ar^4$ represented a $C_{6-10}$ aryl group which may have the same or different 1 to 3 groups selected from the above substitutent group (B1) or a $C_{1-9}$ heteroaryl group which may have the same or different 1 to 3 groups selected from the above substituent group (21); and n represents an integral number from 0 to 2, a $C_{1-6}$ alkyl group which may have the same or different 1 to 3 groups selected from the above substituent group (A1), a $C_{1-6}$ alkoxy group which may have the same or different 1 to 3 groups selected from the above substitutent group (A1), an optionally mono or di($C_{1-6}$ alkyl)-substituted amino group wherein the $C_{1-6}$ alkyl group may have the same or different 1 to 3 groups selected from the above substitutent group (A1), a $C_{3-8}$ cycloalkyl group which may have the same or different 1 to 3 groups selected from the above substitutent group (A1), a $C_{2-9}$ heterocycloalkyl group which may have the same or different 1 to 3 groups selected from the above substituent group (A1), or a heterocycle-fused phenyl group which may have the same or different 1 to 3 groups selected from the above substituent group (B1);

one of $Q^B$ and $T^B$ represents a hydroxy group, and the other represents a group represented by the formula: $-(CH_2)_n-Ar^4$ wherein $Ar^4$ represented a $C_{6-10}$ aryl group which may have the same or different 1 to 3 groups selected from the following substituent group (B1) or a $C_{1-9}$ heteroaryl group which may have the same or different 1 to 3 groups selected from the following substituent group (B1); and n represents an integral number from 0 to 2, a $C_{1-6}$ alkyl group which may have the same or different 1 to 3 groups selected from the above substituent group (A1), a $C_{1-6}$ alkoxy group which may have the same or different 1 to 3 groups selected from the above substituent group (A1), an optionally mono or di($C_{1-6}$ alkyl)-substituted amino group wherein the $C_{1-6}$ alkyl group may have the same or different 1 to 3 groups selected from the above sutstituent group (A1), a $C_{3-8}$ cycloalkyl group which may have the same or different 1 to 3 groups selected from the above substituent group (A1), a $C_{2-9}$ heterocycloalkyl group which may have the same or different 1 to 3 groups selected from the above substituent group (A1), or a heterocycle-fused phenyl group which may have the same or different 1 to 3 groups selected from the above substituent group (B1);

and R, $R^1$, $R^{1A}$, $R^A$, Q and T have the same meanings as defined above.

Process 1

A compound represented by the above general formula (II) can be prepared by subjecting a pyrazole derivative represented by the above general formula (III) to glycosidation using a sugar donor represented by the above general formula (IV) 1) in the presence of a base such as sodium hydroxide, potassium hydroxide, potassium carbonate or the like and a phase transfer catalyst such as benzyltri(n-butyl) ammonium chloride, benzyltri (n-butyl) ammonium bromide, tetra(n-butyl)ammonium hydrogen sulfate or the like in water and an inert solvent, 2) in the presence of silver carbonate in tetrahydrofuran, or 3) in the presence of potassium carbonate in acetonitrile or tetrahydrofuran, and optionally to N-alkylation using an alkylating agent represented by the above general formula (V) in the presence of a base such as cesium carbonate, potassium carbonate or sodium hydride and optionally in the presence of a catalytic amount of sodium iodide in an inert solvent. As the inert solvent used in the glycosidation, for example, dichloromethane, toluene, benzotrifluoride and the like can be illustrated. The reaction temperature is usually from 0° C. to reflux temperature, and the reaction time is usually from 30 minutes to 1 day, varying based on a used starting material, solvent and reaction temperature. As the solvent used in the N-alkylation, for example, acetonitrile, ethanol, 1,2-dimethoxyethane, tetrahydrofuran, N,N-dimethylformamide, N,N-dimethylacetamide, N-methylpyrrolidinone, dimethyl sulfoxide, a mixed solvent thereof and the like can be illustrated. The reaction temperature is usually from room temperature to reflux temperature, and the reaction time is usually from 10 minutes to 1 day, varying based on a used starting material, solvent and reaction temperature. The obtained compound represented by the above general formula (II) can be also used in the process 2 after converting into a salt thereof in the usual way.

Process 2

A compound represented by the above general formula (I) of the present invention can be prepared by subjecting a compound represented by the above general formula (II), after removing the protective group of sugar moiety or the like in accordance with a method used in general organic syntheses such as alkaline hydrolysis, optionally to N-Alkylation using an alkylating agent represented by the above general formula (V) in the presence of a base such as cesium carbonate, potassium carbonate or sodium hydride and optionally in the presence of a catalytic amount of sodium iodide in an inert solvent, and in a case that there is a protective group other than the sugar moiety, by removing the protective group in accordance with a method used in general organic synthesis. As the inert solvent used in the hydrolysis reaction, methanol, ethanol, tetrahydrofuran, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 30 minutes to 1 day, varying based on a used starting material, solvent and reaction temperature. As the solvent used in the N-alkylation, for example, acetonitrile, ethanol, 1,2-dimethoxyethane, tetrahydrofuran, N,N-dimethylformamide, N,N-dimethylacetamide, N-methylpyrrolidinone, dimethyl sulfoxide, a mixed solvent thereof and the like can be illustrated. The reaction temperature is usually from room temperature to reflux temperature, and the reaction time is usually from 10 minutes to 1 day, varying based on a used starting material, solvent and reaction temperature.

Of the compounds represented by the above general formula (I) of the invention, a compound having a $C_{1-6}$ alkoxy group which may have various substituents, for example, can be prepared by subjecting a corresponding hydroxy compound to O-alkylation using an O-alkylating agent such as a corresponding $C_{1-6}$ alkyl halide in the presence of a base such as cesium carbonate, potassium carbonate or sodium hydride and optionally in the presence of a catalytic amount of sodium iodide in an inert solvent. As the inert solvent used in the O-alkylation, for example, acetonitrile, ethanol, 1,2-dimethoxyethane, tetrahydrofuran, N,N-dimethylformamide, N,N-dimethylacetamide, N-methylpyrrolidinone, dimethyl sulfoxide, a mixed solvent thereof and the like can be illustrated. The reaction temperature is usually from room temperature to reflux temperature, and the reaction time is usually from 10 minutes to 1 day, varying based on a used starting material, solvent and reaction temperature. In the above processes 1 to 2, the above O-alkylation can be subjected to a corresponding hydroxy derivative suitably derived as a production intermediate, and the resulting compound can be treated in a similar manner to produce a compound of the present invention.

Of the compounds represented by the above general formula (I) of the invention, a compound wherein one of Q and T represents a β-D-mannopyranosyloxy group, for example, can be also prepared according to the following procedures:

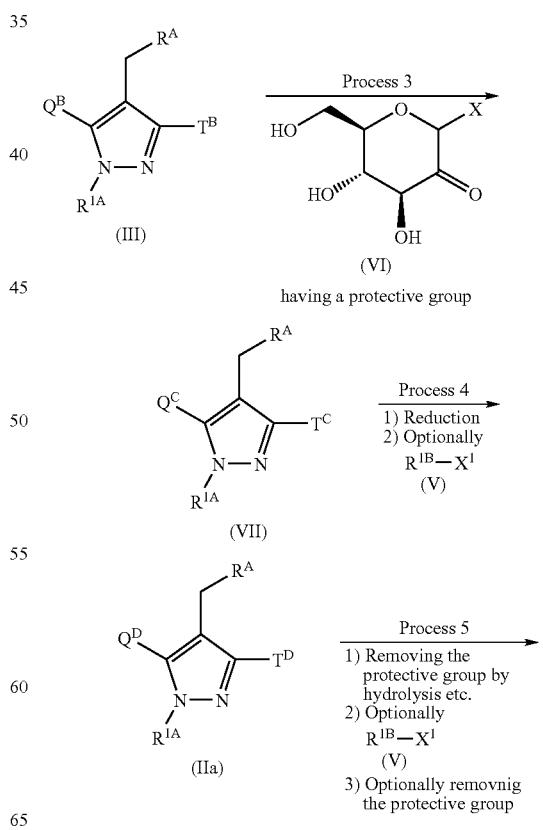

-continued

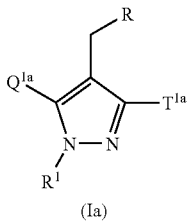

(Ia)

wherein one of $Q^C$ and $T^C$ represents a group of the formula:

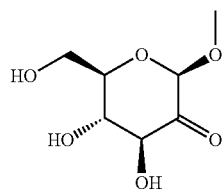

having a protective group, and the other represents a group represented by the formula: —$(CH_2)_n$—$Ar^4$ in which $Ar^4$ and n have the same meanings as defined above, a $C_{1-6}$ alkyl group which may have the same or different 1 to 3 groups selected from the above substituent group (A1), a $C_{1-6}$ alkoxy group which may have the same or different 1 to 3 groups selected from the above substituent group (A1), an optionally mono or di($C_{1-6}$ alkyl)-substituted amino group wherein the $C_{1-6}$ alkyl group may have the same or different 1 to 3 groups selected from the above substituent group (A1), a $C_{3-8}$ cycloalkyl group which may have the same or different 1 to 3 groups selected from the above substituent group (A1), a $C_{2-9}$ heterocycloalkyl group which may have the same or different 1 to 3 groups selected from the above substituent group (A1), or a heterocycle-fused phenyl group which may have the same or different 1 to 3 groups selected from the above substituent group (B1);

one of $Q^D$ and $T^D$ represents a β-D-mannopyranosyloxy group having a protective group, and the other represents a group represented by the formula: —$(CH_2)_n$—$Ar^4$ in which $Ar^4$ and n have the same meanings as defined above, a $C_{1-6}$ alkyl group which may have the same or different 1 to 3 groups selected from the above substituent group (A1), a $C_{1-6}$ alkoxy group which may have the same or different 1 to 3 groups selected from the above substituent group (A1), an optionally mono or di($C_{1-6}$ alkyl)-substituted amino group wherein the $C_{1-6}$ alkyl group may have the same or different 1 to 3 groups selected from the above substituent group (A1), a $C_{3-8}$ cycloalkyl group which may have the same or different 1 to 3 groups selected from the above substituent group (A1), a $C_{2-9}$ heterocycloalkyl group which may have the same or different 1 to 3 groups selected from the above substituent group (A1), or a heterocycle-fused phenyl group which may have the same or different 1 to 3 groups selected from the above substituent group (B1);

one of $Q^{1a}$ and $T^{1a}$ represents a β-D-mannopyranosyloxy group, and the other represents a group represented by the formula: —$(CH_2)_n$—$Ar^4$ in which $Ar^4$ and n have the same meanings as defined above, a $C_{1-6}$ alkyl group which may have the same or different 1 to 3 groups selected from the above substituent group (A1), a $C_{1-6}$ alkoxy group which may have the same or different 1 to 3 groups selected from the above substituent group (A1), an optionally mono or di($C_{1-6}$ alkyl)-substituted amino group wherein the $C_{1-6}$ alkyl group may have the same or different 1 to 3 groups selected from the above substituent group (A1), a $C_{3-8}$ cycloalkyl group which may have the same or different 1 to 3 groups selected from the above substituent group (A1), a $C_{2-9}$ heterocycloalkyl group which may have the same or different 1 to 3 groups selected from the above substituent group (A1), or a heterocycle-fused phenyl group which may have the same or different 1 to 3 groups selected from the above substituent group (B1); and R, $R^1$, $R^{1A}$, $R^{1B}$, $R^A$, $Q^B$, $T^B$, X and $X^1$ have the same meanings as defined above.

Process 3

A compound represented by the above general formula (VII) can be prepared by subjecting a pyrazole derivative represented by the above general formula (III) to glycosidation using a sugar donor represented by the above general formula (VI) in the presence of a base such as silver carbonate in an inert solvent. As the inert solvent used in the glycosidation, for example, dichloromethane, toluene, tetrahydrofuran and the like can be illustrated. The reaction temperature is usually from 0° C. to reflux temperature, and the reaction time is usually from 30 minutes to 1 day, varying based on a used starting material, solvent and reaction temperature.

Process 4

A corresponding compound represented by the above general formula (IIa) can be prepared by subjecting a compound represented by the above general formula (VII) to reduction using a reducing agent such as sodium borohydride, diisobutylaluminum hydride, triisopropoxyalminum hydride or the like in an inert solvent, and optionally to N-alkylation using an alkylating agent represented by the above general formula (V) in the presence of a base such as cesium carbonate, potassium carbonate or sodium hydride and optionally in the presence of a catalytic amount of sodium iodide in an inert solvent. As the inert solvent used in the reduction, for example, methanol, ethanol, tetrahydrofuran, diethyl ether, toluene, a mixed solvent thereof and the like can be illustrated. The reaction temperature is usually from −78° C. to reflux temperature, and the reaction time is usually from 30 minutes to 1 day, varying based on a used starting material, solvent and reaction temperature. As the solvent used in the N-alkylation, for example, acetonitrile, ethanol, 1,2-dimethoxyethane, tetrahydrofuran, N,N-dimethylformamide, N,N-dimethylacetamide, N-methylpyrrolidinone, dimethyl sulfoxide, a mixed solvent thereof and the like can be illustrated. The reaction temperature is usually from room temperature to reflux temperature, and the reaction time is usually from 10 minutes to 1 day, varying based on a used starting material, solvent and reaction temperature. The obtained compound represented by the above general formula (IIa) can be also used in the process 5 after converting into a salt thereof in the usual way.

Process 5

A compound represented by the above general formula (Ia) of the present invention can be prepared by subjecting a compound represented by the above general formula (IIa), after removing the protective group of sugar moiety or the like in accordance with a method used in general organic syntheses such as alkaline hydrolysis, optionally to N-Alkylation using an alkylating agent represented by the above general formula (V) in the presence of a base such as cesium carbonate, potassium carbonate or sodium hydride and optionally in the presence of a catalytic amount of sodium iodide in an inert solvent, and in a case that there is a protective group other than the sugar moiety, by removing the protective group in accordance with a method used in general organic syntheses. As the inert solvent used in the hydrolysis reaction, for example, methanol, ethanol, tetrahydrofuran, water, a mixed solvent thereof and the like can be illustrated. As the base, for example, sodium hydroxide, sodium methoxide, sodium ethoxide, methylamine, dimethylamine and the like can be illustrated. The reaction temperature is usually from 0° C. to reflux temperature, and the reaction time is usually from 30 minutes to 1 day, varying based on a used starting material, solvent and reaction temperature. As the solvent used in the N-alkylation, for example, acetonitrile, ethanol, 1,2-dimethoxyethane, tetrahydrofuran, N,N-dimethylformamide, N,N-dimethylacetamide, N-methylpyrrolidinone, dimethyl sulfoxide, a mixed solvent thereof and the like can be illustrated. The reaction temperature is usually from room temperature to reflux temperature, and the reaction time is usually from 10 minutes to 1 day, varying based on a used starting material, solvent and reaction temperature.

A compound represented by the above general formula (III) of the present invention used as a starting material in the above production processes, for example, can be prepared according to the following procedures:

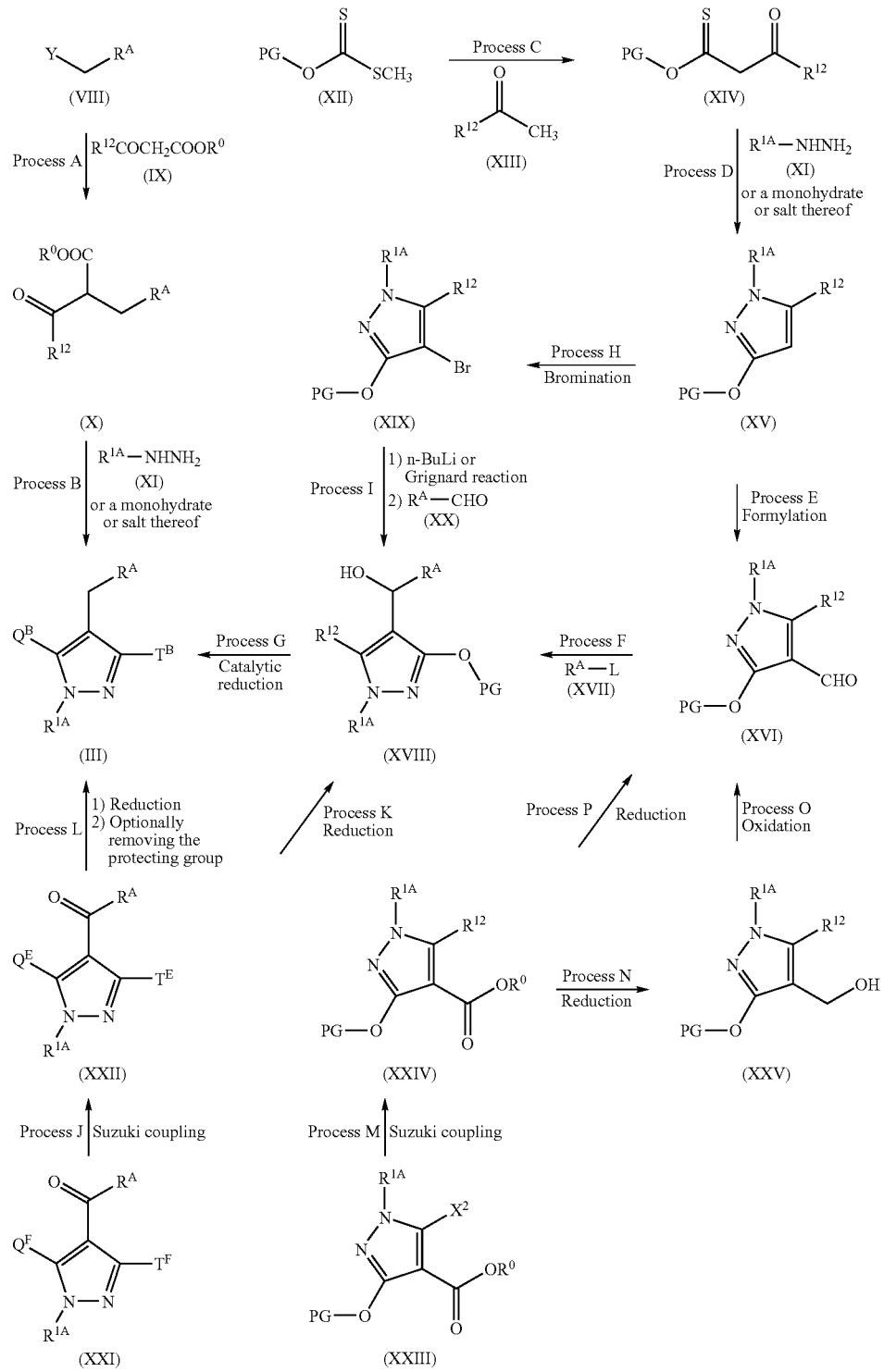

wherein Y represents a leaving group such as a halogen atom, a mesyloxy group, a tosyloxy group; L represents MgBr, MgCl, MgI, ZnI, ZnBr, ZnCl or a lithium atom; $R^{12}$ represents a group represented by the formula: —$(CH_2)_n$—$Ar^4$ in which $Ar^4$ and n have the same meanings as defined above, a $C_{1-6}$ alkyl group which may have the same or different 1 to 3 groups selected from the above substituent group (A1), a $C_{1-6}$ alkoxy group which may have the same or different 1 to 3 groups selected from the above substituent group (A1), an optionally mono or di($C_{1-6}$ alkyl)-substituted amino group wherein the $C_{1-6}$ alkyl group may have the same or different 1 to 3 groups selected from the above substituent group (A1), a $C_{3-8}$ cycloalkyl group which may have the same or different 1 to 3 groups selected from the above substituent group (A1), a $C_{2-9}$ heterocycloalkyl group which may have the same or different 1 to 3 groups selected from the above substituent group (A1), or a heterocycle-fused phenyl group which may have the same or different 1 to 3 groups selected from the above substituent group (B1); $R^0$ represents a $C_{1-6}$ alkyl group; PG represents a hydroxy-protective group; one of $Q^E$ and $T^E$ represents a group represented by the formula: —O—PG, and the other represents $R^{12}$; one of $Q^F$ and $T^F$ represents a group represented by the formula: —O—PG, and the other represents a halogen atom; $X^2$ represents a halogen atom; and $R^{1A}$, $R^A$, $Q^B$ and $T^B$ have the same meanings as defined above.

Process A

A compound represented by the above general formula (X) can be prepared by condensing a compound represented by the above general formula (VIII) with a ketoacetate ester compound represented by the above general formula (IX) in the presence of a base such as sodium hydride, potassium tert-butoxide or the like in an inert solvent. As the inert solvent used in the condensing reaction, for example, 1,2-dimethoxyethane, tetrahydrofuran, N,N-dimethylformamide, a mixed solvent thereof and the like can be illustrated. The reaction temperature is usually from room temperature to reflux temperature, and the reaction time is usually from 1 hour to 1 day, varying based on a used starting material, solvent and reaction temperature.

Process B

A pyrazole derivative represented by the above general formula (III) of the present invention can be prepared by condensing a compound represented by the above general formula (X) with a hydrazine compound represented by the above general formula (XI) or a hydrate thereof or a salt thereof in the presence or absence of a base in an inert solvent, and introducing a protective group in the usual way as occasion demands. As the inert solvent used in the condensing reaction, for example, toluene, tetrahydrofuran, chloroform, methanol, ethanol, a mixed solvent thereof and the like can be illustrated, and as the base, for example, triethylamine, diisopropylethylamine, pyridine, sodium methoxide, sodium ethoxide and the like can be illustrated. The reaction temperature is usually from room temperature to reflux temperature, and the reaction time is usually from 1 hour to 1 day, varying based on a used starting material, solvent and reaction temperature. The obtained pyrazole derivative represented by the above general formula (III) can be also used in the subsequent process after converting into a salt thereof in the usual way.

Process C

A compound represented by the above general formula (XIV) can be prepared by condensing a dithiocarbonate ester compound represented by the above general formula (XII) with a ketone compound represented by the above general formula (XIII) in the presence of a base such as sodium amide in an inert solvent. As the inert solvent used in the condensing reaction, for example, toluene and the like can be illustrated. The reaction temperature is usually from −20° C. to reflux temperature, and the reaction time is usually from 30 minutes to 1 day, varying based on a used starting material, solvent and reaction temperature.

Process D

A pyrazole derivative represented by the above general formula (XV) can be prepared by condensing a compound represented by the above general formula (XIV) with a hydrazine compound represented by the above general formula (XI) or a hydrate thereof or a salt thereof in the presence of a base such as triethylamine or diisopropylethylamine in an inert solvent, and introducing a protective group as occasion demands. As the inert solvent used in the condensing reaction, for example, acetonitrile and the like can be illustrated. The reaction temperature is usually from 0° C. to reflux temperature, and the reaction time is usually from 1 hour to 1 day, varying based on a used starting material, solvent and reaction temperature.

Process E

A pyrazole aldehyde derivative represented by the above general formula (XVI) can be prepared by subjecting a compound represented by the above general formula (XV) to folmylation by a reaction such as Vilsmeier reaction using phosphorus oxychloride and N,N-dimethylformamide. As the solvent used in the folmylating reaction, for example, N,N-dimethylformamide and the like can be illustrated. The reaction temperature is usually from 0° C. to reflux temperature, and the reaction time is usually from 30 minutes to 1 day, varying based on a used starting material, solvent and reaction temperature.

Process F

A compound represented by the above general formula (XVIII) can be prepared by condensing a compound represented by the above general formula (XVI) with a Grignard reagent, a Reformatsky reagent or a lithium reagent represented by the above general formula (XVII) in an inert solvent. As the inert solvent used in the condensing reaction, for example, tetrahydrofuran, diethyl ether, a mixed solvent thereof and the like can be illustrated. The reaction temperature is usually from −78° C. to room temperature, and the reaction time is usually from 30 minutes to 1 day, varying based on a used starting material, solvent and reaction temperature.

Process G

A pyrazole derivative represented by the above general formula (III) of the present invention can be prepared by subjecting a compound represented by the above general formula (XVIII) to catalytic hydrogenation using a palladium catalyst such as palladium-carbon powder in the presence or absence of an acid such as hydrochloric acid in an inert solvent, and in a case that a compound represented by the above general formula (XVIII) has any sulfur atom, subjecting the resulting compound to acid treatment in an aqueous solution of trifluoroacetic acid and dimethyl sulfide usually at 0° C. to reflux temperature for 30 minutes to 1 day as occasion demands. As the inert solvent used in the catalytic hydrogenation, for example, methanol, ethanol, tetrahydrofuran, ethyl acetate, acetic acid, isopropanol, a mixed solvent thereof and the like can be illustrated. The reaction temperature is usually from room temperature to reflux temperature, and the reaction time is usually from 30 minutes to 1 day, varying based on a used starting material, solvent and reaction temperature. The obtained pyrazole derivative represented by the above general formula (III) can be also used in the subsequent process after suitably converting into a salt thereof in the usual way.

Process H

A brominated compound represented by the above general formula (XIX) can be prepared by brominating a compound represented by the above general formula (XV) using bromine in an inert solvent. As the inert solvent used in the brominating reaction, dichloromethane, chloroform, a mixed solvent thereof and the like can be illustrated. The reaction temperature is usually from −40° C. to room temperature, and the reaction time is usually from 30 minutes to 1 day, varying based on a used starting material, solvent and reaction temperature.

Process I

A compound represented by the above general formula (XVIII) can be prepared by converting a compound represented by the above general formula (XIX) into a lithium compound using n-butyllithium in the usual way or a Grignard reagent using magnesium in the usual way, and condensing using a formyl derivative represented by the above general formula (XX) in an inert solvent. As the inert solvent used in the condensing reaction, for example, tetrahydrofuran, diethyl ether, a mixed solvent thereof and the like can be illustrated. The reaction temperature is usually from −78° C. to room temperature, and the reaction time is usually from 30 minutes to 1 day, varying based on a used starting material, solvent and reaction temperature.

Process J

A compound represented by the above general formula (XXII) can be prepared by condensing a compound represented by the above general formula (XXI) with $R^{12}$—B$(OR^3)_2$ wherein $R^3$ represents a hydrogen atom or a lower alkyl group or both $R^3$ bind together to form a lower alkylene group; and $R^{12}$ has the same meaning as defined above, in the presence of a palladium catalyst such as tetrakis(triphenylphosphine)palladium(0) or palladium(II) acetate and a base such as sodium carbonate, cesium fluoride, potassium phosphate or sodium hydroxide and in the presence or absence of a phase transfer catalyst such as tetrabutylammonium bromide. As the inert solvent used in the condensing reaction (Suzuki coupling reaction), for example, N,N-dimethylformamide, tetrahydrofuran, 1,2-dimethoxyethane, water, toluene, a mixed solvent thereof and the like can be illustrated. The reaction temperature is from room temperature to reflux temperature.

Process K

A compound represented by the above general formula (XVIII) can be prepared by subjecting a compound represented by the above general formula (XXII) to reduction using a reducing agent such as sodium borohydride, diisobutylaluminum hydride or lithium aluminum hydride in an inert solvent. As the inert solvent used, for example, toluene, tetrahydrofuran, dichloromethane, methanol, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process L

A compound represented by the above general formula (III) of the present invention can be prepared by subjecting a compound represented by the above general formula (XXII) to reduction using a reducing agent such as triethylsilyl hydride in the presence of a Lewis acid such as trifluoroacetic acid or borontrifluoride diethyl ether complex without solvent or in an inert solvent and then optionally removing the hydroxy-protective group in the usual way. As the inert solvent used in the reducing reaction, for example, toluene, tetrahydrofuran, dichloromethane, a mixed solvent thereof and the like can be illustrated. The reaction temperature is usually from room temperature to reflux temperature, and the reaction time is usually from 30 minutes to 1 day, varying based on a used starting material, solvent and reaction temperature.

Process M

A compound represented by the above general formula (XXIV) can be prepared by condensing a compound represented by the above general formula (XXIII) with $R^{12}$—B$(OR^3)_2$ wherein $R^3$ and $R^{12}$ have the same meanings as defined above, in the presence of a palladium catalyst such as tetrakis(triphenylphosphine)palladium(0) or palladium(II) acetate and a base such as sodium carbonate, cesium fluoride, potassium phosphate or sodium hydroxide and in the presence or absence of a phase transfer catalyst such as tetrabutylammonium bromide. As the inert solvent used in the condensing reaction (Suzuki coupling reaction), for example, N,N-dimethylformamide, tetrahydrofuran, 1,2-dimethoxyethane, water, toluene, a mixed solvent thereof and the like can be illustrated. The reaction temperature is from room temperature to reflux temperature.

Process N

A compound represented by the above general formula (XXV) can be prepared by subjecting a compound represented by the above general formula (XXIV) to reduction using a reducing agent such as lithium aluminum hydride or diisobutylaluminum hydride in an inert solvent. As the inert solvent used in the reduction, for example, toluene, tetrahydrofuran, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process O

A compound represented by the above general formula (XVI) can be prepared by subjecting a compound represented by the above general formula (XXV) to oxidation using dimethylsulfoxide such as Swern oxidation, chromic acid oxidation using pyridinium chlorochromate, pyridinium dichromate or the like in an inert solvent or oxidation using an oxygenating agent such as manganese dioxide. As the inert solvent used in the oxidation, for example, toluene, tetrahydrofuran, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process P

A compound represented by the above general formula (XVI) can be prepared by subjecting a compound represented by the above general formula (XXIV) to reduction using a reducing agent such as triisopropoxyalminum hydride or diisobutylaluminum hydride in an inert solvent. As the inert solvent used in the reduction, for example, toluene, tetrahydrofuran, hexane, diethyl ether, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

A compound represented by the above general formula (XXII) used as a starting material in the above production processes, for example, can be prepared according to the following procedures:

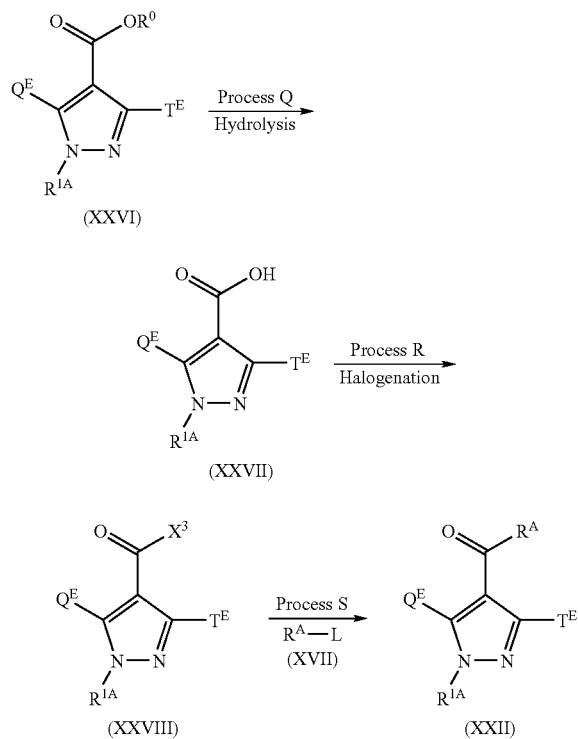

wherein $X^3$ represents a halogen atom such as a chlorine atom; and L, $R^0$, $R^{1A}$, $R^A$, $Q^E$ and $T^E$ have the same meanings as defined above.

Process Q

A compound represented by the above general formula (XXVII) can be prepared by treating a compound represented by the above general formula (XXVI) according to a method used in general organic syntheses such as alkaline hydrolysis. As the solvent used in the hydrolysis reaction, for example, methanol, ethanol, acetonitrile, tetrahydrofuran, dioxane, water, a mixed solvent thereof and the like can be illustrated. As the base, for example, sodium hydroxide, potassium hydroxide, sodium methoxide, sodium ethoxide and the like can be illustrated. The reaction temperature is usually from room temperature to reflux temperature, and the reaction time is usually from 30 minutes to 1 day, varying based on a used starting material, solvent and reaction temperature.

Process R

A compound represented by the above general formula (XXVIII) can be prepared by halogenating a compound represented by the above general formula (XXVII) using an acid halogenating agent such as thionyl chloride, phosphorus trichloride, phosphorus pentachloride, phosphorus oxychloride, phosphorus tribromide or fluorosulfuric acid without solvent or in an inert solvent. As the inert solvent used in the halogenation, for example, toluene, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process S

A compound represented by the above general formula (XXII) can be prepared by condensing a compound represented by the above general formula (XXVIII) with a Grignard reagent, a Reformatsky reagent or a lithium reagent represented by the above general formula (XVII) in an inert solvent. As the inert solvent used in the condensing reaction, for example, tetrahydrofuran, diethyl ether, a mixed solvent thereof and the like can be illustrated. The reaction temperature is usually from −78° C. to room temperature, and the reaction time is usually from 30 minutes to 1 day, varying based on a used starting material, solvent and reaction temperature.

A compound represented by the above general formula (XXI) used as a starting material in the above production processes, for example, can be prepared according to the following procedures:

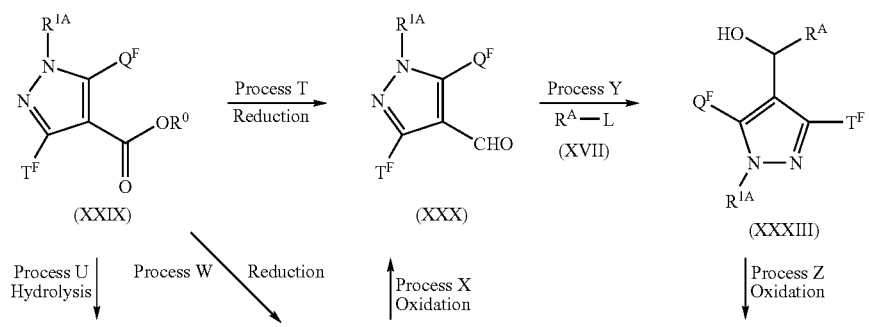

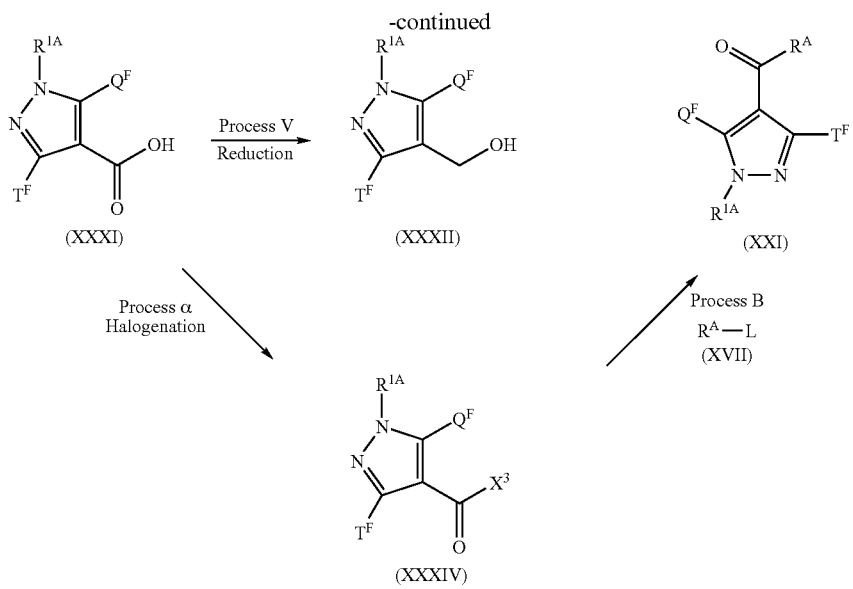

wherein L, $R^0$, $R^{1A}$, $R^A$, $Q^F$, $T^F$ and $X^3$ have the same meanings as defined above.

Process T

A compound represented by the above general formula (XXX) can be prepared by subjecting a compound represented by the above general formula (XXIX) to reduction using a reducing agent such as triisopropoxyalminum hydride or diisobutylaluminum hydride in an inert solvent. As the inert solvent used in the reduction, for example, toluene, tetrahydrofuran, hexane, diethyl ether, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process U

A compound represented by the above general formula (XXXI) can be prepared by treating a compound represented by the above general formula (XXIX) according to a method used in general organic syntheses such as alkaline hydrolysis. As the solvent used in the hydrolysis reaction, for example, methanol, ethanol, acetonitrile, tetrahydrofuran, dioxane, water, a mixed solvent thereof and the like can be illustrated. As the base, for example, sodium hydroxide, sodium methoxide, sodium ethoxide, potassium hydroxide and the like can be illustrated. The reaction temperature is usually from room temperature to reflux temperature, and the reaction time is usually from 30 minutes to 1 day, varying based on a used starting material, solvent and reaction temperature.

Process V

A compound represented by the above general formula (XXXII) can be prepared by subjecting a compound represented by the above general formula (XXXI) to reduction using a reducing agent such as lithium aluminum hydride, borane-dimethylsulfide complex or borane-tetrahydrofuran complex in an inert solvent. As the inert solvent used in the reduction, for example, toluene, tetrahydrofuran, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process W

A compound represented by the above general formula (XXXII) can be prepared by subjecting a compound represented by the above general formula (XXIX) to reduction using a reducing agent such as lithium aluminum hydride or diisobutylaluminum hydride in an inert solvent. As the inert solvent used in the reduction, for example, toluene, tetrahydrofuran, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process X

A compound represented by the above general formula (XXX) can be prepared by subjecting a compound represented by the above general formula (XXXII) to oxidation using dimethylsulfoxide such as Swern oxidation, chromic acid oxidation using pyridinium chlorochromate, pyridinium dichromate or the like in an inert solvent or oxidation using an oxygenating agent such as manganese dioxide. As the inert solvent used in the above oxidation, for example, toluene, tetrahydrofuran, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process Y

A compound represented by the above general formula (XXXIII) can be prepared by condensing a compound represented by the above general formula (XXX) with a Grignard reagent, a Reformatsky reagent or a lithium reagent represented by the above general formula (XVII) in an inert solvent. As the solvent used in the condensing reaction, for example, tetrahydrofuran, diethyl ether, a mixed solvent thereof and the like can be illustrated. The reaction temperature is usually from −78° C. to room temperature, and the reaction time is usually from 30 minutes to 1 day, varying based on a used starting material, solvent and reaction temperature.

Process Z

A compound represented by the above general formula (XXI) can be prepared by subjecting a compound represented by the above general formula (XXXIII) to oxidation using dimethylsulfoxide such as Swern oxidation, chromic acid oxidation using pyridinium chlorochromate, pyridinium dichromate or the like in an inert solvent or oxidation using an oxygenating agent such as manganese dioxide. As the inert solvent used in the oxidation, for example, toluene, tetrahydrofuran, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process α

A compound represented by the above general formula (XXXIV) can be prepared by halogenating a compound represented by the above general formula (XXXI) using an acid halogenating agent such as thionyl chloride, phosphorus trichloride, phosphorus pentachloride, phosphorus oxychloride, phosphorus tribromide or fluorosulfuric acid without solvent or in an inert solvent. As the inert solvent used in the halogenation, for example, toluene, dichloromethane, a mixed solvent thereof and the like can be illustrated. The reaction temperature is usually from −78° C. to reflux temperature, and the reaction time is usually from 30 minutes to 1 day, varying based on a used starting material, solvent and reaction temperature.

Process β

A compound represented by the above general formula (XXI) can be prepared by condensing a compound represented by the above general formula (XXXIV) with a Grignard reagent, a Reformatsky reagent or a lithium reagent represented by the above general formula (XVII) in an inert solvent. As the inert solvent used in the condensing reaction, for example, tetrahydrofuran, diethyl ether, a mixed solvent thereof and the like can be illustrated. The reaction temperature is usually from −78° C. to room temperature, and the reaction time is usually from 30 minutes to 1 day, varying based on a used starting material, solvent and reaction temperature.

A compound represented by the above general formula (XXIX) including a compound represented by the above general formula (XXIII) used as a starting material in the above production processes, for example, can be prepared according to the following procedures:

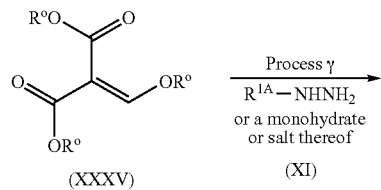

(XXXV)    (XI)

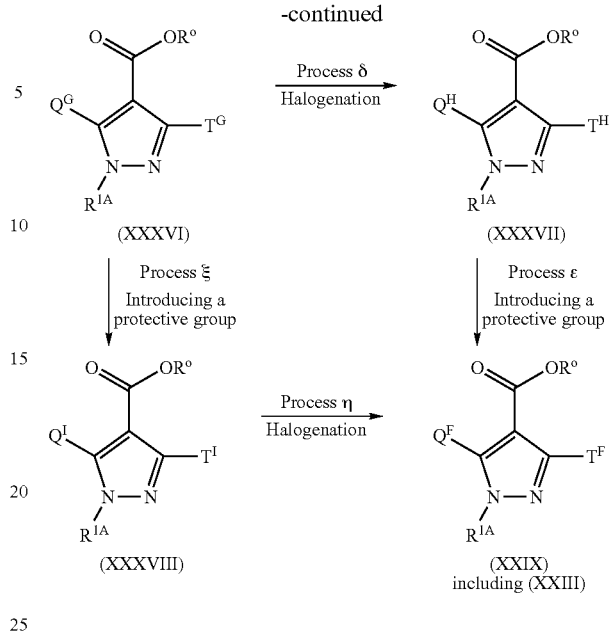

(XXXVI)    (XXXVII)

(XXXVIII)    (XXIX)
including (XXIII)

wherein one of $Q^G$ and $T^G$ represents a hydroxy group, and the other represents a hydrogen atom; one of $Q^H$ and $T^H$ represents a hydroxy group, and the other represents a halogen atom; one of $Q^I$ and $T^I$ represents a group represented by the formula: —O—PG, and the other represents a hydrogen atom; and PG, $R^O$, $R^{1A}$, $Q^F$ and $T^F$ have the same meanings as defined above.

Process γ

A pyrazole derivative represented by the above general formula (XXXVI) can be prepared by condensing a compound represented by the above general formula (XXXV) with a hydrazine compound represented by the above general formula (XI) or a hydrate thereof or a salt thereof in the presence or absence of a base in an inert solvent. As the inert solvent used in the condensing reaction, for example, toluene, tetrahydrofuran, dichloromethane, N,N-dimethylformamide, ethanol, water, a mixed solvent thereof and the like can be illustrated. As the base, for example, sodium hydride, sodium amide, sodium carbonate, sodium ethoxide and the like can be illustrated. The reaction temperature is usually from room temperature to reflux temperature, and the reaction time is usually from 10 minutes to 1 day, varying based on a used starting material, solvent and reaction temperature.

Process δ

A compound represented by the above general formula (XXXVII) can be prepared by halogenating a compound represented by the above general formula (XXXVI) using a halogenating agent such as sulfuryl chloride, N-chlorosuccinimide or N-bromosuccinimide in an inert solvent. As the inert solvent used in the halogenation, for example, tetrahydrofuran, dichloromethane, acetic acid, toluene, N,N-dimethylformamide, a mixed solvent thereof and the like can be illustrated. The reaction temperature is usually from 0° C. to reflux temperature, and the reaction time is usually from 10 minutes to 1 day, varying based on a used starting material, solvent and reaction temperature.

Process ε

A compound represented by the above general formula (XXIX) can be prepared by introducing a hydroxy-protective group to a compound represented by the above general formula (XXXVII) using a hydroxy-protecting agent such as benzyl bromide or chloromethyl methyl ether in the presence or absence of a base in an inert solvent. As the inert solvent used in the introducing reaction, for example, toluene, tetrahydrofuran, dichloromethane, N,N-dimethylformamide, ethanol, water, a mixed solvent thereof and the like can be illustrated. As the base, for example, sodium hydride, sodium amide, sodium carbonate, sodium ethoxide, triethylamine, imidazole and the like can be illustrated. The reaction temperature is usually from 0° C. to reflux temperature, and the reaction time is usually from 10 minutes to 1 day, varying based on a used starting material, solvent and reaction temperature.

Process ζ

A compound represented by the above general formula (XXXVIII) can be prepared by introducing a hydroxy-protective group to a compound represented by the above general formula (XXXVI) using a hydroxy-protecting agent such as benzyl bromide or chloromethyl methyl ether in the presence or absence of a base in an inert solvent. As the inert solvent used in the introducing reaction, for example, toluene, tetrahydrofuran, dichloromethane, N,N-dimethylformamide, ethanol, water, a mixed solvent thereof and the like can be illustrated. As the base, for example, sodium hydride, sodium amide, sodium carbonate, sodium ethoxide, triethylamine, imidazole and the like can be illustrated. The reaction temperature is usually from 0° C. to reflux temperature, and the reaction time is usually from 10 minutes to 1 day, varying based on a used starting material, solvent and reaction temperature.

Process η

A compound represented by the above general formula (XXIX) can be prepared by halogenating a compound represented by the above general formula (XXXVIII) using a halogenating agent such as bromine or iodine after treating with a base such as n-butyllithium in an inert solvent. As the inert solvent used in the halogenation, for example, toluene, tetrahydrofuran, a mixed solvent thereof and the like can be illustrated. The reaction temperature is usually from −78° C. to reflux temperature, and the reaction time is usually from 10 minutes to 1 day, varying based on a used starting material, solvent and reaction temperature.

Among the compounds represented by the above general formula (III) of the present invention, there can be the following tautomers in compounds wherein $T^B$ is a hydroxy group, varying based on difference in the reactions, and both of the compounds are included in the present invention.

Among the compounds represented by the above general formula (III) of the present invention, there can be the following tautomers in compounds wherein $Q^B$ is a hydroxy group, varying based on difference in the reactions, and both of the compounds are included in the present invention:

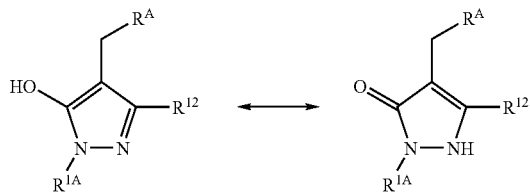

In addition, among the compounds represented by the above general formula (III) of the present invention, there can be the following tautomers in compounds wherein $R^{1A}$ is a hydrogen atom, varying based on difference in the reactions, and all the compounds are included in the present invention:

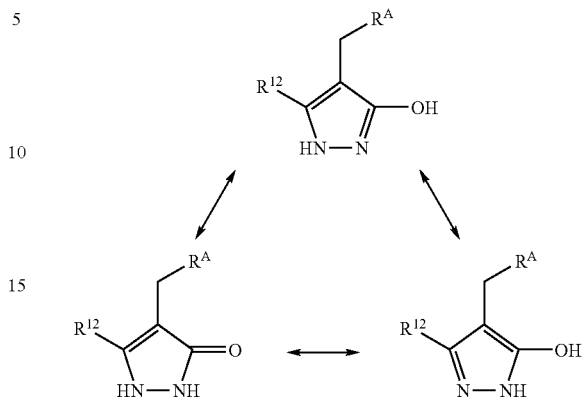

The compounds represented by the above general formula (I) or (I') of the present invention obtained by the above production processes can be isolated and purified by conventional separation means such as fractional recrystallization, purification using chromatography, solvent extraction and solid phase extraction.

The pyrazole derivatives represented by the above general formula (I) of the present invention can be converted into their pharmaceutically acceptable salts in the usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like, salts with inorganic bases such as a sodium salt, a potassium salt and the like, and salts with organic bases such as N-methyl-D-glucamine, N,N'-dibenzyletylenediamine, 2-aminoethanol, tris (hydroxymethyl)aminomethane, arginine, lysine and the like.

The compounds represented by the above general formula (I) of the present invention or pharmaceutically acceptable salts thereof, or prodrugs thereof include their solvates with pharmaceutically acceptable solvents such as ethanol and water.

Of the pyrazole derivatives represented by the above general formula (I) of the present invention and the prodrugs thereof, there are two geometrical isomers in each compound having an unsaturated bond. In the present invention, either of cis(Z)-isomer or trans(E)-isomer can be employed.

Of the pyrazole derivatives represented by the above general formula (I) of the present invention and the prodrugs thereof, there are two optical isomers, R-isomer and S-isomer, in each compound having an asymmetric carbon atom excluding the sugar moiety of glucopyranosyloxy, mannopyranosyloxy and 2-deoxyglucopyranosyloxy moieties. In the present invention, either of the isomers can be employed, and a mixture of both isomers can be also employed. In addition, there can be two rotational isomers in each compound having a rotational barrier. In the present invention, either of the isomers can be employed, and a mixture of both isomers can be also employed.

A prodrug of a compound represented by the above general formula (I) of the present invention can be prepared by introducing an appropriate group forming a prodrug into any one or more groups selected from a hydroxy group in a sugar moiety of glucopyranosyloxy, mannopyranosyloxy and 2-deoxyglucopyranosyloxy moieties, as the case may be a hydroxy group in R, $R^1$, Q or T, a cyclic amino group in case that $R^1$ is a hydrogen atom, an optionally mono($C_{1-6}$ alkyl)-substituted amino group in case that R, $R^1$, Q or T is a substituent having an amino group or a mono($C_{1-6}$ alkyl) amino group, a thiol group and a sulfonamide group of the compound represented by the above general formula (I) using a corresponding reagent to produce a prodrug such as a halide compound or the like in the usual way, and then by suitably isolating and purificating in the usual way as occasion demands. As a group forming a prodrug used in a hydroxy group, for example, a $C_{2-20}$ acyl group, a $C_{1-6}$ alkoxy-substituted ($C_{2-7}$ acyl) group, a $C_{2-7}$ alkoxycarbonyl-substituted ($C_{2-7}$ acyl) group, a $C_{2-7}$ alkoxycarbonyl group, a $C_{1-6}$ alkoxy-substituted ($C_{2-7}$ alkoxycarbonyl) group, a benzoyl group, a ($C_{2-7}$ acyloxy)methyl group, a 1-($C_{2-7}$ acyloxy)ethyl group, a ($C_{2-7}$ alkoxycarbonyl)-oxymethyl group, a 1-[($C_{2-7}$ alkoxycarbonyl)oxy]ethyl group, a ($C_{3-7}$ cycloalkyl)oxycarbonyloxymethyl group, a 1-[($C_{3-7}$ cycloalkyl)oxycarbonyloxy]ethyl group, an ester group condensed with an amino acid, a phosphoric acid derivative or a cinnamic acid derivative or the like can be illustrated. As a group forming a prodrug used in an amino group, for example, a $C_{2-7}$ acyl group, a $C_{1-6}$ alkoxy-substituted ($C_{2-7}$ acyl) group, a $C_{2-7}$ alkoxycarbonyl-substituted ($C_{2-7}$ acyl) group, a $C_{2-7}$ alkoxycarbonyl group, a $C_{1-6}$ alkoxy-substituted ($C_{2-7}$ alkoxycarbonyl) group, a benzoyl group, a ($C_{2-7}$ acyloxy)methyl group, a 1-($C_{2-7}$ acyloxy)ethyl group, a ($C_{2-7}$ alkoxycarbonyl)-oxymethyl group, a 1-[($C_{2-7}$ alkoxycarbonyl)oxy]ethyl group, a ($C_{3-7}$ cycloalkyl)oxycarbonyloxymethyl group, a 1-[($C_{3-7}$ cycloalkyl)oxycarbonyloxy]ethyl group, an amide group condensed with an amino acid or the like can be illustrated. As a group forming a prodrug used in a cyclic amino group, for example, a $C_{2-7}$ acyl group, a $C_{1-6}$ alkoxy-substituted ($C_{2-7}$ acyl) group, a $C_{2-7}$ alkoxycarbonyl-substituted ($C_{2-7}$ acyl) group, a $C_{2-7}$ alkoxycarbonyl group, a $C_{1-6}$ alkoxy-substituted ($C_{2-7}$ alkoxycarbonyl) group, a ($C_{2-7}$ acyloxy)methyl group, a 1-($C_{2-7}$ acyloxy)ethyl group, a ($C_{2-7}$ alkoxycarbonyl)oxymethyl group, a 1-[($C_{2-7}$ alkoxycarbonyl)oxy]ethyl group, a ($C_{3-7}$ cycloalkyl)oxycarbonyloxymethyl group, a 1-[($C_{3-7}$ cycloalkyl)-oxycarbonyloxy]ethyl group, a benzoyl group or the like can be illustrated. As a group forming a prodrug used in a thiol group, for example, a $C_{2-20}$ acyl group, a $C_{1-6}$ alkoxy-substituted ($C_{2-7}$ acyl) group, a $C_{2-7}$ alkoxycarbonyl-substituted ($C_{2-7}$ acyl) group, a $C_{2-7}$ alkoxycarbonyl group, a $C_{1-6}$ alkoxy-substituted ($C_{2-7}$ alkoxycarbonyl) group, a benzoyl group, a ($C_{2-7}$ acyloxy)methyl group, a 1-($C_{2-7}$ acyloxy)ethyl group, a ($C_{2-7}$ alkoxycarbonyl)-oxymethyl group, a 1-[($C_{2-7}$ alkoxycarbonyl)oxy]ethyl group, a ($C_{3-7}$ cycloalkyl)oxycarbonyloxymethyl group, a 1-[($C_{3-7}$ cycloalkyl)oxycarbonyloxy]ethyl group, an ester group condensed with an amino acid, a phosphoric acid derivative or a cinnamic acid derivative or the like can be illustrated. As a group forming a prodrug used in a sulfonamide group, for example, a ($C_{2-7}$ acyloxy)methyl group, a 1-($C_{2-7}$ acyloxy)ethyl group, a ($C_{2-7}$ alkoxycarbonyl) oxymethyl group, a 1-[($C_{2-7}$ alkoxycarbonyl)oxy]ethyl group, a ($C_{3-7}$ cycloalkyl)oxycarbonyloxymethyl group, a 1-[($C_{3-7}$ cycloalkyl)oxycarbonyloxy]ethyl group or the like can be illustrated. The term "$C_{2-7}$ acyl group" means a straight-chained or branched acyl group having 2 to 7 carbon atoms such as an acetyl group, a propionyl group, a butyryl group, an isobutyryl group, a valeryl group, a pivaloyl group, a hexanoyl group or the like; the term "$C_{2-20}$ acyl group" means a straight-chained or branched acyl group having 2 to 20 carbon atoms such as an acetyl group, a propionyl group, a butyryl group, an isobutyryl group, a valeryl group, a pivaloyl group, a hexanoyl group, a lauroyl group, a myristoyl group, a palmitoyl group, a stearoyl group or the like; the term "$C_{1-6}$ alkoxy-substituted ($C_{2-7}$ acyl) group" means the above $C_{2-7}$ acyl group substituted by the above $C_{1-6}$ alkoxy group; the term "$C_{2-7}$ alkoxycarbonyl group" means a straight-chained or branched alkoxycarbonyl group having 2 to 7 carbon atoms such as a methoxycarbonyl group, an ethoxycarbonyl group, a propoxycarbonyl group, an isopropoxycarbonyl group, a butoxycarbonyl group, an isobutyloxycarbonyl group, a sec-butoxycarbonyl group, a tert-butoxycarbonyl group, a pentyloxycarbonyl group, an isopentyloxycarbonyl group, a neopentyloxycarbonyl group, a tert-pentyloxycarbonyl group, a hexyloxycarbonyl group or the like or a cyclic alkoxycarbonyl group having a 3 to 6-membered cycloalkyl group such as a cyclopropyloxycarbonyl group, a cyclobutyloxycarbonyl group, a cyclopentyloxycarbonyl group, a cyclohexyloxycarbonyl group or the like; the term "$C_{2-7}$ alkoxycarbonyl-substituted ($C_{2-7}$ acyl) group" means the above $C_{2-7}$ acyl group substituted by the above $C_{2-7}$ alkoxycarbonyl group; the term "$C_{1-6}$ alkoxy-substituted ($C_{2-7}$ alkoxycarbonyl) group" means the above $C_{2-7}$ alkoxycarbonyl group substituted by the above $C_{1-6}$ alkoxy group; the term "($C_{2-7}$ acyloxy)methyl group" means a hydroxymethyl group O-substituted by the above $C_{2-7}$ acyl group; the term "1-($C_{2-7}$ acyloxy)ethyl group" means a 1-hydroxyethyl group O-substituted by the above $C_{2-7}$ acyl group; the term "($C_{2-7}$ alkoxycarbonyl)oxymethyl group" means a hydroxymethyl group O-substituted by the above $C_{2-7}$ alkoxy-carbonyl group; and the term "1-[($C_{2-7}$ alkoxycarbonyl)oxy]ethyl group" means a 1-hydroxyethyl group O-substituted by the above $C_{2-7}$ alkoxycarbonyl group. In addition, the term "($C_{3-7}$ cycloalkyl)oxycarbonyl group" means an ester group having the above $C_{3-7}$ cycloalkyl group; the term "($C_{3-7}$ cycloalkyl)-oxycarbonyloxymethyl group" means a hydroxymethyl group O-substituted by the above ($C_{3-7}$ cycloalkyl)oxycarbonyl group; and the term "1-[($C_{3-7}$ cycloalkyl)oxycarbonyloxy]ethyl group" means a 1-hydroxyethyl group O-substituted by the above ($C_{3-7}$ cycloalkyl)oxycarbonyl group. Furthermore, as a group forming a prodrug, a sugar residue of a glucopyranosyl group, a galactopyranosyl group or the like can be illustrated. For example, these groups are preferably introduced into the hydroxy group at the 4 or 6 position of the sugar moiety of glucopyranosyloxy group or the like.

The pyrazole derivatives represented by the above general formula (I) of the present invention, for example, showed a potent inhibitory activity in human 1,5-anhydroglucitol/fructose/mannose transporter inhibitory activity confirmatory test as described below. Thus, the pyrazole derivatives represented by the above general formula (I) of the present invention exhibit an excellent inhibitory activity on 1,5-anhydroglucitol/fructose/mannose transporter found highly in the kidney and small intestine, and can remarkably inhibit blood glucose level increase by inhibiting the reabsorption at the kidney or uptake into cells of glucose, mannose and fructose or inhibiting the sugar absorption in the small intestine. Therefore, a pyrazole derivative represented by the above general formula (I) of the present invention, a pharmaceutically acceptable salt and a prodrug thereof is extremely useful as an agent for prevention or inhibition of progression of a disease associated with the excess uptake of at least a kind of carbohydrates selected from glucose, fructose and mannose or a disease associated with hyperglycemia such as diabetic complications (e.g. retinopathy, neuropathy, nephropathy, ulcer, macroangiopathy), diabetes, impaired glucose tolerance, obesity, hyperinsulinemia, hyperlipidemia, hypercholesterolemia, hypertriglyceridemia, lipid metabolism disorder, atherosclerosis, hypertension, congestive heart failure, edema, hyperuricemia, gout or the like, especially for prevention or inhibition of progression of diabetic complications such as diabetic nephropathy.

Furthermore, the compounds of the present invention can be suitably used in combination with at least one member selected from drugs other than 1,5-anhydroglucitol/fructose/mannose transporter inhibitors. Examples of the drugs which can be used in combination with the compounds of the present invention include an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor (PDGF), a platelet-derived growth factor (PDGF) analogue (e.g., PDGF-AA, PDGF-BB, PDGF-AB), epidermal growth factor (EGF), nerve growth factor, a carnitine derivative, uridine, 5-hydroxy-1-methylhidantoin, EGB-761, bimoclomol, sulodexide, Y-128, a hydroxymethylglutaryl coenzyme A reductase inhibitor, a fibric acid derivative, a $β_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an antiplatelets agent, a uric acid synthesis inhibitor, a uricosuric agent and a urinary alkalinizer.

In case of uses of the compound of the present invention in combination with the above one or more drugs, the present invention includes either dosage forms of simultaneous administration as a single preparation or separated preparations in way of the same or different administration route, and administration at different dosage intervals as separated preparations in way of the same or different administration route. A pharmaceutical combination comprising the compound of the present invention and the above drug(s) includes both dosage forms as a single preparation and separated preparations for combination as mentioned above.

The compounds of the present invention can obtain more advantageous effects than additive effects in the prevention or treatment of the above diseases when using suitably in combination with the above one or more drugs. Also, the administration dose can be decreased in comparison with administration of either drug alone, or adverse effects of coadministrated drugs other than 1,5-anhydroglucitol/fructose/mannose transporter inhibitors can be avoided or declined.

Concrete compounds as the drugs used for combination and preferable diseases to be treated are exemplified as follows. However, the present invention is not limited thereto, and the concrete compounds include their free compounds, and their or other pharmaceutically acceptable salts.

As insulin sensitivity enhancers, peroxisome proliferator-activated receptor-γagonists such as troglitazone, pioglitazone hydrochloride, rosiglitazone maleate, sodium darglitazone, GI-262570, isaglitazone, LG-100641, NC-2100, T-174, DRF-2189, CLX-0921, CS-011, GW-1929, ciglitazone, sodium englitazone and NIP-221, peroxisome proliferator-activated receptor-αagonists such as GW-9578 and BM-170744, peroxisome proliferator-activated receptor-α/γagonists such as GW-409544, KRP-297, NN-622, CLX-0940, LR-90, SB-219994, DRF-4158 and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, NN-2344, BM-13125, BM-501050, HQL-975, CLX-0900, MBX-668, MBX-675, S-15261, GW-544, AZ-242, LY-510929, AR-H049020 and GW-501516 are illustrated. Insulin sensitivity enhancers are used preferably for diabetes, impaired glucose tolerance, diabetic complications, obesity, hyperinsulinemia, hyperlipidemia, hypercholesterolemia, hypertriglyceridemia, lipid metabolism disorder or atherosclerosis, and more preferably for diabetes, impaired glucose tolerance or hyperinsulinemia because of improving the disturbance of insulin signal transduction in peripheral tissues and enhancing glucose uptake into the tissues from the blood, leading to lowering of blood glucose level.

As glucose absorption inhibitors, for example, α-glucosidase inhibitors such as acarbose, voglibose, miglitol, CKD-711, emiglitate, MDL-25,637, camiglibose and MDL-73,945, α-amylase inhibitors such as AZM-127, and SGLT1 inhibitors are illustrated. Glucose absorption inhibitors are used preferably for diabetes, impaired glucose tolerance, diabetic complications, obesity or hyperinsulinemia, and more preferably for impaired glucose tolerance because of inhibiting the gastrointestinal enzymatic digestion of carbohydrates contained in foods, and inhibiting or delaying the absorption of glucose into the body.

As biguanides, phenformin, buformin hydrochloride, metformin hydrochloride or the like are illustrated. Biguanides are used preferably for diabetes, impaired glucose tolerance, diabetic complications or hyperinsulinemia, and more preferably for diabetes, impaired glucose tolerance or hyperinsulinemia because of lowering blood glucose level by inhibitory effects on hepatic gluconeogenesis, accelerating effects on anaerobic glycolysis in tissues or improving effects on insulin resistance in peripheral tissues.

As insulin secretion enhancers, tolbutamide, chlorpropamide, tolazamide, acetohexamide, glyclopyramide, glyburide (glibenclamide), gliclazide, 1-butyl-3-metanilylurea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide or the like are illustrated. Insulin secretion enhancers are used preferably for diabetes, impaired glucose tolerance or diabetic complications, and more preferably for diabetes or impaired glucose tolerance because of lowering blood glucose level by acting on pancreatic β-cells and enhancing the insulin secretion.

As SGLT2 inhibitors, T-1095 and compounds described in Japanese patent publications Nos. Hei 10-237089 and 2001-288178, and International Publications Nos. WO01/16147, WO01/27128, WO01/68660, WO01/74834, WO01/74835, WO02/28872, WO02/36602, WO02/44192, WO02/053573, WO02/064606, WO02/068439, WO02/068440 or the like are illustrated. SGLT2 inhibitors are used preferably for diabetes, impaired glucose tolerance, diabetic complications, obesity or hyperinsulinemia, and more preferably for diabetes, impaired glucose tolerance, obesity or hyperinsulinemia because of lowering blood glucose level by inhibiting the reabsorption of glucose at the kidney's proximal tubule.

As insulin or insulin analogues, human insulin, animal-derived insulin, human or animal-derived insulin analogues or the like are illustrated. These preparations are used preferably for diabetes, impaired glucose tolerance or diabetic complications, and more preferably for diabetes or impaired glucose tolerance.

As glucagon receptor antagonists, BAY-27-9955, NNC-92-1687 or the like are illustrated; as insulin receptor kinase stimulants, TER-17411, L-783281, KRX-613 or the like are illustrated; as tripeptidyl peptidase II inhibitors, UCL-1397 or the like are illustrated; as dipeptidyl peptidase IV inhibitors, NVP-DPP728A, TSL-225, P-32/98 or the like are illustrated; as protein tyrosine phosphatase 1B inhibitors, PTP-112, OC-86839, PNU-177496 or the like are illustrated; as glycogen phosphorylase inhibitors, NN-4201, CP-368296 or the like are illustrated; as fructose-bisphosphatase inhibitors, R-132917 or the like are illustrated; as pyruvate dehydrogenase inhibitors, AZD-7545 or the like are illustrated; as hepatic gluconeogenesis inhibitors, FR-225659 or the like are illustrated; as glucagon-like peptide-1 analogues, exendin-4, CJC-1131 or the like are illustrated; as glucagon-like peptide 1 agonists; AZM-134, LY-315902 or the like are illustrated; and as amylin, amylin analogues or amylin agonists, pramlintide acetate or the like are illustrated. These drugs, glucose-6-phosphatase inhibitors, D-chiroinsitol, glycogen synthase kinase-3 inhibitors and glucagon-like peptide-1 are used preferably for diabetes, impaired glucose tolerance, diabetic complications or hyperinsulinemia, and more preferably for diabetes or impaired glucose tolerance.

As aldose reductase inhibitors, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat or the like are illustrated. Aldose reductase inhibitors are preferably used for diabetic complications because of inhibiting aldose reductase and lowering excessive intracellular accumulation of sorbitol in accelerated polyol pathway which are in continuous hyperglycemic condition in the tissues in diabetic complications.

As advanced glycation end products formation inhibitors, pyridoxamine, OPB-9195, ALT-946, ALT-711, pimagedine hydrochloride or the like are illustrated. Advanced glycation end products formation inhibitors are preferably used for diabetic complications because of inhibiting formation of advanced glycation end products which are accelerated in continuous hyperglycemic condition in diabetes and declining of cellular damage.

As protein kinase C inhibitors, LY-333531, midostaurin or the like are illustrated. Protein kinase C inhibitors are preferably used for diabetic complications because of inhibiting of protein kinase C activity which is accelerated in continuous hyperglycemic condition in diabetes.

As γ-aminobutyric acid receptor antagonists, topiramate or the like are illustrated; as sodium channel antagonists, mexiletine hydrochloride, oxcarbazepine or the like are illustrated; as transcript factor NF-κB inhibitors, dexlipotam or the like are illustrated; as lipid peroxidase inhibitors, tirilazad mesylate or the like are illustrated; as N-acetylated-α-linked-acid-dipeptidase inhibitors, GPI-5693 or the like are illustrated; and as carnitine derivatives, carnitine, levacecarnine hydrochloride, levocarnitine chloride, levocarnitine, ST-261 or the like are illustrated. These drugs, insulin-like growth factor-I, platelet-derived growth factor, platelet derived growth factor analogues, epidermal growth factor, nerve growth factor, uridine, 5-hydroxy-1-methylhidantoin, EGB-761, bimoclomol, sulodexide and Y-128 are preferably used for diabetic complications.

As hydroxymethylglutaryl coenzyme A reductase inhibitors, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin or the like are illustrated. Hydroxymethylglutaryl coenzyme A reductase inhibitors are used preferably for hyperlipidemia, hypercholesterolemia, hypertriglyceridemia, lipid metabolism disorder or atherosclerosis, and more preferably for hyperlipidemia, hypercholesterolemia or atherosclerosis because of lowering blood cholesterol level by inhibiting hydroxymethylglutaryl coenzyme A reductase.

As fibric acid derivatives, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 or the like are illustrated. Fibric acid derivatives are used preferably for hyperinsulinemia, hyperlipidemia, hypercholesterolemia, hypertriglyceridemia, lipid metabolism disorder or atherosclerosis, and more preferably for hyperlipidemia, hypertriglyceridemia or atherosclerosis because of activating hepatic lipoprotein lipase and enhancing fatty acid oxidation, leading to lowering of blood triglyceride level.

As $β_3$-adrenoceptor agonists, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696, YM178 or the like are illustrated. $β_3$-Adrenoceptor agonists are used preferably for obesity, hyperinsulinemia, hyperlipidemia, hypercholesterolemia, hypertriglyceridemia or lipid metabolism disorder, and more preferably for obesity or hyperinsulinemia because of stimulating $β_3$-adrenoceptor in adipose tissue and enhancing the fatty acid oxidation, leading to induction of energy expenditure.

As acyl-coenzyme A cholesterol acyltransferase inhibitors, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe or the like are illustrated. Acyl-coenzyme A cholesterol acyltransferase inhibitors are used preferably for hyperlipidemia, hypercholesterolemia, hypertriglyceridemia or lipid metabolism disorder, and more preferably for hyperlipidemia or hypercholesterolemia because of lowering blood cholesterol level by inhibiting acyl-coenzyme A cholesterol acyltransferase.

As thyroid hormone receptor agonists, sodium liothyronine, sodium levothyroxine, KB-2611 or the like are illustrated; as cholesterol absorption inhibitors, ezetimibe, SCH-48461 or the like are illustrated; as lipase inhibitors, orlistat, ATL-962, AZM-131, RED-103004 or the like are illustrated; as carnitine palmitoyl transferase inhibitors, etomoxir or the like are illustrated; as squalene synthase inhibitors, SDZ-268-198, BMS-188494, A-87049, RPR-101821, ZD-9720, RPR-107393, ER-27856 or the like are illustrated; as nicotinic acid derivatives, nicotinic acid, nicotinamide, nicomol, niceritrol, acipimox, nicorandil or the like are illustrated; as bile acid sequestrants, colestyramine, colestilan, colesevelam hydrochloride, GT-102-279 or the like are illustrated; as sodium/bile acid cotransporter inhibitors, 264W94, S-8921, SD-5613 or the like are illustrated; and as cholesterol ester transfer protein inhibitors, PNU-107368E, SC-795, JTT-705, CP-529414 or the like are illustrated. These drugs, probcol, microsomal triglyceride transfer protein inhibitors, lipoxygenase inhibitors and low-density lipoprotein receptor enhancers are preferably used for hyperlipidemia, hypercholesterolemia, hypertriglyceridemia or lipid metabolism disorder.

As appetite suppressants, monoamine reuptake inhibitors, serotonin reuptake inhibitors, serotonin releasing stimulants, serotonin agonists (especially $5HT_{2C}$-agonists), noradrenaline reuptake inhibitors, noradrenaline releasing stimulants, $\alpha_1$-adrenoceptor agonists, $\beta_2$-adrenoceptor agonists, dopamine agonists, cannabinoid receptor antagonists, γ-aminobutyric acid receptor antagonists, $H_3$-histamine antagonists, L-histidine, leptin, leptin analogues, leptin receptor agonists, melanocortin receptor agonists (especially, MC3-R agonists, MC4-R agonists), α-melanocyte stimulating hormone, cocaine-and amphetamine-regulated transcript, mahogany protein, enterostatin agonists, calcitonin, calcitonin-gene-related peptide, bombesin, cholecystokinin agonists (especially CCK-A agonists), corticotropin-releasing hormone, corticotrophin-releasing hormone analogues, corticotropin-releasing hormone agonists, urocortin, somatostatin, somatostatin analogues, somatostatin receptor agonists, pituitary adenylate cyclase-activating peptide, brain-derived neurotrophic factor, ciliary neurotrophic factor, thyrotropin-releasing hormone, neurotensin, sauvagine, neuropeptide Y antagonists, opioid peptide antagonists, galanin antagonists, melanin-concentrating hormone antagonists, agouti-related protein inhibitors and orexin receptor antagonists are illustrated. Concretely, as monoamine reuptake inhibitors, mazindol or the like are illustrated; as serotonin reuptake inhibitors, dexfenfluramine hydrochloride, fenfluramine, sibutramine hydrochloride, fluvoxamine maleate, sertraline hydrochloride or the like are illustrated; as serotonin agonists, inotriptan, (+)-norfenfluramine or the like are illustrated; as noradrenaline reuptake inhibitors, bupropion, GW-320659 or the like are illustrated; as noradrenaline releasing stimulants, rolipram, YM-992 or the like are illustrated; as $\beta_2$-adrenoceptor agonists, amphetamine, dextroamphetamine, phentermine, benzphetamine, methamphetamine, phendimetrazine, phenmetrazine, diethylpropion, phenylpropanolamine, clobenzorex or the like are illustrated; as dopamine agonists, ER-230, doprexin, bromocriptine mesylate or the like are illustrated; as cannabinoid receptor antagonists, rimonabant or the like are illustrated; as γ-aminobutyric acid receptor antagonists, topiramate or the like are illustrated; as $H_3$-histamine antagonists, GT-2394 or the like are illustrated; as leptin, leptin analogues or leptin receptor agonists, LY-355101 or the like are illustrated; as cholecystokinin agonists (especially CCK-A agonists), SR-146131, SSR-125180, BP-3.200, A-71623, FPL-15849, GI-248573, GW-7178, GI-181771, GW-7854, A-71378 or the like are illustrated; and as neuropeptide Y antagonists, SR-120819-A, PD-160170, NGD-95-1, BIBP-3226, 1229-U-91, CGP-71683, BIBO-3304, CP-671906-01, J-115814 or the like are illustrated. Appetite suppressants are used preferably for diabetes, impaired glucose tolerance, diabetic complications, obesity, hyperlipidemia, hypercholesterolemia, hypertriglyceridemia, lipid metabolism disorder, atherosclerosis, hypertension, congestive heart failure, edema, hyperuricemia or gout, and more preferably for obesity because of stimulating or inhibiting the activities of intracerebral monoamines or bioactive peptides in central appetite regulatory system and suppressing the appetite, leading to reduction of energy intake.

As angiotensin-converting enzyme inhibitors, captopril, enalapri maleate, alacepril, delapril hydrochloride, ramipril, lisinopril, imidapril hydrochloride, benazepril hydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril or the like are illustrated. Angiotensin-converting enzyme inhibitors are preferably used for diabetic complications or hypertension.

As neutral endopeptidase inhibitors, omapatrilat, MDL-100240, fasidotril, sampatrilat, GW-660511X, mixanpril, SA-7060, E-4030, SLV-306, ecadotril or the like are illustrated. Neutral endopeptidase inhibitors are preferably used for diabetic complications or hypertension.

As angiotensin II receptor antagonists, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 or the like are illustrated. Angiotensin II receptor antagonists are preferably used for diabetic complications or hypertension.

As endothelin-converting enzyme inhibitors, CGS-31447, CGS-35066, SM-19712 or the like are illustrated; as endothelin receptor antagonists, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 or the like are illustrated. These drugs are preferably used for diabetic complications or hypertension, and more preferably for hypertension.

As diuretic agents, chlorthalidone, metolazone, cyclopenthiazide, trichloromethiazide, hydrochlorothiazide, hydroflumethiazide, benzylhydrochlorothiazide, penflutizide, methyclothiazide, indapamide, tripamide, mefruside, azosemide, etacrynic acid, torasemide, piretanide, furosemide, bumetanide, meticrane, potassium canrenoate, spironolactone, triamterene, aminophylline, cicletanine hydrochloride, LLU-α, PNU-80873A, isosorbide, D-mannitol, D-sorbitol, fructose, glycerin, acetazolamide, methazolamide, FR-179544, OPC-31260, lixivaptan, conivaptan hydrochloride or the like are illustrated. Diuretic drugs are preferably used for diabetic complications, hypertension, congestive heart failure or edema, and more preferably for hypertension, congestive heart failure or edema because of reducing blood pressure or improving edema by increasing urinary excretion.

As calcium antagonists, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride or the like are illustrated; as vasodilating antihypertensive agents, indapamide, todralazinehydrochloride, hydralazine hydrochloride, cadralazine, budralazine or the like are illustrated; as sympathetic blocking agents, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin or the like are illustrated; as centrally acting antihypertensive agents, reserpine or the like are illustrated; and as $\alpha_2$-adrenoceptor agonists, clonidine hydrochloride, methyldopa, CHF-1035, guanabenz acetate, guanfacine hydrochloride, moxonidine, lofexidine, talipexole hydrochloride or the like are illustrated. These drugs are preferably used for hypertension.

As antiplatelets agents, ticlopidine hydrochloride, dipyridamole, cilostazol, ethyl icosa pentate, sarpogrelate hydrochloride, dilazep dihydrochloride, trapidil, beraprost sodium, aspirin or the like are illustrated. Antiplatelets agents are preferably used for atherosclerosis or congestive heart failure.

As uric acid synthesis inhibitors, allopurinol, oxypurinol or the like are illustrated; as uricosuric agents, benzbromarone, probenecid or the like are illustrated; and as urinary alkalinizers, sodium hydrogen carbonate, potassium citrate, sodium citrate or the like are illustrated. These drugs are preferably used for hyperuricemia or gout.

In case of uses in combination with drugs other than 1,5-anhydroglucitol/fructose/mannose transporter inhibitors, for example, in the use for diabetic complications, the combination with at least one member of the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, glycogen synthase kinase-3 inhibitors, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid antagonist, a sodium channel antagonist, a transcript factor NF-κB inhibitor, alipidperoxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhidantoin, EGB-761, bimoclomol, sulodexide, Y-128, an angiotensin-converting enzyme inhibitor, a neutral endopeptidase inhibitor, an angiotensin II receptor antagonist, an endothelin-converting enzyme inhibitor, an endothelin receptor antagonist and a diuretic agent is preferable; and the combination with at least one member of the group consisting of an aldose reductase inhibitor, an angiotensin-converting enzyme inhibitor, a neutral endopeptidase inhibitor and an angiotensin II receptor antagonist is more preferable. Similarly, in the use for diabetes, the combination with at least one member of the group consisting of an insulin sensitivity enhancer, a glucose absorption inhibitor, a biguanide, an insulin secretion enhancer, a SGLT2 inhibitors, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructosebisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist and an appetite suppressant is preferable; the combination with at least one member of the group consisting of an insulin sensitivity enhancer, a biguanide, an insulin secretion enhancer, a SGLT2 inhibitors, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3inhibitor, glucagon-like peptide-1, a glucagon-like peptide-1 analogue, a glucagon-like peptide-1 agonist, amylin, an amylin analogue and an amylin agonist is more preferable; and the combination with at least one member of the group consisting of an insulin sensitivity enhancer, a biguanide, an insulin secretion enhancer, a SGLT2 inhibitor and an insulin or insulin analogue is most preferable. Furthermore, in the use for obesity, the combination with at least one member of the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, a $\beta_3$-adrenoceptor agonist and an appetite suppressant is preferable; and the combination with at least one member of the group consisting of a SGLT2 inhibitor, a $\beta_3$-adrenoceptor agonist and an appetite suppressant is more preferable.

When the pharmaceutical compositions of the present invention are employed in the practical treatment, various dosage forms are used depending on their uses. As examples of the dosage forms, powders, granules, fine granules, dry syrups, tablets, capsules, topical dosages (e.g., transdermal absorption preparations), injections, suppositories, solutions and the like are illustrated, which are orally or parenterally administered. The pharmaceutical compositions of the present invention can also include sustained release formulation and enteric coated preparation.

These pharmaceutical compositions can be prepared optionally by admixing, diluting, dissolving and then coating using an appropriate pharmaceutical additive such as excipients, disintegrators, binders, lubricants, diluents, buffers, isotonicities, antiseptics, moistening agents, emulsifiers, dispersing agents, stabilizing agents, dissolving aids, viscosity-increasing agents, gelling agents, hardening agents, absorbents, viscosing agents, elasticating agents, plasticizers, coating agents, sustained-releasing agent, antioxidants, light shielding agents, antistatic agents, fragrances, sweetening agents, flavors, coloring agents, soothing agents and the like, and formulating the mixture in accordance with conventional methods. In case of the uses of the compound of the present invention in combination with the drug(s) other than 1,5-anhydroglucitol/fructose/mannose transporter inhibitors, they can be prepared by formulating each active ingredient together or individually.

When the pharmaceutical compositions of the present invention are employed in the practical treatment, the dosage of a compound represented by the above general formula (I), or a pharmaceutically acceptable salt thereof or a prodrug thereof as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably. Also, in case of the uses of the compound of the present invention in combination with the drug(s) other than 1,5-anhydroglucitol/fructose/mannose transporter inhibitors, the dosage of the compound of the present invention can be decreased, depending on the dosage of the drug(s) other than 1,5-anhydroglucitol/fructose/mannose transporter inhibitors.

In addition, the present invention also includes a screening method for an agent for the prevention, inhibition of progression or treatment of a disease associated with the excess uptake of at least a kind of carbohydrates selected from glucose, fructose and mannose, characterized by using a protein relating to 1,5-anhydroglucitol/fructose/mannose transporter.

The present invention includes a screening method for an agent for the prevention or inhibition of progression of diabetic complications such as diabetic nephropathy, characterized by using a protein relating to 1,5-anhydroglucitol/fructose/mannose transporter.

The present invention also includes an agent for prevention, inhibition of progression or treatment of a disease associated with the excess uptake of at least a kind of carbohydrates selected from glucose, fructose and mannose, comprising as an active ingredient an inhibitor of 1,5-anhydroglucitol/fructose/mannose transporter.

The present invention includes an agent for prevention or inhibition of progression of diabetic complications such as diabetic nephropathy, comprising as an active ingredient an inhibitor of 1,5-anhydroglucitol/fructose/mannose transporter.

Furthermore, the present invention includes an agent for prevention, inhibition of progression or treatment of a disease associated with hyperglycemia such as diabetes, comprising as an active ingredient an inhibitor of 1,5-anhydroglucitol/fructose/mannose transporter.

The details are illustrated below regarding the screening method for an agent for the prevention, inhibition of progression or treatment of a disease associated with the excess uptake of at least a kind of carbohydrates selected from glucose, fructose and mannose, or an agent for the prevention or inhibition of progression of diabetic complications such as diabetic nephropathy, characterized by using a protein relating to 1,5-anhydroglucitol/fructose/mannose transporter.

SMINT and SGLTh have 1,5-anhydroglucitol/fructose/mannose transporting activities. In relative diseases such as diabetic complications, diabetes or obesity in which a flow of carbohydrates, especially glucose and mannose, have varied with the changes of lifestyles, energy accumulation in the body is one of contributing factors in pathologic conditions. The 1,5-anhydroglucitol/fructose/mannose transporter relates to reabsorption in the kidney or uptake into a cell of glucose, fructose and mannose or absorption in the small intestine of these carbohydrates, and controls the energy flow by controlling the flow of carbohydrates. Therefore, it is considered that the flow of carbohydrate energy can be controlled by inhibiting 1,5-anhydroglucitol/fructose/mannose transporter. Thus, an inhibitor of 1,5-anhydroglucitol/fructose/mannose transporter is useful for prevention, inhibition of progression or treatment of a disease which pathological conditions are associated with disturbance in the energy balance, that is, diabetic complications such as diabetic nephropathy or a disease associated with hyperglycemia.

A screening method of the present invention can be conducted in the following way.

Firstly, DNA molecule encoding the protein with 1,5-anhydroglucitol/fructose/mannose transporter activity is ligated to appropriate expression vectors; it is transfected into appropriate host cells; the cells are cultured under appropriate conditions to express the protein of the present invention. As appropriate expression vectors available for expression of the protein to carry out screening, for example, pCI-neo, pcDNA and pME18S can be illustrated in the case of animal cells as host cells; pBluescript II and pGEMEX-1 can be illustrated in the case of *Escherichia coli* as host cells; pBacPAK8-GUS (transfer vector)/BacPAK6 (virus DNA) and the like can be illustrated in the case of insect cells as host cells. As appropriate host cells, animal cells such as COS-7 cells, insect cells such as Sf9 cells, prokaryote LB medium (*Escherichia coli*) such as *Escherichia coli* and the like can be illustrated.

Secondly, by using previously prepared cells expressing the protein (for example, COS-7 cells expressing SMINT and the like), for example, the following operation can be done. First of all, to Uptake Buffer containing sodium chloride is added methyl-α-D-glucopyranoside as a mixture of its non-radiolabeled form and $^{14}$C-labeled form at a final concentration of 1 mM. Test compound is dissolved in dimethylsulfoxide, then it is diluted properly with distilled water, and it is added to the Uptake Buffer containing 1 mM methyl-α-D-glucopyranoside to prepare Assay Buffer. For control group, Assay Buffer without test compound is prepared; for the determination of basal uptake, Basal Buffer containing choline chloride instead of sodium chloride of the Uptake Buffer is prepared. Culture medium is removed from cultured cells, and Pretreatment Buffer (Basal Buffer without methyl-α-D-glucopyranoside) is added to the cells, and the cells are incubated at 37° C. for 10 minutes. After repeating once the same operation, Pretreatment Buffer is removed, and each of Assay Buffer and Basal Buffer is added to the cells followed by incubation at 37° C. After 1 hour incubation, the Assay Buffer is removed and the cells are washed twice with Washing Buffer (Basal Buffer containing 10 mM non-radiolabeled methyl-α-D-glucopyranoside). The cells are lysed with 0.2 mol/L sodium hydroxide, and the lysate is transferred to PicoPlate. MicroScint 40 is added to the lysate, and the radioactivity is measured in a microscintillation counter TOP- COUNT. Methyl-α-D-glucopyranoside uptake by the cells treated with each concentration of test compounds is calculated as relative activity to control group, which is set as 100% uptake after deducting the basal uptake. When methyl-α-D-glucopyranoside uptake by the cells treated with a test compound is extremely low or virtually zero, the test compound is judged to be an effective inhibitor.

The above screening method can be optionally modified within common knowledge of a person skilled in the art. In addition, an agent for the prevention, inhibition of progression or treatment of a disease associated with the excess uptake of at least a kind of carbohydrates selected from glucose, fructose and mannose; an agent for the prevention or inhibition of progression of diabetic complications such as diabetic nephropathy; or an agent for prevention, inhibition of progression or treatment of a disease associated with hyperglycemia such as diabetes can be prepared by comprising as an active ingredient an inhibitor of 1,5-anhydroglucitol/fructose/mannose transporter of which activity of inhibiting 1,5-anhydroglucitol/fructose/mannose transporter can be confirmed by the above screening method or the like.

BEST MODE FOR CARRYING OUT THE INVENTION

Figure 1:
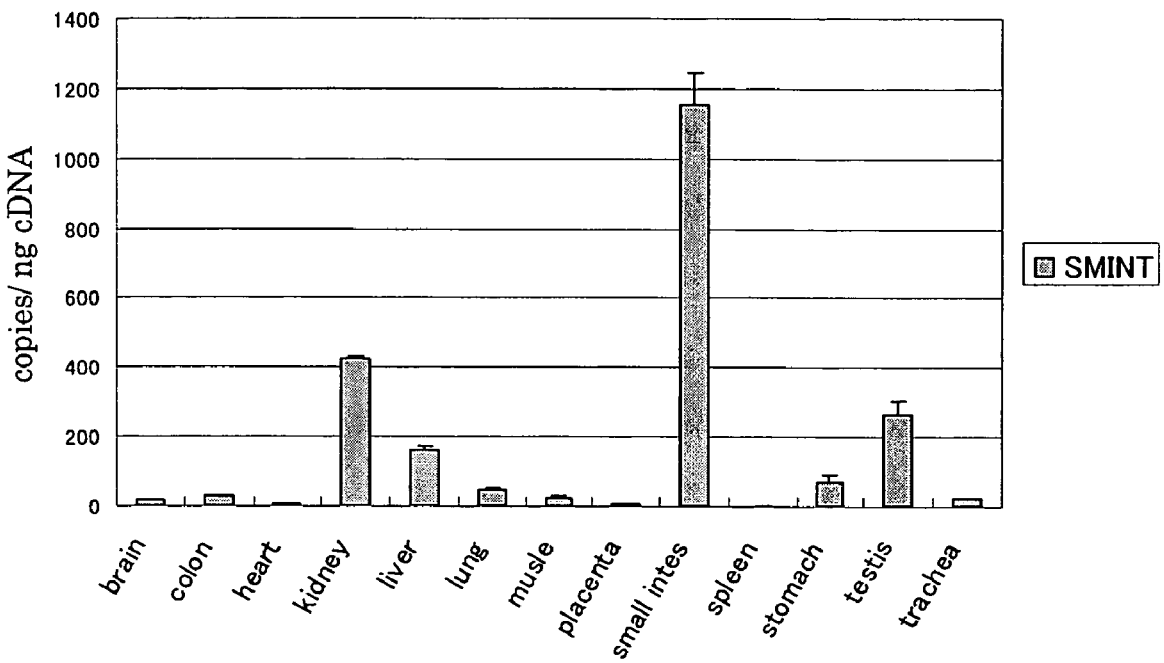
FIG. 1 is a graph showing the distribution pattern of SMINT gene expression among human organs. The vertical axis indicates copy number/ng cDNA, and the horizontal axis indicates the name of human organ.

The present invention is further illustrated in more detail by way of the following Examples and Test Examples. However, the present invention is not limited thereto.

EXAMPLE 1

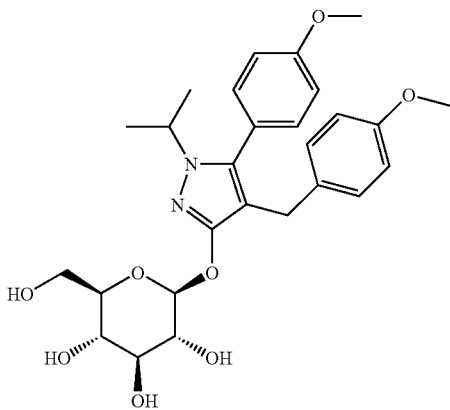

Process 1

3-(4-Methoxyphenyl)-3-oxothiopropionic acid O-benzyl ester

To a suspension of sodium amide (1.6g) in toluene (50 mL) was added a mixture of dithiocarbonic acid O-benzyl ester S-methyl ester (4.0 g) and 4-methoxybenzophenone (3.0 g) at room temperature and the mixture was stirred at room temperature overnight. Hydrochloric acid solution (2 mol/L, 80 mL) was added to the reaction mixture and the mixture was extracted with diethyl ether. The organic layer was washed with brine and dried over anhydrous magnesium sulfate, and the solvent was removed under reduced pressure. The residue was purified by column chromatography on silica gel (eluent: hexane/dichloromethane=5/1-2/1) to give the title compound (3.4 g).

Process 2

3-Benzyloxy-1-isopropyl-5-(4-methoxyphenyl)-1H-pyrazole

To a suspension of 3-(4-methoxyphenyl)-3-oxothiopropionic acid O-benzyl ester (0.60 g) and isopropylhydrazine hydrochloride (0.29 g) in acetonitrile (2 mL) was added triethylamine (0.81 g) and the mixture was stirred at room temperature overnight. Water was added to the reaction mixture and the mixture was extracted with dichloromethane. The solvent of the organic layer was removed under reduced pressure and the residue was purified by column chromatography on silica gel (eluent: hexane/dichloromethane=3/1-1/3) to give the title compound (0.40 g).

$^1$H-NMR (CDCl$_3$) δ ppm:
1.41 (6H, d, J=6.6 Hz), 3.85 (3H, s), 4.30-4.45 (1H, m), 5.21 (2H, s), 5.63 (1H, s), 6.90-7.00 (2H, m), 7.20-7.40 (5H, m), 7.40-7.55 (2H, m)

Process 3

3-Benzyloxy-4-formyl-1-isopropyl-5-(4-methoxyphenyl)-1H-pyrazole

To a solution of 3-benzyloxy-1-isopropyl-5-(4-methoxyphenyl)-1H-pyrazole (0.40 g) in N,N-dimethylformamide (1.5 mL) was added phosphorus oxychloride (0.23 g) at 80° C. and the mixture was stirred at 80° C. for 1 hour. After cooling to room temperature, a sodium hydroxide aqueous solution (1 mol/L, 5 mL) was added to the reaction mixture and the mixture was extracted with diethyl ether. The organic layer was dried over anhydrous magnesium sulfate and the solvent was removed under reduced pressure to give the title compound (0.42 g).

$^1$H-NMR (CDCl$_3$) δ ppm:
1.39 (6H, d, J=6.5 Hz), 3.87 (3H, s), 4.25-4.40 (1H, m), 5.41 (2H, s), 6.95-7.05 (2H, m), 7.25-7.40 (5H, m), 7.50-7.60 (2H, m), 9.57 (1H, s)

Process 4

[3-Benzyloxy-1-isopropyl-5-(4-methoxyphenyl)-1H-pyrazol-4-yl]4-methoxyphenyl methanol To a solution of 3-benzyloxy-4-formyl-1-isopropyl-5-(4-methoxyphenyl)-1H-pyrazole (0.14 g) in tetrahydrofuran (1.8 mL) was added a solution of 4-methoxyphenylmagnesium bromide in tetrahydrofuran (0.5 mol/L, 0.96 mL) at room temperature and the mixture was stirred at room temperature for 1 hour. A small amount of water was added to the reaction mixture and the mixture was purified by column chromatography on aminopropylated silica gel (eluent: tetrahydrofuran). Further purification by column chromatography on silica gel (eluent: hexane/ethyl acetate=10/1-2/1) gave the title compound (0.11 g).

Process 5

1-Isopropyl-5-(4-methoxyphenyl)-4-[(4-methoxyphenyl)-methyl]-1,2-dihydro-3H-pyrazole-3-on To a solution of [3-benzyloxy-1-isopropyl-5-(4-methoxyphenyl)-1H-pyrazol-4-yl]4-methoxy-phenyl methanol (0.11 g) in ethanol (4 mL) was added a catalytic amount of 10% palladium-carbon powder and the mixture was stirred at room temperature under a hydrogen atmosphere overnight. Dichloromethane was added to the mixture and the insoluble material was removed by filtration. The solvent of filtrate was removed under reduced pressure to give the title compound (0.076 g).

$^1$H-NMR (CDCl$_3$) δ ppm:

1.36 (6H, d, J=6.6 Hz), 3.55 (2H, s), 3.75 (3H, s), 3.85 (3H, s), 4.10-4.25 (1H, m), 6.70-6.80 (2H, m), 6.90-7.00 (2H, m), 7.05-7.20 (5H, m)

Process 6

3-(β-D-Glucopyranosyloxy)-1-isopropyl-5-(4-methoxyphenyl)-4-[(4-methoxyphenyl)methyl-1H-pyrazole To a suspension of 1-isopropyl-5-(4-methoxyphenyl)-4-[(4-methoxyphenyl)methyl]-1,2-dihydro-3H-pyrazole-3-one (0.066 g), acetobromo-α-D-glucose (0.39 g) and benzyl-(n-tributyl)ammonium bromide (0.033 g) in dichloromethane (4 mL) was added sodium hydroxide (5 mol/L, 0.37 mL) and the mixture was stirred at room temperature for 1.5 hours. The reaction mixture was purified by column chromatography on aminopropylated silica gel (eluent: tetrahydrofuran). The obtained semi purified 1-isopropyl-5-(4-methoxyphenyl)-4-[(4-methoxyphenyl)methyl]-3-(2,3,4,6-tetra-O-acethyl-β-D-glucopyranosyloxy)-1H-pyrazole was dissolved in methanol (3 mL) and sodium methoxide (28% methanol solution, 0.36 mL) was added to the solution and the mixture was stirred at room temperature for 2 hours. The solvent of the reaction mixture was removed and methanol (0.5 mL), water (2 mL) and 10% citric acid solution (3 mL) were added to the residue. The mixture was purified by solid phase extraction on ODS (washing solvent: water, eluent: methanol). Preparative reverse phase column chromatography (Shiseido CAPSELL-PAC C18 UG80, 5 μM, 20×50 mm, flow rate 30 mL/min linear gradient, water/methanol=90/10-10/90) was used for further purification to give the title compound (0.047 g).

$^1$H-NMR (CD$_3$OD) δ ppm:

1.32 (3H, d, J=7.8 Hz), 1.33 (3H, d, J=6.5 Hz), 3.25-3.50 (4H, m), 3.56 (1H, d, J=15.9 Hz), 3.61 (1H, d, J=15.9 Hz), 3.65-3.75 (1H, m), 3.71 (3H, s), 3.75-3.86 (1H, m), 3.82 (3H, s), 4.15-4.35 (1H, m), 5.10-5.25 (1H, m), 6.65-6.75 (2H, m), 6.90-7.00 (4H, m), 7.05-7.15 (2H, m)

EXAMPLES 2-74

The compounds described in Tables 1-14 were prepared in a similar manner to that described in Example 1 using corresponding starting materials and optionally by introducing a protective group.

TABLE 1

| Example number | Chemical structure | $^1$H-NMR (CD$_3$OD) δ ppm: |
|---|---|---|
| Example 2 | 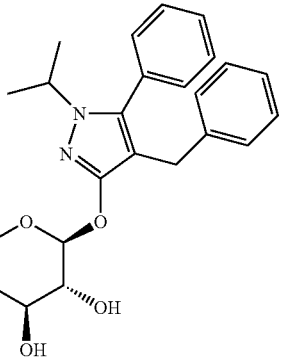 | 1.32 (3H, d, J=6.7 Hz), 1.34 (3H, J=6.5 Hz), 3.25–3.50 (4H, m), 3.60–3.75 (3H, m), 3.82 (1H, dd, J=2.5. 12.0 Hz), 4.20–4.30 (1H, m), 5.15–5.25 (1H, m), 6.95–7.25 (7H, m), 7.35–7.50 (3H, m) |
| Example 3 | 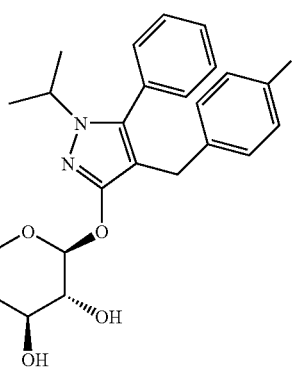 | 1.33 (3H, d, J=6.7 Hz), 1.34 (3H, d, J=6.7 Hz), 3.30–3.50 (4H, m), 3.56 (1H, d, J=15.7 Hz), 3.62 (1H, d, J=15.7 Hz), 3.69 (1H, dd, J=5.7, 12.2 Hz), 3.71 (3H, s), 3.82 (1H, dd, J=2.2, 12.2 Hz), 4.20–4.30 (1H, m), 5.15–5.25 (1H, m), 6.65–6.75 (2H, m), 6.90–7.00 (2H, m), 7.15–7.25 (2H, m), 7.40–7.50 (3H, m) |

| Example number | Chemical structure | $^1$H-NMR (CD$_3$OD) δ ppm: |
|---|---|---|
| Example 4 | 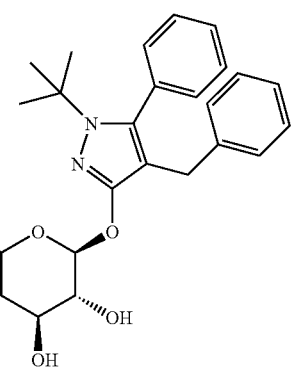 | 1.34 (9H, s), 3.25–3.55 (6H, m), 3.69 (1H, dd, J=5.6, 12.1 Hz), 3.83 (1H, dd, J=2.3, 12.1 Hz), 5.25–5.35 (1H, m), 6.90–7.00 (2H, m), 7.00–7.20 (5H, m), 7.30–7.45 (3H, m) |
| Example 5 | 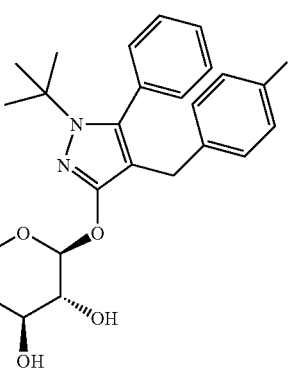 | 1.34 (9H, s), 3.25–3.50 (6H, m), 3.65–3.75 (1H, m), 3.71 (3H, s), (1H, dd, J=2.3, 12.1 Hz), 5.20–5.35 (1H, m), 6.60–6.70 (2H, m), 6.80–6.90 (2H, m), 7.10–7.20 (2H, m), 7.30–7.45 (3H, m) |
| Example 6 | 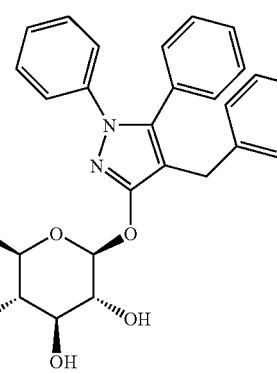 | 3.30–3.50 (4H, m), 3.67 (1H, d, J=15.6 Hz), 3.70 (1H, dd, J=5.2, 12.0 Hz), 3.73 (3H, s), 3.76 (1H, d, J=15.6 Hz), 3.87 (1H, dd, J=1.9, 12.0 Hz), 5.35–5.45 (1H, m), 6.70–6.80 (2H, m), 7.00–7.15 (4H, m), 7.15–7.40 (8H, m) |

TABLE 2

| Example number | Chemical structure | ¹H-NMR (CD₃OD) δ ppm: |
| --- | --- | --- |
| Example 7 | 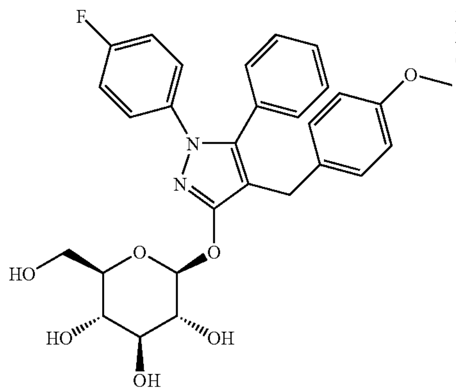 | 3.30–3.55 (4H, m), 3.60–3.80 (6H, m), 3.80–3.95 (1H, m), 5.35–5.45 (1H, m), 6.70-6.80 (2H, m), 6.95–7.40 (11H, m) |
| Example 8 | 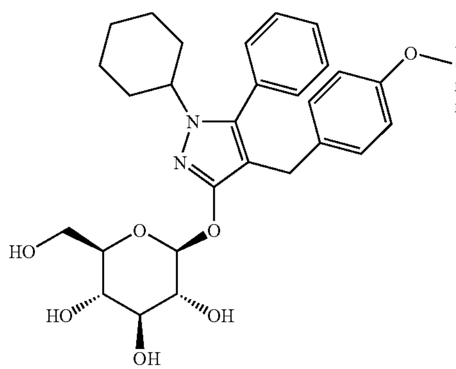 | 1.34 (9H, s), 3.25–3.50 (6H, m), 3.65–3.75 (1H, m), 3.71 (3H, s), 3.83 (1H, dd, J=2.3, 12.1 Hz), 5.20–5.35 (1H, m), 6.60–6.70 (2H, m), 6.80–6.90 (2H, m), 7.10–7.20 (2H, m), 7.30–7.45 (3H, m) |
| Example 9 | 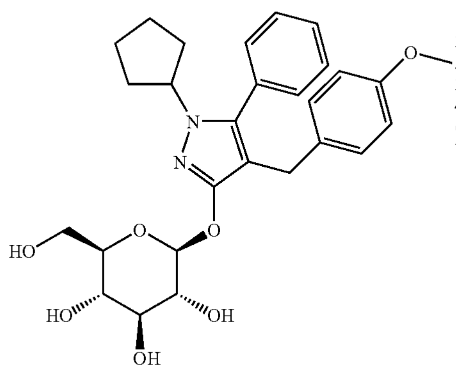 | 1.45–1.65 (2H, m), 1.80–2.10 (6H, m), 3.30–3.50 (4H, m), 3.56 (1H, d, J=15.6 Hz), 3.61 (1H, d, J=15.6 Hz), 3.65–3.72 (1H, m), 3.71 (3H, s), 4.30–4.45 (1H, m), 5.20–5.30 (1H, m), 6.65–6.75 (2H, m), 6.90–7.00 (2H, m), 7.15–7.25 (2H, m), 7.35–7.50 (3H, m) |
| Example 10 | 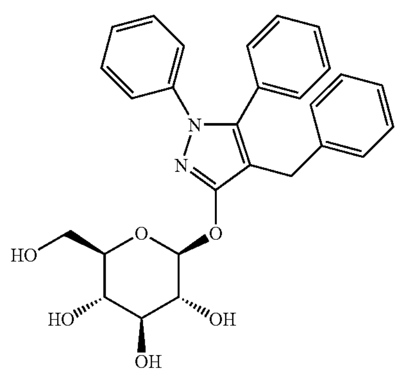 | 3.20–3.55 (4H, m), 3.69 (1H, dd, J=5.3, 11.9 Hz), 3.73 (1H, d, J=15.8 Hz), 3.83 (1H, d, J=15.8 Hz), 3.87 (1H, dd, J=1.7, 11.9 Hz), 5.35–5.45 (1H, m), 7.00–7.40 (15H, m) |

TABLE 2-continued
| Example number | Chemical structure | $^1$H-NMR (CD$_3$OD) δ ppm: |
|---|---|---|
| Example 11 | 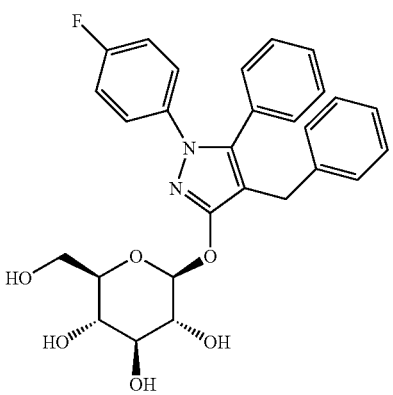 | 3.30–3.50 (4H, m), 3.69, (1H, dd, J=4.9, 12.0 Hz), 3.73 (1H, d, J=15.7 Hz), 3.82 (1H, d, J=15.7 Hz), 3.87 (1H, dd, J=1.9, 12.0 Hz), 5.35–5.45 (1H, m), 6.95–7.05 (2H, m), 7.05–7.15 (5H, m), 7.15–7.25 (4H, m), 7.25–7.40 (3H, m) |
| Example 12 | 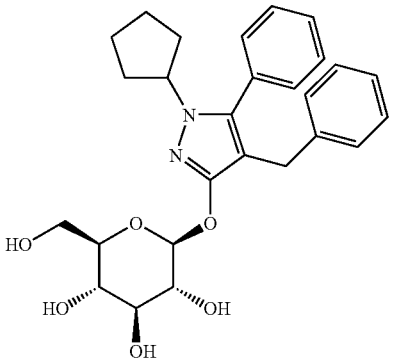 | 1.45–1.60 (2H, m), 1.80–2.10 (6H, m), 3.30–3.50 (4H, m), 3.63 (1H, d, J=15.5 Hz), 3.68 (1H, d, J=15.5 Hz), 3.69 (1H, dd, J=5.3, 12.2 Hz), 3.82 (1H, dd, J=2.5, 12.2 Hz), 4.30–4.45 (1H, m), 5.20–5.30 (1H, m), 7.00–7.10 (3H, m), 7.10–7.25 (4H, m), 7.35–7.50 (3H, m) |
TABLE 3
| Example number | Chemical structure | $^1$H-NMR (CD$_3$OD) δ ppm: |
|---|---|---|
| Example 13 | 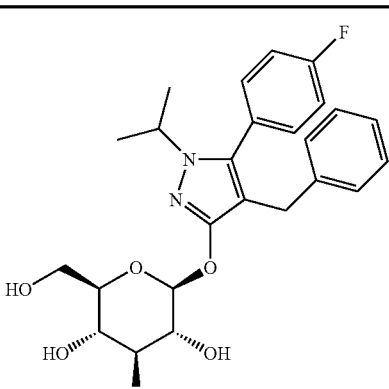 | 1.30–1.40 (6H, m), 3.25–3.50 (4H, m), 3.50–3.75 (3H, m), 3.75–3.90 (1H, m), 4.15–4.30 (1H, m), 5.15–5.30 (1H, m), 6.95–7.25 (9H, m) |

TABLE 3-continued

| Example number | Chemical structure | $^1$H-NMR (CD$_3$OD) δ ppm: |
| --- | --- | --- |
| Example 14 | 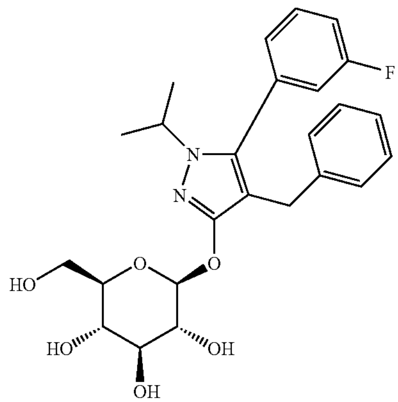 | 1.34 (3H, d, J=6.8 Hz), 1.34 (3H, d, J=6.7 Hz), 3.25–3.50 (4H, m), 3.60–3.75 (3H, m), 3.83 (1H, dd, J=2.6, 12.0 Hz), 4.15–4.35 (1H, m), 5.15–5.30 (1H, m), 6.80–7.25 (8H, m), 7.35–7.50 (1H, m) |
| Example 15 | 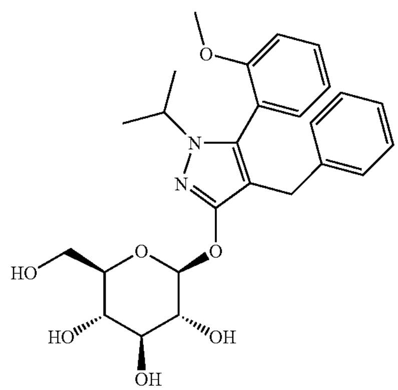 | 1.20–1.40 (6H, m), 3.25–3.50 (4H, m), 3.50–3.75 (6H, m), 3.75–3.90 (1H, m), 3.95–4.10 (1H, m), 5.10–5.20 (1H, m), 6.90–7.15 (8H, m), 7.35–7.45 (1H, m) |
| Example 16 | 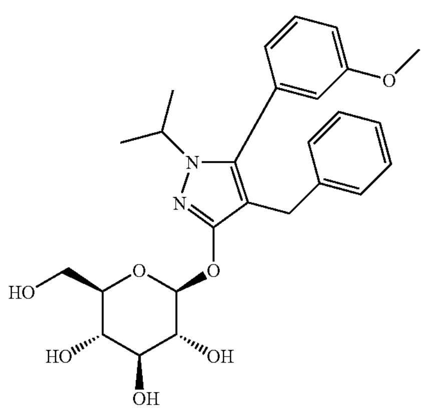 | 1.33 (3H, d, J=6.5 Hz), 1.34 (3H, d, J=6.7 Hz), 3.25–3.50 (4H, m), 3.55–3.75 (6H, m), 3.82 (1H, dd, J=2.6, 12.2 Hz), 4.20–4.35 (1H, m), 5.15–5.30 (1H, m), 6.60–6.70 (1H, m), 6.70–6.80 (1H, m), 6.90–7.00 (1H, m), 7.00–7.10 (3H, m), 7.10–7.20 (2H, m), 7.25–7.40 (1H, m) |

TABLE 3-continued

| Example number | Chemical structure | $^1$H-NMR (CD$_3$OD) δ ppm: |
|---|---|---|
| Example 17 | 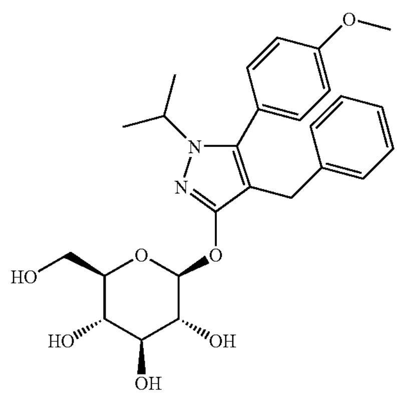 | 1.32 (3H, d, J=6.6 Hz), 1.33 (3H, d, J=6.5 Hz), 3.25–3.50 (4H, m), 3.55–3.75 (3H, m), 3.75–3.90 (4H, m), 4.20–4.30 (1H, m), 5.15–5.25 (1H, m), 6.90–7.20 (9H, m) |
| Example 18 | 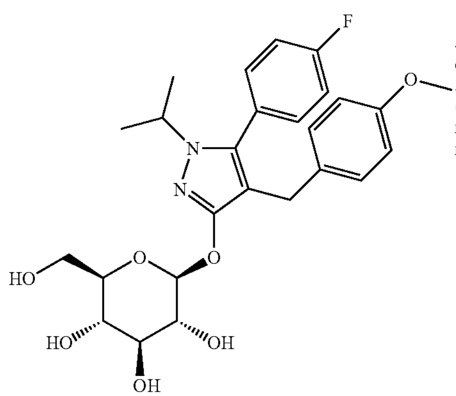 | 1.32 (3H, d, J=6.5 Hz), 1.33 (3H, d, J=6.7 Hz), 3.25–3.50 (4H, m), 3.56 (1H, d, J=15.8 Hz), 3.61 (1H, d, J=15.8 Hz), 3.65–3.75 (1H, m), 3.71 (3H, s), 3.82 (1H, dd, J=2.5, 12.0 Hz), 4.15–4.30 (1H, m), 5.15–5.25 (1H, m), 6.65–6.75 (2H, m), 6.90–6.95 (2H, m), 7.10–7.25 (4H, m) |

TABLE 4

| Example number | Chemical structure | $^1$H-NMR (CD$_3$OD) δ ppm: |
|---|---|---|
| Example 19 | 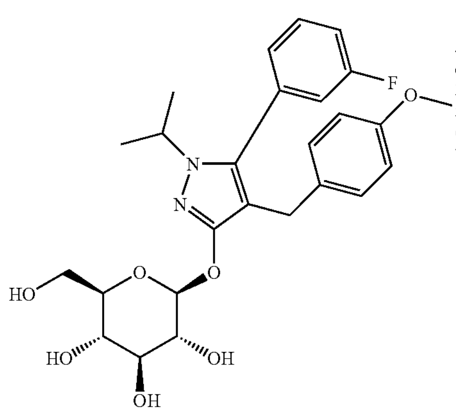 | 1.33 (3H, d, J=6.6 Hz), 1.34 (3H, d, J=6.7 Hz), 3.30–3.50 (4H, m), 3.58 (1H, d, J=15.7 Hz), 3.63 (1H, d, J=15.7 Hz), 3.65–3.75 (4H, m), 4.15–4.30 (1H, m), 5.15–5.30 (1H, m), 6.60–6.80 (2H, m), 6.80–7.10 (4H, m), 7.10–7.20 (1H, m), 7.40–7.50 (1H, m) |

TABLE 4-continued

| Example number | Chemical structure | $^1$H-NMR (CD$_3$OD) δ ppm: |
|---|---|---|
| Example 20 | 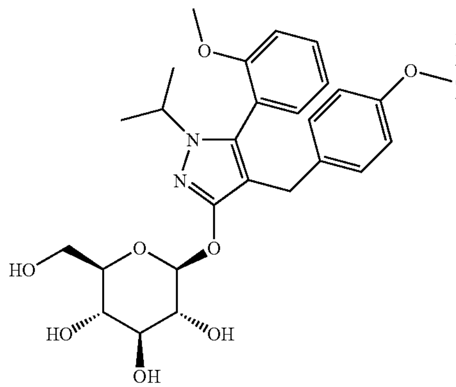 | 1.20–1.40 (6H, m), 3.20–3.60 (6H, m), 3.60–3.75 (7H, m), 3.80–3.90 (1H, m), 3.95–4.10 (1H, m), 5.10–5.20 (1H, m), 6.60–6.70 (2H, m), 6.85–7.10 (5H, m), 7.35–7.45 (1H, m) |
| Example 21 | 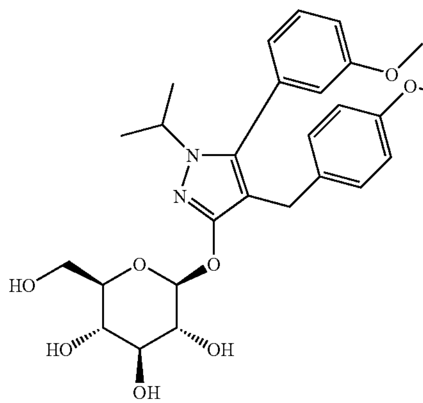 | 1.33 (3H, d, J=6.6 Hz), 1.34 (3H, d, J=6.4 Hz), 3.25–3.50 (4H, m), 3.57 (1H, d, J=15.7 Hz), 3.62 (1H, d, J=15.7 Hz), 3.65–3.75 (7H, m), 3.83 (1H, dd, J=2.2, 12.1 Hz), 4.20–4.35 (1H, m), 5.15–5.25 (1H, m), 6.60–6.80 (4H, m), 6.90–7.00 (3H, m), 7.30–7.40 (1H, m) |
| Example 22 | 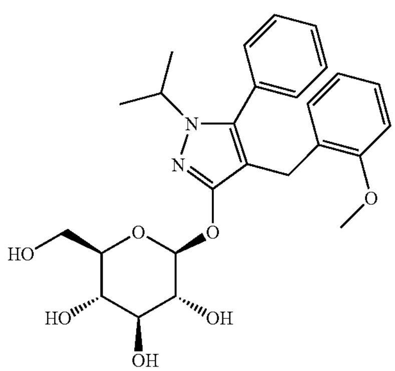 | 1.30–1.40 (6H, m), 3.20–3.30 (1H, m), 3.30–3.45 (3H, m), 3.55–3.75 (7H, m), 3.79 (1H, dd, J=2.4, 12.0 Hz), 4.20–4.35 (1H, m), 5.10–5.25 (1H, m), 6.70–6.85 (2H, m), 6.90–7.00 (1H, m), 7.00–7.12 (1H, m), 7.13–7.25 (2H, m), 7.35–7.45 (3H, m) |
| Example 23 | 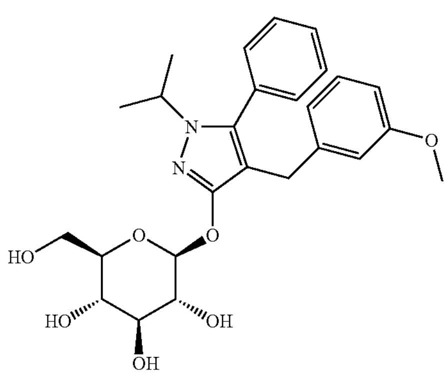 | 1.33 (3H, d, J=6.9 Hz), 1.34 (3H, d, J=6.5 Hz), 3.25–3.55 (4H, m), 3.55–3.75 (3H, m), 3.68 (3H, s), 3.82 (1H, dd, J=2.2, 12.0 Hz), 4.15–4.35 (1H, m), 5.20–5.30 (1H, m), 6.55–6.70 (3H, m), 7.00–7.10 (1H, m), 7.15–7.25 (2H, m), 7.35–7.50 (3H, m) |

TABLE 4-continued
| Example number | Chemical structure | $^1$H-NMR (CD$_3$OD) δ ppm: |
|---|---|---|
| Example 24 | 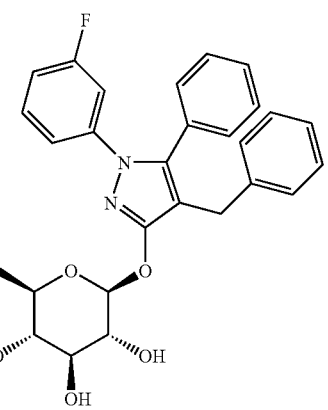 | 3.20–3.55 (4H, m), 3.55–3.85 (4H, m), 3.88 (1H, dd, J=2.0, 12.0 Hz), 5.40–5.50 (1H, m), 6.80–7.50 (14H, m) |
TABLE 6
| Example number | Chemical structure | $^1$H-NMR (CD$_3$OD) δ ppm: |
|---|---|---|
| Example 25 | 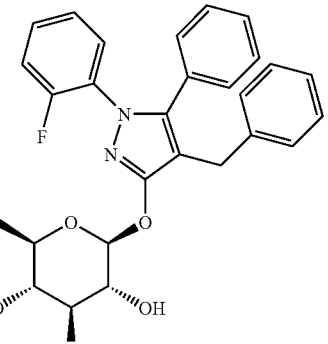 | 3.30–3.50 (4H, m), 3.69 (1H, dd, J=4.8, 12.0 Hz), 3.77 (1H, d, J=15.8 Hz), 3.86 (1H, dd, J=1.8, 12.0 Hz), 3.87 (1H, d, J=15.8 Hz), 5.30–3.40 (1H, m), 7.00–7.50 (14H, m) |
| Example 26 | 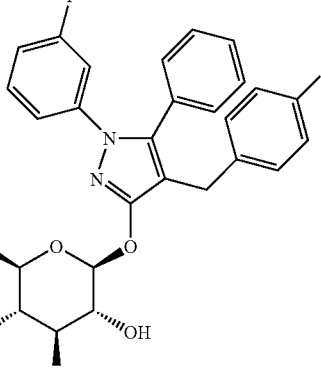 | 3.30–3.55 (4H, m), 3.65 (1H, d, J=15.4 Hz), 3.70 (1H, dd, J=5.4, 12.0 Hz), 3.73 (1H, d, J=15.4 Hz), 3.88 (1H, dd, J=2.2, 12.0 Hz), 5.40–5.50 (1H, m), 6.70–6.80 (2H, m), 6.90–7.05 (5H, m), 7.05–7.15 (2H, m), 7.15–7.30 (1H, m), 7.30–7.45 (3H, m) |

TABLE 6-continued

| Example number | Chemical structure | ¹H-NMR (CD₃OD) δ ppm: |
|---|---|---|
| Example 27 | 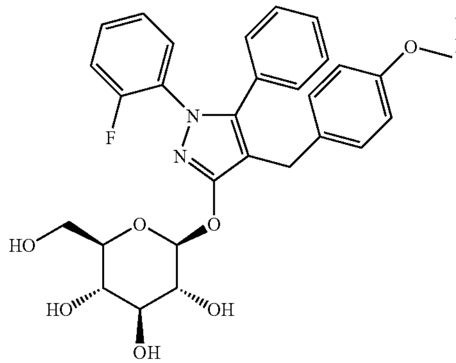 | 3.30–3.55 (4H, m), 3.55–3.95 (7H, m), 5.30–5.40 (1H, m), 6.70–6.85 (2H, m), 7.00–7.55 (11H, m) |
| Example 28 | 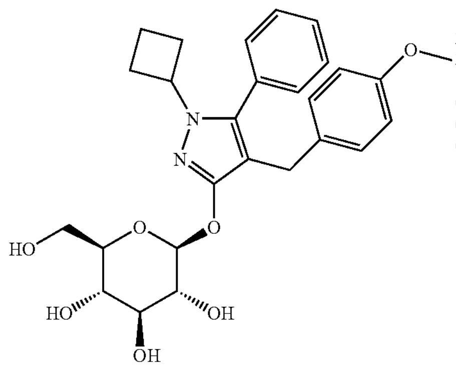 | 1.55–1.85 (2H, m), 2.05–2.25 (2H, m), 2.55–2.75 (2H, m), 3.30–3.50 (4H, m), 3.50–3.75 (6H, m), 3.85 (1H, dd, J=1.9, 12.2 Hz), 4.45–4.60 (1H, m), 5.25–5.35 (1H, m), 6.65–6.80 (2H, m), 6.90–7.00 (2H, m), 7.10–7.2 (2H, m), 7.35–7.50 (3H, m) |
| Example 29 | 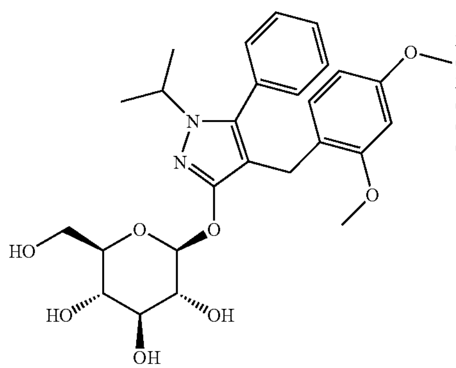 | 1.30–1.40 (6H, m), 3.20–3.45 (4H, m), 3.45–3.60 (2H, m), 3.62 (3H, s), 3.68 (1H, dd, J=5.1, 12.2 Hz), 3.72 (3H, s), 3.80 (1H, dd J=2.3, 12.2 Hz), 4.20–4.35 (1H, m), 5.10–5.20 (1H, m), 6.30–6.40 (2H, m), 6.80–6.90 (1H, m), 7.10–7.25 (2H, m), 7.35–7.45 (3H, m) |
| Example 30 | 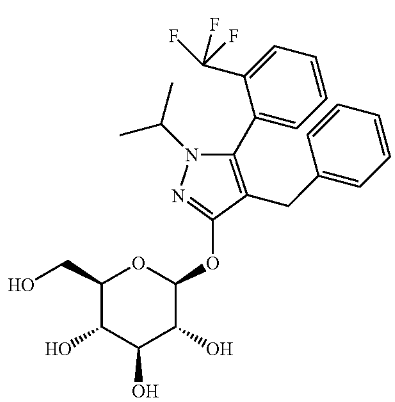 | 1.15–1.40 (6H, m), 3.25–3.50 (5H, m), 3.65–3.90 (4H, m), 5.15–5.35 (1H, m), 6.85–6.95 (2H, m), 6.95–7.10 (4H, m), 7.45–7.70 (2H, m), 7.75–7.85 (1H, m) |

TABLE 6-continued
| Example number | Chemical structure | $^1$H-NMR (CD$_3$OD) δ ppm: |
|---|---|---|
| Example 31 | 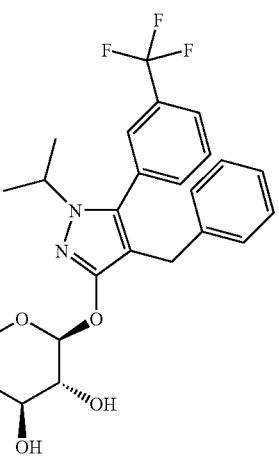 | 1.34 (3H, d, J=6.5 Hz). 1.35 (3H, d, J=6.7 Hz), 3.30–3.55 (4H, m), 3.63 (1H, d, J=15.8 Hz), 3.71 (1H, dd, J=5.4, 12.1 Hz), 3.84 (1H, dd, J=2.3, 12.1 Hz), 4.10–4.25 (1H, m), 5.25–5.35 (1H, m), 6.95–7.20 (5H, m), 7.30–7.40 (1H, m), 7.40–7.50 (1H, m), 7.55–7.65 (1H, m), 7.65–7.55 (1H, m) |
TABLE 6
| Example number | Chemical structure | $^1$H-NMR (CD$_3$OD) δ ppm: |
|---|---|---|
| Example 32 | 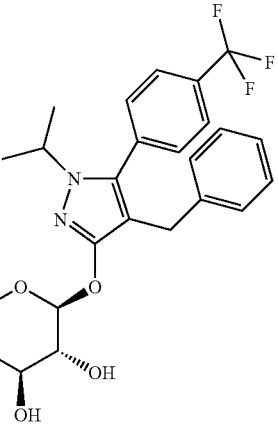 | 1.34 (3H, d, J=6.5 Hz), 1.35 (3H, d, J=6.4 Hz), 3.25–3.50 (4H, m), 3.60–3.75 (3H, m), 3.83 (1H, dd, J=2.5, 12.0 Hz), 4.10–4.30 (1H, m), 5.20–5.30 (1H, m), 6.95–7.20 (5H, m), 7.30–7.45 (2H, m), 7.65–7.75 (2H, m) |
| Example 33 | 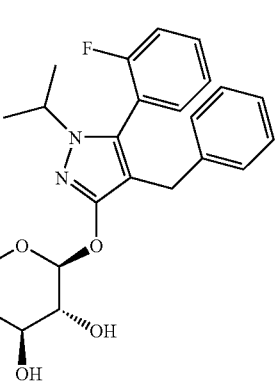 | 1.20–1.45 (6H, m), 3.25–3.50 (4H, m), 3.50–3.90 (4H, m), 4.00–4.15 (1H, m), 5.15–5.30 (1H, m), 6.90–7.30 (8H, m), 7.40–4.55 (1H, m) |

TABLE 6-continued

| Example number | Chemical structure | ¹H-NMR (CD₃OD) δ ppm: |
|---|---|---|
| Example 34 | 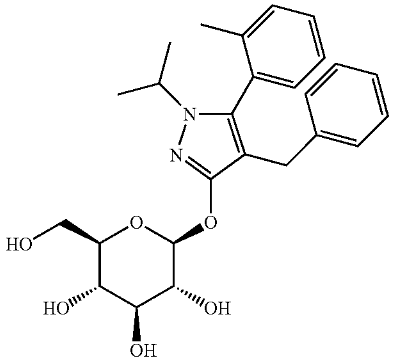 | 1.15–1.40 (6H, m), 1.80–1.90 (3H, m), 3.30–3.5 (6H, m), 3.65–3.80 (1H, m), 3.80–3.95 (2H, m), 5.20–5.30 (1H, m), 6.88–6.96 (2H, m), 6.98–7.12 (4H, m), 7.16–7.28 (2H, m), 7.30–7.38 (1H, m) |
| Example 35 | 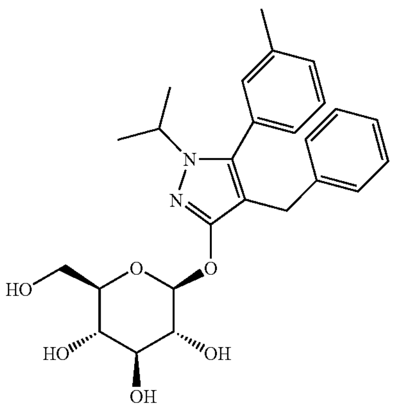 | 1.32 (3H, d, J=6.6 Hz), 1.33 (3H, d, J=6.5 Hz), 2.31 (3H, s), 3.25–3.50 (4H, m), 3.55–3.75 (3H, m), 3.83 (1H, dd, J=2.2, 11.9 Hz), 4.20–4.30 (1H, m), 5.15–5.2 (1H, m), 6.90–6.95 (1H, m), 6.95–7.00 (1H, m), 7.00–7.10 (3H, m), 7.10–7.20 (2H, m), 7.20–7.35 (2H, m) |
| Example 36 | 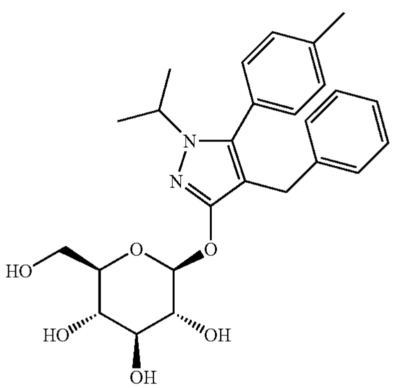 | 1.32 (3H, d, J=6.7 Hz), 1.33 (3H, d, J=6.8 Hz), 2.38 (3H, s), 3.25–3.50 (4H, m), 3.55–3.75 (3H, m), 3.82 (1H, dd, J=2.2, 12.1 Hz), 4.20–4.35 (1H, m), 5.15–5.25 (1H, m), 6.95–7.20 (7H, m), 7.20–7.30 (2H, m) |
| Example 37 | 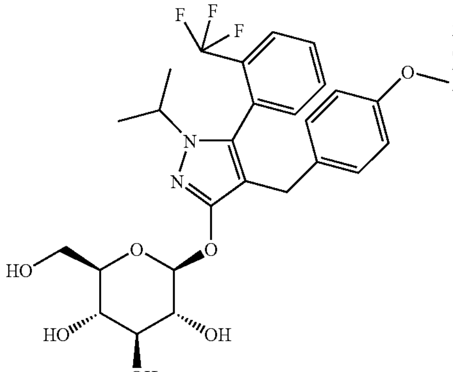 | 1.15–1.40 (6H, m), 3.20–3.50 (5H, m), 3.60–3.90 (7H, m), 5.15–5.35 (1H, m), 6.55–6.70 (2H, m), 6.75–6.90 (2H, m), 7.00–7.10 (1H, m), 7.50–7.70 (2H, m), 7.75–7.85 (1H, m) |

TABLE 7
| Example number | Chemical structure | ¹H-NMR (CD₃OD) δ ppm: |
|---|---|---|
| Example 38 | 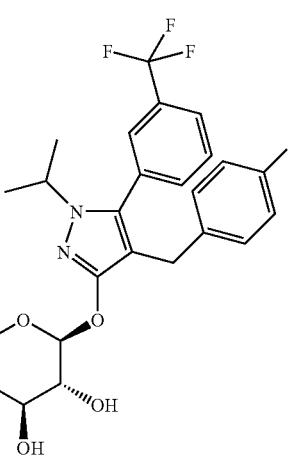 | 1.34 (3H, d, J=6.6 Hz), 1.35 (3H, d, J=6.7 Hz), 3.25–3.50 (4H, m), 3.57 (1H, d, J=15.7 Hz), 3.62 (1H, d, J=15.7 Hz), 3.65–3.75 (4H, m), 3.85 (1H, dd, J=2.3, 12.1 Hz), 4.10–4.25 (1H, m), 5.20–5.35 (1H, m), 6.60–6.80 (2H, m), 6.85–7.00 (2H, m), 7.30–7.50 (2H, m), 7.55–7.80 (2H, m) |
| Example 39 | 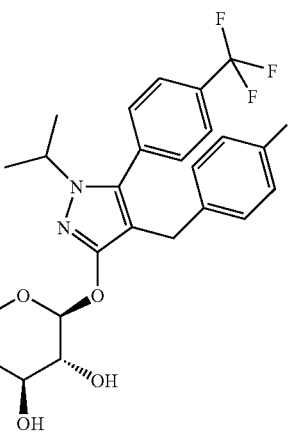 | 1.34 (3H, d, J=6.4 Hz), 1.35 (3H, d, J=6.8 Hz), 3.25–3.50 (4H, m), 3.59 (1H, d, J=15.7 Hz), 3.64 (1H, d, J=15.7 Hz), 3.65–3.75 (4H, m), 4.15–4.30 (1H, m), 5.20–5.30 (1H, m), 6.60–6.80 (2H, m), 6.85–7.00 (2H, m), 7.30–7.45 (2H, m), 7.65–7.80 (2H, m) |
| Example 40 | 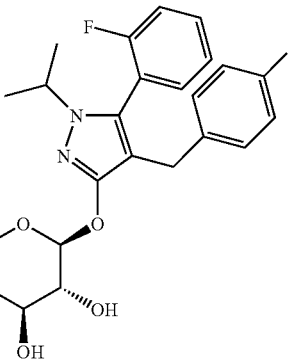 | 1.20–1.40 (6H, m), 3.25–3.75 (10H, m), 3.80–3.90 (1H, m), 4.00–4.15 (1H, m), 5.15–5.30 (1H, m), 6.60–6.70 (2H, m), 6.85–6.95 (2H, m), 7.05–7.25 (3H, m), 7.40–7.55 (1H, m) |

TABLE 7-continued
| Example number | Chemical structure | $^1$H-NMR (CD$_3$OD) δ ppm: |
|---|---|---|
| Example 41 | 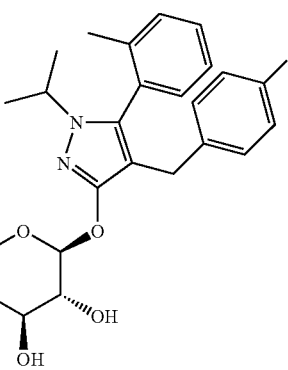 | 1.15–1.40 (6H, m), 1.85–1.95 (3H, m), 3.30–3.60 (6H, m), 3.60–3.80 (4H, m), 3.80–4.00 (2H, m), 5.20–5.30 (1H, m), 6.60–6.70 (2H, m), 6.80–6.90 (2H, m), 6.95–7.10 (1H, m), 7.15–7.40 (3H, m) |
| Example 42 | 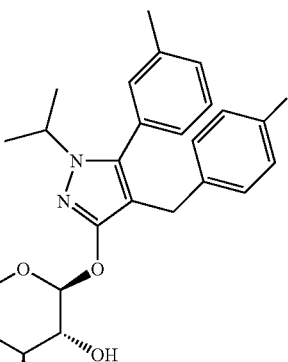 | 1.32 (3H, d, J=6.3 Hz), 1.33 (3H, d, J=6.7 Hz), 2.32 (3H, s), 3.30–3.50 (4H, m), 3.55 (1H, d, J=15.8 Hz), 3.60 (1H, d, J=15.8 Hz), 3.65–3.75 (4H, m), 3.83 (1H, dd, J=2.3, 12.4 Hz), 4.15–4.30 (1H, m), 5.15–5.25 (1H, m), 6.65–6.75 (2H, m), 6.90–7.05 (4H, m), 7.20–7.35 (2H, m) |
| Example 43 | 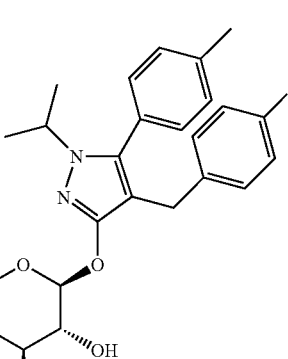 | 1.31 (3H, d, J=6.5 Hz), 1.32 (3H, d, J=6.7 Hz), 2.38 (3H, s), 3.25–3.50 (4H, m), 3.56 (1H, d, J=15.5 Hz), 3.61 (1H, d, J=15.5 Hz), 3.65–3.75 (4H, m), 4.15–4.35 (1H, m), 5.10–5.25 (1H, m), 6.65–6.75 (2H, m), 6.90–7.00 (2H, m), 7.00–7.15 (2H, m), 7.15–7.30 (2H, m) |

TABLE 8
| Example number | Chemical structure | $^1$H-MMR (CD$_3$OD) δ ppm: |
|---|---|---|
| Example 44 | 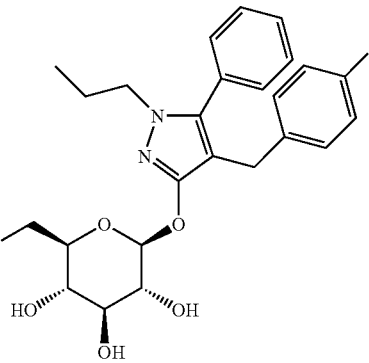 | 0.72 (3H, t, J=7.5 Hz), 1.60–1.75 (2H, m), 3.30–3.50 (4H, m), 3.56 (1H, d, J=15.8 Hz), 3.63 (1H, d, J=15.8 Hz), 3.60–2.74 (1H, m), 3.71 (3H, s), 5.15–5.25 (1H, m), 6.65–6.75 (2H, m), 6.90–7.00 (2H, m), 7.15–7.25 (2H, m), 7.40–7.50 (3H, m) |
| Example 45 | 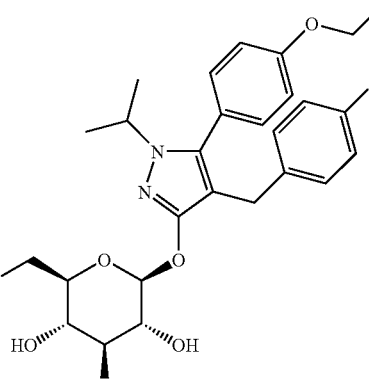 | 1.32 (3H, d, J=6.3 Hz), 1.33 (3H, d, J=6.2 Hz), 1.35–1.45 (3H, m), 3.20–3.55 (4H, m), 3.56 (1H, d, J=15.8 Hz), 3.61 (1H, d, J=15.8 Hz), 3.65–3.75 (4H, m), 4.00–4.15 (2H, m), 4.15–4.35 (1H, m), 5.10–5.25 (1H, m), 6.65–6.75 (2H, m), 6.90–7.00 (4H, m), 7.05–7.15 (2H, m) |
| Example 46 | 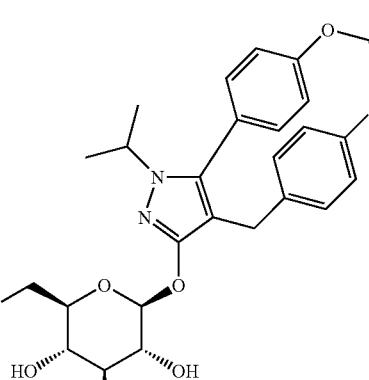 | 1.25–1.40 (12H, m), 3.20–3.50 (4H, m), 3.56 (1H, d, J=15.6 Hz), 3.61 (1H, d, J=15.6 Hz), 3.75–3.85 (1H, m), 4.20–4.35 (1H, m), 4.55–4.70 (1H, m), 5.10–5.25 (1H, m), 6.65–6.75 (2H, m), 6.85–7.00 (4H, m), 7.00–7.15 (2H, m) |

TABLE 8-continued

| Example number | Chemical structure | $^1$H-MMR (CD$_3$OD) δ ppm: |
|---|---|---|
| Example 47 | 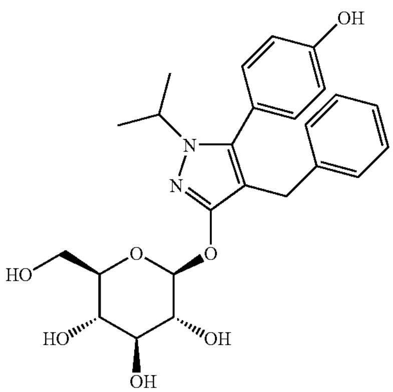 | 1.32 (3H, d, J=6.7 Hz), 1.33 (3H, d, J=6.2 Hz), 3.20–3.55 (4H, m), 3.55–3.75 (3H, m), 3.81 (1H, dd, J=2.1, 12.0 Hz), 4.20–4.35 (1H, m), 5.10–5.25 (1H, m), 6.75–6.85 (2H, m), 6.95–7.10 (5H, m), 7.10–7.20 (2H, m) |
| Example 48 | 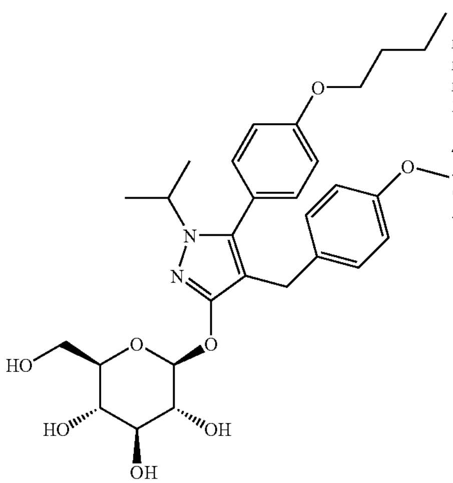 | 1.00 (3H, t, J=7.4 Hz), 1.25–1.40 (6H, m), 1.45–1.60 (2H, m), 1.70–1.85 (2H, m), 3.20–3.47 (4H, m), 3.52–3.64 (2H, m), 3.68 (1H, dd, J=5.4 Hz, 12.0 Hz), 3.71 (3H, s), 3.82 (1H, dd, J=2.3 Hz, 12.0 Hz), 4.01 (2H, t, J=6.6 Hz), 4.15–4.35 (1H, m), 5.18 (1H, d, J=7.3 Hz), 6.71 (2H, d, J=9.0 Hz), 6.85–7.05 (4H, d, m), 7.08 (2H, d, J=9.0 Hz) |

TABLE 9

| Example number | Chemical structure | $^1$H–NMR (CD$_3$OD) δ ppm: |
|---|---|---|
| Example 49 | 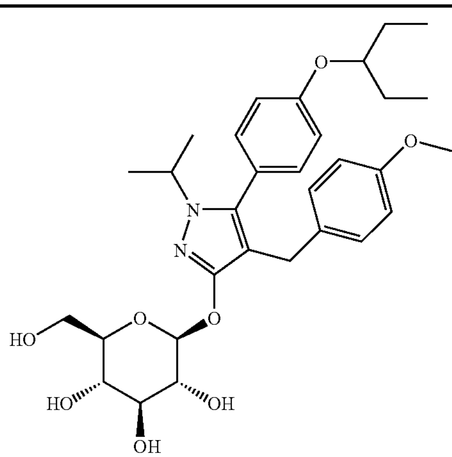 | 0.90–1.03 (6H, m), 1.25–1.40 (6H, m), 1.60–1.79 (4H, m), 3.20–3.48 (4H, m), 3.52–3.65 (2H, m), 3.69 (1H, dd, J=5.4 Hz, 12.1 Hz), 3.71 (3H, s), 3.82 (1H, dd, J=2.1 Hz, 12.1 Hz), 4.15–4.35 (2H, m), 5.17 (1H, d, J=7.1 Hz), 6.70 (2H, d, J=8.8 Hz), 6.85–7.00 (4H, d, m), 7.07 (2H, d, J=8.8 Hz), |

TABLE 9-continued
| Example number | Chemical structure | $^1$H–NMR (CD$_3$OD) δ ppm: |
|---|---|---|
| Example 50 | 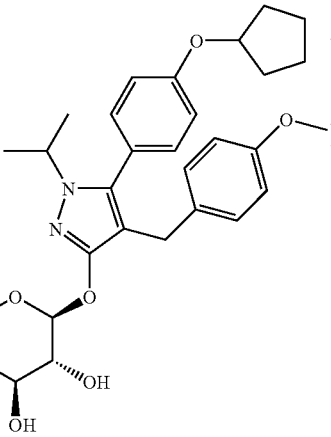 | 1.32 (3H, d, J=6.7 Hz), 1.33 (3H, d, J=6.3 Hz), 1.55–2.05 (8H, m), 3.25–3.50 (5H, m), 3.56 (1H, d, J=15.7 Hz), 3.61 (1H, d, J=15.7 Hz), 3.69 (1H, dd, J=5.5, 12.0 Hz), 3.71 (3H, s), 3.82 (1H, dd, J=2.5, 12.0 Hz), 4.20–4.35 (1H, m), 5.15–5.20 (1H, m), 6.65–6.75 (2H, m), 6.85–7.00 (4H, m), 7.00–7.15 (2H, m) |
| Example 51 | 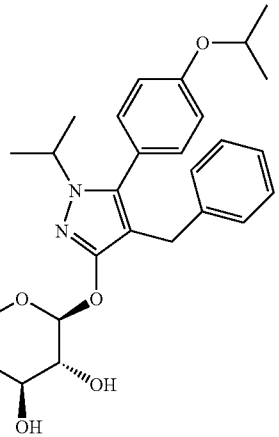 | 1.30–1.35 (12H, m), 3.25–3.50 (4H, m), 3.60–3.75 (3H, m), 3.75–3.85 (1H, m), 4.20–4.35 (1H, m), 4.55–4.70 (1H, m), 5.15–5.20 (1H, m), 6.90–7.00 (2H, m), 7.00–7.10 (5H, m), 7.10–7.20 (2H, m) |
| Example 52 | 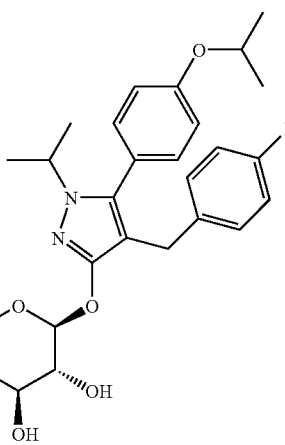 | 1.25–1.35 (12H, m), 3.25–3.50 (4H, m), 3.55–3.75 (3H, m), 3.83 (1H, dd, J=2.1, 12.0 Hz), 4.20–4.30 (1H, m), 4.55–4.70 (1H, m), 5.15–5.25 (1H, m), 6.80–6.90 (2H, m), 6.90–6.98 (2H, m), 6.99–7.10 (4H, m) |

TABLE 9-continued

| Example number | Chemical structure | $^1$H–NMR (CD$_3$OD) δ ppm: |
|---|---|---|
| Example 53 | 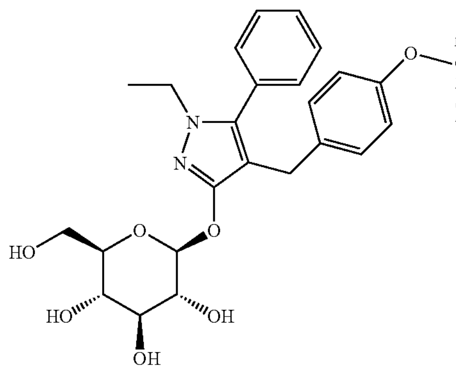 | 1.23 (3H, q, J=7.2 Hz), 3.30–3.50 (4H, m), 3.56 (1H, d, J=15.6 Hz), 3.63 (1H, d, J=15.6 Hz), 3.65–3.75 (4H, m), 3.80–3.95 (3H, m), 5.15–5.25 (1H, m), 6.65–6.75 (2H, m), 6.90–7.00 (2H, m), 7.15–5.25 (2H, m), 7.40–7.50 (3H, m) |

TABLE 10

| Example number | Chemical structure | $^1$H–NMR (CD$_3$OD) δ ppm: |
|---|---|---|
| Example 54 | 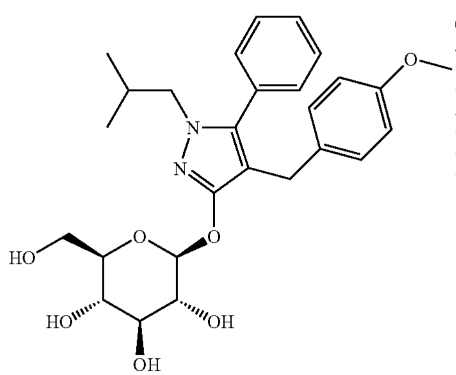 | 0.69 (3H, d, J=6.6 Hz), 0.71 (3H, d, J=6.9 Hz), 1.90–2.10 (1H, m), 3.25–3.50 (4H, m), 3.58 (1H, d, J=15.7 Hz), 3.63 (1H, d, J=15.7 Hz), 3.65–3.75 (6H, m), 3.84 (1H, dd, J=2.1, 12.1 Hz), 5.15–5.25 (1H, m), 6.65–6.75 (2H, m), 6.90–7.00 (2H, m), 7.15–7.25 (2H, m), 7.35–7.45 (3H, m) |
| Example 55 | 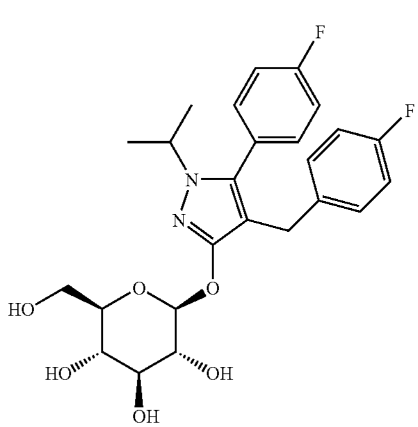 | 1.30–1.35 (6H, m), 3.20–3.50 (4H, m), 3.61 (1H, d, J=15.6 Hz), 3.66 (1H, d, J=15.6 Hz), 3.70 (1H, dd, J=5.4, 12.0 Hz), 3.84 (1H, dd, J=2.2, 12.0 Hz), 4.15–4.25 (1H, m), 5.20–5.30 (1H, m), 6.80–6.90 (2H, m), 6.95–7.05 (2H, m), 7.10–7.25 (4H, m) |

TABLE 10-continued

| Example number | Chemical structure | ¹H–NMR (CD₃OD) δ ppm: |
|---|---|---|
| Example 56 | 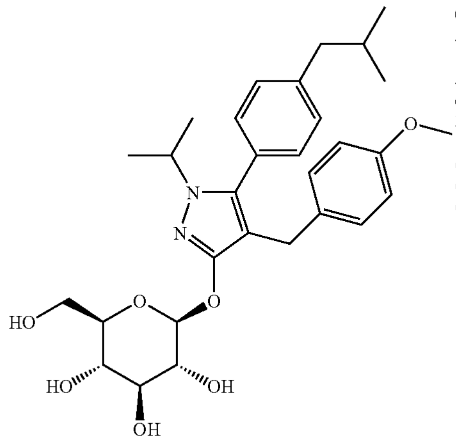 | 0.93 (6H, d, J=6.6 Hz), 1.32 (3H, d, J=6.7 Hz), 1.33 (3H, d, J=6.4 Hz), 1.80–1.95 (1H, m), 2.53 (2H, d, J=7.3 Hz), 3.25–3.50 (4H, m), 3.57 (1H, d, J=15.8 Hz), 3.62 (1H, d, J=15.8 Hz), 3.65–3.75 (4H, m), 3.83 (1H, dd, J=2.0, 11.9 Hz), 4.20–4.30 (1H, m), 5.15–5.25 (1H, m), 6.60–6.75 (2H, m), 6.85–6.95 (2H, m), 7.05–7.15 (2H, m), 7.15–7.25 (2H, m) |
| Example 57 | 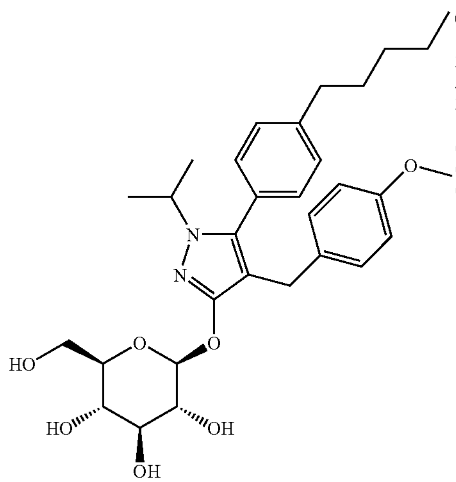 | 0.85–0.95 (3H, m), 1.20–1.45 (10H, m), 1.55–1.75 (2H, m), 2.60–2.70 (2H, m), 3.25–3.50 (4H, m), 3.56 (1H, d, J=15.7 Hz), 3.61 (1H, d, J=15.7 Hz), 3.65–3.75 (4H, m), 3.82 (1H, dd, J=2.4, 12.0 Hz), 4.15–4.35 (1H, m), 5.15–5.25 (1H, m), 6.65–6.75 (2H, m), 6.85–7.00 (2H, m), 7.05–7.15 (2H, m), 7.20–7.30 (2H, m) |
| Example 58 | 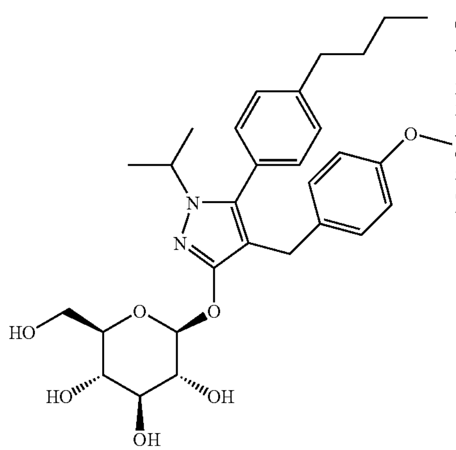 | 0.96 (3H, t, J=7.5 Hz), 1.32 (3H, d, J=6.7 Hz), 1.33 (3H, d, J=6.8 Hz), 1.30–1.45 (2H, m), 1.55–1.70 (2H, m), 2.60–2.70 (2H, m), 3.25–3.50 (4H, m), 3.56 (1H, d, J=15.7 Hz), 3.61 (1H, d, J=15.7 Hz), 3.65–3.75 (4H, m), 3.82(1H, dd, J=2.3, 12.9 Hz), 4.20–4.35 (1H, m), 5.15–5.25 (1H, m), 6.65–6.75 (2H, m), 6.90–7.00 (2H, m), 7.05–7.15 (2H, m), 7.20–7.30 (2H, m) |

TABLE 11

| Example number | Chemical structure | $^1$H-NMR (CD$_3$OD) δ ppm: |
|---|---|---|
| Example 59 | 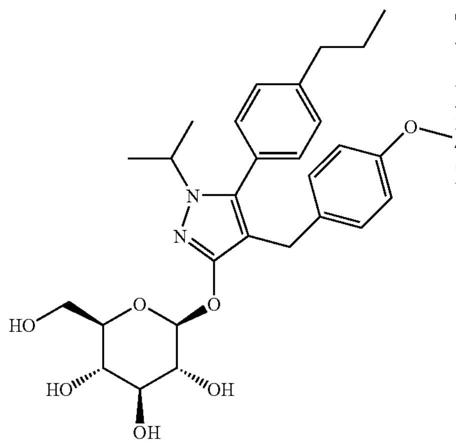 | 0.96 (3H, t, J=7.4Hz), 1.32 (3H, d, J=6.5Hz), 1.33 (3H, d, J=6.6Hz), 1.60–1.75 (2H, m), 2.60–2.70 (2H, m), 3.25–3.50 (4H, m), 3.56 (1H, d, J=15.6Hz), 3.61 (1H, d, J=15.6Hz), 3.65–3.75 (4H, m), 3.75–3.90 (1H, m), 4.20–4.30 (1H, m), 5.15–5.25 (1H, m), 6.65–6.75 (2H, m), 6.85–7.00 (2H, m), 7.05–7.15 (2H, m), 7.20–7.30 (2H, m) |
| Example 60 | 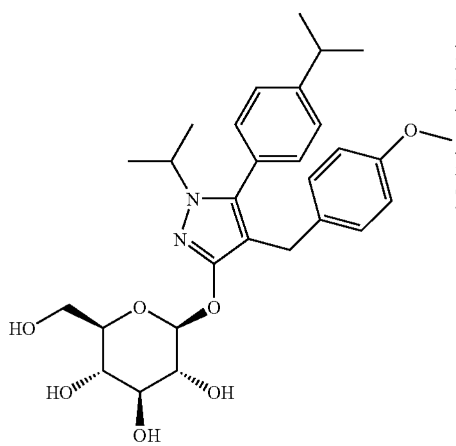 | 1.28 (6H, d, J=6.9Hz), 1.32 (3H, d, J=6.6Hz), 1.33 (3H, d, J=6.6Hz), 2.85–3.05 (1H, m), 3.25–3.50 (4H, m), 3.56 (1H, d, J=15.7Hz), 3.61 (1H, d, J=15.7Hz), 3.69 (1H, dd, J=5.4, 12.0Hz), 3.71 (3H, s), 3.82 (1H, dd, J=2.3, 12.0Hz), 4.20–4.35 (1H, m), 5.15–5.25 (1H, m), 6.65–6.75 (2H, m), 6.90–7.00 (2H, m), 7.05–7.15 (2H, m), 7.25–7.35 (2H, m) |
| Example 61 | 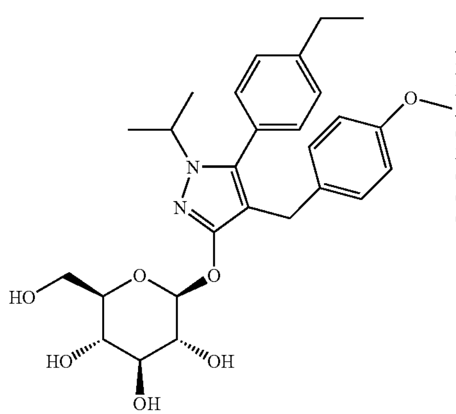 | 1.26 (3H, t, J=7.6Hz), 1.32 (3H, d, J=6.3Hz), 1.33 (3H, d, J=6.6Hz), 2.69 (2H, q, J=7.7Hz), 3.25–3.35 (1H, m), 3.35–3.50 (3H, m), 3.56 (1H, d, J=15.7Hz), 3.61 (1H, d, J=15.7Hz), 3.69 (1H, dd, J=5.4, 12.1Hz), 3.71 (3H, s), 3.82 (1H, dd, J=2.2, 12.1Hz), 4.20–4.35 (1H, m), 5.15–5.25 (1H, m), 6.65–6.75 (2H, m), 6.90–7.00 (2H, m), 7.05–7.15 (2H, m), 7.20–7.35 (2H, m) |

TABLE 11-continued

| Example number | Chemical structure | $^1$H-NMR (CD$_3$OD) δ ppm: |
|---|---|---|
| Example 62 | 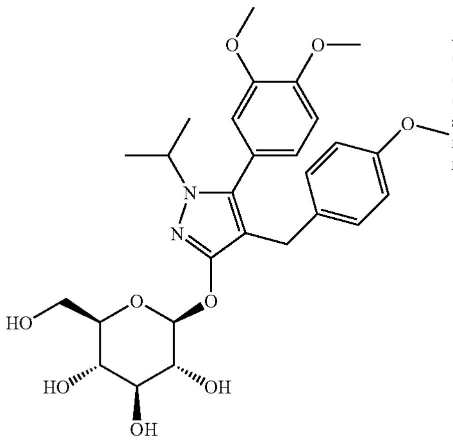 | 1.34 (3H, d, J=6.7Hz), 1.34 (3H, d, J=6.6Hz), 3.25–3.35 (1H, m), 3.35–3.50 (3H, m), 3.57 (1H, d, J=15.8Hz), 3.62 (3H, s), 3.63 (1H, d, J=15.7Hz), 3.69 (1H, dd, J=2.7, 12.2Hz), 3.85 (3H, s), 4.25–4.40 (1H, m), 5.15–5.25 (1H, m), 6.55–6.65 (1H, m), 6.70–6.80 (3H, m), 6.90–7.05 (3H, m) |
| Example 63 | 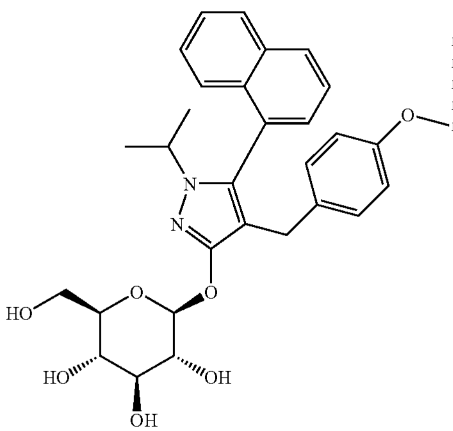 | 1.20–1.30 (6H, m), 3.30–3.70 (9H, m), 3.70–3.80 (1H, m), 3.80–3.95 (2H, m), 5.25–5.35 (1H, m), 6.45–6.55 (2H, m), 6.65–6.75 (2H, m), 7.20–7.30 (1H, m), 7.30–7.45 (2H, m), 7.45–7.55 (2H, m), 7.90–8.00 (2H, m) |

TABLE 12

| Example number | Chemical structure | $^1$H-NMR (CD$_3$OD) δ ppm: |
|---|---|---|
| Example 64 | 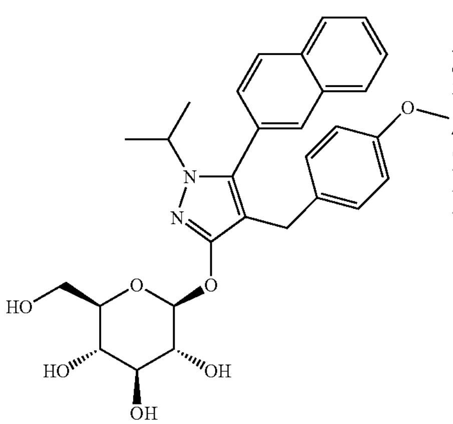 | 1.35 (3H, d, J=6.5Hz), 1.36 (3H, d, J=6.5Hz), 3.25–3.50 (4H, m), 3.61 (1H, d, J=15.7Hz), 3.66 (1H, d, J=15.7Hz), 3.69 (3H, s), 3.71 (1H, dd, J=5.4, 12.1 Hz), 3.85 (1H, dd, J=2.5, 12.1Hz), 4.25–4.40 (1H, m), 5.20–5.30 (1H, m), 6.65–6.70 (2H, m), 6.90–7.00 (2H, m), 7.25–7.30 (1H, m), 7.50–7.60 (3H, m), 7.60–7.65 (1H, m), 7.75–7.85 (1H, m), 7.85–7.95 (2H, m) |

TABLE 12-continued
| Example number | Chemical structure | $^1$H-NMR (CD$_3$OD) δ ppm: |
|---|---|---|
| Example 65 | 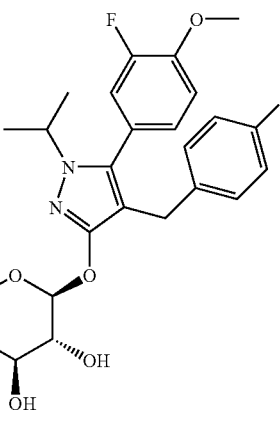 | 1.32 (3H, d, J=6.7Hz), 1.33 (3H, d, J=6.7Hz), 3.30–3.50 (4H, m), 3.57 (1H, d, J=15.8Hz), 3.62 (1H, d, J=15.8Hz), 3.69 (1H, dd, J=5.4, 11.9Hz), 3.71 (3H, s), 3.83 (1H, dd, J=2.2, 11.9Hz), 3.90 (3H, s), 4.15–4.30 (1H, m), 5.15–5.25 (1H, m), 6.65–6.75 (2H, m), 6.85–6.90 (1H, m), 6.90–7.00 (3H, m), 7.10–7.20 (1H, m) |
| Example 66 | 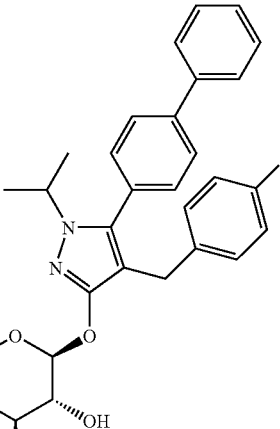 | 1.35 (3H, d, J=6.5Hz), 1.36 (3H, d, J=6.2Hz), 3.30–3.50 (4H, m), 3.62 (1H, d, J=16.2Hz), 3.67 (1H, d, J=16.2Hz), 3.65–3.75 (4H, m), 3.84 (1H, dd, J=2.7, 12.0Hz), 4.25–4.40 (1H, m), 5.20–5.30 (1H, m), 6.65–6.75 (2H, m), 6.95–7.05 (2H, m), 7.20–7.30 (2H, m), 7.30–7.40 (1H, m), 7.40–7.50 (4H, m) |
| Example 67 | 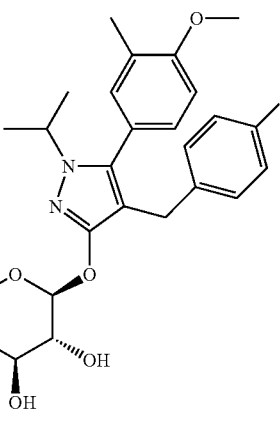 | 1.31 (3H, d, J=6.6Hz), 1.32 (3H, d, J=6.6Hz), 2.15 (3H, s), 3.25–3.50 (4H, m), 3.55 (1H, d, J=15.5Hz), 3.60 (1H, dd, J=15.5Hz), 3.69 (1H, dd, J=5.4, 12.1 Hz), 3.71 (3H, s), 3.83 (1H, dd, J=2.3, 12.1 Hz), 3.85 (3H, s), 4.20–4.35 (1H, m), 5.10–5.25 (1H, m), 6.65–6.75 (2H, m), 6.85–6.90 (1H, m), 6.90–7.05 (4H, m) |

TABLE 12-continued
| Example number | Chemical structure | $^1$H-NMR (CD$_3$OD) δ ppm: |
|---|---|---|
| Example 68 | 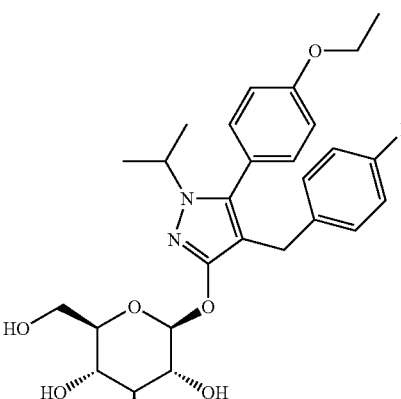 | 1.32 (6H, t, J=6.2Hz), 1.40 (3H, t, J=7.0Hz), 3.25–3.50 (4H, m), 3.60 (1H, d, J=15.7Hz), 3.65 (1H, d, J=15.7Hz), 3.69 (1H, dd, J=5.4, 12.0Hz), 3.83 (1H, dd, J=2.2, 12.0Hz), 4.07 (2H, q, J=7.0Hz), 4.15–4.30 (1H, m), 5.15–5.25 (1H, m), 6.80–6.90 (2H, m), 6.90–7.00 (2H, m), 7.00–7.10 (4H, m) |
TABLE 13
| Example number | Chemical structure | $^1$H-NMR (CD$_3$OD) δ ppm: |
|---|---|---|
| Example 69 | 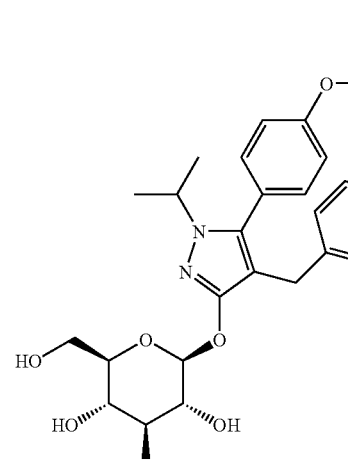 | 1.30–1.35 (6H, m), 3.25–3.50 (4H, m), 3.61 (1H, d, J=15.7Hz), 3.66 (1H, d, J=15.7Hz), 3.69 (1H, dd, J=5.3, 12.1Hz), 3.83 (1H, dd, J=2.2, 12.1Hz), 4.15–4.30 (1H, m), 4.58 (2H, q, J=8.5Hz), 5.15–5.30 (1H, m), 6.80–6.90 (2H, m), 7.00–7.06 (2H, m), 7.06 (2H, m), 7.06–7.12 (2H, m), 7.13–7.20 (2H, m) |
| Example 70 | 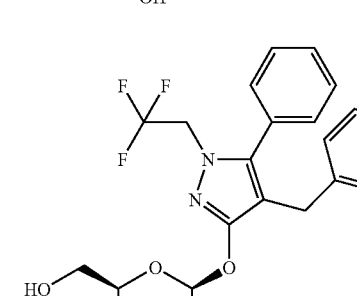 | 3.25–3.50 (4H, m), 3.57 (1H, d, J=15.7Hz), 3.63 (1H, d, J=15.7Hz), 3.65–3.75 (4H, m), 3.85 (1H, dd, J=2.1, 12.1Hz), 4.45–4.60 (2H, m), 5.32–5.38 (1H, m), 6.65–6.75 (2H, m), 6.90–7.00 (2H, m), 7.15–7.30 (2H, m), 7.40–7.50 (3H, m) |

TABLE 13-continued

| Example number | Chemical structure | $^1$H-NMR (CD$_3$OD) δ ppm: |
|---|---|---|
| Example 71 | 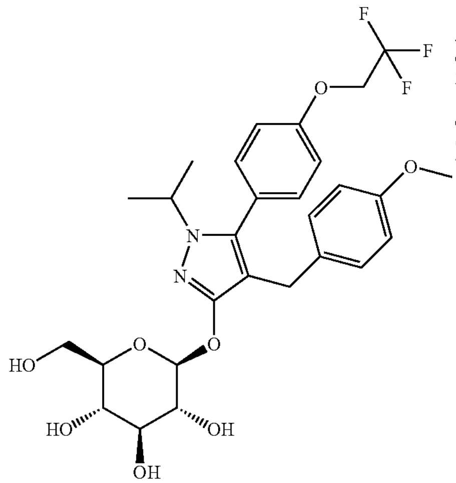 | 1.32 (3H, d, J=6.3Hz), 1.33 (3H, d, J=6.6Hz), 3.25–3.50 (4H, m), 3.56 (1H, d, J=15.9Hz), 3.61 (1H, d, J=15.9Hz), 3.65–3.75 (4H, m), 3.82 (1H, dd, J=2.2, 11.9Hz), 4.15–4.30 (1H, m), 4.58 (2H, q, J=8.5Hz), 5.15–5.25 (1H, m), 6.65–6.75 (2H, m), 6.90–7.00 (2H, m), 7.00–7.10 (2H, m), 7.10–7.20 (2H, m) |
| Example 72 | 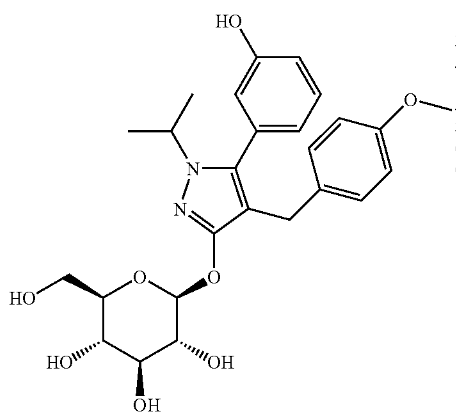 | 1.30–1.40 (6H, m), 3.25–3.50 (4H, m), 3.60 (1H, d, J=15.7Hz), 3.62 (1H, d, J=15.7Hz), 3.69 (1H, dd, J=5.4, 12.2Hz), 3.71 (3H, s), 3.82 (1H, dd, J=2.1, 12.2Hz), 4.25–4.35 (1H, m), 5.15–5.25 (1H, m), 6.60–6.67 (2H, m), 6.68–6.75 (2H, m), 6.80–6.90 (1H, m), 6.90–7.00 (2H, m), 7.20–7.30 (1H, m) |
| Example 73 | 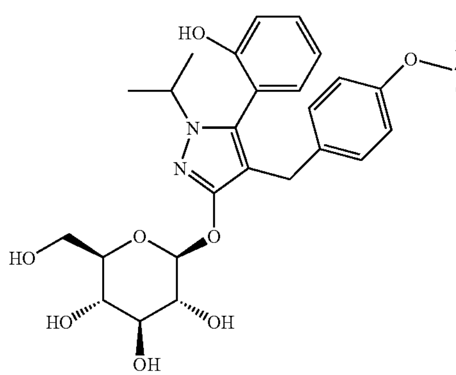 | 1.20–2.30 (3H, m), 1.35–1.45 (3H, m), 3.20–3.90 (10H, m), 3.75–3.85 (1H, m), 4.05–4.20 (1H, m), 5.05–5.20 (1H, m), 6.60–7.40 (8H, m) |

TABLE 14

| Example number | Chemical structure | $^1$H-NMR (CD$_3$OD) δ ppm: |
|---|---|---|
| Example 74 | 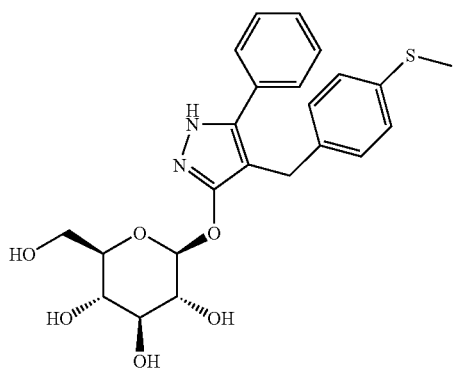 | 1.15–1.30 (6H, m), 3.25–3.75 (10H, m), 3.75–3.85 (1H, m), 4.00–4.15 (1H, m), 4.75–5.20 (3H, m), 6.50–7.50 (13H, m) |

EXAMPLE 75

Process 1

4-[(4-Methylthiophenyl)methyl]-5-phenyl-1,2-dihydro-3H-pyrazole-3-one

To a solution of methyltiobenzylalcohol (0.31 g) and triethylamine (0.20 g) in tetrahydrofuran (2 mL) was added methanesulfonyl chloride (0.23 g) and the mixture was stirred at room temperature for 1 hour and then the insoluble material was removed by filtration. The obtained tetrahydrofuran solution of methanesulfonic acid 4-(methylthio)benzyl ester was added to a suspension of sodium hydride (60%, 0.080 g) and 3-oxo-3-phenylpropionic acid ethyl ester (0.38 g) in 1,2-dimethoxyethane (1 mL) and the mixture was stirred at 60° C. overnight. Hydrazine monohydrate (0.60 g) was added to the reaction mixture and the reaction mixture was stirred at 60° C. for 6 hours. The solvent of the reaction mixture was removed, and water was added to the residue. The mixture was stirred. After the mixture was left at rest, water was removed by decantation and water was added to the residue again. The mixture was stirred and then left at rest, and water was removed by decantation. The residue was dried under reduced pressure. Diethyl ether and hexane were added. The precipitated material was collected by filtration and washed with water and hexane, and dried under reduced pressure to give the title compound (0.37 g).

$^1$H-NMR (DMSO-d$_6$) δ ppm:

2.41 (3H, s), 3.76 (2H, s), 7.05-7.50 (9H, m)

Process 2

3-(β-D-Glucopyranosyloxy)-4-[(4-methylthiophenyl)methyl]-1H-pyrazole

To a suspension of 4-[(4-methylthiophenyl)methyl]-5-phenyl-1,2-dihydro-3H-pyrazole-3-one (0.087 g), acetobromo-α-D-glucose (0.62 g) and benzyltri(n-butyl)ammonium bromide (0.054 g) in dichloromethane (3 mL) was added a sodium hydroxide aqueous solution (5 mol/L, 0.9 mL), and the mixture was stirred at room temperature overnight. The reaction mixture was purified by column chromatography on aminopropylated silica gel (eluent: tetrahydrofuran). The obtained semi purified 4-[(4-methylthiophenyl)methyl]-3-(2,3,4,6-tetraacethyl-β-D-glucopyranosyloxy)-1H-pyrazole was dissolved in methanol (5 mL), and sodium methoxide (28% methanol solution, 0.28 mL) was added to the solution. The mixture was stirred at room temperature for 2 hours. Acetic acid (0.090 g) was added to the reaction mixture, and the solvent was removed. Water (5 mL) was added to the residue, and the mixture was purified by solid phase extraction on ODS (washing solvent: water/methanol=5/1, eluent: methanol). Column chromatography on silica gel (eluent: dichloromethane/methanol=20/1-7/1) was used for further purification to give the title compound (0.033 g).

$^1$H-NMR (CD$_3$OD) δ ppm:

3.30-3.45 (4H, m), 3.69 (1H, dd, J=4.7, 11.8 Hz), 3.80-3.95 (3H, m), 5.15-5.25 (1H, m), 7.05-7.20 (4H, m), 7.30-7.45 (5H, m)

EXAMPLES 76-85

The compounds described in Tables 15-16 were prepared in a similar manner to that described in Example 75 by using corresponding starting materials.

TABLE 15

| Example number | Chemical structure | $^1$H–NMR (CD$_3$OD) δ ppm: |
|---|---|---|
| Example 76 | 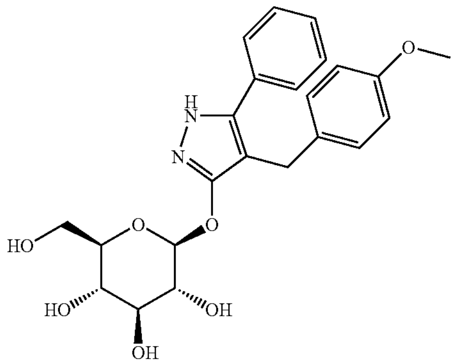 | 3.30–3.45 (4H, m), 3.60–3.75 (1H, m), 3.73 (3H, s), 3.78–3.95 (3H, m), 5.10–5.30 (1H, m), 6.75–6.85 (2H, m), 7.05–7.15 (2H, m), 7.30–7.45 (5H, m) |
| Example 77 | 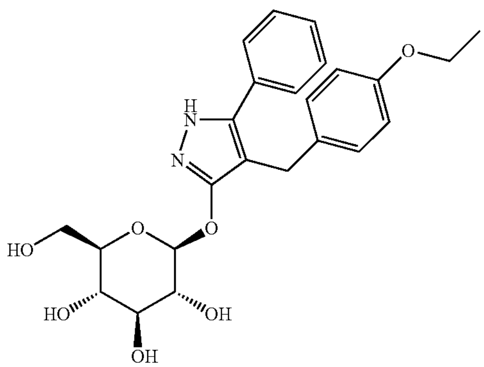 | 1.34 (3H, t, J=6.9Hz), 3.30–3.50 (4H, m), 3.65–3.75 (1H, m), 3.75–3.95 (3H, m), 3.96 (2H, q, J=7.1Hz), 5.10–5.25 (1H, m), 6.70–6.80 (2H, m), 7.00–7.15 (2H, m), 7.30–7.45 (5H, m) |
| Example 78 | 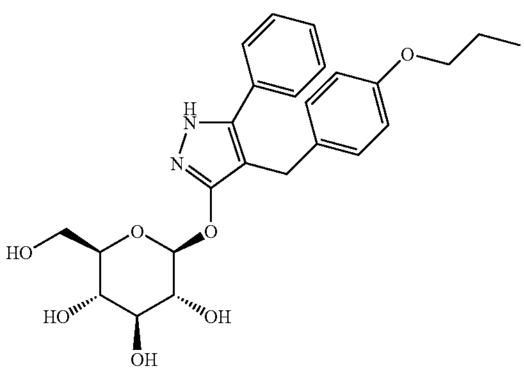 | 1.01 (3H, t, J=7.4Hz), 1.65–1.80 (2H, m), 3.30–3.50 (4H, m), 3.65–3.75 (1H, m), 3.75–3.95 (5H, m), 5.10–5.25 (1H, m), 6.70–6.80 (2H, m), 7.00–7.15 (2H, m), 7.30–7.50 (5H, m) |
| Example 79 | 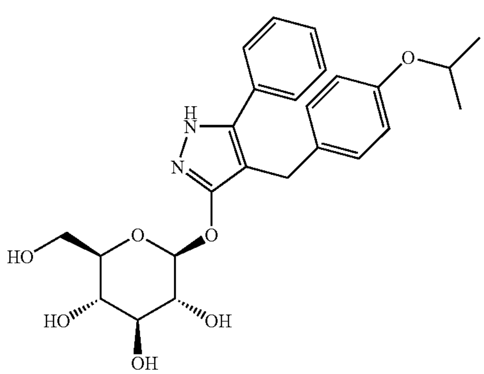 | 1.20–1.30 (6H, m), 3.30–3.50 (4H, m), 3.65–3.75 (1H, m), 3.75–3.95 (3H, m), 4.45–4.55 (1H, m), 5.15–5.25 (1H, m), 6.70–6.80 (2H, m), 7.00–7.10 (2H, m), 7.30–7.50 (5H, m) |

TABLE 15-continued

| Example number | Chemical structure | $^1$H–NMR (CD$_3$OD) δ ppm: |
|---|---|---|
| Example 80 | 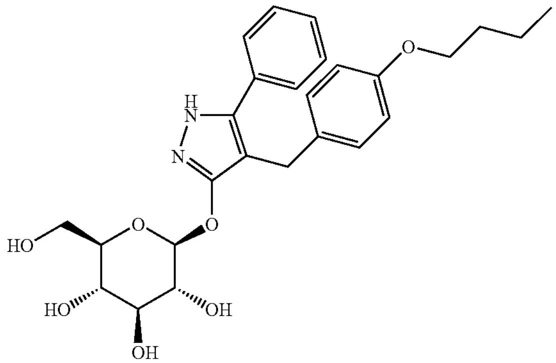 | 0.97 (3H, t, J=7.4Hz), 1.40–1.55 (2H, m), 1.65–1.80 (2H, m), 3.30–3.50 (4H, m), 3.65–3.75 (1H, m), 3.75–3.95 (5H, m), 5.10–5.25 (1H, m), 6.70–7.85 (2H, m), 7.0–7.15 (2H, m), 7.30–7.45 (5H, m) |
| Example 81 | 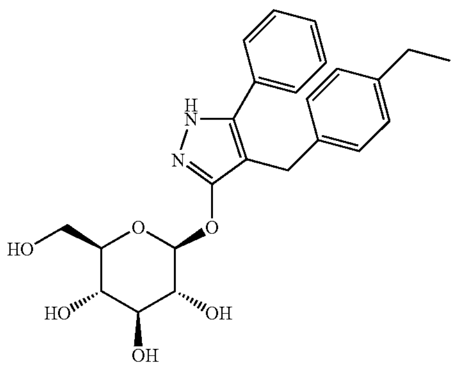 | 1.18 (3H, t, J=7.6Hz), 2.57 (2H, q, J=7.5Hz), 3.30–3.45 (4H, m), 3.65–3.75 (1H, m), 3.80–3.95 (3H, m), 5.15–5.25 (1H, m), 7.00–7.15 (4H, m), 7.30–7.45 (5H, m) |

TABLE 16

| Example number | Chemical structure | $^1$H-NMR (CD$_3$OD) δ ppm: |
|---|---|---|
| Example 82 | 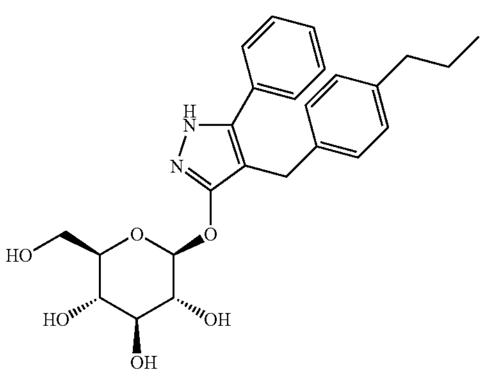 | 0.90 (3H, t, J=7.3Hz), 1.50–1.65 (2H, m), 2.45–4.55 (2H, m), 3.30–3.50 (4H, m), 3.65–3.75 (1H, m), 3.80–4.00 (3H, m), 5.10–5.25 (1H, m), 7.00–7.15 (4H, m), 7.30–7.50 (5H, m) |

TABLE 16-continued
| Example number | Chemical structure | $^1$H-NMR (CD$_3$OD) δ ppm: |
|---|---|---|
| Example 83 | 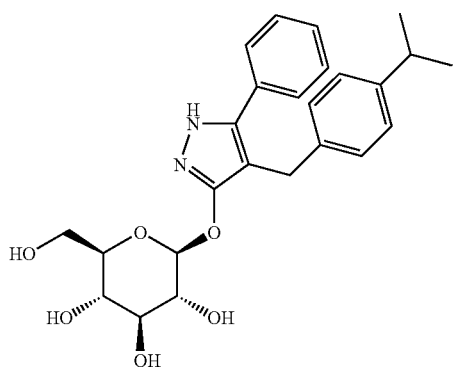 | 1.15–1.25 (6H, m), 2.75–2.90 (1H, m), 3.30–3.45 (4H, m), 3.65–3.75 (1H, m), 3.80–4.00 (3H, m), 5.10–5.25 (1H, m), 7.00–7.20 (4H, m), 7.30–7.50 (5H, m) |
| Example 84 | 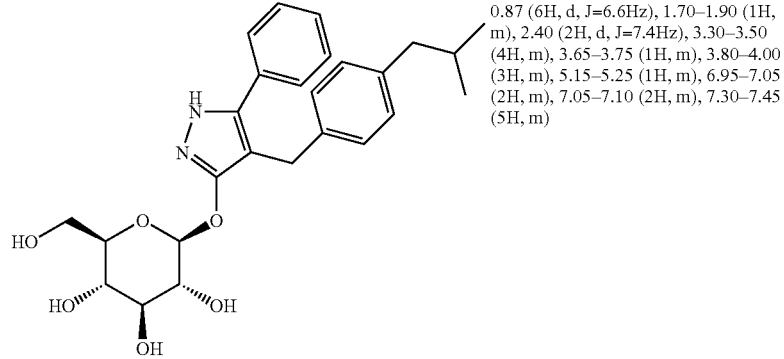 | 0.87 (6H, d, J=6.6Hz), 1.70–1.90 (1H, m), 2.40 (2H, d, J=7.4Hz), 3.30–3.50 (4H, m), 3.65–3.75 (1H, m), 3.80–4.00 (3H, m), 5.15–5.25 (1H, m), 6.95–7.05 (2H, m), 7.05–7.10 (2H, m), 7.30–7.45 (5H, m) |
| Example 85 | 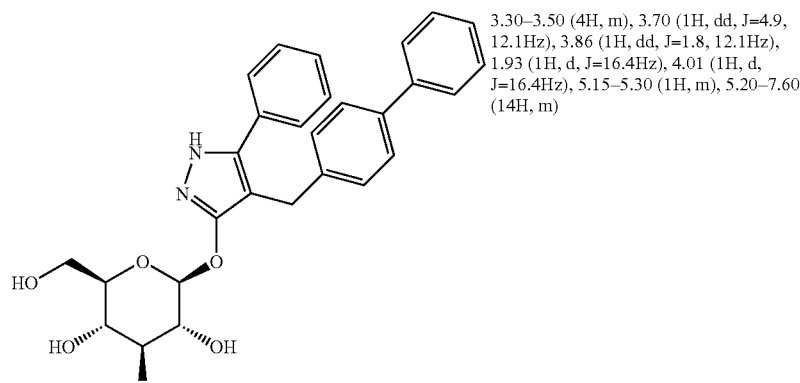 | 3.30–3.50 (4H, m), 3.70 (1H, dd, J=4.9, 12.1Hz), 3.86 (1H, dd, J=1.8, 12.1Hz), 1.93 (1H, d, J=16.4Hz), 4.01 (1H, d, J=16.4Hz), 5.15–5.30 (1H, m), 5.20–7.60 (14H, m) |

EXAMPLE 86

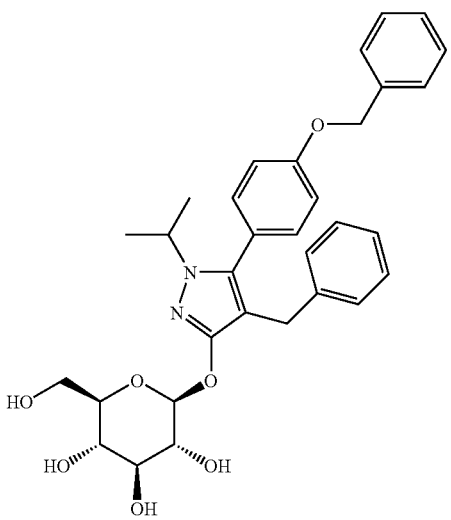

4-Benzyl-5-(4-benzyloxyphenyl)-3-(β-D-glucopyranosyloxy)-1-isopropyl-1H-pyrazole To a suspension of 4-benzyl-3-(β-D-glucopyranosyloxy)-5-(4-hydroxyphenyl)-1-isopropyl-1H-pyrazole (0.02 g) and potassium carbonate (0.017 g) in N,N-dimethylformamide (20 mL) was added benzyl bromide at room temperature. The reaction mixture was stirred at 50° C. for 3 hours. After the reaction mixture was acidified by adding a hydrochloric acid aqueous solution (1 mol/L), the mixture was extracted with ethyl acetate. The organic layer was washed with brine and dried over anhydrous magnesium sulfate. The solvent was removed under reduced pressure and the residue was purified by column chromatography on silica gel (eluent: hexane/ethyl acetate=5/1) to give the title compound.

$^1$H-NMR (CD$_3$OD) δ ppm:
1.32 (3H, d, J=6.4 Hz), 1.33 (3H, d, J=6.3 Hz), 3.20-3.50 (4H, m), 3.55-3.75 (3H, m), 3.81 (1H, dd, J=2.5, 12.2 Hz), 4.20-4.35 (1H, m), 5.10-5.15 (2H, m), 5.15-5.25 (1H, m), 6.95-7.20 (9H, m), 7.20-7.50 (5H, m)

EXAMPLE 87

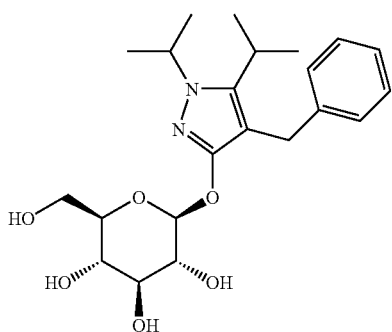

Process 1

4-Methyl-3-oxothiopentanoic acid O-benzyl ester

To a suspension of sodium amide (3.9 g) in toluene (150 mL) was added a mixture of dithiocarbonic acid O-benzyl ester S-methyl ester (9.9 g) and 3-methyl-2-butanone (4.3 g) at room temperature and the mixture was stirred at room temperature overnight. The reaction mixture was poured into a hydrochloric acid aqueous solution (1 mol/L, 500 mL), and the mixture was extracted with diethyl ether. The organic layer was washed with brine and dried over anhydrous magnesium sulfate. The solvent was removed under reduced pressure. The residue was purified by column chromatography on silica gel (eluent:hexane—hexane/ethyl acetate=20/1) to give the title compound (4.6 g).

Process 2

3-Benzyloxy-1,5-diisopropyl-1H-pyrazole

To a suspension of 4-methyl-3-oxothiopentanoic acid O-benzyl ester (0.84 g) and isopropylhydrazine hydrochloride (0.52 g) in acetonitrile (4 mL) was added triethylamine (1.4 g), and the mixture was stirred at room temperature overnight. Water was added to the reaction mixture, and the mixture was extracted with diethyl ether. The solvent of the organic layer was removed under reduced pressure, and the residue was purified by column chromatography on silica gel (hexane/dichloromethane=1/1-2/3) to give the title compound (0.44 g).

$^1$H-NMR (CDCl$_3$) δ ppm:
1.23 (6H, d, J=6.9 Hz), 1.43 (6H, d, J=6.6 Hz), 2.80-3.00 (1H, m), 4.25-4.40 (1H, m), 5.14 (2H, s), 5.43 (1H, s), 7.25-7.40 (3H, m), 7.40-7.50 (2H, m).

Process 3

3-Benzyloxy-4-formyl-1,5-diisopropyl-1H-pyrazole

To a solution of 3-benzyloxy-1,5-diisopropyl-1H-pyrazole (0.44 g) in N,N-dimethylformamide (3 mL) was added phosphorus oxychloride (0.31 g) at 80° C., and the mixture was stirred at 80° C. for 30 minutes. After the reaction mixture was cooled to room temperature, a sodium hydroxide aqueous solution (1 mol/L) was added to the reaction mixture. The mixture was extracted with diethyl ether. The organic layer was dried over anhydrous magnesium sulfate, and the solvent was removed under reduced pressure to give the title compound (0.42 g).

$^1$H-NMR (CDCl$_3$) δ ppm:
1.36 (6H, d, J=7.5 Hz), 1.45 (6H, d, J=6.5 Hz), 3.40-3.60 (1H, m), 4.40-4.60 (1H, m), 5.30 (2H, s), 7.25-7.43 (3H, m), 7.44-7.52 (2H, m), 9.82 (1H, s)

Process 4

4-Benzyl-1,5-diisopropyl-1,2-dihydro-3H-pyrazole-3-one

To a solution of 3-benzyloxy-4-formyl-1,5-diisopropyl-1H-pyrazole (0.21 g) in tetrahydrofuran (10 mL) was added a solution of phenylmagnesium bromide in tetrahydrofuran (1 mol/L, 1.5 mL) at room temperature, and the mixture was stirred at room temperature for 2 hours. A saturated ammonium chloride aqueous solution and water were added to the reaction mixture, and the mixture was purified by column chromatography on aminopropylated silica gel (eluent:tetrahydrofuran). Further purification by column chromatography on silica gel (eluent:hexane/ethyl acetate=10/1-2/1) to give the adduct material, [3-benzyloxy-1,5-diisopropyl-1H-pyrazole-4-yl] phenyl methanol. The obtained adduct material was dissolved in ethanol, and a catalytic amount of 10% palladium-carbon powder was added to the solution. The mixture was stirred at room temperature under a hydrogen atmosphere overnight. The insoluble material was removed by filtration, and the solvent of the filtrate was removed under reduced pressure to give the title compound (0.16 g).

¹H-NMR (CDCl₃) δ ppm:

1.16 (6H, d, J=7.0 Hz), 1,41 (6H, d, J=6.7 Hz), 2.95-3.10 (1H, m), 3.77 (2H, s), 4.25-4.45 (1H, m), 7.10-7.7.18 (1H, m), 7.20-7.30 (4H, m)

Process 5

4-Benzyl-3-(β-D-glucopyranosyloxy)-1,5-diisopropyl-1H-pyrazole

To a suspension of 4-benzyl-1,5-diisopropyl-1,2-dihydro-3H-pyrazole-3-one (0.078 g), acetobromo-α-D-glucose (0.62 g) and benzyl (n-tributyl)ammonium bromide (0.054 g) in dichloromethane (4 mL) was added a sodium hydroxide aqueous solution (5 mol/L, 0.6 mL) and the mixture was stirred at room temperature for 2 hours. The reaction mixture was purified by column chromatography on aminopropylated silica gel (eluent: tetrahydrofuran). The obtained semi purified 4-benzyl-1,5diisopropyl-3-(2,3,4,6-tetraacetyl-1β-D-glucopyranosyloxy)-1H-pyrazole was dissolved in methanol (3 mL), and sodium methoxide (28% methanol solution, 0.58 mL) was added to the solution. The mixture was stirred at room temperature for 2 hours. The solvent of the reaction mixture was removed under reduced pressure, and the residue was acidified by adding 10% citric acid aqueous solution. The mixture was purified by solid phase extraction on ODS (washing solvent: water, eluent: methanol). Further purification by column chromatography on silica gel (eluent: dichloromethane/methanol=10/1) gave the title compound (0.11 g).

¹H-NMR (CD₃OD) δ ppm:

1.10-1.20 (6H, m), 1.39 (3H, d, J=6.6 Hz), 1.40 (3H, d, J=6.8 Hz), 3.05-3.15 (1H, m), 3.20-3.45 (4H, m), 3.65 (1H, dd, J=5.4, 12.1 Hz), 3.77 (1H, dd, J=2.5, 12.1 Hz), 3.79 (1H, d, J=16.7 Hz), 3.85 (1H, d, J=16.7 Hz), 4.45-4.55 (1H, m), 5.05-5.15 (1H, m), 7.05-7.25 (5H, m)

EXAMPLES 88-101

The compounds described in Tables 17-19 were prepared in a similar manner to that described in Example 87 using corresponding starting materials.

TABLE 17

| Example number | Chemical structure | ¹H-NMR (CD₃OD) δ ppm: |
|---|---|---|
| Example 88 | 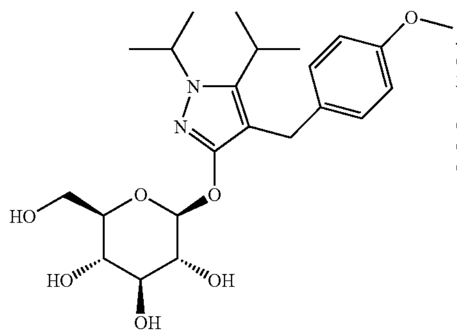 | 1.14 (3H, d, J=7.4Hz), 1.15 (3H, d, J=7.0Hz), 1.38 (3H, d, J=7.0Hz), 1.40 (3H, d, J=6.8Hz), 3.05–3.15 (1H, m), 3.20–3.45 (4H, m), 3.66 (1H, dd, J=5.3, 11.9Hz), 3.68–3.90 (6H, m), 4.45–4.55 (1H, m), 5.05–5.15 (1H, m), 6.75–6.85 (2H, m), 7.00–7.10 (2H, m) |
| Example 89 | 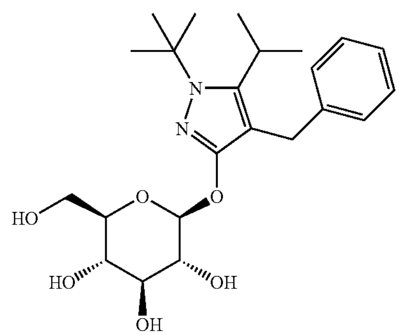 | 1.14 (3H, d, J=7.1Hz), 1.17 (3H, d, J=7.1Hz), 1.60 (9H, s), 3.20–3.45 (4H, m), 3.45–3.60 (1H, m), 3.64 (1H, dd, J=5.2, 12.1Hz), 3.79 (1H, dd, J=2.0, 12.1Hz), 3.86 (1H, d, J=16.7Hz), 3.92 (1H, d, J=16.7Hz), 5.18 (1H, d, J=7.6Hz), 7.05–7.25 (5H, m) |
| Exampel 90 | 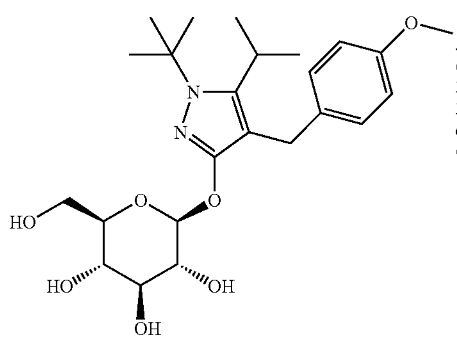 | 1.15 (3H, d, J=7.2Hz), 1.18 (3H, d, J=7.2Hz), 3.20–3.45 (4H, m), 3.45–3.60 (1H, m), 3.65 (1H, dd, J=5.5, 12.0Hz), 3.73 (3H, s), 3.78 (1H, d, J=16.6Hz), 3.80 (1H, dd, J=2.2, 12.0Hz), 3.84 (1H, d, J=16.6Hz), 5.18 (1H, d, J=7.1Hz), 6.75–6.80 (2H, m), 7.00–7.10 (2H, m) |

TABLE 18

| Example number | Chemical structure | ¹H-NMR (CD$_3$OD) δ ppm: |
|---|---|---|
| Example 91 | 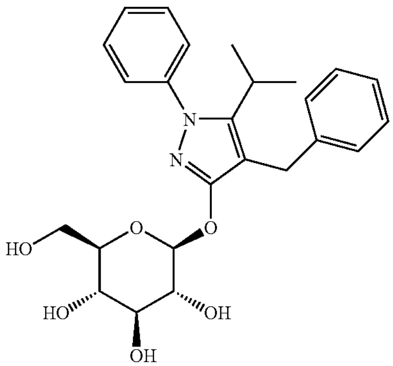 | 1.04 (3H, d, J=7.0Hz), 1.06 (3H, d, J=7.1Hz), 2.90–3.00 (1H, m), 3.25–3.45 (4H, m), 3.66 (1H, dd, J=5.3, 11.9Hz), 3.83 (1H, dd, J=1.9, 11.9Hz), 3.89 (1H, d, J=16.4Hz), 5.15–5.25 (1H, m), 7.10–7.20 (1H, m), 7.20–7.30 (4H, m), 7.35–7.55 (5H, m) |
| Example 92 | 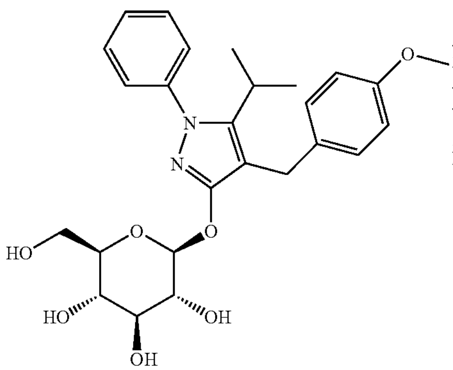 | 1.05 (3H, d, J=7.1Hz), 1.07 (3H, d, J=7.9Hz), 2.90–3.00 (1H, m), 3.25–3.50 (4H, m), 3.66 (1H, dd, J=5.3, 11.9Hz), 3.82 (1H, d, J=16.1Hz), 3.83 (1H, dd, J=2.0, 11.9Hz), 3.90 (1H, d, J=16.1Hz), 5.15–5.25 (1H, m), 6.75–6.85 (2H, m), 7.10–7.20 (2H, m), 7.30–7.55 (5H, m) |
| Example 93 | 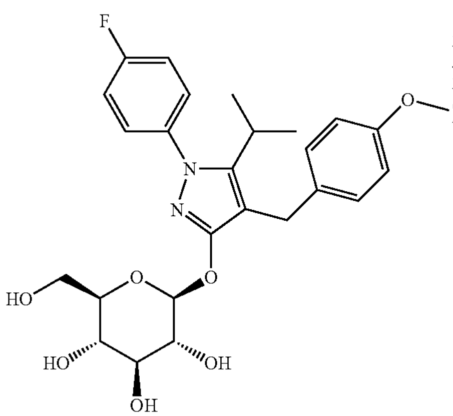 | 1.00–1.10 (6H, m), 2.80–3.00 (1H, m), 3.25–3.45 (4H, m), 3.66 (1H, dd, J=5.5, 11.9Hz), 3.75 (3H, s), 3.77–3.95 (3H, m), 5.15–5.30 (1H, m), 6.75–6.85 (2H, m), 7.10–7.20 (2H, m), 7.20–7.30 (2H, m), 7.35–7.50 (2H, m) |
| Example 94 | 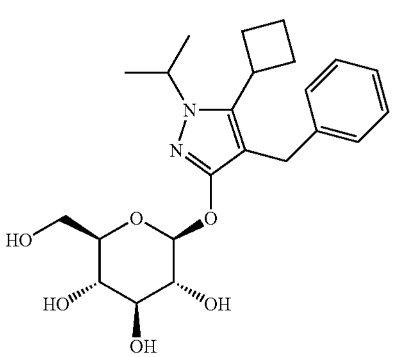 | 1.36 (3H, d, J=6.9Hz), 1.39 (3H, d, J=6.3Hz), 1.65–1.80 (1H, m), 1.85–2.05 (1H, m), 2.10–2.35 (4H, m), 3.15–3.45 (4H, m), 3.50–3.65 (1H, m), 3.64 (1H, dd, J=5.5, 12.1Hz), 3.75 (1H, dd, J=2.5Hz), 3.85 (1H, d, J=16.7Hz), 3.91 (1H, d, J=16.7Hz), 4.35–4.50 (1H, m), 5.00–5.10 (1H, m), 7.05–7.30 (5H, m) |

TABLE 18-continued

| Example number | Chemical structure | $^1$H-NMR (CD$_3$OD) δ ppm: |
|---|---|---|
| Example 95 | 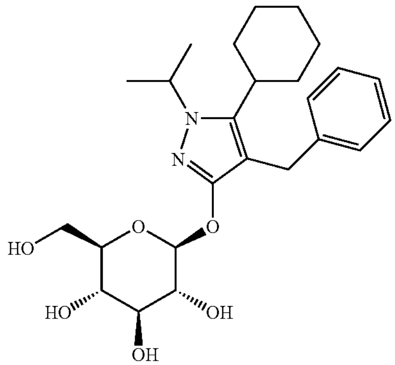 | 1.05–1.35 (3H, m), 1.38 (3H, d, J=6.4Hz), 1.39 (3H, d, J=6.9Hz), 1.40–1.80 (7H, m), 2.60–2.80 (1H, m), 3.20–3.45 (4H, m), 3.65 (1H, dd, J=5.5, 12.1Hz), 3.78 (1H, dd, J=2.4, 12.1Hz), 3.80 (1H, d, J=16.3Hz), 3.86 (1H, d, J=16.3Hz), 4.45–4.60 (1H, m), 5.05–5.15 (1H, m), 7.05–7.25 (5H, m) |
| Example 96 | 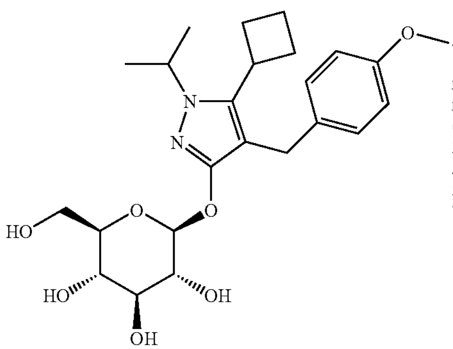 | 1.36 (3H, d, J=7.3Hz), 1.37 (3H, d, J=7.4Hz), 1.65–1.80 (1H, m), 1.85–2.05 (1H, m), 2.10–2.35 (4H, m), .3.20–3.40 (4H, m), 3.50–3.65 (1H, m), 3.65 (1H, dd, J=5.4, 12.1Hz), 3.74 (3H, s), 3.76 (1H, dd, J=2.3, 12.1Hz), 3.78 (1H, d, J=16.8Hz), 3.84 (1H, d, J=16.8Hz), 4.35–4.50 (1H, m), 5.00–5.10 (1H, m), 6.75–6.85 (2H, m), 7.00–7.10 (2H, m) |

TABLE 19

| Example number | Chemical structure | $^1$HNMR (CD$_3$OD) δ ppm: |
|---|---|---|
| Example 97 | 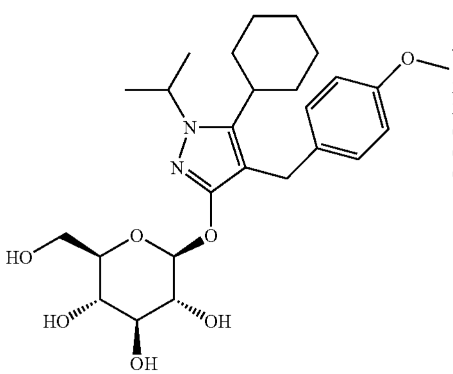 | 1.05–1.35 (3H, m). 1.328 (3H, d, J=6.6Hz),1.39 (3H, d, J=7.1Hz), 1.40–1.80 (7H, m), 2.65–2.80 (1H, m), 3.20–3.30 (1H, m), 3.30–3.45 (3H, m), 3.66 (1H, dd, J=5.5, 12.1), 3.70–3.85 (6H, m), 4.45–4.60 (1H, m), 5.05–5.15 (1H, m), 6.75–6.85 (2H, m), 7.00–7.10 (2H, m) |

TABLE 19-continued

| Example number | Chemical structure | $^1$HNMR (CD$_3$OD) δ ppm: |
|---|---|---|
| Example 98 | 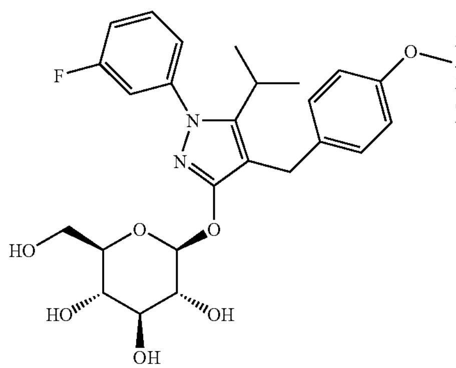 | 1.05–1.15 (6H, m), 2.90–3.10 (1H, m), 3.25–3.45 (4H, m), 3.67 (1H, dd, J=5.3, 11.9Hz), 3.75 (3H, s), 3.74–3.95 (3H, m), 5.20–5.30 (1H, m), 6.75–6.85 (2H, m), 7.10–7.30 (5H, m), 7.45–7.60 (1H, m) |
| Example 99 | 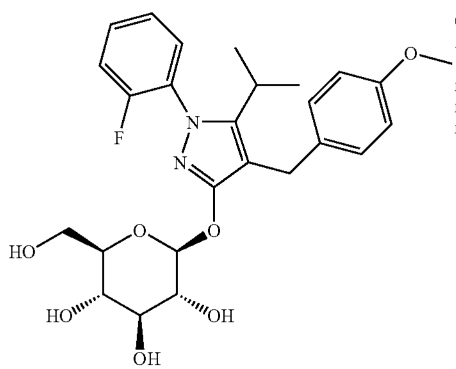 | 0.95–1.10 (6H, m), 2.70–2.85 (1H, m), 3.30–3.45 (4H, m), 3.66 (1H, dd, 5.0, 11.8Hz), 3.75 (3H, s), 3.76–3.95 (4H, m), 5.15–5.25 (1H, m), 6.75–6.90 (2H, m), 7.10–7.20 (2H, m), 7.25–7.40 (2H, m), 7.40–7.60 (2H, m) |
| Example 100 | 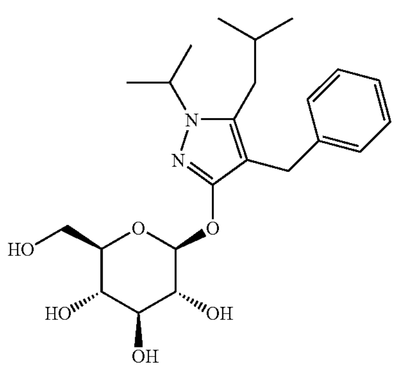 | 0.82 (3H, d, J=6.7Hz), 0.83 (3H, d, J=6.7Hz), 1.36 (3H, d, J=7.1Hz), 1.37 (3H, d, J=6.7Hz), 1.60–1.80 (1H, m), 2.25–2.40 (2H, m), 3.25–3.45 (4H, m), 3.67 (1H, dd, J=5.5, 12.0Hz), 3.70–3.85 (3H, m), 4.30–4.45 (1H, m), 5.05–5.15 (1H, m), 7.05–7.25 (5H, m) |
| Example 101 | 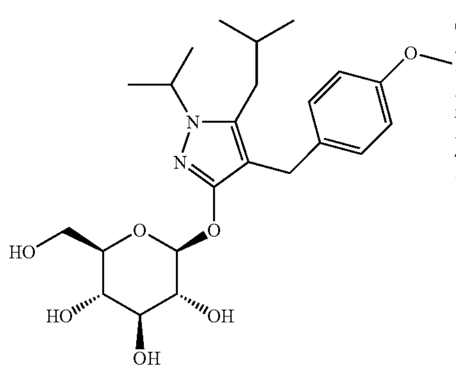 | 0.83 (3H, d, J=6.6Hz), 0.83 (3H, d, J=6.6Hz), 1.35 (3H, d, J=6.7Hz), 1.37 (3H, d, J=7.0Hz), 1.65–1.80 (1H, m), 2.34 (1H, d, J=7.6Hz), 3.25–3.45 (4H, m), 3.60–3.75 (3H, m), 3.73 (3H, s), 3.80 (1H, dd, J=2.1, 12.1Hz), 4.30–4.45 (1H, m), 5.00–5.15 (1H, m), 6.70–6.85 (2H, m), 7.00–7.15 (2H, m) |

EXAMPLE 102

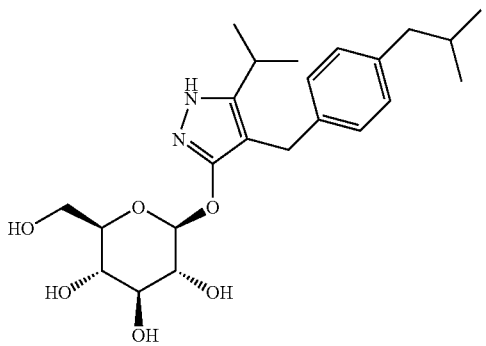

Process 1

4-Isobutylbenzylalcohol

To a solution of 4-isobutylbenzaldehyde (2.4 g) in methanol (10 mL) was added sodium borohydride (0.85 g) at room temperature, and the mixture was stirred at room temperature overnight. Water was added to the reaction mixture, and the mixture was extracted with diethyl ether. The organic layer was washed with water and brine, and dried over anhydrous magnesium sulfate. The solvent was removed under reduced pressure to give the title compound (2.3 g).

$^1$H-NMR (CDCl$_3$) δ ppm:
0.90 (6H, d, J=6.6 Hz), 1.62 (1H, t, J=6.0 Hz), 1.75-1.95 (1H, m), 2.47 (1H, d, J=7.0 Hz), 4.66 (1H, d, J=6.0 Hz), 7.10-7.20 (2H, m), 7.20-7.35 (2H, m)

Process 2

4-[(4-Isobutylphenyl)methyl]-5-isopropyl-1,2-dihydro-3H-pyrazole-3-one

To a solution of 4-isobutylbenzylalcohol (0.33 g) and triethylamine (0.20 g) in tetrahydrofuran (2 mL) was added methanesulfonyl chloride (0.23 g). After the mixture was stirred at room temperature for 1 hour, the insoluble material of the reaction mixture was removed by filtration. The obtained solution of methanesulfonic acid 4-isobutylbenzyl ester in tetrahydrofuran was added to a suspension of sodium hydride (60%, 0.080 g) and 4-methyl-3-oxopentanoic acid methyl ester (0.29 g) in 1,2-dimethoxyethane (3 mL), and the mixture was stirred at 60° C. overnight. Hydrazine monohydrate (0.60 g) was added to the reaction mixture, and the mixture was stirred at 60° C. overnight. The solvent of the reaction mixture was removed under reduced pressure, and water was added to the residue. The mixture was stirred and then left at rest. Water was removed by decantation. Water was added to the residue again, and the mixture was stirred and then left at rest. Water was removed by decantation. The residue was dried under reduced pressure, and diethyl ether and hexane were added to the residue. The precipitated material was collected by filtration, washed with water and then hexane, and dried under reduced pressure to give the title compound (0.25 g).

$^1$H-NMR (DMSO-d$_6$) δ ppm:
0.82 (6H, d, J=6.6 Hz), 1.05 (6H, d, J=7.3 Hz), 1.70-1.85 (1H, m), 2.37 (2H, d, J=7.0 Hz), 2.75-2.90 (1H, m), 3.53 (2H, s), 6.95-7.10 (4H, m)

Process 3

3-(β-D-Glucopyranosyloxy)-4-[(4-isobutyphenyl)methyl]-5-isopropyl-1H-pyrazole

To a suspension of 4-[(4-isobutylphenyl)methyl]-5-isopropyl-1,2-dihydro-3H-pyrazole-3-one (0.082 g), acetobromo-α-D-glucose (0.62 g) and benzyl(n-tributyl)ammonium bromide (0.054 g) in dichloromethane (3 mL) was added a sodium hydroxide aqueous solution (5 mol/L, 0.9 mL), and the mixture was stirred at room temperature overnight. The reaction mixture was purified by column chromatography on aminopropylated silica gel (eluent:tetrahydrofuran). The obtained semi purified 5-isopropyl-4-[(4-isobutylphenyl)methyl]-3-(2,3,4,6-tetraacetyl-β-D-glucopyranosyloxy)-1H-pyrazole was dissolved in methanol (5 mL), and sodium methoxide (28% methanol solution, 0.29 mL) was added to the solution. The mixture was stirred at room temperature for 2 hours. The solvent of the reaction mixture was removed under reduced pressure, and water was added to the residue. The mixture was purified by solid phase extraction (washing solvent:water, eluent:methanol). Further purification by column chromatography on silica gel (eluent:dichloromethane/methanol=20/1-7/1) gave the title compound (0.080 g).

$^1$H-NMR (CD$_3$OD) δ ppm:
0.87 (6H, d, J=6.6 Hz), 1.10 (3H, d, J=7.3 Hz), 1.11 (3H, d, J=7.2 Hz), 1.70-1.90 (1H, m), 2.41 (2H, d, J=7.0 Hz), 2.80-2.95 (1H, m), 3.30-3.45 (4H, m), 3.60-3.80 (3H, m), 3.80-3.90 (1H, m), 5.00-5.15 (1H, m), 6.95-7.05 (2H, m), 7.05-7.15 (2H, m)

EXAMPLES 103-118

The compounds described in Tables 20-22 were prepared in a similar manner to that described in Example 102 using corresponding starting materials.

TABLE 20

| Example number | Chemical structure | $^1$H-NNR (CD$_3$OD) δ ppm: |
|---|---|---|
| Example 103 | 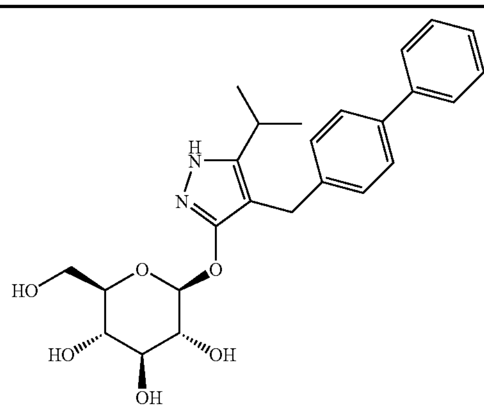 | 1.16 (3H, d, J=7.4Hz), 1.16 (3H, d, J=7.2Hz), 2.85–3.00 (1H, m), 3.30–3.45 (4H, m), 3.68 (1H, dd, J=5.0, 12.0Hz), 3.75–3.90 (3H, m), 5.05–5.15 (1H, m), 7.25–7.35 (3H, m), 7.35–7.45 (2H, m), 7.45–7.52 (2H, m), 7.5–7.60 (2H, m) |

TABLE 20-continued

| Example number | Chemical structure | ¹H-NNR (CD₃OD) δ ppm: |
|---|---|---|
| Example 104 | 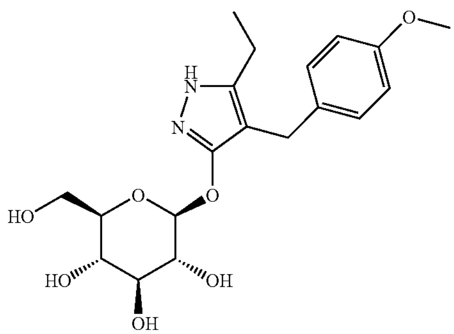 | 1.05 (3H, t, J=7.5Hz), 2.47 (2H, q, J=7.5Hz), 3.30–3.45 (4H, m), 3.60–3.80 (6H, m), 3.80–3.90 (1H, m), 5.00–5.10 (1H, m), 6.75–6.85 (2H, m), 7.05–7.14 (2H, m) |
| Example 105 | 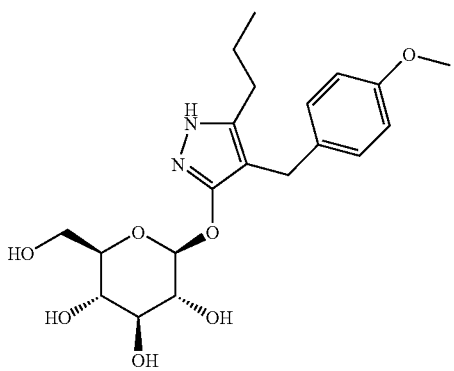 | 0.82 (3H, t, J=7.3Hz), 1.40–1.55 (2H, m), 2.35–2.45 (2H, m), 3.30–3.45 (4H, m), 3.60–3.80 (6H, m), 3.80–3.90 (1H, m), 5.00–5.10 (1H, m), 6.75–6.85 (2H, m), 7.05–7.15 (2H, m) |
| Example 106 | 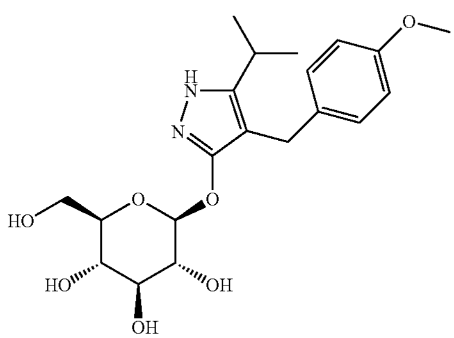 | 1.12 (3H, d, J=7.4Hz), 1.13 (3H, d, J=7.2Hz), 2.80–2.95 (1H, m), 3.30–3.45 (4H, m), 3.60–3.80 (6H, m), 3.80–3.90 (1H, m), 5.00–5.15 (1H, m), 6.75–7.85 (2H, m), 7.05–7.15 (2H, m) |
| Example 107 | 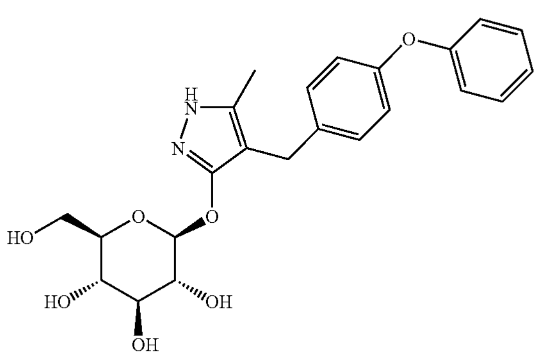 | 2.09 (3H, s), 3.30–3.45 (4H, m), 3.60–3.80 (3H, m), 3.80–3.90 (1H, m), 5.00–5.10 (1H, m), 6.80–6.90 (2H, m), 6.90–6.95 (2H, m), 7.00–7.10 (1H, m), 7.15–7.25 (2H, m), 7.25–7.35 (2H, m) |

TABLE 21

| Example number | Chemical structure | ¹H-NMR (CD$_3$OD) δ ppm: |
|---|---|---|
| Example 108 | 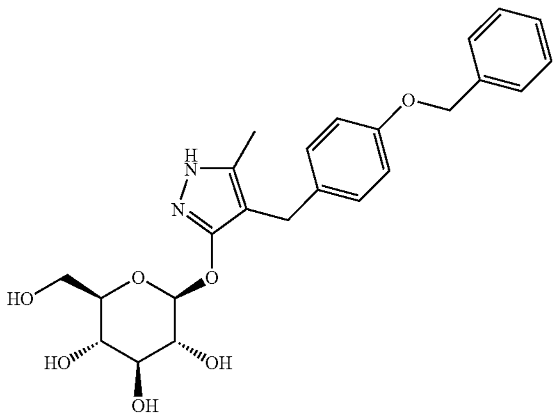 | 2.04 (3H, s), 3.30–3.45 (4H, m), 3.60–3.75 (3H, m), 3.80–3.90 (1H, m), 4.95–5.10 (3H, m), 6.80–6.90 (2H, m), 7.05–7.15 (2H, m), 7.20–7.50 (5H, m) |
| Example 109 | 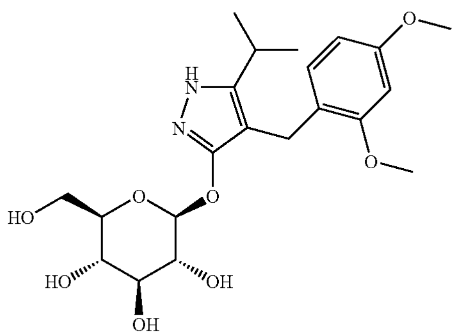 | 1.10–1.20 (6H, m), 2.58–3.00 (1H, m), 3.25–3.40 (4H, m), 3.60–3.70 (3H, m), 3.74 (3H, s), 3.80–3.90 (1H, m), 3.82 (3H, s), 5.00–5.10 (1H, m), 6.37 (1H, dd, J=2.6, 8.1Hz), 6.47 (1H, d, J=2.6Hz), 6.89 (1H, d, J=8.1Hz) |
| Exampel 110 | 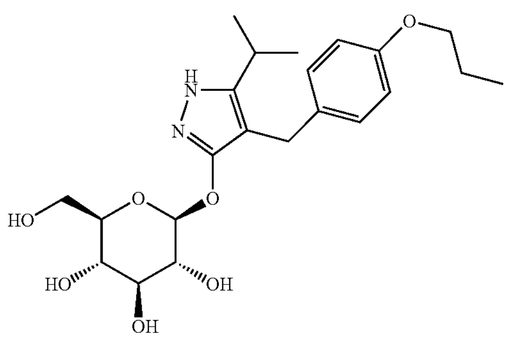 | 1.02 (3H, t, J=7.6Hz), 1.12 (3H, d, J=7.1Hz), 1.13 (3H, d, J=7.4Hz), 1.70–1.80 (2H, m), 2.80–3.00 (1H, m), 3.30–3.45 (4H, m), 3.66 (1H, d, J=16.1Hz), 3.67 (1H, dd, J=5.1, 12.1Hz), 3.73 (1H, d, J=16.1Hz), 3.84 (1H, dd, J=1.8, 12.1Hz), 3.87 (2H, d, J=6.3Hz), 5.00–5.15 (1H, m), 6.70–6.80 (2H, m), 7.05–7.15 (2H, m) |
| Example 111 | 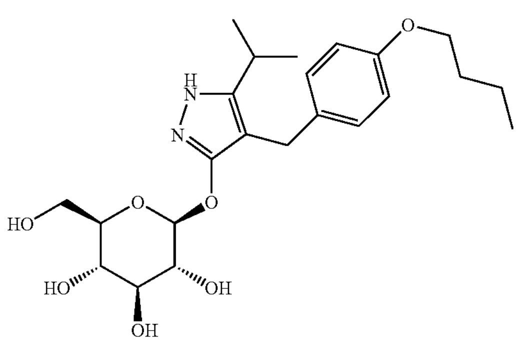 | 0.97 (3H, t, J=7.4Hz), 1.12 (3H, d, J=6.9Hz), 1.13 (3H, d, J=7.1Hz), 1.40–1.55 (2H, m), 1.65–1.80 (2H, m), 2.80–3.00 (1H, m), 3.30–3.45 (4H, m), 3.60–3.80 (3H, m), 3.80–3.90 (1H, m), 3.91 (2H, t, J=6.4Hz), 5.00–5.15 (1H, m), 6.70–6.80 (2H, m), 7.05–7.15 (2H, m) |

TABLE 21-continued
| Example number | Chemical structure | $^1$H-NMR (CD$_3$OD) δ ppm: |
|---|---|---|
| Example 112 | 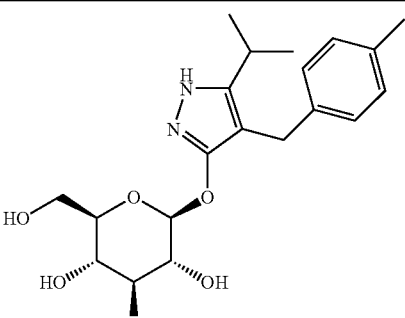 | 1.11 (3H, d, J=7.2Hz), 1.12 (3H, d, J=7.4Hz), 2.26 (3H, s), 2.80–2.95 (1H, m), 3.30–3.45 (4H, m), 3.60–3.80 (3H, m), 3.80–3.90 (1H, m), 5.00–5.15 (1H, m), 7.0–7.10 (4H, m) |
| Example 113 | 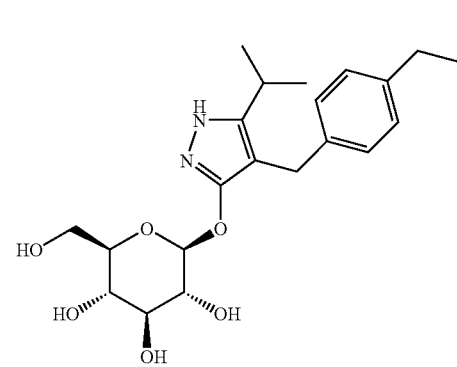 | 0.90 (3H, t, J=7.5Hz), 1.11 (3H, d, J=7.4Hz), 1.12 (3H, d, J=7.4Hz), 1.50–1.65 (2H, m), 2.45–2.55 (2H, m), 2.80–2.95 (1H, m), 3.30–3.45 (4H, m), 3.60–3.80 (3H, m), 3.80–3.90 (1H, m), 5.00–5.15 (1H, m), 6.95–7.15 (4H, m) |
TABLE 22
| Example number | Chemical structure | $^1$H-NMR (CD$_3$OD) δ ppm: |
|---|---|---|
| Example 114 | 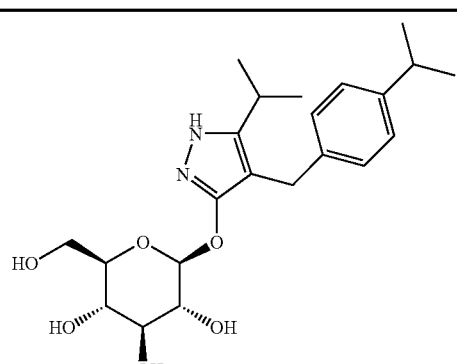 | 1.12 (3H, d, J=7.9Hz), 1.13 (3H, d, J=6.7Hz), 1.20 (6H, d, J=7.0Hz), 2.75–2.95 (2H, m), 3.30–3.45 (4H, m), 3.60–3.90 (4H, m), 5.00–5.15 (1H, m), 7.05–7.15 (4H, m) |
| Example 115 | 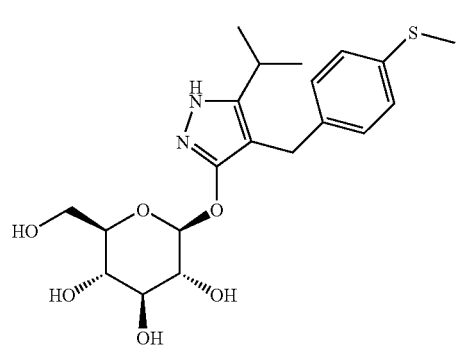 | 1.13 (3H, d, J=7.2Hz), 1.13 (3H, d, J=7.1Hz), 2.42 (3H, s), 2.80–2.95 (1H, m), 3.30–3.45 (4H, m), 3.67 (1H, dd, J=5.3, 12,2Hz), 3.70 (1H, d, J=15.8Hz), 3.76 (1H, d, J=15.8Hz), 3.84 (1H, dd, J=1.7, 12.2Hz), 5.05–5.15 (1H, m), 7.15–7.20 (4H, m) |

TABLE 22-continued

| Example number | Chemical structure | $^1$H-NMR (CD$_3$OD) δ ppm: |
|---|---|---|
| Example 116 | 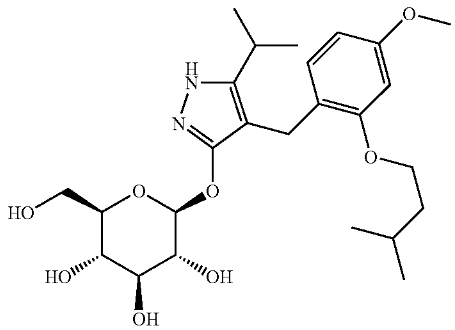 | 0.95–1.00 (6H, m), 1.65–1.75 (2H, m), 2.02 (3H, s), 3.25–3.40 (4H, m), 3.55–3.70 (3H, m), 3.74 (3H, s), 4.00 (2H, d, J=6.6Hz), 4.95–5.10 (1H, m), 6.37 (1H, dd, J=2.5, 8.3Hz), 6.46 (1H, d, J=2.5Hz), 6.90 (1H, d, J=8.3Hz) |
| Example 117 | 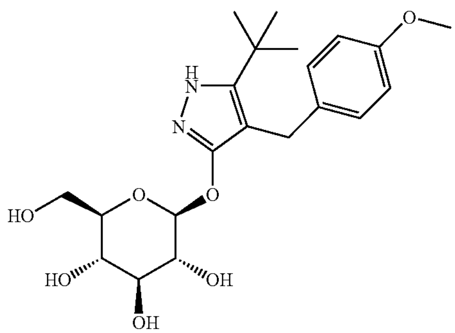 | 1.22 (9H, s), 3.25–3.45 (4H, m), 3.67 (1H, dd, J=5.1, 11.8Hz), 3.73 (3H, s), 3.75–3.95 (3H, m), 5.05–5.15 (1H, m), 6.75–6.80 (2H, m), 7.00–7.10 (2H, m) |
| Example 118 | 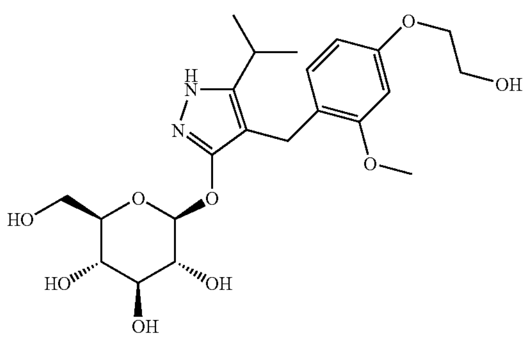 | 1.05–1.20 (6H, m), 2.80–3.00 (1H, m), 3.25–3.45 (4H, m), 3.50–3.75 (3H m), 3.75–3.95 (7H, m), 3.95–4.05 (2H, m), 5.00–5.10 (1H, m), 6.35–6.45 (1H, m), 6.50–6.60 (1H, m), 6.85–6.95 (1H, m) |

EXAMPLE 119

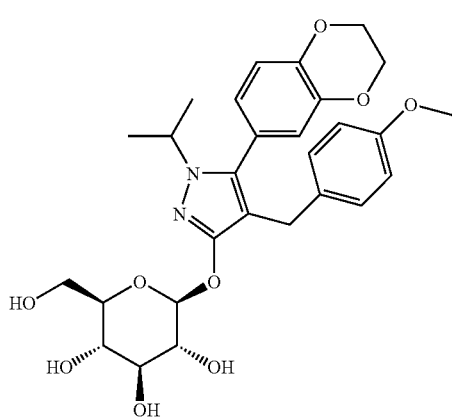

Process 1

3-Benzyloxy-5-(2,3-dihydrobenzo[1,4]dioxin-6-yl)-1-isopropyl-1H-pyrazole

To a solution of dithiocarbonic acid O-benzyl ester S-methyl ester (0.99 g) and 1-(2,3-dihydrobenzo[1,4]dioxin-6-yl)ethanone (0.89 g) in toluene (20 mL) was added sodium amide (0.39 g) at room temperature, and the mixture was stirred at room temperature for 3 days. A hydrochloric acid aqueous solution (2 mol/L) was added to the reaction mixture, and the mixture was extracted with diethyl ether. The organic layer was washed with brine and dried over anhydrous magnesium sulfate, and the solvent was removed under reduced pressure. Acetonitrile (5 mL), triethylamine (2.5 g) and isopropylhydrazine hydrochloride (0.55 g) were added to the residue, and the mixture was stirred at room temperature overnight. Water and diethyl ether was added to the reaction mixture, and the organic layer was separated. The organic layer was washed with brine and dried over anhydrous magnesium sulfate, and the solvent was removed under reduced pressure. The residue was purified by column chromatography on aminopropylated silica gel (eluent:dichloromethane) to give the title compound (1.8 g).

Process 2

3-Benzyloxy-5-(2,3-dihydrobenzo[1,4]dioxin-6-yl)-5-formyl-1-isopropyl-1H-pyrazole To a solution of 3-benzyloxy-5-(2,3-dihydrobenzo-[1,4]dioxin-6-yl)-1-isopropyl-1H-pyrazole (1.8 g) in N,N-dimethylformamide (3 mL) was added phosphorus oxychloride (0.97 g) at 80° C., and the mixture was stirred at 80° C. for 2 hours. After the reaction mixture was cooled to room temperature, a sodium hydroxide aqueous solution (2 mol/L, 10 mL) was added to the reaction mixture. The mixture was extracted with diethyl ether. The organic layer was dried over anhydrous magnesium sulfate, and the solvent was removed under reduced pressure. The residue was purified by column chromatography on silica gel (eluent:hexane/dichloromethane=1/4-dichloromethane) to give the title compound (0.86 g).

Process 3

1-Isopropyl-5-(2,3-dihydrobenzo[1,4]dioxin-6-yl)-4-[(4-methoxyphenyl)methyl]-1,2-dihydro-3H-pyrazole-3-one To a solution of 3-benzyloxy-5-(2,3-dihydrobenzo[1,4]-dioxin-6-yl)-5-formyl-1-isopropyl-1H-pyrazole (0.19 g) in tetrahydrofuran (2 mL) was added a solution of 4-methoxyphenyl-magnesium bromide in tetrahydrofuran (1 mol/L, 0.60 mL) at room temperature, and the mixture was stirred at room temperature for 2 hours. A small amount of water was added to the reaction mixture, and the mixture was purified by column chromatography on aminopropylated silica gel (eluent:tetrahydrofuran). The obtained compound was dissolved in ethanol (10 mL). Ten percent (10%) Palladium-carbon powder was added to the solution, and the mixture was stirred at room temperature under a hydrogen atmosphere overnight. Dichloromethane was added to the reaction mixture, and the insoluble material was removed by filtration. The solvent of the filtrate was removed under reduced pressure, and ethanol and hexane were added to the residue. The precipitated material was collected by filtration and dried under reduced pressure to give the title compound (0.056 g).

$^1$H-NMR (CDCl$_3$) δ ppm:
1.35 (6H, d, J=6.7 Hz), 3.56 (2H, s), 3.75 (3H, s), 4.15-4.35 (5H, m), 6.64-6.70 (1H, m), 6.70-6.78 (3H, m), 6.86-6.92 (1H, m), 7.60-7.12 (2H, m)

Process 4

5-(2,3-Dihydrozenzo[1,4]dioxin-6-yl)-3-(β-D-glucopyranosyloxy)-1-isopropyl-4-[(4-methoxyphenyl)methyl-1H-pyrazole To a suspension of 1-isopropyl-5-(2,3-dihydrobenzo[1,4]-dioxin-6-yl)-4-[(4-methoxyphenyl)methyl]-1,2-dihydro-3H-pyrazole-3-one (0.052 g), acetobromo-α-D-glucose (0.28 g) and benzyl(n-tributyl)ammonium chloride (0.021 g) in dichloromethane (4 mL) was added sodium hydroxide (5 mol/L, 0.27 mL), and the mixture was stirred at room temperature for 2 hours. The reaction mixture was purified by column chromatography on aminopropylated silica gel (eluent:tetrahydrofuran). The obtained semi purified 5-(2,3-dihydrobenzo[1,4]dioxin-6-yl)-1-isopropyl-3-(2,3,4,6-tetra-O-acetyl-β-D-glucopyranosyloxy)-4-[(4-methoxyphenyl) methyl-1H-pyrazole was dissolved in methanol (4 mL), and sodium methoxide (28% methanol solution, 0.26 mL) was added to the solution. The mixture was stirred at room temperature for 2 hours. The solvent of the reaction mixture was removed, and methanol (1 mL) and 10% citric acid aqueous solution (10 mL) were added to the residue. The mixture was purified by solid phase extraction on ODS (washing solvent: water, eluent:methanol). Further purification by preparative reverse phase column chromatography (Shiseido CAPSELL-PAC C18 UG80, 5μM, 20×50 mm, flow rate 30 mL/min linear gradient, water/methanol=90/10-10/90) gave the title compound (0.022 g).

$^1$H-NMR (CD$_3$OD) δ ppm:
1.31 (3H, d, J=6.3 Hz), 1.32 (3H, d, J=6.6 Hz), 3.25-3.50 (4H, m), 3.56 (1H, d, J=15.6 Hz), 3.61 (1H, d, J=15.6 Hz), 3.68 (1H, dd, J=5.3, 12.0 Hz), 3.72 (3H, s), 3.82 (1H, dd, J=2.2, 12.0 Hz), 4.20-4.35 (5H, m), 5.10-5.20 (1H, m), 6.60-6.66 (2H, m), 6.80-6.74 (2H, m), 6.84-6.90 (1H, m), 6.92-6.98 (2H, m)

EXAMPLE 120

The following compound was prepared in a similar manner to that described in Example 119 using a corresponding starting material.

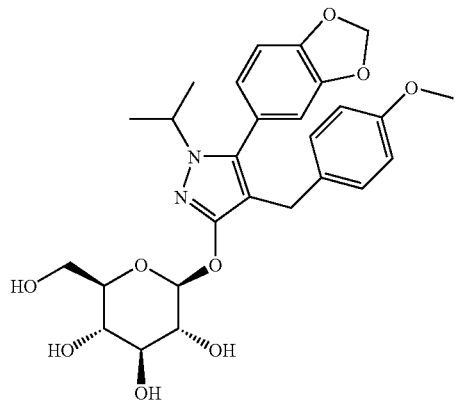

5-(Benzo[1,3]dioxolene-5-yl)-3-(β-D-glucopyranosyloxy)-1-isopropyl-4-[(4-methoxyphenyl)methyl]-1H-pyrazole $^1$H-NMR (CD$_3$OD) δ ppm:
1.32 (3H, d, J=6.7 Hz), 1.33 (3H, d, J=6.7 Hz), 3.25-3.50 (4H, m), 3.57 (1H, d, J=15.7 Hz), 3.61 (1H, d, J=15.7 Hz), 3.65-3.75 (4H, m), 3.82 (1H, dd, J=2.5, 12.2 Hz), 4.20-4.35 (1H, m), 5.14-5.22 (1H, m), 5.99 (2H, s), 6.60 (1H, d, J=1.8 Hz), 6.65 (1H, dd, J=1.8, 7.9 Hz), 6.68-6.74 (2H, m), 6.87 (1H, d, J=8.0 Hz), 6.92-6.98 (2H, m)

EXAMPLE 121

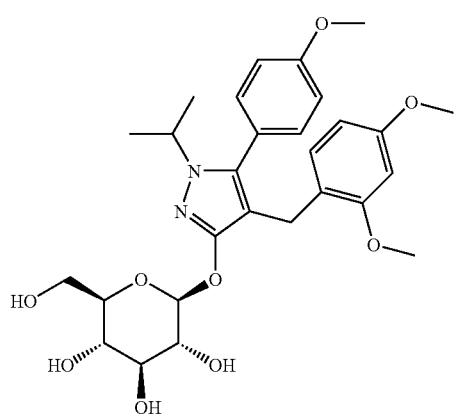

Process 1

3-Benzyoxy-4-bromo-1-isopropyl-5-(4-methoxyphenyl)-1H-pyrazole

To a solution of 3-benzyloxy-1-isopropyl-5-(4-methoxyphenyl)-1H-pyrazole (3.7 g) in dichloromethane (50 mL) was added bromine (0.98 mL) at 0° C., and the mixture was stirred for 1 hour. A saturated sodium hydrogen carbonate aqueous solution was added to the reaction mixture, and the organic layer was separated. The organic layer was dried over anhydrous magnesium sulfate, and the solvent was removed under reduced pressure. The residue was purified by column chromatography on silica gel (eluent:hexane/dichloromethane=2/1) to give the title compound (3.3 g).

$^1$H-NMR (CDCl$_3$) δ ppm:

1.35 (6H, d, J=6.6 Hz), 3.86 (3H, s), 4.25-4.40 (1H, m), 5.33 (2H, s), 6.95-7.05 (2H, m), 7.25-7.40 (5H, m), 7.50-7.55 (2H, m)

Process 2

1-Isopropyl-5-(4-methoxyphenyl)-4-[(2,4-dimethoxyphenyl)-methyl]-1,2-dihydro-3H-pyrazole-3-one To a solution of 3-benzyloxy-4-bromo-1-isopropyl-5-(4-methoxyphenyl)-1H-pyrazole in tetrahydrofuran (2 mL) was added n-butyllithium (2.6 mol/L hexane solution, 0.89 mL) at −78° C. under argon atmosphere, and the mixture was stirred for 30 minutes. A solution of 2,4-dimethoxybenzaldehyde (0.51 g) in tetrahydrofuran (2 mL) was added to the reaction mixture, and the mixture was stirred at −78° C. for 1 hour. The reaction mixture was directly purified by column chromatography on aminopropylated silica gel (eluent:tetrahydrofuran). The obtained semi purified [3-benzyloxy-1-isopropyl-5-(4-methoxyphenyl)-1H-pyrazol-4-yl] (2,4-dimethoxyphenyl) methanol was dissolved in ethanol (9 mL), and a catalytic amount of 10% palladium-carbon powder was added to the solution. The mixture was stirred at room temperature under a hydrogen atmosphere overnight. Dichloromethane was added to the reaction mixture, and the insoluble material was removed by filtration. The solvent of the filtrate was removed, and diethyl ether and hexane were added to the residue. The insoluble material was collected by filtration and dried under reduced pressure to give the title compound (0.09 g).

$^1$H-NMR (CDCl$_3$) δ ppm:

1.34 (6H, d, J=6.7 Hz), 3.51 (2H, s), 3.73 (3H, s), 3.76 (3H, s), 3.84 (3H, s), 4.10-4.25 (1H, m), 6.30-6.40 (2H, m), 6.90-7.00 (3H, m), 7.10-7.20 (2H, m)

Process 3

3-(β-D-Glucopyranosyloxy)-1-isopropyl-5-(4-methoxyphenyl)-4-[(2,4-dimethoxyphenyl)methyl]-1H-pyrazole To a suspension of 1-isopropyl-5-(4-methoxypheny)-4-[(2,4-dimethoxyphenyl)methyl]-1,2-dihydro-3H-pyrazole-3-one (0.090 g), acetobromo-α-D-glucose (0.48 g) and benzyl-(n-tributyl)ammonium chloride (0.037 g) in dichloromethane (2 mL) was added sodium hydroxide (5 mol/L, 0.47 mL), and the mixture was stirred at room temperature for 3 hours. The reaction mixture was purified by column chromatography on aminopropylated silica gel (eluent:tetrahydrofuran). The obtained semi purified 1-isopropyl-5-(4-methoxyphenyl)-4-[(2,4-dimethylphenyl)-methyl]-3-(2,3,4,6-tetra-O-acetyl-β-D-glucopyranosyloxy)-1H-pyrazole was dissolved in methanol (5 mL), and sodium methoxide (28% methanol solution, 0.45 mL) was added to the solution. The mixture was stirred at room temperature overnight. The solvent of the reaction mixture was removed, and methanol (0.5 mL) and 10% citric acid aqueous solution (5 mL) were added to the residue. The mixture was purified by solid phase extraction on ODS (washing solvent:water, eluent:methanol). Further purification by preparative reverse phase column chromatography (Shiseido CAPSELLPAC C18 UG80, 5μM, 20×50 mm, flow rate 30 mL/min linear gradient, water/methanol=90/10-10/90) gave the title compound (0.065 g).

$^1$H-NMR (CD$_3$OD) δ ppm:

1.33 (3H, d, J=6.8 Hz), 1.34 (3H, d, J=6.4 Hz), 3.15-3.30 (1H, m), 3.30-3.45 (3H, m), 3.51 (1H, d, J=16.8 Hz), 3.55 (1H, d, J=16.8 Hz), 3.64 (3H, s), 3.68 (1H, dd, J=5.4, 12.1 Hz), 3.72 (3H, s), 3.75-3.85 (4H, m), 4.20-4.35 (1H, m), 5.10-5.20 (1H, m), 6.30-6.40 (2H, m), 6.80-7.00 (3H, m), 7.00-7.15 (2H, m)

EXAMPLES 122-128

The compounds described in Tables 23-24 were prepared in a similar manner to that described in Example 121 using corresponding starting materials.

TABLE 23

| Example number | Chemical structure | $^1$H-NMR (CD$_3$OD) δ ppm: |
|---|---|---|
| Example 122 | 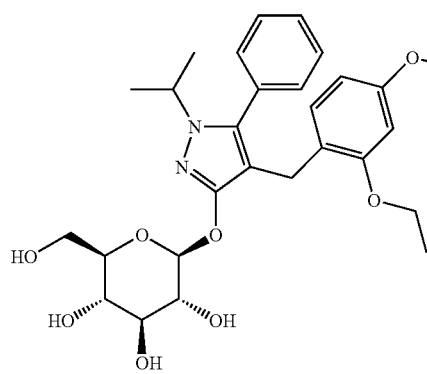 | 1.26 (3H, t, J=6.9Hz), 1.34 (3H, d, J=6.6Hz), 1.35 (3H, d, J=6.6Hz), 3.20–3.30 (1H, m), 3.30–3.45 (3H, m), 3.53 (1H, d, J=16.8Hz), 3.68 (1H, dd, J=5.2, 12.0Hz), .3.71 (3H, s), 3.80 (1H, dd, J=2.4, 12.0Hz), 3.87 (2H, q, J=7.0Hz), 4.20–4.35 (1H, m), 5.10–5.20 (1H, m), 6.30–6.40 (2H, m), 6.80–6.90 (1H, m), 7.10–7.20 (2H, m), 7.30–7.45 (3H, m) |

TABLE 23-continued

| Example number | Chemical structure | $^1$H-NMR (CD$_3$OD) δ ppm: |
|---|---|---|
| Example 123 | 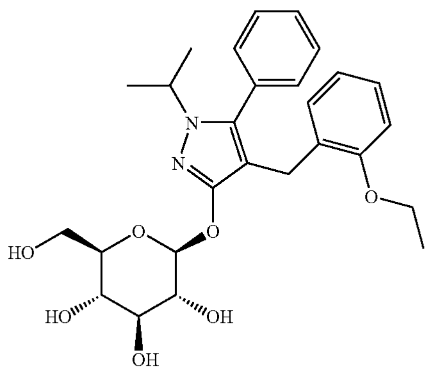 | 1.26 (3H, t, J=7.0Hz), 1.34 (3H, d, J=6.6Hz), 1.35 (3H, d, J=6.6Hz), 3.20–3.30 (1H, m), 3.30–3.45 (3H, m), 3.55–3.75 (3H, m), 3.80 (1H, dd, J=2.5, 12.1Hz), 3.85–3.95 (2H, m), 5.10–5.25 (1H, m), 6.65–6.80 (2H, m), 6.90–7.00 (1H, m), 7.00–7.10 (1H, m), 7.10–7.20 (2H, m), 7.30–7.40 (3H, m) |

TABLE 24

| Example number | Chemical structure | $^1$H-NMR (CD$_3$OD) δ ppm: |
|---|---|---|
| Example 124 | 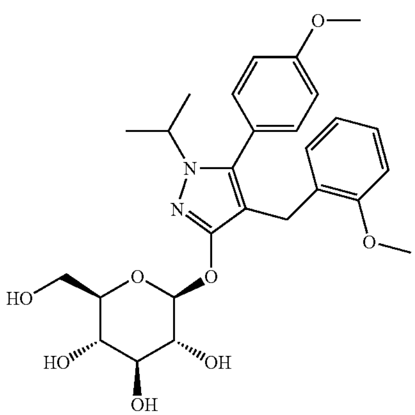 | 1.34 (3H, d, J=6.6Hz), 1.35 (3H, d, J=6.3Hz), 3.15–3.30 (1H, m), 3.30–3.45 (3H, m), 3.55–3.70 (6H, m), 3.75–7.85 (4H, m), 4.20–4.35 (1H, m), 5.10–5.20 (1H, m), 6.70–6.85 (2H, m), 6.85–7.00 (3H, m), 7.00–7.15 (3H, m) |
| Example 125 | 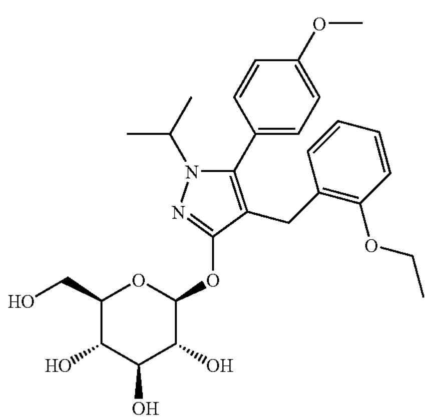 | 1.27 (3H, t, J=6.9Hz), 1.34 (3H, d, J=6.6Hz), 1.35 (3H, d, J=6.6Hz), 3.15–3.30 (1H, m), 3.30–3.45 (3H, m), 3.61 (1H, d, J=17.0Hz), 3.65 (1H, d, J=17.0Hz), 3.67 (1H, dd, J=5.2, 12.0Hz), 3.75–3.85 (4H, m), 3.85–3.95 (2H, m), 4.20–4.35 (1H, m), 5.10–5.20 (1H, m), 6.70–7.80 (2H, m), 6.85–7.00 (3H, m), 7.00–7.10 (3H, m) |

TABLE 24-continued
| Example number | Chemical structure | $^1$H-NMR (CD$_3$OD) δ ppm: |
|---|---|---|
| Example 126 | 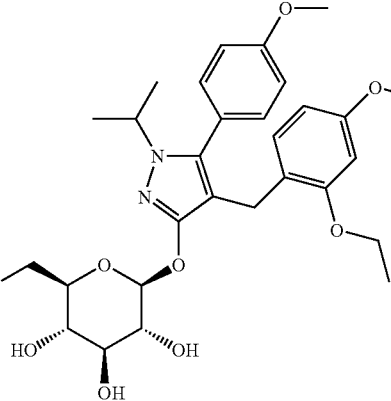 | 1.26 (3H, t, J=7.1Hz), 1.33 (3H, d, J=6.6Hz), 1.34 (3H, d, J=6.6Hz), 3.15–3.30 (1H, m), 3.30–3.45 (3H, m), 3.52 (1H, d, J=16.7Hz), 3.57 (1H, d, J=16.7Hz), 3.68 (1H, dd, J=5.1, 11.9Hz), 3.71 (3H, s), 3.78 (3H, s), 3.80 (1H, dd, J=2.6, 11.9Hz), 3.87 (1H, q, J=7.1Hz), 4.20–4.35 (1H, m), 5.10–5.20 (1H, m), 6.30–6.40 (2H, m), 6.80–6.95 (3H, m), 7.00–7.10 (2H, m) |
| Example 127 | 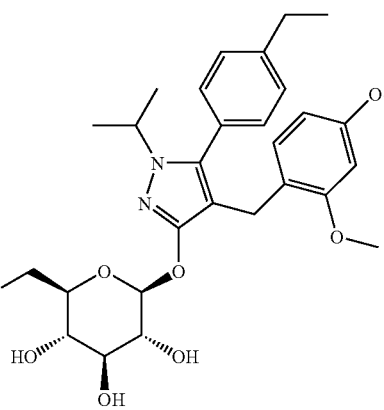 | 1.24 (3H, t, J=7.6Hz), 1.30–1.40 (6H, m), 2.67 (2H, q, J=7.6Hz), 3.15–3.45 (4H, m), 3.52 (1H, d, J=16.4Hz), 3.56 (1H, d, J=16.4Hz), 3.63 (3H, s), 3.68 (1H, dd, J=5.0, 12.0Hz), 3.72 (3H, s), 3.80 (1H, dd, J=2.5, 12.0Hz), 4.20–4.35 (1H, m), 5.10–5.20 (1H, m), 6.30–6.40 (2H, m), 6.80–6.90 (1H, m), 7.00–7.10 (2H, m), 7.15–7.30 (2H, m) |
| Example 128 | 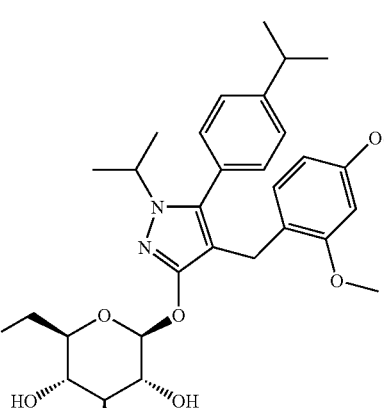 | 1.26 (6H, d, J=6.9Hz), 1.30–1.40 (6H, m), 2.85–3.00 (1H, m), 3.15–3.45 (4H, m), 3.52 (1H, d, J=16.7Hz), 3.56 (1H, dd, J=16.7Hz), 3.62 (3H, s), 3.68 (1H, dd, J=5.3, 12.0Hz), 3.72 (3H, s), 3.80 (1H, dd, J=2.5, 12.0Hz), 4.20–4.35 (1H, m), 5.10–5.20 (1H, m), 6.30–6.40 (2H, m), 6.80–6.90 (1H, m), 7.00–7.10 (2H, m), 7.20–7.30 (2H, m) |

EXAMPLE 129

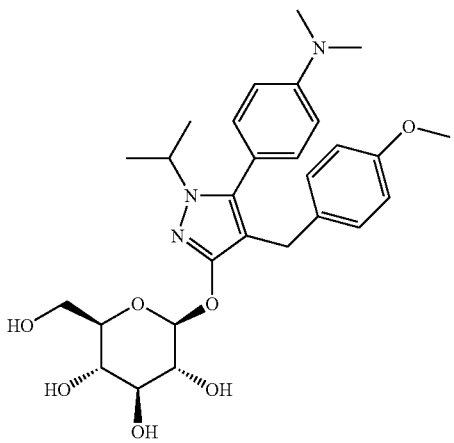

Process 1

3-Hydroxy-1-isopropylpyrazole-4-carboxylic acid ethyl ester

To a solution of sodium ethoxide (23 g) in ethanol (150 mL) were added ethoxymethylene malonic acid diethyl ester (32.7 g) and isopropylhydrazine (11.2 g) at room temperature, and the mixture was stirred at 80° C. for 4 hours and then at 100° C. for 2 hours. The reaction mixture was poured into 2 mol/L hydrochloric acid (300 mL), the mixture was diluted with brine and extracted with ethyl acetate. The organic layer was washed with brine and dried over anhydrous magnesium sulfate. The solvent was removed under reduced pressure, and the obtained residue was purified by column chromatography on silica gel (eluent:ethyl acetate/hexane=1/5) to give the title compound (10.5 g).

$^1$H-NMR (CDCl$_3$) δ ppm:
1.35 (3H, t, J=7.0 Hz), 1.48 (6H, d, J=6.7 Hz), 4.20-4.40 (3H, m), 7.60 (1H, s)

Process 2

5-Bromo-3-hydroxy-1-isopropylpyrazole-4-carboxylic acid ethyl ester

3-Hydroxy-1-isopropylpyrazole-4-carboxylic acid ethyl ester (10.5 g) was dissolved in dichloromethane (100 mL), and N-bromosuccinimide (14.1 g) was added to the solution under ice cooling. The mixture was stirred at room temperature for 6 hours. The solvent was removed under reduced pressure, and the obtained residue was purified by column chromatography on silica gel (eluent:ethyl acetate/hexane=1/5) to give the title compound (5.9 g)

$^1$H-NMR (CDCl$_3$) δ ppm:
1.39 (3H, t, J=7.0 Hz), 1.44 (6H, d, J=6.6 Hz), 4.37 (2H, q, J=7.0 Hz), 4.60-4.80 (1H, m), 8.34 (1H, s)

Process 3

3-Benzyloxy-5-bromo-1-isopropylpyrazole-4-carboxylic acid ethyl ester

5-Bromo-3-hydroxy-1-isopropylpyrazole-4-carboxylic acid ethyl ester (5.8 g) and potassium carbonate (3.5 g) were suspended in N,N-dimethylformamide (50 mL), and benzyl bromide (2.76 mL) was added to the suspension under ice cooling. The mixture was stirred at room temperature for 6 hours. The reaction mixture was poured into 1 mol/L hydrochloric acid (100 mL), and the mixture was extracted with ethyl acetate. The organic layer was washed with brine and dried over anhydrous magnesium sulfate. The solvent was removed under reduced pressure, and the obtained residue was purified by column chromatography on silica gel (eluent: ethyl acetate/hexane=1/5) to give the title compound (7.7 g)

$^1$H-NMR (CDCl$_3$) δ ppm:
1.35(3H, t, J=7.1 Hz), 1.42 (6H, d, J=6.6 Hz), 4.30 (2H, q, J=7.1 Hz), 4.60-4.80 (1H, m), 5.32 (2H, s), 7.20-7.60 (5H, m)

Process 4

3-Benzyloxy-5-bromo-1-isopropylpyrazole-4-carboxylic acid

3-Benzyloxy-5-bromo-1-isopropylpyrazole-4-carboxylic acid ethyl ester (7.7 g) was suspended into 1,4-dioxan (19 mL), and 20% sodium hydroxide aqueous solution (19 mL) was added to the suspension. The mixture was stirred at 100° C. for 8 hours. After the mixture was cooled, the reaction mixture was poured into 2 mol/L hydrochloric acid (100 mL). The mixture was extracted with ethyl acetate. The organic layer was washed with brine and dried over anhydrous magnesium sulfate. The solvent was removed under reduced pressure to give the title compound (4.6 g).

$^1$H-NMR (CDCl$_3$) δ ppm:
1.43 (6H, d, J=6.7 Hz), 4.60-4.85 (1H, m), 5.34 (2H, s), 7.20-7.65 (5H, m)

Process 5

3-Benzyloxy-5-bromo-4-hydroxymethyl-1-isopropyl-1H-pyrazole

3-Benzyloxy-5-bromo-1-isopropylpyrazole-4-carboxylic acid (4.6 g) was dissolved in tetrahydrofuran (30 mL), and borane-tetrahydrofuran complex, 1M tetrahydrofuran solution (21 mL) was delivered by drops into the stirred solution under ice cooling. The mixture was stirred at room temperature for 1 hour. The reaction mixture was cooled with ice bath, and water (50 mL) was delivered by drops into the mixture. Hydrochloric acid (1 mol/L, 20 mL) was delivered by drops into the mixture, and the mixture was extracted with ethyl acetate. The organic layer was washed with brine and dried over anhydrous magnesium sulfate. The solvent was removed under reduced pressure, and the obtained residue was purified by column chromatography on silica gel (eluent:ethyl acetate/hexane =1/5) to give the title compound (3.0 g).

$^1$H-NMR (CDCl$_3$) δ ppm:
1.41 (6H, d, J=6.6 Hz), 1.51 (1H, t, J=6.1 Hz), 4.43 (2H, d, J=6.1 Hz), 4.50-4.68 (1H, m), 5.25 (2H, s), 7.20-7.60 (5H, m)

Process 6

3-Benzyloxy-5-bromo-4-formyl-1-isopropyl-1H-pyrazole

3-Benzyloxy-5-bromo-4-hydroxymethyl-1-isopropyl-1H-pyrazole (3.0 g) was dissolved in dichloromethane (30 mL), and manganese dioxide (4 g) was added to the stirred solution at room temperature. The mixture was stirred at 50° C. for 1 hour. After the insoluble material was removed by filtration, the filtrate was concentrated under reduced pressure to give the title compound (2.7 g).

$^1$H-NMR (CDCl$_3$) δ ppm:
1.44 (6H, d, J=6.7 Hz), 4.55-4.75 (1H, m), 5.34 (2H, s), 7.20-7.60 (5H, m), 9.75 (1H, s)

Process 7

3-Benzyloxy-5-bromo-4-[hydroxyl(4-methoxyphenyl)methyl]-1-isopropyl-1H-pyrazole

3-Benzyloxy-5-bromo-4-formyl-1-isopropyl-1H-pyrazole (0.7 g) was dissolved in tetrahydrofuran (5 mL), and a solution of 4-methoxyphenyl magnesium bromide in tetrahydrofuran (0.5 mL/L, 4.3 mL) was added to the stirred solution. The mixture was stirred at room temperature for 1 hour. A small amount of a saturated ammonium chloride aqueous solution was added to the reaction mixture, and the mixture was purified by column chromatography on aminopropylated silica gel (eluent:tetrahydrofuran) to give the title compound (0.6 g).

¹H-NMR (CDCl₃) δ ppm:
1.40 (6H, d, J=6.6 Hz),2.65 (1H, d, J=7.5 Hz), 3.79 (3H, s),4.45-4.65 (1H, m), 5.15-5.35 (2H, m), 5.66 (1H, d, J=7.5Hz), 6.83 (2H, d, J=9.0 Hz), 7.20-7.45 (7H, m)

Process 8

3-Benzyloxy-5-bromo-1-isopropyl-4-(4-methoxybenzoyl)-1H-pyrazole

3-Benzyloxy-5-bromo-4-[hydroxyl(4-methoxyphenyl)-methyl]-1-isopropyl-1H-pyrazole (0.6 g) was dissolved in dichloromethane (10 mL), and manganese dioxide was added to the stirred solution at room temperature. The mixture was stirred at 50° C. for 1 hour. The insoluble material was removed by filtration, and the filtrate was concentrated under reduced pressure to give the title compound (0.4 g).

¹H-NMR (CDCl₃) δ ppm:
1.47 (6H, d, J=6.6 Hz), 3.86 (3H, s), 4.60-4.80 (1H, m), 5.23 (2H, s), 6.87 (2H, d, J=8.9 Hz), 7.15-7.40 (5H, m), 7.81 (2H, d, J=8.9 Hz)

Process 9

3-Benzyloxy-5-[4-(N,N-dimethylamino)phenyl]-1-isopropyl-4-(4-methyoxybenzoyl)-1 H-pyrazole A suspension of 3-benzyloxy-5-bromo-1-isopropyl-4-(4-methoxybenzoyl)-1H-pyrazole (0.11 g), 4-N,N-dimethylamino)-phenylboronic acid (0.061 g), tetrakis(triphenylphosphine)-palladium (0.034 g), potassium carbonate (0.078 g) and water (0.2 mL) in N,N-dimethylformamide (4 mL) was stirred at 80° C. for 12 hours. Water was added to the reaction mixture, and the mixture was extracted with ethyl acetate. The organic layer was washed with brine and dried over anhydrous magnesium sulfate, and the solvent was removed under reduced pressure. The residue was purified by column chromatography on aminopropylated silica gel (eluent:hexane/ethyl acetate=5/1) to give the title compound (0.098 g).

Process 10

5-[4-(N,N-Dimethylamino)phenyl]-1-isopropyl-4-(4-methoxyphenyl)methyl-3H-pyrazole-3-on hydrochloride To a suspension of sodium borohydride (0.016 g) in tetrahydrofuran (4 mL) was added 3-benzyloxy-5-[4-(N,N-dimethylamino)phenyl]-1-isopropyl-4-(4-methoxybenzoyl)-1H-pyrazole (0.098 g) in tetrahydrofuran (1 mL) at 0° C., and the mixture was stirred for 1 hour. Diluted hydrochloric acid was added to the reaction mixture, and the mixture was extracted with ethyl acetate. The organic layer was washed with brine and dried over anhydrous magnesium sulfate and the solvent was removed under reduced pressure. The residue was dissolved in methanol (5 mL), and 10% palladium-carbon powder (10 mg) and a hydrochloric acid aqueous solution (2 mol/L, 0.1 mL) were added to the solution. The mixture was stirred at room temperature under a hydrogen atmosphere for 6 hours. The insoluble material was removed by filtration and the solvent of the filtrate was removed under reduced pressure to give the title compound (0.051 g).

Process 11

1-Isopropyl-4-(4-methoxyphenylmethyl)-5-[4-(N,N-dimethyl-amino)phenyl]-3-(β-D-glucopyranosyloxy)-1H-pyrazole To a suspension of 5-[4-(N,N-dimethylamino)phenyl]-1-isopropyl-4-(4-methoxyphenyl)methyl-3H-pyrazole-3-on hydrochloride (0.051 g), acetobromo-α-D-glucose (0.16 g) and benzyl(n-tributyl)ammonium chloride (0.12 g) in dichloromethane (3 mL) was added sodium hydroxide (2 mol/L, 0.19 mL), and the mixture was stirred at room temperature for 3 hours. The reaction mixture was extracted with ethyl acetate, and the organic layer was washed with brine and dried over anhydrous magnesium sulfate. The solvent was removed under reduced pressure, and the residue was purified by column chromatography on aminopropylated silica gel (eluent:ethyl acetate). The obtained semi purified 1-isopropyl-4-(4-methoxyphenylmethyl)-5-[4-(N,N-dimethylamino)phenyl]-3-(2,3,4,6-tetraacetyl-β-D-glucopyranosyloxy)-1H-pyrazoel was dissolved in methanol, and sodium methoxide (28% methanol solution, 0.02 mL) was added to the solution. The mixture was stirred at room temperature for 1 hour. The reaction mixture was concentrated under reduced pressure, and the residue was purified by preparative reverse phase column chromatography (Shiseido CAPSELLPAC C18UG80, 5µM, 20×50 mm, flowrate 30 mL/min linear gradient, water/methanol=90/10-10/90) to give the title compound (0.040 g).

¹H-NMR (CD₃OD) δ ppm:
1.32 (3H, d, J=6.6 Hz), 1.33 (3H, d, J=6.6 Hz),2.97 (6H, s), 3.25-3.50 (4H, m), 3.56 (1H, d, J=15.6 Hz), 3.61 (1H, d, J=15.6 Hz), 3.68 (1H, dd, J=5.7, 12.1 Hz), 3.72 (3H, s), 3.81 (1H, dd, J=2.7, 12.1 Hz), 4.25-4.35 (1H, m), 5.10-5.20 (1H, m), 6.65-6.75 (2H, m), 6.75-6.85 (2H, m), 6.90-7.10 (4H, m)

EXAMPLES 130-139

The compounds described in Tables 25-27 were prepared in a similar manner to that described in Example 129 using corresponding starting materials and optionally introducing a protective group.

TABLE 25

| Example number | Chemical structure | ¹HNMR (CD₃OD) δ ppm: |
|---|---|---|
| Example 130 | 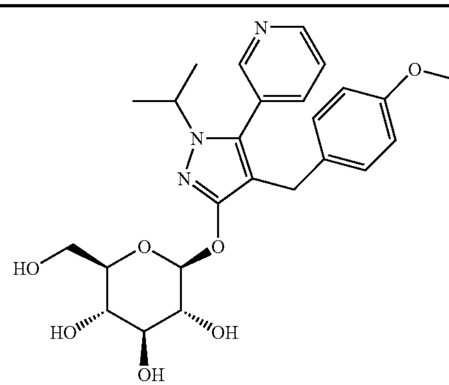 | 1.35 (3H, d, J=6.7Hz), 1.36 (3H, d, J=6.7Hz), 3.25–3.50 (4H, m), 3.59 (1H, d, J=14.9Hz), 3.65 (1H, d, J=14.9Hz), 3.71(1H, dd, J=5.2, 12.0Hz), 3.71 (3H, s), 3.84 (1H, dd, J=2.4, 12.0Hz), 4.10–4.25 (1H, m), 5.25–5.35 (1H, m), 6.65–6.75 (2H, m), 6.85–6.95 (2H, m), 7.45–7.55 (1H, m), 7.60–7.70 (1H, m), 8.25–8.35 (1H, m), 8.50–8.60 (1H, m) |

TABLE 25-continued
| Example number | Chemical structure | $^1$HNMR (CD$_3$OD) δ ppm: |
|---|---|---|
| Example 131 | 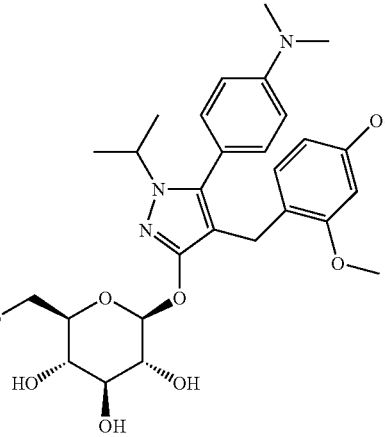 | 1.25–1.40 (6H, m), 2.95 (6H, s), 3.10–3.25 (1H, m), 3.28–3.43 (3H, m), 3.60–3.70 (4H, m), 3.73 (3H, s), 3.78 (1H, dd, J=2.3Hz, 12.2Hz), 4.25–4.40 (1H, m), 5.09 (1H, d, J=7.5Hz), 6.35 (1H, dd, J=2.3Hz, 8.5Hz), 6.38 (1H, d, J=2.3Hz), 6.74 (2H, d, J=9.0Hz), 6.83 (1H, d, J=8.5Hz), 6.99 (2H, d, J=9.0Hz) |
TABLE 26
| Example number | Chemical structure | $^1$H-NMR (CD$_3$OD) δ ppm: |
|---|---|---|
| Example 132 | 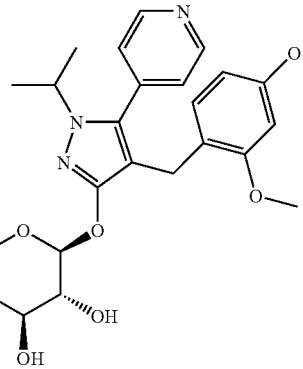 | 1.25–1.45 (6H, m), 3.24–3.50 (4H, m), 3.55–3.65 (6H, m), 3.69 (1H, dd, J=5.4Hz, 12.0Hz), 3.72 (3H, s), 3.82 (1H, dd, J=2.6Hz, 12.0Hz), 4.25–4.45 (1H, m), 5.26 (1H, d, J=7.8Hz), 6.25–6.40 (2H, m), 6.89 (1H, d, J=9.0Hz), 7.23 (2H, d, J=6.1Hz), 8.55 (2H, d, J=6.1Hz) |
| Example 133 | 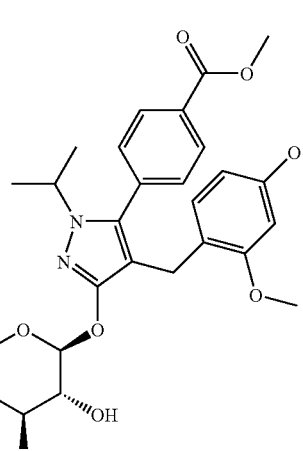 | 1.30–1.40 (6H, m), 3.25–3.45 (4H, m), 3.52–3.62 (5H, m), 3.65–3.75 (4H, m), 3.82 (1H, dd, J=2.3Hz, 12.1Hz), 3.92 (3H, s), 4.15–4.30 (1H, m), 5.22 (1H, d, J=7.6Hz), 6.25–6.40 (2H, m), 6.87 (1H, d, J=8.6Hz), 7.28 (2H, d, J=8.4z), 8.02 (2H, d, J=8.4Hz) |

TABLE 26-continued

| Example number | Chemical structure | $^1$H-NMR (CD$_3$OD) δ ppm: |
|---|---|---|
| Example 134 | 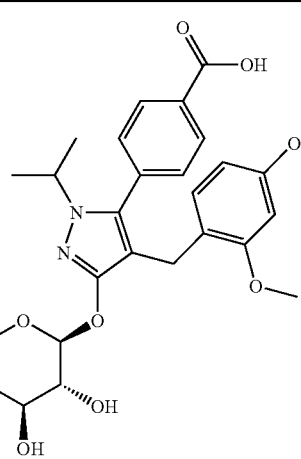 | 1.25–1.40 (6H, m), 3.25–3.50 (4H, m), 3.52–3.64 (5H, m), 3.69 (1H, dd, J=5.3Hz, 12.1Hz), 3.72 (3H, s), 3.82 (1H, dd, J=2.3Hz, 12.1Hz), 4.15–4.32 (1H, m), 5.21 (1H, d, J=7.8Hz), 6.25–6.40 (2H, m), 6.87 (1H, d, J=9.0Hz), 7.25 (2H, d, J=8.0Hz), 8.01 (2H, d, J=8.0Hz) |
| Example 135 | 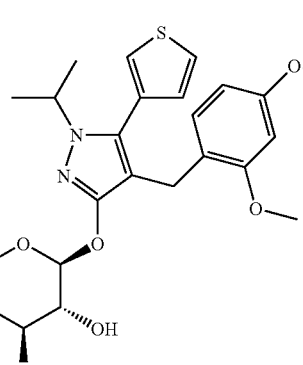 | 1.30–1.45 (6H, m), 3.15–3.47 (4H, m), 3.51–3.63 (2H, m), 3.67 (1H, dd, J=5.1Hz, 12.1Hz), 3.69 (3H, s), 3.73 (3H, s), 3.79 (1H, dd, J=2.3Hz, 12.1Hz), 4.25–4.45 (1H, m), 5.13 (1H, d, J=7.3Hz), 6.35 (1H, dd, J=2.4Hz, 8.3Hz), 6.41 (1H, d, J=2.4Hz), 6.84 (2H, d, J=8.3Hz), 6.96 (1H, dd, J=0.9Hz, 4.7Hz), 7.25 (1H, dd, J=0.9Hz, 2.9Hz), 7.48 (1H, dd, J=2.9Hz, 4.7Hz) |
| Example 136 | 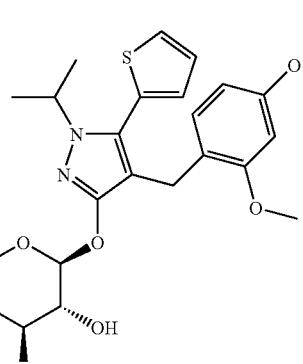 | 1.30–1.45 (6H, m), 3.10–3.50 (4H, m), 3.52–3.64 (2H, m), 3.67 (1H, dd, J=5.2Hz, 12.0Hz), 3.69 (3H, s), 3.73 (3H, s), 3.79 (1H, dd, J=2.6Hz, 12.0Hz), 4.35–4.55 (1H, m), 5.17 (1H, d, J=7.7Hz), 6.34 (1H, dd, J=2.2Hz, 8.2Hz), 6.40 (1H, d, J=2.2Hz), 6.80 (2H, d, J=8.2Hz), 6.94 (1H, dd, J=1.0Hz, 3.7Hz), 7.09 (1H, dd, J=3.7Hz, 5.2Hz), 7.54 (1H, dd, J=1.0Hz, 5.2Hz) |

TABLE 27
| Example number | Chemical structure | ¹H-NMR (CD₃OD) δ ppm: |
|---|---|---|
| Example 137 | 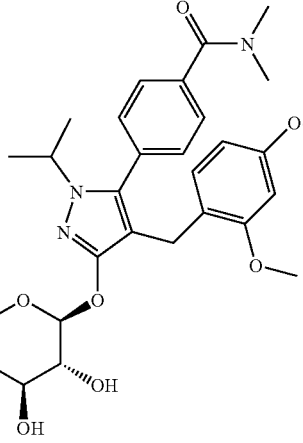 | 1.25–1.45 (6H, m), 3.01 (3H, s), 3.10 (3H, s), 3.15–3.47 (4H, m), 3.53–3.62 (2H, m), 3.64 (3H, s), 3.66–3.75 (4H, m), 3.82 (1H, dd, J=2.1Hz, 12.0Hz), 4.15–4.35 (1H, m), 5.20 (1H, d, J=7.7Hz), 6.25–6.40 (2H, m), 6.84 (1H, d, J=8.1Hz), 7.26 (2H, d, J=8.3Hz), 7.44 (2H, d, J=8.3Hz) |
| Example 138 | 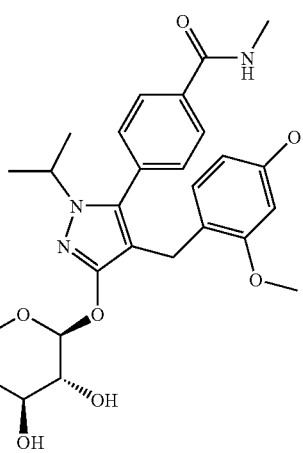 | 1.25–1.45 (6H, m), 2.92 (3H, s), 3.15–3.47 (4H, m), 3.51–3.58 (2H, m), 3.60 (3H, s), 3.68 (1H, dd, J=5.2Hz, 11.9Hz), 3.72 (3H, s), 3.81 (1H, dd, J=2.1Hz, 11.9Hz), 4.15–4.35 (1H, m), 5.20 (1H, d, J=7.1Hz), 6.25–6.40 (2H, m), 6.86 (1H, d, J=8.7Hz), 7.26 (2H, d, J=8.2Hz), 7.81 (2H, d, J=8.2Hz) |
| Example 139 | 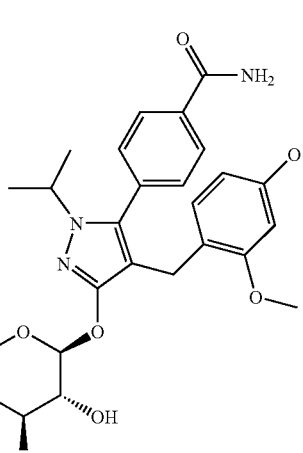 | 1.25–1.45 (6H, m), 3.15–3.47 (4H, m), 3.52–3.65 (5H, m), 3.69 (1H, dd, J=4.8Hz, 12.0Hz), 3.72 (3H, s), 3.81 (1H, dd, J=2.2Hz, 12.0Hz), 4.15–4.35 (1H, m), 5.20 (1H, d, J=7.4Hz), 6.25–6.40 (2H, m), 6.87 (1H, d, J=8.2Hz), 7.27 (2H, d, J=8.2Hz), 7.88 (2H, d, J=8.2Hz) |

EXAMPLE 140

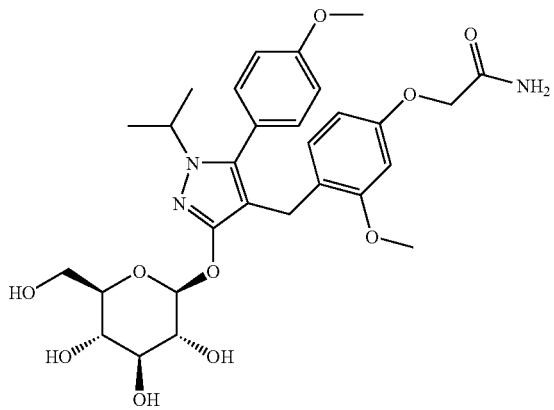

Process 1

[3-Benzyloxy-1-isopropyl-5-(4-methoxyphenyl)-1H-pyrazole-4-yl](2-methoxy-4-triisopropylsilyloxyphenyl)methanol To a solution of 3-benzyloxy-4-bromo-1-isopropyl-5-(4-methoxyphenyl)-1H-pyrazole (2.4 g) in tetrahydrofuran (15 mL) was added n-butyllithium (2.66 mol/L, tetrahydrofuran solution, 2.2 mL) at −78° C. under an argon atmosphere, and the mixture was stirred for 30 minutes. A solution of 2-methoxy-4-triisopropyl-silyloxybenzaldehyde (2.0 g) in tetrahydrofuran (3 mL) was added to the reaction mixture and the mixture was stirred at −78° C. for 30 minutes. The reaction mixture was purified by column chromatography on aminopropylated silica gel (eluent:tetrahydrofuran), and further purification by column chromatography on silica gel (eluent: hexane/ethyl acetate) gave the title compound (3.0 g).

Process 2

5-(4-Methoxypheny)-1-isopropyl-4-(2-methoxy-4-triisopropyl-silyloxyphenyl)methyl-3H-pyrazole-3-on To a solution of [3-benzyloxy-1-isopropyl-5-(4-methoxyphenyl)-1H-pyrazole-4-yl] (2-methoxy-4-triisopropyl-silyloxyphenyl)methanol (3.0 g) in ethanol was added a catalytic amount of 10% palladium-carbon powder, and the mixture was stirred at room temperature under a hydrogen atmosphere overnight. Dichloromethane (20 mL) was added to the reaction mixture and the insoluble material was removed by filtration. The solvent of the filtrate was removed under reduced pressure and hexane was added to the residue. The insoluble material was collected by filtration and dried under reduced pressure to give the title compound (1.8 g).

$^1$H-NMR (CDCl$_3$) δ ppm:
1.09 (18H, d, J=7.2 Hz), 1.15-1.30 (3H, m), 1.33 (6H, d, J=6.6 Hz), 3.48 (2H, s), 3.74 (3H, s), 3.85 (3H, s), 4.10-4.25 (1H, m), 6.30-6.40 (2H, m), 6.75-6.80 (1H, m), 6.90-7.00 (2H, m), 7.10-7.20 (2H, m)

Process 3

3-(2,3,4,6-Tetrapivaroyl-β-D-glucopyranosyloxy)-1-isopropyl-5-(4-methoxypheny)-4-[(4-hydroxy-2-methoxyphenyl)-methyl]-1H-pyrazole To a suspension of 5-(4-methoxyphenyl)-1-isopropyl-4-(2-methoxy-4-triisopropylsilyloxyphenyl)methyl-3H-pyrazole-3-on (1.5 g), 2,3,4,6-tetrapivaroyl-1-bromo-α-D-glucose (9.2 g) and benzyl(n-tributyl)ammonium chloride (0.46 g) in dichloromethane (2 mL) was added sodium hydroxide (5 mol/L, 5.9 mL) and the mixture was stirred at room temperature for 2 hours. The reaction mixture was purified by column chromatography on aminopropylated silica gel (eluent:tetrahydrofuran). Further purification by column chromatography on silica gel (eluent:dichloromethane—hexane/ethyl acetate=8/1) gave 1-isopropyl-5-(4-methoxyphenyl)-4-[(2-methoxy-4-triisopropyloxypheny)methyl]-3-(2,3,4,6-tetra-O-pivaroyl-β-D-glucopyranosyloxy)-1H-pyrazole. The obtained 1-isopropyl-5-(4-methoxyphenyl)-4-[(2-methoxy-4-triisopropyloxypheny)-methyl]-3-(2,3,4,6-tetra-O-pivaroyl-β-D-glucopyranosyloxy)-1H-pyrazole was dissolved in tetrahydrofuran (10 mL), and tetra-n-butylammonium fluoride (1 mol/L tetrahydrofuran solution, 3.5 mL) was added to the solution. The mixture was stirred at room temperature for 1 hour. The reaction mixture was concentrated under reduced pressure, and the residue was purified by column chromatography on silica gel (eluent:hexane/ethyl acetate=4/1-3/1-1/1) to give the desired title compound (0.82 g).

$^1$H-NMR (CDCl$_3$) δ ppm:
1.08 (9H, s), 1.12 (9H, s), 1.15 (9H, s), 1.19 (9H, s), 1.29 (1H, d, J=6.7 Hz), 1.32 (1H, d, J=6.7 Hz), 3.42 (1H, d, J=16.3 Hz), 3.46 (1H, d, J=16.3 Hz), 3.59 (3H, s), 3.75-3.85 (1H, m), 3.82 (3H, s), 4.10 (1H, dd, J=4.7, 12.2 Hz), 4.17 (1H, dd, J=1.7, 12.2 Hz), 4.15-4.25 (1H, m), 5.15-5.30 (2H, m), 5.35-5.45 (1H, m), 5.77 (1H, d, J=8.1 Hz), 6.15-6.30 (2H, m), 6.75-6.85 (1H, m), 6.85-6.95 (2H, m), 7.00-7.10 (2H, m)

Process 4

1-Isopropyl-5-(4-methoxyphenyl)-4-[(2-methoxy-4-carbamoyl-methyloxypheny)methyl]-3-(2,3,4,6-tetra-O-pivaroyl-β-D-glucopyranosyloxy)-1H-pyrazole To a suspension of 3-(2,3,4,6-tetrapivaroyl-β-D-glucopyranosyloxy)-1-isopropyl-5-(4-methoxyphenyl)-4-[(4-hydroxy-2-methoxyphenyl)methyl]-1H-pyrazole (0.13 g) and cesium carbonate (0.10 g) in N,N-dimethylformamide (1 mL) was added 2-bromoacetoamide (0.031 g), and the mixture was stirred at room temperature for 2 hours. Water (10 mL) was added to the reaction and the mixture was stirred at room temperature. After 1 hour, the precipitated solid was collected by filtration and dried under reduced pressure to give the title compound (0.13 g).

Process 5

1-Isopropyl-5-(4-methoxyphenyl)-4-[(2-methoxy-4-carbamoylmethyloxyphenyl)methyl]-3-(β-D-glucopyranosyloxy)-1H-pyrazole To a solution of 1-isopropyl-5-(4-methoxyphenyl)-4-[(2-methoxy-4-carbamoylmethyloxyphenyl)methyl]-3-(2,3,4,6-tetra-O-pivaroyl-p-β-glucopyranosyloxy)-1H-pyrazole (0.13 g) in methanol (2 mL) was added sodium methoxide (28% methanol solution, 0.13 mL), and the mixture was stirred at 55° C. for 30 minutes. A citric acid aqueous solution (10%) was added to the reaction mixture, and the mixture was purified by solid phase extraction on ODS (washing solvent: water, eluent:methanol). Further purification by preparative reverse phase column chromatography (Shiseido CAPSELL-PAC C18 UG80, 5 μM, 20×50 mm, flow rate 30 mL/min linear gradient, water/methanol=90/10-10/90) gave the title compound (0.051 g).

$^1$H-NMR (CD$_3$OD) δ ppm:
1.33 (3H, d, J=6.3 Hz), 1.34 (3H, d, J=6.8 Hz), 3.15-3.30 (1H, m), 3.30-3.45 (3H, m), 3.45-3.60 (2H, m), 3.60-3.75 (4H, m), 3.75-3.85 (4H, m), 4.20-4.35 (1H, m), 4.43 (2H, s), 5.05-5.20 (1H, m), 6.35-6.40 (1H, m), 6.45-6.55 (1H, m), 6.80-6.90 (1H, m), 6.90-7.00 (2H, m), 7.00-7.10 (2H, m)

EXAMPLES 141-142

The compounds described in Table 28 were prepared in a similar manner to that described in Example 140 using corresponding starting materials.

Process 1

3-(2,3,4,6Tetra-O-pivaroyl-β-D-glucopyranosyloxy)-1-isopropyl-5-(4-methoxyphenyl)-4-{[4-(2-benzyloxyethyloxy)-2-methoxyphenyl]methyl}-1H-pyrazole To a suspension of 3-(2,3,4,6-tetra-O-pivaroyl-β-D-glucopyranosyloxy)-1-isopropyl-5-(4-methoxyphenyl)-4-[(4-

TABLE 28

| Example number | Chemical structure | $^1$H–NMR (CD$_3$OD) δ ppm: |
|---|---|---|
| Example 141 | 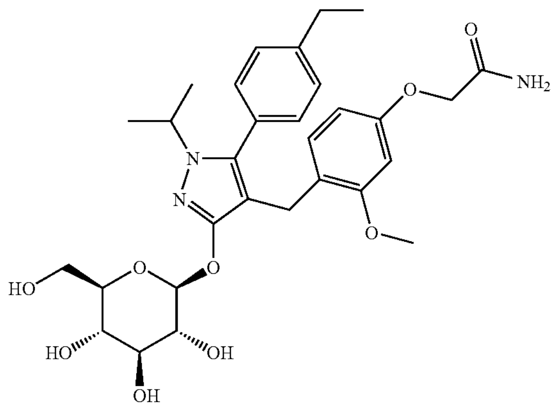 | 1.25 (3H, t, J=7.6Hz), 1.30–1.40 (6H, m), 2.67 (1H, q, J=7.6Hz), 3.10–3.45 (4H, m), 3.45–3.60 (2H, m), 3.60–3.75 (5H, m), 3.79 (1H, dd, J=2.1, 11.9Hz), 4.20–4.35 (1H, m), 4.43 (2H, s), 5.10–5.20 (1H, m), 6.35–6.40 (1H, m), 6.45–6.55 (1H, m), 6.85–6.95 (1H, m), 7.00–7.10 (2H, m), 7.20–7.30 (2H, m) |
| Example 142 | 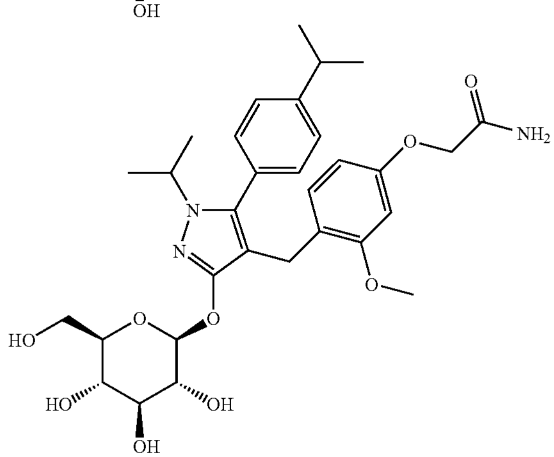 | 1.26 (6H, d, J=6.9Hz), 1.30–1.40 (6H, m), 2.80–3.00 (1H, m), 3.15–3.3.45 (4H, m), 3.50–3.60 (2H, m), 3.64 (3H, s), 3.67 (1H, dd, J=5.4, 12.0Hz), 3.80 (1H, dd, J=2.1, 12.0Hz), 4.20–4.35 (1H, m), 4.43 (2H, s), 5.10–5.20 (1H, m), 6.35–6.40 (1H, m), 6.45–6.50 (1H, m), 6.85–6.95 (1H, m), 7.05–7.10 (2H, m), 7.20–7.30 (2H, m) |

EXAMPLE 143

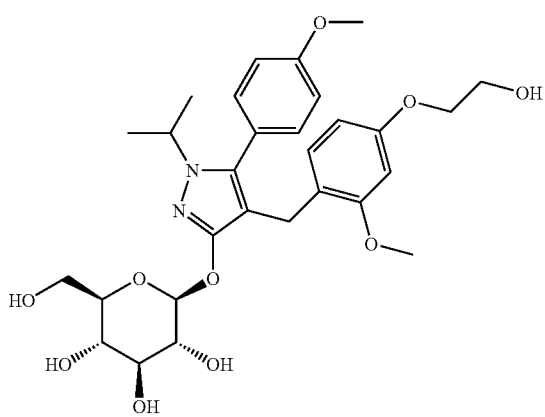

hydroxy-2-methoxypheny)methyl]-1H-pyrazole (0.13 g) and cesium carbonate (0.10 g) in N,N-dimethylformamide (1 mL) was added benzyl 2-bromoethyl ether (0.049 g), and the mixture was stirred at room temperature for 2 hours. Water was added to the reaction mixture, and the mixture was extracted with dichloromethane. The solvent of the organic layer was removed under reduced pressure, and the residue was purified by column chromatography on silica gel (eluent: hexane/ethyl acetate=4/1) to give the title compound (0.11 g).

Process 2

3-(β-D-Glucopyranosyloxy)-1-isopropyl-5-(4-methoxyphenyl)-4-{[4-(2-hydoxyethyloxy)-2-methoxyphenyl]methyl}-1H-pyrazole To a solution of 3-(2,3,4,6-tetrapivaroyl-β-D-glucopyranosyloxy)-1-isopropyl-5-(4-methoxyphenyl)-4-{[4-(2-benzyloxyethyloxy)-2-methoxyphenyl]methyl}-1H-pyrazole (0.11 g) in methanol (2 mL) was added sodium methoxide (28% methanol solution, 0.13 mL), and the mixture was stirred at 55° C. for 30 minutes. A citric acid aqueous solution (10%) was added to the reaction mixture and the mixture was purified by solid phase extraction on ODS (washing solvent: water, eluent:methanol). The obtained semi purified 3-(β-D-glucopyranosyloxy)-1-isopropyl-5-(4-methoxyphenyl)-4-{[4-(2-benzyloxyethyloxy)-2-methoxyphenyl]methyl}-1H-pyrazole was dissolved in methanol (2 mL), a catalytic amount of 10% palladium-carbon powder was added to the solution. The mixture was stirred at room temperature for 1 hour. The insoluble material was removed by filtration, and the solvent of filtrate was removed under reduced pressure. The residue was purified by preparative reverse phase column chromatography (Shiseido CAPSELLPAC C18 UG80, 5 μM, 20×50 mm, flow rate 30 mL/min linear gradient, water/methanol=90/10-10/90) to give the title compound (0.043 g).

$^1$H-NMR (CD$_3$OD) δ ppm:

1.33 (3H, d, J=6.7 Hz), 1.34 (3H, d, J=6.8 Hz), 3.15-3.45 (4H, m), 3.51 (1H, d, J=16.2 Hz), 3.55 (1H, d, J=16.2 Hz), 3.60-3.70 (4H, m), 3.75-3.85 (6H, m), 3.95-4.05 (2H, m), 4.20-4.35 (1H, m), 5.05-5.20 (1H, m), 6.30-6.40 (1H, m), 6.40-6.45 (1H, m), 6.80-6.87 (1H, m), 6.90-7.00 (2H, m), 7.05-7.10 (2H, m)

EXAMPLES 144-148

The compounds described in Table 29 were prepared in a similar manner to that described in Example 143 using corresponding starting materials.

TABLE 29

| Example number | Chemical structure | $^1$H-NMR (CD$_3$OD) δ ppm: |
|---|---|---|
| Example 144 | 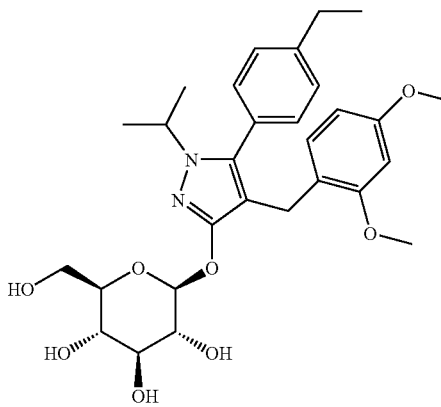 | 1.25 (6H, t, J=7.7Hz), 1.30–1.40 (6H, m), 2.67 (1H, q, J=7.7Hz), 3.15–3.45 (4H, m), 3.51 (1H, d, J=16.6Hz), 3.56 (1H, d, J=16.6Hz), 3.63 (3H, s), 3.67 (1H, dd, J=1H, dd, J=5.4, 12.0Hz), 3.80 (1H, dd, J=2.6, 12.0Hz), 3.80–3.85 (2H, m), 3.95–4.05 (2H, m), 4.20–4.35 (1H, m), 5.10–5.20 (1H, m), 6.40–6.6.39 (1H, m), 6.40–6.45 (1H, m), 6.80–6.90 (1H, m), 7.00–7.10 (2H, m), 7.20–7.25 (2H, m) |
| Example 145 | 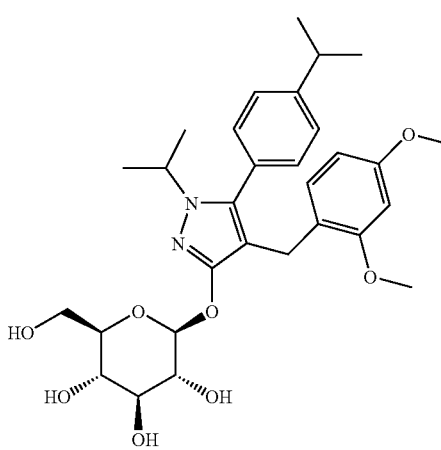 | 1.26 (6H, d, J=7.0Hz), 1.30–1.40 (6H, m), 2.85–3.00 (1H, m), 3.15–3.45 (4H, m), 3.45–3.60 (2H, m), 3.63 (3H, s), 3.68 (1H, dd, J=5.2, 12.0Hz), 3.75–3.85 (3H, m), 3.95–7.05 (2H, m), 4.20–4.35 (1H, m), 5.10–5.20 (1H, m), 6.30–6.45 (2H, m), 6.80–6.90 (1H, m), 7.00–7.15 (2H, m), 7.20–7.30 (2H, m) |

TABLE 29-continued

| Example number | Chemical structure | ¹H-NMR (CD₃OD) δ ppm: |
|---|---|---|
| Example 146 | 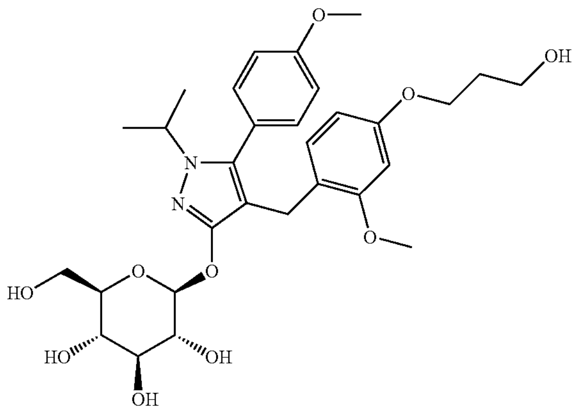 | 1.33 (3H, d, J=6.5Hz), 1.34(3H, d, J=6.6Hz), 1.90–2.00 (1H, m), 3.15–3.45 (4H, m), 3.50 (1H, d, J=16.4Hz), 3.55 (1H, d, J=16.4Hz), 3.60–3.75 (6H, m), 3.75–3.85 (2H, m), 4.20–4.35 (1H, m), 5.10–5.15 (1H, m), 6.30–6.40 (2H, m), 6.80–6.85 (1H, m), 6.90–7.00 (2H, m), 7.05–7.15 (2H, m) |
| Example 147 | 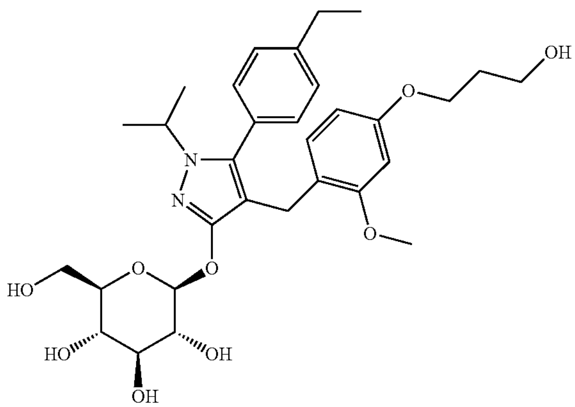 | 1.25 (3H, t, J=7.6Hz), 1.33 (3H, d, J=6.4Hz), 1.34 (3H, d, J=6.8Hz), 1.90–2.00 (1H, m), 2.60–2.75 (2H, q, J=7.6Hz), 3.15–3.45 (I4H, m), 3.51 (1H, d, J=16.5Hz), 3.55 (1H, d, J=16.5Hz), 3.63 (3H, s), 3.67 (3H, dd, J=5.0, 12.0Hz), 3.72 (2H, t, J=6.4Hz), 3.80 (1H, dd, J=2.2Hz, 12.0Hz), 4.01 (2H,t, 6.4Hz), 4.20–4.35 (1H, m), 5.10–5.20 (1H, m), 6.30–6.40 (2H, m), 6.80–6.90 (1H, m), 7.00–7.10 (2H, m), (2H, m), 7.20–7.25 (2H, m) |
| Example 148 | 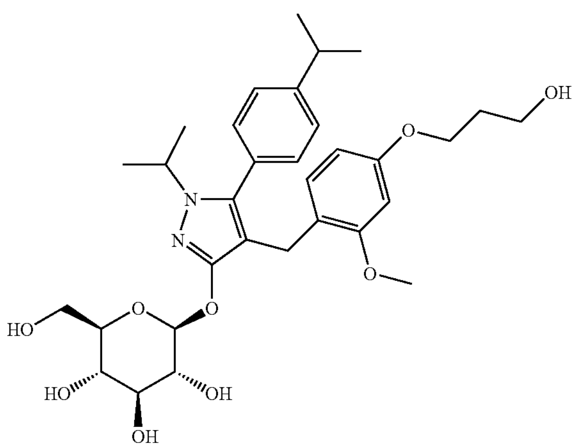 | 1.26 (6H, d, J=7.0Hz), 1.33 (3H, d, J=6.5Hz), 1.34 (3H, d, J=6.4Hz), 1.90–2.00 (2H, m), 2.85–3.00 (1H, m), 3.15–3.45 (4H, m), 3.51 (1H, d, J=16.6Hz), 3.56 (1H, d, J=16.6Hz), 3.62 (3H, s), 3.68 (1H, dd, J=5.5, 12.0Hz), 3.72 (2H, t, J=6.3Hz), 3.80 (1H, dd, J=2.7, 12.0H), 4.01 (2H, t, J=6.2Hz), 4.20–4.35 (1H, m), 5.10–5.20 (1H, m), 6.30–6.40 (2H, m), 6.80–6.90 (1H, m), 7.05–7.10 (2H, m), 7.20–7.30 (2H, m) |

TEST EXAMPLE 1

Distribution Pattern of SMINT Gene Expression Among Human Organs 1) cDNA Synthesis Total RNA (tRNA) from human liver, colon, testis, pancreas, lung, small intestine, stomach, placenta, and skeletal muscle were obtained from Sawady Technology, and tRNA from the trachea, brain, kidney and heart were purchased from CLONTECH. Concentrations of these tRNAs were determined by using RiboGreen RNA quantification reagent and kit (Molecular Probes), and then each of cDNA was synthesized (i.e. reverse-transcription reaction). Reaction mixture at a volume of 16.5 µL, which included 1.5 µg of tRNA and 1.5 µL of 500 ng/µL random hexamer (Invitrogen), was incubated at 70° C. for 5 minutes, then kept at room temperature for 5 minutes. After the incubation, to the above reaction mixture was added 13.5 µL of another reaction mixture containing 6 µL of 5×BRL 1$^{st}$ strand buffer (Invitrogen), 3.25 µL of distilled water (Nippon Gene), 1.5 µL of 10 mM dNTP mix (Invitrogen), 0.75 µL of RNase inhibitor (Invitrogen), and 2 μL of SuperScript II (Invitrogen). Simultaneously, another reaction mixture added 2 μL of distilled water (Nippon Gene) instead of the same volume of SuperScript II (Invitrogen) was mixed similarly with the above reaction mixture. All of the mixtures were incubated at room temperature for 10 minutes followed by the reaction at 42° C. for 1 hour. After the reaction, these mixtures were incubated at 95° C. for 10 minutes to inactivate SuperScript II (Invitrogen) immediately followed by standing on ice. Then, to the mixtures was added 1.5 μL of RNase H, and the mixture was incubated at 37° C. for 30 minutes. After the reactions, to the mixtures was added 170 μL of distilled water. The synthesized cDNA were extracted with 200 μL of phenol:chloroform:isoamylalcohol=25:24:1 (Invitrogen), and extracted again with 200 μL of chloroform:isoamylalcohol=24:1. After ethanol precipitation, the cDNA were diluted in 100 μL of distilled water (Nippon Gene).

2) Determination of SMINT Gene Expression By Real-time Quantitative PCR

Primer sequences used for real-time quantitative PCR were as follows: Forward primer: 5'-TGT CAC AGT CCC CAA CAC CA-3' (SEQ ID NO:2), Reverse primer: 5'-CCG AAG CAT GTG GAA AGC A-3' (SEQ ID NO: 3), and Probe: 5'-TGT CAC CTC CCA CGG CCC G-3' (SEQ ID NO: 4). The probe was labeled its 5'-end with fluorescence dye FAN, and its 3'-end with fluorescence dye TAMPA. Twenty-five μL of reaction mixture was prepared with 2.5 ng of cDNA prepared as described above, 1× Taqman Universal master mix (Applied Biosystems), 500 nM each of the forward and the reverse primers, and 200 nM of the probe. PCR condition was as follows: 1 cycle at 50° C. for 2 minutes, 1 cycle at 95° C. for 10 minutes, and 40 cycles at 95° C. for 15 seconds and at 60° C. for 1 minutes. Gene expression level was detected by GeneAmp 5700 Sequence Detection System (Applied Biosystems) in reaction tubes composed of MicroAmp optical 96-well reaction plate (Applied Biosystems) and MicroAmp optical cap (Applied Biosystems). Fluorescence signals were detected according to the manufacturer's instruction (Christian A. Heid, et al., in "Genome Research", 1996, Vol. 6, pp. 986-994). Serially 10-fold diluted plasmid DNA ($3.5 \times 10^6$, $3.5 \times 10^5$, $3.5 \times 10^4$, $3.5 \times 10^3$, $3.5 \times 10^2$ and $3.5 \times 10$ molecules/well, extracted from Escherichia coli/SMINT2010324 host cells, which is described in Test Example 2) was used to draw a standard curve for the expression analysis.

The obtained results were shown in FIG. 1. FIG. 1 indicates that human SMINT gene is expressed highly in the small intestine and the kidney. Therefore, human SMINT plays important roles in sugar absorption at the small intestine, sugar reabsorption and/or sugar uptake into the cells at the kidney.

TEST EXAMPLE 2

Confirmatory Test for Substrate Specificity of Human SMINT

1) Preparation of Cells Transiently Expressing Human SMINT

Human SMINT-carrying expression plasmid SMINT/pME18S-FL (denotation of bacteria: *Escherichia coli*/SMINT2010324), which was deposited with NITE Patent Microorganisms Depositary on Mar. 12, 2002, was transfected to COS-7 cells (RIKEN CELL BANK RCB0539) by lipofection method. LIPOFECTAMINE PLUS reagent (Invitrogen) was used as the lipofection reagent. A day before the lipofection, COS-7 cells were suspended in D-MEM medium (Invitrogen) at $6 \times 10^6$ cells per 1 mL, and dispensed 50 μL per well of 96-well plate. The lipofection was performed by the following methods. For each well, 0.1 μg of the plasmid was diluted with 10 μL of D-MEM, added 0.5 μL of PLUS reagent, mixed gently, and kept stand for 15 minutes to prepare Plasmid Dilute Solution. For each well, 0.5 μL of LIPOFECTAMINE reagent was diluted with 10 μL of D-MEM to prepare LIPOFECTAMINE Dilute Solution. The Plasmid Dilute Solution was mixed with an equal volume of the LIPOFECTAMINE Dilute Solution, kept stand for 15 minutes, dispensed 20 μL per well of cell culture medium, and incubated at 37° C. under 5% $CO_2$ for 5 hours. Then D-MEM containing 16.7% fetal bovine serum (Sanko Jun-yaku) was dispensed 100 μL per well. After 2 days culture, the cells were used for the inhibition assay of methyl-α-D-glucopyranoside uptake activity.

2) Inhibition Assay of methyl-α-D-glucopyranoside Uptake Activity

Figure 2:
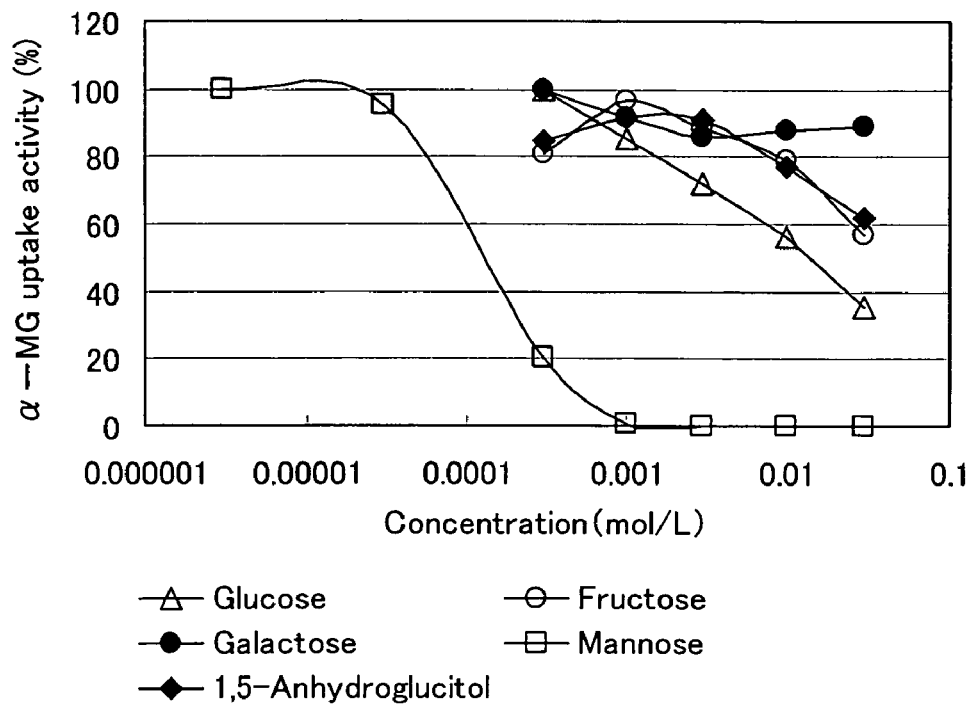
FIG. 2 is a graph showing substrate specificity of human SMINT. The vertical axis indicates methyl-α-D-glucopyranoside (α-MG) uptake activity (%), and the horizontal axis indicates concentration (mol/L). In the graph, an open triangle shows glucose, an open circle shows fructose, a black circle shows galactose, an open square shows mannose and a black diamond shows 1,5-anhydroglucitol.

To Uptake Buffer consisting of 140 mM sodium chloride, 2 mM potassium chloride, 1 mM calcium chloride, 1 mM magnesium chloride, 10 mM 2-[2-(2-hydroxyethyl)-1-piperazinyl]-ethanesulfonic acid, and 5 mM tris(hydroxymethyl)aminomethane (pH 7.4), was added methyl-α-D-glucopyranoside (α-MG) composed of its non-radiolabeled form and $^{14}C$-labeled form at 1 mM as the final concentration. For measurement of basal uptake, Basal Buffer was prepared by the addition of 140 mM choline chloride instead of sodium chloride of the Uptake Buffer. In order to determine the substrate specificity among natural sugars, natural sugars were solubilized in distilled water, diluted with distilled water into appropriate concentrations, and added to the Uptake Buffer to prepare Assay Buffer. Culture medium was discarded from the cells with transient SMINT expression, Pretreatment Buffer (Basal Buffer without α-MG) was added to the cells at 200 μL per well, and the cells were incubated at 37° C. for 10 minutes. After repeating once the same operation, Pretreatment Buffer was removed, Assay Buffer, Uptake Buffer or Basal Buffer was added to the cells at 75 μL per well, and the cells were incubated at 37° C. After the incubation for 1 hour, Assay Buffer was removed, and the cells were washed twice with 150 μL per well of Wash Buffer (Basal Buffer containing 10 mM non-radiolabeled α-MG). Cell lysates were prepared by addition of 75 μL per well of 0.2 mol/L sodium hydroxide to the cells, and transferred to PicoPlate (Packard). To the cell lysates were added 150 μL per well of MicroScint 40 (Packard), mixed well, and the radioactivity was measured in a microscintillation counter TOPCOUNT (Packard). α-MG uptake by the cells treated with each concentration of test compounds was calculated as relative activity to control group, which is set as 100% uptake after deducting the basal uptake. A half-maximal inhibitory concentration of each test compound ($IC_{50}$ value) was derived from logit plot analysis. The results were shown in FIG. 2. FIG. 2 indicates that SMINT recognizes 1,5-anhydroglucitol, fructose, and mannose in addition to glucose, but not galactose as substrates. Therefore, it is suggested that SMINT may be 1,5-anhydroglucitol/fructose/mannose transporter expressed in the kidney and the other human tissues.

TEST EXAMPLE 3

Confirmatory Test for Inhibitory Activity on Human 1,5-anhydroglucitol/fructose/mannose Transporter 1) Preparation of Cells Transiently Expressing Human SMINT The cells were prepared according to the method described in 1) of Test Example 2.

2) Inhibition Assay of methyl-α-D-glucopyranoside Uptake Activity

To Uptake Buffer consisting of 140 mM sodium chloride, 2 mM potassium chloride, 1 mM calcium chloride, 1 mM magnesium chloride, 10 mM 2-[2-(2-hydroxyethyl)-1-piperazinyl]-ethanesulfonic acid, and 5 mM tris(hydroxymethyl) aminomethane (pH 7.4), was added methyl-α-D-glucopyranoside (α-MG) composed of its non-radiolabeled form and $^{14}C$-labeled form at 1 mM as the final concentration. For measurement of basal uptake, Basal Buffer was prepared by the addition of 140 mM choline chloride instead of sodium chloride of the Uptake Buffer. In order to determine the substrate specificity among natural sugars, natural sugars were solubilized in distilled water, diluted with distilled water into appropriate concentrations, and added to the Uptake Buffer to prepare Assay Buffer. Culture medium was discarded from the cells with transient SMINT expression, Pretreatment Buffer (Basal Buffer without α-MG) was added to the cells at 200 μL per well, and the cells were incubated at 37° C. for 10 minutes. After repeating once the same operation, Pretreatment Buffer was removed, Assay Buffer, Uptake Buffer or Basal Buffer was added to the cells at 75 μL per well, and the cells were incubated at 37° C. After the incubation for 1 hour, Assay Buffer was removed, and the cells were washed twice with 150 μL per well of Wash Buffer (Basal Buffer containing 10 mM non-radiolabeled α-MG). Cell lysates were prepared by addition of 75 μL per well of 0.2 mol/L sodium hydroxide to the cells, and transferred to PicoPlate (Packard). To the cell lysates were added 150 μL per well of MicroScint 40 (Packard), mixed well, and the radioactivity was measured in a microscintillation counter TOPCOUNT (Packard). α-MG uptake by the cells treated with each concentration of test compounds was calculated as relative activity to control group, which is set as 100% uptake after deducting the basal uptake. A half-maximal inhibitory concentration of each test compound ($IC_{50}$ value) was derived from logit plot analysis. The results were shown in Table 30. The compounds of the invention exhibited a potent inhibitory activity on 1,5-anhydroglucitol/fructose/mannose transporter.

TABLE 30

| Test compounds | IC50 value (nM) |
| --- | --- |
| Example 1 | 92 |
| Example 87 | 444 |
| Example 99 | 245 |
| Example 119 | 296 |

INDUSTRIAL APPLICABILITY

The pyrazole derivatives represented by the above general formula (I) of the present invention, pharmaceutically acceptable salts thereof and prodrugs thereof exert an inhibitory activity in human 1,5-anhydroglucitol/fructose/mannose transporter and exhibit an excellent inhibitory activity on 1,5-anhydroglucitol/fructose/mannose transporter found highly in the kidney and small intestine, and can inhibit blood glucose level increase by inhibiting the reabsorption at the kidney or uptake into cells of glucose, mannose and fructose or inhibiting the sugar absorption in the small intestine. Therefore, the present invention can provide an agent for prevention, inhibition of progression or treatment of a disease associated with the excess uptake of at least a kind of carbohydrates selected from glucose, fructose and mannose or a disease associated with hyperglycemia such as diabetic complications, diabetes and obesity. In addition, since the pyrazole derivatives represented by the above general formula (II) or (III) of the present invention and salts thereof are important as intermediates in the production of the pyrazole derivatives represented by the above general formula (I), the compounds represented by the above general formula (I) of the present invention can be readily prepared via such compounds.

The invention claimed is:

1. A pyrazole derivative represented by the following general formula (Iα):

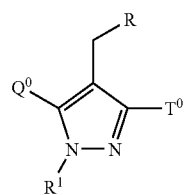

wherein

R$^1$ represents a hydrogen atom, a C$_{1-6}$ alkyl group which may have the same or different 1 to 3 groups selected from the following substituent group (A), a C$_{2-6}$ alkenyl group which may have the same or different 1 to 3 groups selected from the following substituent group (A), a C$_{2-6}$ alkynyl group which may have the same or different 1 to 3 groups selected from the following substituent group (A), a C$_{3-8}$ cycloalkyl group which may have the same or different 1 to 3 groups selected from the following substituent group (A), a C$_{6-10}$ aryl group which may have the same or different 1 to 3 groups selected from the following substituent group (B), a C$_{2-9}$ heterocycloalkyl group which may have the same or different 1 to 3 groups selected from the following substituent group (A), or a C$_{1-9}$ heteroaryl group which may have the same or different 1 to 3 groups selected from the following substituent group (B);

one of Q$^0$ and T$^0$ represents a group selected from

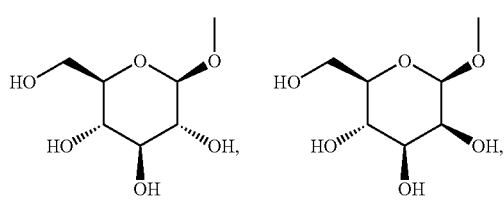

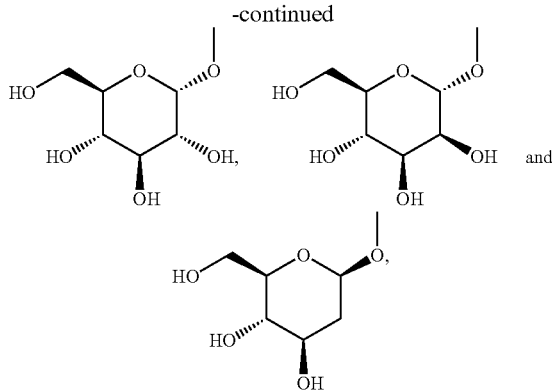

and the other represents a group represented by the formula: —(CH$_2$)$_n$—Ar wherein Ar represents a C$_{6-10}$ aryl group which may have the same or different 1 to 3 groups selected from the following substituent group (B) or a C$_{1-9}$ heteroaryl group which may have the same or different 1 to 3 groups selected from the following substituent group (B); and n represents an integral number from 0 to 2, a C$_{1-6}$ alkoxy group which may have the same or different 1 to 3 groups selected from the following substituent group (A), an optionally mono or di(C$_{1-6}$ alkyl)-substituted amino group wherein the C$_{1-6}$ alkyl group may have the same or different 1 to 3 groups selected from the following substituent group (A), a C$_{2-9}$ heterocycloalkyl group which may have the same or different 1 to 3 groups selected from the following substituent group (A), or a heterocycle-fused phenyl group which may have the same or different 1 to 3 groups selected from the following substituent group (B);

R represents a C$_{3-8}$ cycloalkyl group which may have the same or different 1 to 3 groups selected from the following substituent group (A), a C$_{6-10}$ aryl group which may have the same or different 1 to 3 groups selected from the following substituent group (B), a C$_{2-9}$ heterocycloalkyl group which may have the same or different 1 to 3 groups selected from the following substituent group (A), or a C$_{1-9}$ heteroaryl group which may have the same or different 1 to 3 groups selected from the following substituent group (B);

[Substituent Group (A)]:

a halogen atom, a nitro group, a cyano group, an oxo group, -G$^1$, —OG$^2$, —SG$^2$, —N(G$^2$)$_2$, —C(=O)G$^2$, —C(=O)OG$^2$, —C(=O)N(G$^2$)$_2$, —S(=O)$_2$G$^2$, —S(=O)$_2$OG$^2$, —S(=O)$_2$N(G$^2$)$_2$, —S(=O)G$^1$, —OC(=O)G$^1$, —OC(=O)N(G$^2$)$_2$, —NHC(=O)G$^2$, —OS(=O)$_2$G$^1$, —NHS(=O)$_2$G$^1$ and —C(=O)NHS(=O)$_2$G$^1$;

[Substituent Group (B)]:

a halogen atom, a nitro group, a cyano group, -G$^1$, —OG$^2$, —SG$^2$, —N(G$^2$)$_2$, -G$^3$OG$^4$, -G$^3$N(G$^4$)$_2$, —C(=O)G$^2$, —C(=O)OG$^2$, —C(=O)N(G$^2$)$_2$, —S(=O)$_2$G$^2$, —S(=O)$_2$OG$^2$, —S(=O)$_2$N(G$^2$)$_2$, —S(=O)G$^1$, —OC(=O)G$^1$, —OC(=O)N(G$^2$)$_2$, —NHC(=O)G$^2$, —OS(=O)$_2$G$^1$, —NHS(=O)$_2$G$^1$ and —C(=O)NHS(=O)$_2$G$^1$;

in the above substituent group (A) and/or (B),

G$^1$ represents a C$_{1-6}$ alkyl group which may have the same or different 1 to 3 groups selected from the following substituent group (C), a C$_{2-6}$ alkenyl group which may have the same or different 1 to 3 groups selected from the following substituent group (C), a C$_{2-6}$ alkynyl group which may have the same or different 1 to 3 groups selected from the following substituent group (C), a C$_{3-8}$ cycloalkyl group which may have the same or different 1 to 3 groups selected from the following substituent group (C), a C$_{6-10}$ aryl group which may have the same or different 1 to 3 groups selected from the following substituent group (D), a C$_{2-9}$ heterocycloalkyl group which may have the same or different 1 to 3 groups selected from the following substituent group (C), or a C$_{1-9}$ heteroaryl group which may have the same or different 1 to 3 groups selected from the following substituent group (D);

G$^2$ represents a hydrogen atom, a C$_{1-6}$ alkyl group which may have the same or different 1 to 3 groups selected from the following substituent group (C), a C$_{2-6}$ alkenyl group which may have the same or different 1 to 3 groups selected from the following substituent group (C), a C$_{2-6}$ alkynyl group which may have the same or different 1 to 3 groups selected from the following substituent group (C), a C$_{3-8}$ cycloalkyl group which may have the same or different 1 to 3 groups selected from the following substituent group (C), a C$_{6-10}$ aryl group which may have the same or different 1 to 3 groups selected from the following substituent group (D), a C$_{2-9}$ heterocycloalkyl group which may have the same or different 1 to 3 groups selected from the following substituent group (C), or a C$_{1-9}$ heteroaryl group which may have the same or different 1 to 3 groups selected from the following substituent group (D), and with the proviso that G$^2$ may be the same or different when there are 2 or more G$^2$ in the substituents;

G$^3$ represents a C$_{1-6}$ alkyl group;

G$^4$ represents a C$_{1-6}$ alkyl group which may have the same or different 1 to 3 groups selected from the following substituent group (C), and with the proviso that G$^4$ may be the same or different when there are 2 or more G$^4$ in the substituents;

[Substituent Group (C)]:

a halogen atom, a nitro group, a cyano group, an oxo group, -G$^5$, —OG$^6$, —SG$^6$, —N(G$^6$)$_2$, —C(=O)G$^6$, —C(=O)OG$^6$, —C(=O)N(G$^6$)$_2$, —S(=O)$_2$G$^6$, —S(=O)$_2$OG$^6$, —S(=O)$_2$N(G$^6$)$_2$, —S(=O)G$^5$, —OC(=O)G$^5$, —OC(=O)N(G$^6$)$_2$, —NHC(=O)G$^6$, —OS(=O)$_2$G$^5$, —NHS(=O)$_2$G$^5$ and —C(=O)NHS(=O)$_2$G$^5$; and

[Substituent Group (D)]:

a halogen atom, a nitro group, a cyano group, -G$^5$, —OG$^6$, —SG$^6$, —N(G$^6$)$_2$, —C(=O)G$^6$, —C(=O)OG$^6$, —C(=O)N(G$^6$)$_2$, —S(=O)$_2$G$^6$, —S(=O)$_2$OG$^6$, —S(=O)$_2$N(G$^6$)$_2$, —S(=O)G$^5$, —OC(=O)G$^5$, —OC(=O)N(G$^6$)$_2$, —NHC(=O)G$^6$, —OS(=O)$_2$G$^5$, —NHS(=O)$_2$G$^5$ and —C(=O)NHS(=O)$_2$G$^5$;

in the substituent group (C) and/or (D),

G$^5$ represents a C$_{1-6}$ alkyl group, a C$_{2-6}$ alkenyl group, a C$_{2-6}$ alkynyl, a C$_{3-8}$ cycloalkyl group, a C$_{6-10}$ aryl group, a C$_{2-9}$ heterocycloalkyl group or a C$_{1-9}$ heteroaryl group; and G$^6$ represents a hydrogen atom, a C$_{1-6}$ alkyl group, a C$_{2-6}$ alkenyl group, a C$_{2-6}$ alkynyl, a C$_{3-8}$ cycloalkyl group, a C$_{6-10}$ aryl group, a C$_{2-9}$ heterocycloalkyl group or a C$_{1-9}$ heteroaryl group, and with the proviso that G$^6$ may be the same or different when there are 2 or more G$^6$ in the substituents, or a pharmaceutically acceptable salt thereof or a prodrug thereof.

2. A pyrazole derivative as claimed in claim 1, wherein

R$^1$ represents a hydrogen atom, a C$_{1-6}$ alkyl group which may have the same or different 1 to 3 groups selected from the substituent group (A), a C$_{3-8}$ cycloalkyl group which may have the same or different 1 to 3 groups selected from the substituent group (A), or a C$_{6-10}$ aryl group which may have the same or different 1 to 3 groups selected from the substituent group (B); Q$^0$ represents a C$_{6-10}$ aryl group which may have the same or different 1 to 3 groups selected from the substituent group (B); T$^0$ represents a group:

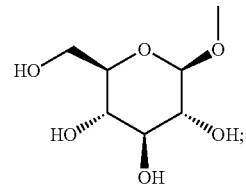

R represents a C$_{6-10}$ aryl group which may have the same or different 1 to 3 groups selected from the substituent group (B); substituent group (A) consists of a halogen atom, —OG$^2$, —SG$^2$, —N(G$^2$)$_2$, —C(=O)OG$^2$, —C(=O)N(G$^2$)$_2$, —S(=O)$_2$OG$^2$ and —S(=O)$_2$N(G$^2$)$_2$ in which G$^2$ represents a hydrogen atom, a C$_{1-6}$ alkyl group which may have the same or different 1 to 3 groups selected from the substituent group (C); or a C$_{6-10}$ aryl group which may have the same or different 1 to 3 groups selected from the substituent group (D); and substituent group (B) consists of a halogen atom, a nitro group, a cyano group, -G$^1$, —OG$^2$, —SG$^2$, —C(=O)OG$^2$ in which G$^1$ represents a C$_{1-6}$ alkyl group which may have the same or different 1 to 3 groups selected from the substituent group (C) or a C$_{6-10}$ aryl group which may have the same or different 1 to 3 groups selected from the substituent group (D); and G has the same meaning as defined above, or a pharmaceutically acceptable salt thereof or a prodrug thereof.

3. A pyrazole derivative as claimed in claim 1, wherein one of Q$^0$ and T$^0$ represents a group selected from

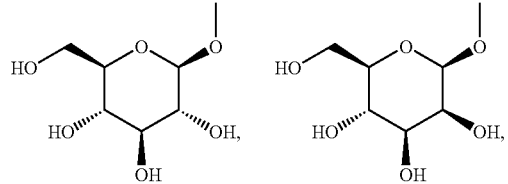

-continued

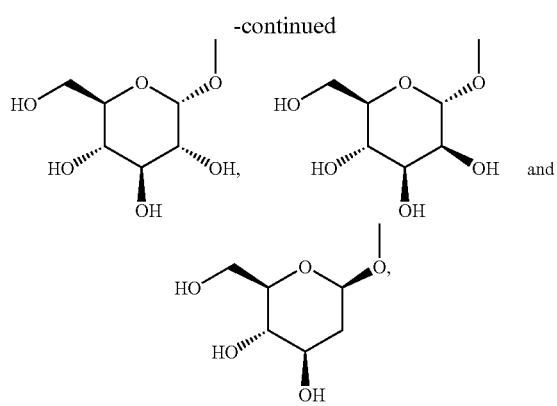

and the other represents a group represented by the formula: —(CH$_2$)$_n$—Ar, or a pharmaceutically acceptable salt thereof or a prodrug thereof.

4. A pyrazole derivative as claimed in claim 3, wherein wherein Q$^0$ represents a C$_{6-10}$ aryl group which may have the same or different 1 to 3 groups selected from the substituent group (B); T$^0$ represents a group selected from

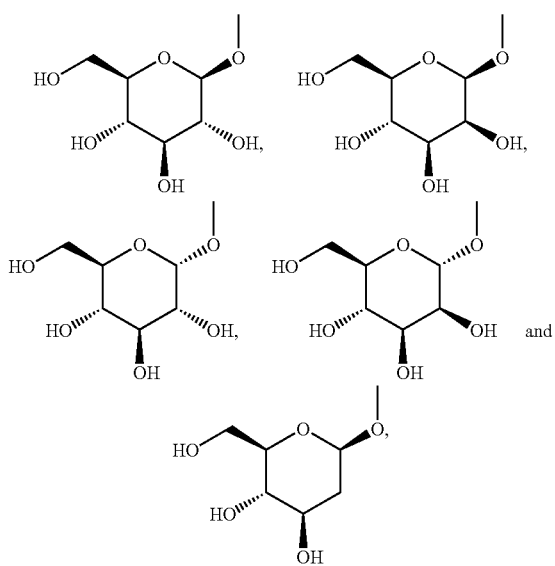

and R represents a C$_{6-10}$ aryl group which may have the same or different 1 to 3 groups selected from the substituent group (B), or a pharmaceutically acceptable salt thereof or a prodrug thereof.

5. A pyrazole derivative as claimed in claim 4, wherein T$^0$ represents a group:

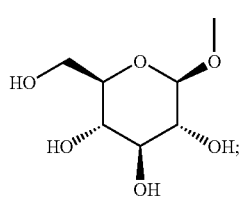

and substituent group (B) consists of a halogen atom, a nitro group, a cyano group, -G$^1$, —OG$^2$, —SG$^2$ and —C(=O)OG$^2$ in which G$^1$ represents a C$_{1-6}$ alkyl group which may have the same or different 1 to 3 groups selected from the substituent group (C) or a C$_{6-10}$ aryl group which may have the same or different 1 to 3 groups selected from the substituent group (D); and G$^2$ represents a hydrogen atom, a C$_{1-6}$ alkyl group which may have the same or different 1 to 3 groups selected from the substituent group (C) or a C$_{6-10}$ aryl group which may have the same or different 1 to 3 groups selected from the substituent group (D), or a pharmaceutically acceptable salt thereof or a prodrug thereof.

6. A pyrazole derivative as claimed in claim 1, wherein one of Q$^0$ and T$^0$ represents a group selected from

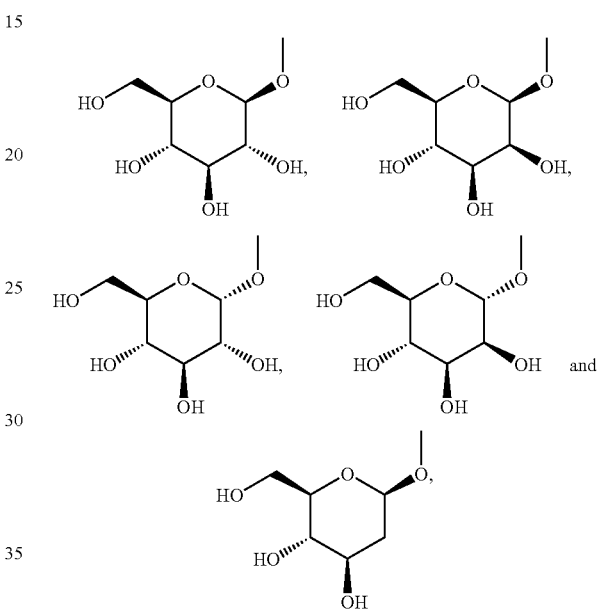

and the other represents a C$_{1-6}$ alkoxy group which may have the same or different 1 to 3 groups selected from the substituent group (A), an optionally mono or di(C$_{1-6}$ alkyl)-substituted amino group in which the C$_{1-6}$ alkyl group may have the same or different 1 to 3 groups selected from the substituent group (A), or a C$_{2-9}$ heterocycloalkyl group which may have the same or different 1 to 3 groups selected from the substituent group (A), or a pharmaceutically acceptable salt thereof or a prodrug thereof.

7. A pyrazole derivative as claimed in claim 6, wherein Q$^0$ represents an optionally mono or di(C$_{1-6}$ alkyl)-substituted amino group in which the C$_{1-6}$ alkyl group may have the same or different 1 to 3 groups selected from the substituent group (A), or a C$_{2-9}$ heterocycloalkyl group which may have the same or different 1 to 3 groups selected from the substituent group (A); and T$^0$ represents a group selected from

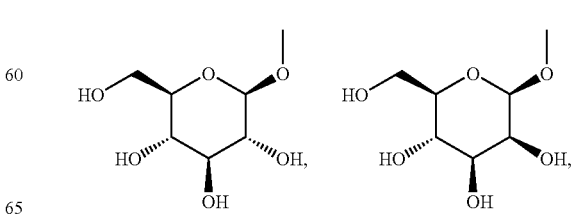

-continued

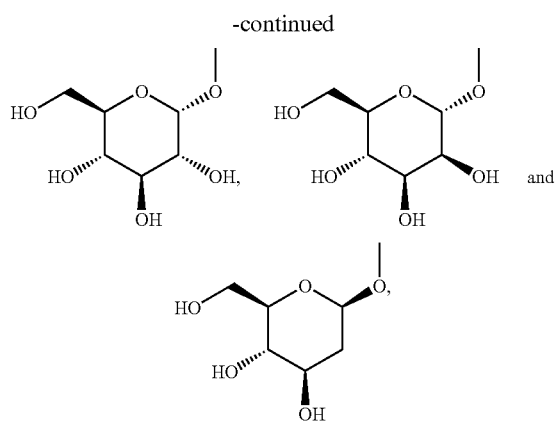

or a pharmaceutically acceptable salt thereof or a prodrug thereof.

8. A pyrazole derivative as claimed in claim 1, wherein one of $Q^0$ and $T^0$ represents a group selected from

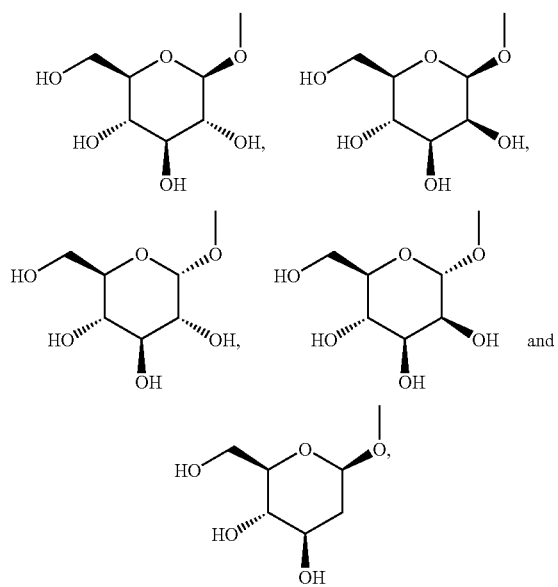

and the other represents a heterocycle-fused phenyl group which may have the same or different 1 to 3 groups selected from the substituent group (B), or a pharmaceutically acceptable salt thereof or a prodrug thereof.

9. A pyrazole derivative as claimed in claim 8, wherein $Q^0$ represents a heterocycle-fused phenyl group which may have the same or different 1 to 3 groups selected from the substituent group (B); and $T^0$ represents a group selected from

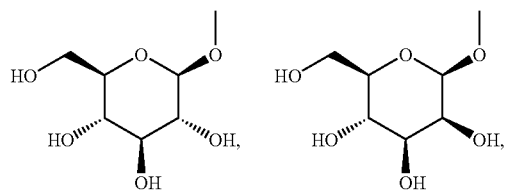

-continued

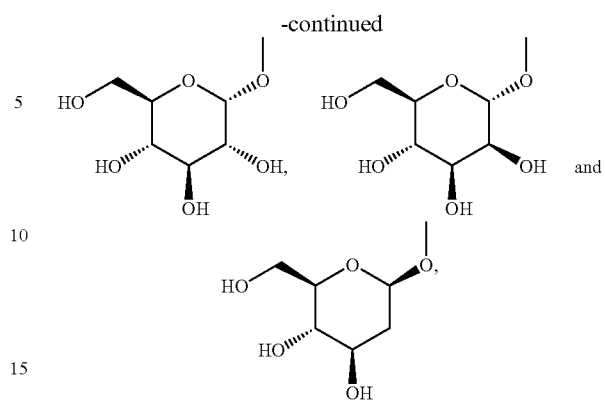

or a pharmaceutically acceptable-salt thereof or a prodrug thereof.

10. A pharmaceutical composition comprising as an active ingredient a pyrazole derivative as claimed in claim 1, or a pharmaceutically acceptable salt thereof or a prodrug thereof.

11. A method for inhibiting 1,5-anhydroglucitol/fructose/mannose transporter activity, which comprises administering to a subject in need thereof an effective amount of a pyrazole derivative represented by the following general formula (I):

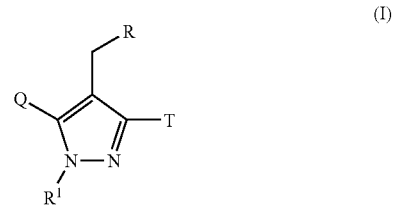

(I)

wherein $R^1$ represents a hydrogen atom, a $C_{1-6}$ alkyl group which may have the same or different 1 to 3 groups selected from the following substituent group (A), a $C_{2-6}$ alkenyl group which may have the same or different 1 to 3 groups selected from the following substituent group (A), a $C_{2-6}$ alkynyl group which may have the same or different 1 to 3 groups selected from the following substituent group (A), a $C_{3-8}$ cycloalkyl group which may have the same or different 1 to 3 groups selected from the following substituent group (A), a $C_{6-10}$ aryl group which may have the same or different 1 to 3 groups selected from the following substituent group (B), a $C_{2-9}$ heterocycloalkyl group which may have the same or different 1 to 3 groups selected from the following substituent group (A), or a $C_{1-9}$ heteroaryl group which may have the same or different 1 to 3 groups selected from the following substituent group (B);

one of Q and T represents a group selected from

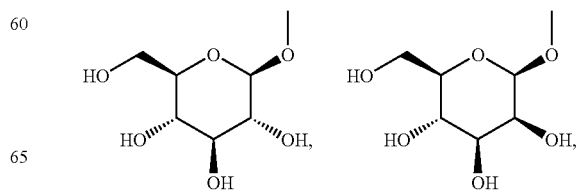

-continued

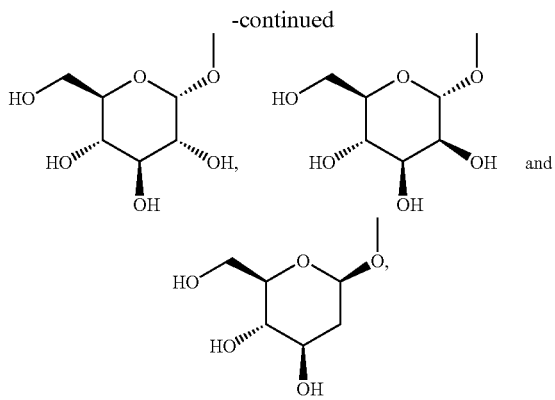

and the other represents a group represented by the formula: —(CH$_2$)$_n$—Ar wherein Ar represents a C$_{6-10}$ aryl group which may have the same or different 1 to 3 groups selected from the following substituent group (B) or a C$_{1-9}$ heteroaryl group which may have the same or different 1 to 3 groups selected from the following substituent group (B); and n represents an integral number from 0 to 2, a C$_{1-6}$ alkyl group which may have the same or different 1 to 3 groups selected from the following substituent group (A), a C$_{1-6}$ alkoxy group which may have the same or different 1 to 3 groups selected from the following substituent group (A), an optionally mono or di(C$_{1-6}$ alkyl)-substituted amino group wherein the C$_{1-6}$ alkyl group may have the same or different 1 to 3 groups selected from the following substituent group (A), a C$_{3-8}$ cycloalkyl group which may have the same or different 1 to 3 groups selected from the following substituent group (A), a C$_{2-9}$ heterocycloalkyl group which may have the same or different 1 to 3 groups selected from the following substituent group (A), or a heterocycle-fused phenyl group which may have the same or different 1 to 3 groups selected from the following substituent group (B);

R represents a C$_{3-8}$ cycloalkyl group which may have the same or different 1 to 3 groups selected from the following substituent group (A), a C$_{6-10}$ aryl group which may have the same or different 1 to 3 groups selected from the following substituent group (B), a C$_{2-9}$ heterocycloalkyl group which may have the same or different 1 to 3 groups selected from the following substituent group (A), or a C$_{1-9}$ heteroaryl group which may have the same or different 1 to 3 groups selected from the following substituent group (B);

[Substituent Group (A)]:
a halogen atom, a nitro group, a cyano group, an oxo group, -G$^1$, —OG$^2$, —SG$^2$, —N(G$^2$)$_2$, —C(=O)G$^2$, —C(=O)OG$^2$, —C(=O)N(G$^2$)$_2$, —S(=O)$_2$G$^2$, —S(=O)$_2$OG$^2$, —S(=O)$_2$N(G$^2$)$_2$, —S(=O)G$^1$, —OC(=O)G$^1$, —OC(=O)N(G$^2$)$_2$, —NHC(=O)G$^2$, —OS(=O)$_2$G$^1$, —NHS(=O)$_2$G$^1$ and —C(=O)NHS(=O)$_2$G$^1$;

[Substituent Group[Substituent Group (B)]:
a halogen atom, a nitro group, a cyano group, -G$^1$, —OG$^2$, —SG$^2$, —N(G$^2$)$_2$, -G$^3$OG$^4$, -G$^3$N(G$^4$)$_2$, —C(=O)G$^2$, —C(=O)OG$^2$, —C(=O)N(G$^2$)$_2$, —S(=O)$_2$G$^2$, —S(=O)$_2$OG$^2$, —S(=O)$_2$N(G$^2$)$_2$, —S(=O)G$^1$, —OC(=O)G$^1$, —OC(=O)N(G$^2$)$_2$, —NHC(=O)G$^2$, —OS(=O)$_2$G$^1$, —NHS(=O)$_2$G$^1$ and —C(=O)NHS(=O)$_2$G$^1$;

in the above substituent group (A) and/or (B),
G$^1$ represents a C$_{1-6}$ alkyl group which may have the same or different 1 to 3 groups selected from the following substituent group (C), a C$_{2-6}$ alkenyl group which may have the same or different 1 to 3 groups selected from the following substituent group (C), a C$_{2-6}$ alkynyl group which may have the same or different 1 to 3 groups selected from the following substituent group (C), a C$_{3-8}$ cycloalkyl group which may have the same or different 1 to 3 groups selected from the following substituent group (C), a C$_{6-10}$ aryl group which may have the same or different 1 to 3 groups selected from the following substituent group (D), a C$_{2-9}$ heterocycloalkyl group which may have the same or different 1 to 3 groups selected from the following substituent group (C), or a C$_{1-9}$ heteroaryl group which may have the same or different 1 to 3 groups selected from the following substituent group (D);

G$^2$ represents a hydrogen atom, a C$_{1-6}$ alkyl group which may have the same or different 1 to 3 groups selected from the following substituent group (C), a C$_{2-6}$ alkenyl group which may have the same or different 1 to 3 groups selected from the following substituent group (C), a C$_{2-6}$ alkynyl group which may have the same or different 1 to 3 groups selected from the following substituent group (C), a C$_{3-8}$ cycloalkyl group which may have the same or different 1 to 3 groups selected from the following substituent group (C), a C$_{6-10}$ aryl group which may have the same or different 1 to 3 groups selected from the following substituent group (D), a C$_{2-9}$ heterocycloalkyl group which may have the same or different 1 to 3 groups selected from the following substituent group (C), or a C$_{1-9}$ heteroaryl group which may have the same or different 1 to 3 groups selected from the following substituent group (D), and with the proviso that G$^2$ may be the same or different when there are 2 or more G$^2$ in the substituents;

G$^3$ represents a C$_{1-6}$ alkyl group;

G$^4$ represents a C$_{1-6}$ alkyl group which may have the same or different 1 to 3 groups selected from the following substituent group (C), and with the proviso that G$^4$ may be the same or different when there are 2 or more G$^4$ in the substituents;

[Substituent Group[Substituent Group (C)]:
a halogen atom, a nitro group, a cyano group, an oxo group, -G$^5$, —OG$^6$, —SG$^6$, —N(G$^6$)$_2$, —C(=O)G$^6$, —C(=O)OG$^6$, —C(=O)N(G$^6$)$_2$, —S(=O)$_2$G$^6$, —S(=O)$_2$OG$^6$, —S(=O)$_2$N(G$^6$)$_2$, —S(=O)G$^5$, —OC(=O)G$^5$, —OC(=O)N(G$^6$)$_2$, —NHC(=O)G$^6$, —OS(=O)$_2$G$^5$, —NHS(=O)$_2$G$^5$ and —C(=O)NHS(=O)$_2$G$^5$; and

[Substituent Group[Substituent Group (D)]:
a halogen atom, a nitro group, a cyano group, -G$^5$, —OG$^6$, —SG$^6$, —N(G$^6$)$_2$, —C(=O)G$^6$, C(=O)OG$^6$, —C(=O)N(G$^6$)$_2$, —S(=O)$_2$G$^6$, —S(=O)$_2$OG$^6$, —S(=O)$_2$N(G$^6$)$_2$, —S(=O)G$^5$, —OC(=O)G$^5$, —OC(=O)N(G$^6$)$_2$, —NHC(=O)G$^6$, —OS(=O)$_2$G$^5$, —NHS(=O)$_2$G$^5$ and —C(=O)NHS(=O)$_2$G$^5$;

in the substituent group (C) and/or (D),
G$^5$ represents a C$_{1-6}$ alkyl group, a C$_{2-6}$ alkenyl group, a C$_{2-6}$ alkynyl, a C$_{3-8}$ cycloalkyl group, a C$_{6-10}$ aryl group, a C$_{2-9}$ heterocycloalkyl group or a C$_{1-9}$ heteroaryl group; and G$^6$ represents a hydrogen atom, a C$_{1-6}$ alkyl group, a C$_{2-6}$ alkenyl group, a C$_{2-6}$ alkynyl, a C$_{3-8}$ cycloalkyl group, a C$_{6-10}$ aryl group, a C$_{2-9}$ heterocycloalkyl group or a C$_{1-9}$ heteroaryl group, and with the proviso that G$^6$ may be the same or different when there are 2 or more G$^6$ in the substituents, or a pharmaceutically acceptable salt thereof or a prodrug thereof.

12. A method for inhibiting 1,5-anhydroglucitol/fructose/mannose transporter activity, which comprises administering to a subject in need thereof an effective amount of a pyrazole derivative as claimed in claim 1, or a pharmaceutically acceptable salt thereof or a prodrug thereof.

13. A method for treatment of a disease associated with the excess uptake of at least a kind of carbohydrate selected from glucose, fructose and mannose, which comprises administering to a subject in need thereof an effective amount of a pyrazole derivative represented by the following general formula (I):

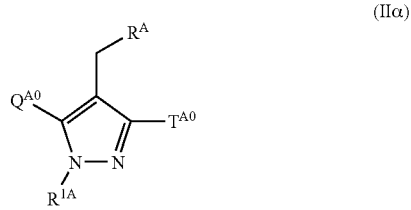

wherein
R[1] represents a hydrogen atom, a $C_{1-6}$ alkyl group which may have the same or different 1 to 3 groups selected from the following substituent group (A), a $C_{2-6}$ alkenyl group which may have the same or different 1 to 3 groups selected from the following substituent group (A), a $C_{2-6}$ alkynyl group which may have the same or different 1 to 3 groups selected from the following substituent group (A), a $C_{3-8}$ cycloalkyl group which may have the same or different 1 to 3 groups selected from the following substituent group (A), a $C_{6-10}$ aryl group which may have the same or different 1 to 3 groups selected from the following substituent group (B), a $C_{2-9}$ heterocycloalkyl group which may have the same or different 1 to 3 groups selected from the following substituent group (A), or a $C_{1-9}$ heteroaryl group which may have the same or different 1 to 3 groups selected from the following substituent group (B);
one of Q and T represents a group selected from

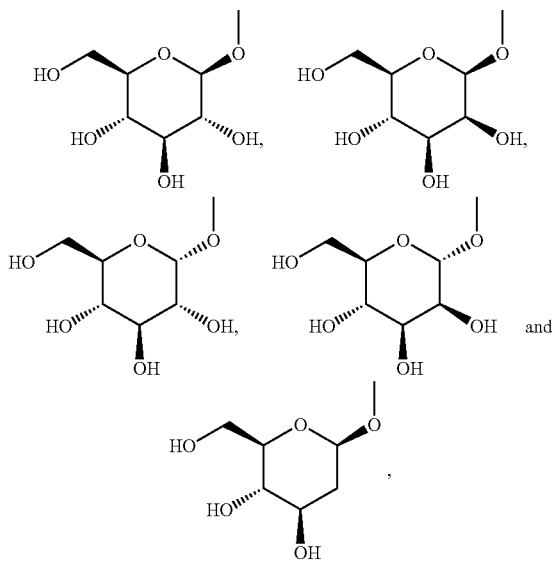

and the other represents a group represented by the formula: $-(CH_2)_n-Ar$ wherein Ar represents a $C_{6-10}$ aryl group which may have the same or different 1 to 3 groups selected from the following substituent group (B) or a $C_{1-9}$ heteroaryl group which may have the same or different 1 to 3 groups selected from the following substituent group (B); and n represents an integral number from 0 to 2, a $C_{1-6}$ alkyl group which may have the same or different 1 to 3 groups selected from the following substituent group (A), a $C_{1-6}$ alkoxy group which may have the same or different 1 to 3 groups selected from the following substituent group (A), an optionally mono or di($C_{1-6}$ alkyl)-substituted amino group wherein the $C_{1-6}$ alkyl group may have the same or different 1 to 3 groups selected from the following substituent group (A), a $C_{3-8}$ cycloalkyl group which may have the same or different 1 to 3 groups selected from the following substituent group (A), a $C_{2-9}$ heterocycloalkyl group which may have the same or different 1 to 3 groups selected from the following substituent group (A), or a heterocycle-fused phenyl group which may have the same or different 1 to 3 groups selected from the following substituent group (B);
R represents a $C_{3-8}$ cycloalkyl group which may have the same or different 1 to 3 groups selected from the following substituent group (A), a $C_{6-10}$ aryl group which may have the same or different 1 to 3 groups selected from the following substituent group (B), a $C_{2-9}$ heterocycloalkyl group which may have the same or different 1 to 3 groups selected from the following substituent group (A), or a $C_{1-9}$ heteroaryl group which may have the same or different 1 to 3 groups selected from the following substituent group (B);
[Substituent Group[Substituent Group (A)]:
a halogen atom, a nitro group, a cyano group, an oxo group, $-G^1$, $-OG^2$, $-SG^2$, $-N(G^2)_2$, $-C(=O)G^2$, $-C(=O)OG^2$, $-C(=O)N(G^2)_2$, $-S(=O)_2G^2$, $-S(=O)_2OG^2$, $-S(=O)_2N(G^2)_2$, $-S(=O)G^1$, $-OC(=O)G^1$, $-OC(=O)N(G^2)_2$, $-NHC(=O)G^2$, $-OS(=O)_2G^1$, $-NHS(=O)_2G^1$ and $-C(=O)NHS(=O)_2G^1$;
[Substituent Group[Substituent Group (B)]:
a halogen atom, a nitro group, a cyano group, $-G^1$, $-OG^2$, $-SG^2$, $-N(G^2)_2$, $-G^3OG^4$, $-G^3N(G^4)_2$, $-C(=O)G^2$, $-C(=O)OG^2$, $-C(=O)N(G^2)_2$, $-S(=O)_2G^2$, $-S(=O)_2OG^2$, $-S(=O)_{N(G^2)}_2$, $-S(=O)G^1$, $-OC(=O)G^1$, $-OC(=O)N(G^2)_2$, $-NHC(=O)G^2$, $-OS(=O)_2G^1$, $-NHS(=O)_2G^1$ and $-C(=O)NHS(=O)_2G^1$;
in the above substituent group (A) and/or (B),
G[1] represents a $C_{1-6}$ alkyl group which may have the same or different 1 to 3 groups selected from the following substituent group (C), a $C_{2-6}$ alkenyl group which may have the same or different 1 to 3 groups selected from the following substituent group (C), a $C_{2-6}$ alkynyl group which may have the same or different 1 to 3 groups selected from the following substituent group (C), a $C_{3-8}$ cycloalkyl group which may have the same or different 1 to 3 groups selected from the following substituent group (C), a $C_{6-10}$ aryl group which may have the same or different 1 to 3 groups selected from the following substituent group (D), a $C_{2-9}$ heterocycloalkyl group which may have the same or different 1 to 3 groups selected from the following substituent group (C), or a $C_{1-9}$ heteroaryl group which may have the same or different 1 to 3 groups selected from the following substituent group (D);
G[2] represents a hydrogen atom, a $C_{1-6}$ alkyl group which may have the same or different 1 to 3 groups selected from the following substituent group (C), a $C_{2-6}$ alkenyl group which may have the same or different 1 to 3 groups selected from the following substituent group (C), a $C_{2-6}$ alkynyl group which may have the same or different 1 to 3 groups selected from the following substituent group (C), a $C_{3-8}$ cycloalkyl group which may have the same or different 1 to 3 groups selected from the following substituent group (C), a $C_{6-10}$ aryl group which may have the same or different 1 to 3 groups selected from the following substituent group (D), a $C_{2-9}$ heterocycloalkyl group which may have the same or different 1 to 3 groups selected from the following substituent group (C). or a $C_{1-9}$ heteroaryl group which may have the same or different 1 to 3 groups selected from the following substituent group (D), and with the proviso that $G^2$ may be the same or different when there are 2 or more $G^2$ in the substituents;

$G^3$ represents a $C_{1-6}$ alkyl group;

$G^4$ represents a $C_{1-6}$ alkyl group which may have the same or different 1 to 3 groups selected from the following substituent group (C), and with the proviso that $G^4$ may be the same or different when there are 2 or more $G^4$ in the substituents;

[Substituent Group[Substituent Group (C)]:

a halogen atom, a nitro group, a cyano group, an oxo group, $-G^5$, $-OG^6$, $-SG^6$, $-N(G^6)_2$, $-C(=O)G^6$, $-C(=O)OG^6$, $-C(=O)N(G^6)_2$, $-S(=O)_2G^6$, $-S(=O)_2OG^6$, $-S(=O)_2N(G^6)_2$, $-S(=O)G^5$, $-OC(=O)G^5$, $-OC(=O)N(G^6)_2$, $-NHC(=O)G^6$, $-OS(=O)_2G^5$, $-NHS(=O)_2G^5$ and $-C(=O)NHS(=O)_2G^5$; and

[Substituent Group[Substituent Group (D)]:

a halogen atom, a nitro group, a cyano group, $-G^5$, $-OG^6$, $-SG^6$, $-N(G^6)_2$, $-C(=O)G^6$, $-C(=O)OG^6$, $-C(=O)N(G^6)_2$, $-S(=O)_2G^6$, $-S(=O)_2OG^6$, $-S(=O)_2N(G^6)_2$, $-S(=O)G^5$, $-OC(=O)G^5$, $-OC(=O)N(G^6)_2$, $-NHC(=O)G^6$, $-OS(=O)_2G^5$, $-NHS(=O)_2G^5$ and $-C(=O)NHS(=O)_2G^5$;

in the substituent group (C) and/or (D), $G^5$ represents a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group; and $G^6$ represents a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group, and with the proviso that $G^6$ may be the same or different when there are 2 or more $G^6$ in the substituents, or a pharmaceutically acceptable salt thereof or a prodrug thereof.

14. A method for the treatment of a disease associated with the excess uptake of at least a kind of carbohydrate selected from glucose, fructose and mannose, which comprises administering to a subject in need thereof an effective amount of a pyrazole derivative as claimed in claim 1, or a pharmaceutically acceptable salt thereof or a prodrug thereof.

15. A method as claimed in claim 13, wherein the disease associated with the excess uptake of at least a kind of carbohydrate selected from glucose, fructose and mannose is diabetic complications.

16. A method as claimed in claim 14, wherein the disease associated with the excess uptake of at least a kind of carbohydrate selected from glucose, fructose and mannose is diabetic complications.

17. A method as claimed in claim 15, wherein the diabetic complications is diabetic nephropathy.

18. A method as claimed in claim 16, wherein the diabetic complications is diabetic nephropathy.

19. A method as claimed in claim 13, wherein the disease associated with the excess uptake of at least a kind of carbohydrate selected from glucose, fructose and mannose is diabetes.

20. A method as claimed in claim 14, wherein the disease associated with the excess uptake of at least a kind of carbohydrate selected from glucose, fructose and mannose is diabetes.

21. A pharmaceutical combination which comprises (component a) a pyrazole derivative as claimed in claim 1, or a pharmaceutically acceptable salt thereof or a prodrug thereof, and (component b) at least one member selected from the group consisting of an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethylglutaryl coenzyme A reductase inhibitor, a fibric acid derivative, a $β_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an antiplatelets agent, a uric acid synthesis inhibitor, a uricosuric agent and a urinary alkalinizer.

22. A pyrazole derivative represented by the following general formula (IIα):

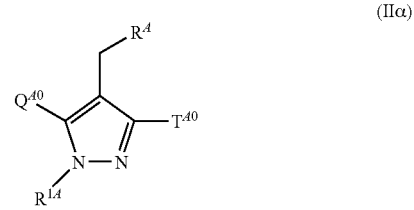

wherein $R^{14}$ represents a hydrogen atom, a $C_{1-6}$ alkyl group which may have the same or different 1 to 3 groups selected from the following substituent group (A1), a $C_{2-6}$ alkenyl group which may have the same or different 1 to 3 groups selected from the following substituent group (A1), a $C_{2-6}$ alkynyl group which may have the same or different 1 to 3 groups selected from the following substituent group (A1), a $C_{3-8}$ cycloalkyl group which may have the same or different 1 to 3 groups selected from the following substituent group (A1), a $C_{6-10}$ aryl group which may have the same or different 1 to 3 groups selected from the following substituent group (B1), a $C_{2-9}$ heterocycloalkyl group which may have the same or different 1 to 3 groups selected from the following substituent group (A1), or a $C_{1-9}$ heteroaryl group which may have the same or different 1 to 3 groups selected from the following substituent group (B1);
one of $Q^{40}$ and $T^{40}$ represents a group selected from

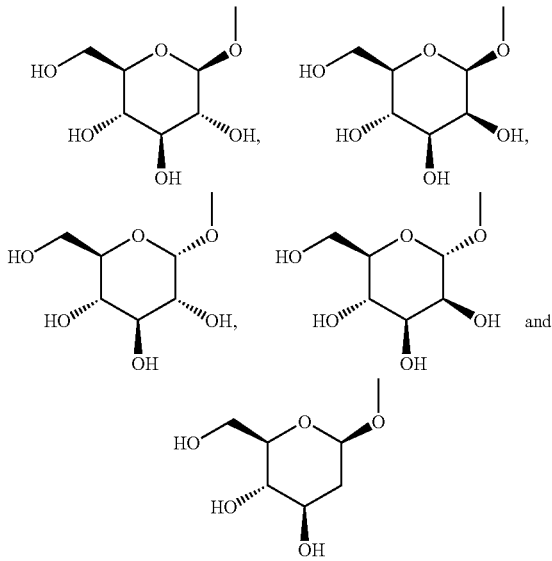

having protective group(s), and the other represents a group represented by the formula: —$(CH_2)_n$—$Ar^4$ wherein $Ar^4$ represents a $C_{6-10}$ aryl group which may have the same or different 1 to 3 groups selected from the following substituent group (B1) or a $C_{1-9}$ heteroaryl group which may have the same or different 1 to 3 groups selected from the following substituent group (B1); and n represents an integral number from 0 to 2, a $C_{1-6}$ alkoxy group which may have the same or different 1 to 3 groups selected from the following substituent group (A1), an optionally mono or di($C_{1-6}$ alkyl)-substituted amino group wherein the $C_{1-6}$ alkyl group may have the same or different 1 to 3 groups selected from the following substituent group (A1), a $C_{2-9}$ heterocycloalkyl group which may have the same or different 1 to 3 groups selected from the following substituent group (A1), or a heterocycle-fused phenyl group which may have the same or different 1 to 3 groups selected from the following substituent group (B1);

$R^A$ represents a $C_{3-8}$ cycloalkyl group which may have the same or different 1 to 3 groups selected from the following substituent group (A1), a $C_{6-10}$ aryl group which may have the same or different 1 to 3 groups selected from the following substituent group (B1), a $C_{2-9}$ heterocycloalkyl group which may have the same or different 1 to 3 groups selected from the following substituent group (A1), or a $C_{1-9}$ heteroaryl group which may have the same or different 1 to 3 groups selected from the following substituent group (B1);

[Substituent Group (A1)]:
a halogen atom, a nitro group, a cyano group, an oxo group, -$G^{1A}$, —$OG^{2B}$, —$SG^{2B}$, —$N(G^{2B})_2$, —$C(=O)G^{2A}$, —$C(=O)OG^{2B}$, —$C(=O)N(G^{2B})_2$, —$S(=O)_2G^{2A}$, —$S(=O)_2OG^{2A}$, —$S(=O)_2N(G^{2B})_2$, —$S(=O)G^{1A}$, —$OC(=O)G^{1A}$, —$OC(=O)N(G^{2B})_2$, —$NHC(=O)G^{2A}$, —$OS(=O)_2G^{1A}$, —$NHS(=O)_2G^{1A}$ and —$C(=O)NHS(=O)_2G^{1A}$;

[Substituent Group (B1)]:
a halogen atom, a nitro group, a cyano group, -$G^{1A}$, —$OG^{2B}$, —$SG^{2B}$, —$N(G^{2B})_2$, -$G^3OG^{4A}$, -$G^3N(G^{4A})_2$, —$C(=O)G^{2A}$, —$C(=O)OG^{2B}$, —$C(=O)N(G^{2B})_2$, —$S(=O)_2G^{2A}$, —$S(=O)_2OG^{2A}$, —$S(=O)_2N(G^{2B})_2$, —$S(=O)G^{1A}$, —$OC(=O)G^{1A}$, —$OC(=O)N(G^{2B})_2$, —$NHC(=O)G^{2A}$, —$OS(=O)_2G^{1A}$, —$NHS(=O)_2G^{1A}$ and —$C(=O)NHS(=O)_2G^{1A}$;

in the above substituent group (A1) and/or (B1),
$G^{1A}$ represents a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1);

$G^{2A}$ represents a hydrogen atom, a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1);

$G^{2B}$ represents a protective group, a hydrogen atom, a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1), and with the proviso that $G^{2B}$ may be the same or different when there are 2 or more $G^{2B}$ in the substituents;

$G^3$ represents a $C_{1-6}$ alkyl group;

$G^{4A}$ represents a $C_{1-6}$ alkyl group which may have the same or different 1 to 3 groups selected from the following substituent group (C1), and with the proviso that $G^{4A}$ may be the same or different when there are 2 or more $G^{4A}$ in the substituents;

[Substituent Group (C1)]:
a halogen atom, a nitro group, a cyano group, -$G^5$, —$OG^{6A}$, —$SG^{6A}$, —$N(G^{6A})_2$, —$C(=O)G^6$, —$C(=O)OG^{6A}$, —$C(=O)N(G^{6A})_2$, —$S(=O)_2G^6$, —$S(=O)_2OG^6$, —$S(=O)_2N(G^{6A})_2$, —$S(=O)G^5$, —$OC(=O)G^5$, —$OC(=O)N(G^{6A})_2$, —$NHC(=O)G^6$, —$OS(=O)_2G^5$, —$NHS(=O)_2G^5$ and —$C(=O)NHS(=O)_2G^5$; and

[Substituent Group (D1)]:
  a halogen atom, a nitro group, a cyano group, -$G^5$, —$OG^{6A}$, —$SG^{6A}$, —$N(G^{6A})_2$, —$C(=O)G^6$, —$C(=O)OG^{6A}$, —$C(=O)N(G^{6A})_2$, —$S(=O)_2G^6$, —$S(=O)_2OG^6$, —$S(=O)_2N(G^{6A})_2$, —$S(=O)G^5$, —$OC(=O)G^5$, —$OC(=O)N(G^{6A})_2$, —$NHC(=O)G^6$, —$OS(=O)_2G^5$, —$NHS(=O)_2G^5$ and —$C(=O)NHS(=O)_2G^5$;

in the substituent group (C1) and/or (D1),
  $G^5$ represents a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group;
  $G^6$ represents a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group; and
  $G^{6A}$ represents a protective group, a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group, and with the proviso that $G^{6A}$ may be the same or different when there are 2 or more $G^{6A}$ in the substituents, or a pharmaceutically acceptable salt thereof.

23. A pyrazole derivative represented by the following general formula (IIIα):

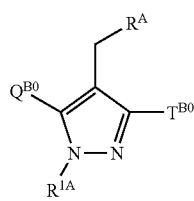

(IIIα)

wherein
  $R^{1A}$ represents a hydrogen atom, a $C_{1-6}$ alkyl group which may have the same or different 1 to 3 groups selected from the following substituent group (A1), a $C_{2-6}$ alkenyl group which may have the same or different 1 to 3 groups selected from the following substituent group (A1), a $C_{2-6}$ alkynyl group which may have the same or different 1 to 3 groups selected from the following substituent group (A1), a $C_{3-8}$ cycloalkyl group which may have the same or different 1 to 3 groups selected from the following substituent group (A1), a $C_{6-10}$ aryl group which may have the same or different 1 to 3 groups selected from the following substituent group (B1), a $C_{2-9}$ heterocycloalkyl group which may have the same or different 1 to 3 groups selected from the following substituent group (A1), or a $C_{1-9}$ heteroaryl group which may have the same or different 1 to 3 groups selected from the following substituent group (B1);
  one of $Q^{B0}$ and $T^{B0}$ represents a hydroxy group, and the other represents a group represented by the formula: —$(CH_2)_n$—$Ar^A$ wherein $Ar^A$ represents a $C_{6-10}$ aryl group which may have the same or different 1 to 3 groups selected from the following substituent group (B1) or a $C_{1-9}$ heteroaryl group which may have the same or different 1 to 3 groups selected from the following substituent group (B1); and n represents an integral number from 0 to 2, a $C_{1-6}$ alkoxy group which may have the same or different 1 to 3 groups selected from the following substituent group (A1), an optionally mono or di($C_{1-6}$ alkyl)-substituted amino group wherein the $C_{1-6}$ alkyl group may have the same or different 1 to 3 groups selected from the following substituent group (A1), a $C_{2-9}$ heterocycloalkyl group which may have the same or different 1 to 3 groups selected from the following substituent group (A1), or a heterocycle-fused phenyl group which may have the same or different 1 to 3 groups selected from the following substituent group (B1);
  $R^A$ represents a $C_{3-8}$ cycloalkyl group which may have the same or different 1 to 3 groups selected from the following substituent group (A1), a $C_{6-10}$ aryl group which may have the same or different 1 to 3 groups selected from the following substituent group (B1), a $C_{2-9}$ heterocycloalkyl group which may have the same or different 1 to 3 groups selected from the following substituent group (A1), or a $C_{1-9}$ heteroaryl group which may have the same or different 1 to 3 groups selected from the following substituent group (B1);

[Substituent Group (A1)]:
  a halogen atom, a nitro group, a cyano group, an oxo group, -$G^{1A}$, —$OG^{2B}$, —$SG^{2B}$, —$N(G^{2B})_2$, —$C(=O)G^{2A}$, —$C(=O)OG^{2B}$, —$C(=O)N(G^{2B})_2$, —$S(=O)_2G^{2A}$, —$S(=O)_2OG^{2A}$, —$S(=O)_2N(G^{2B})_2$, —$S(=O)G^{1A}$, —$OC(=O)G^{1A}$, —$OC(=O)N(G^{2B})_2$, —$NHC(=O)G^{2A}$, —$OS(=O)_2G^{1A}$, —$NHS(=O)_2G^{1A}$ and —$C(=O)NHS(=O)_2G^{1A}$;

[Substituent Group (B1)]:
  a halogen atom, a nitro group, a cyano group, -$G^{1A}$, —$OG^{2B}$, —$SG^{2B}$, —$N(G^{2B})_2$, -$G^3OG^{4A}$, -$G^3N(G^{4A})_2$, —$C(=O)G^{2A}$, —$C(=O)OG^{2B}$, —$C(=O)N(G^{2B})_2$, —$S(=O)_2G^{2A}$, —$S(=O)_2OG^{2A}$, —$S(=O)_2N(G^{2B})_2$, —$S(=O)G^{1A}$, —$OC(=O)G^{1A}$, —$OC(=O)N(G^{2B})_2$, —$NHC(=O)G^{2A}$, —$OS(=O)_2G^{1A}$, —$NHS(=O)_2G^{1A}$ and —$C(=O)NHS(=O)_2G^{1A}$;

in the above substituent group (A1) and/or (B1),
  $G^{1A}$ represents a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1);
  $G^{2A}$ represents a hydrogen atom, a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1);
  $G^{2B}$ represents a protective group, a hydrogen atom, a $C_{1-6}$ alkyl group which may have the same or different 1 to 3 groups selected from the following substituent group (C1), a $C_{2-6}$ alkenyl group which may have the same or different 1 to 3 groups selected from the following substituent group (C1), a $C_{2-6}$ alkynyl group which may have the same or different 1 to 3 groups selected from the following substituent group (C1), a $C_{3-8}$ cycloalkyl group which may have the same or different 1 to 3 groups selected from the following substituent group (C1), a $C_{6-10}$ aryl group which may have the same or different 1 to 3 groups selected from the following substituent group (D1), a $C_{2-9}$ heterocycloalkyl group which may have the same or different 1 to 3 groups selected from the following substituent group (C1), or a $C_{1-9}$ heteroaryl group which may have the same or different 1 to 3 groups selected from the following substituent group (D1), and with the proviso that $G^{2B}$ may be the same or different when there are 2 or more $G^{2B}$ in the substituents;

$G^3$ represents a $C_{1-6}$ alkyl group;

$G^{4A}$ represents a $C_{1-6}$ alkyl group which may have the same or different 1 to 3 groups selected from the following substituent group (C1), and with the proviso that $G^{4A}$ may be the same or different when there are 2 or more $G^{4A}$ in the substituents;

[Substituent Group (C1)]:

a halogen atom, a nitro group, a cyano group, an oxo group, -$G^5$, —$OG^{6A}$, —$SG^{6A}$, —$N(G^{6A})_2$, —$C(=O)G^6$, —$C(=O)OG^{6A}$, —$C(=O)N(G^{6A})_2$, —$S(=O)_2G^6$, —$S(=O)_2OG^g$, —$S(=O)_2N(G^{6A})_2$, —$S(=O)G^5$, —$OC(=O)G^5$, —$OC(=O)N(G^{6A})_2$, —$NHC(=O)G^6$, —$OS(=O)_2G^5$, —$NHS(=O)_2G^5$ and —$C(=O)NHS(=O)_2G^5$; and

[Substituent Group (D1)]:

a halogen atom, a nitro group, a cyano group, -$G^5$, —$OG^{6A}$, —$SG^{6A}$, —$N(G^{6A})_2$, —$C(=O)G^6$, —$C(=O)OG^{6A}$, —$C(=O)N(G^{6A})_2$, —$S(=O)_2G^6$, —$S(=O)_2G^6$, —$S(=O)_2N(G^{6A})_2$, —$S(=O)G^5$, —$OC(=O)G^5$, —$OC(=O)N(G^{6A})_2$, —$NHC(=O)G^6$, —$OS(=O)_2G^5$, —$NHS(=O)_2G^5$ and —$C(=O)NHS(=O)_2G^5$;

in the substituent group (C1) and/or (D1), $G^5$ represents a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group;

$G^6$ represents a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group; and $G^{6A}$ represents a protective group, a hydrogen atom, a $C_{1-6}$ alkyl group, a $C_{2-6}$ alkenyl group, a $C_{2-6}$ alkynyl, a $C_{3-8}$ cycloalkyl group, a $C_{6-10}$ aryl group, a $C_{2-9}$ heterocycloalkyl group or a $C_{1-9}$ heteroaryl group, and with the proviso that $G^{6A}$ may be the same or different when there are 2 or more $G^{6A}$ in the substituents, or a pharmaceutically acceptable salt thereof.

\* \* \* \* \*

SEQUENCE LISTING

<160> NUMBER OF SEQ ID NOS: 4

<210> SEQ ID NO 1
<211> LENGTH: 7
<212> TYPE: PRT
<213> ORGANISM: Homo sapien

<400> SEQUENCE: 1

Met Ser Lys Glu Leu Ala Ala
1               5

<210> SEQ ID NO 2
<211> LENGTH: 20
<212> TYPE: DNA
<213> ORGANISM: Artificial Sequence
<220> FEATURE:
<223> OTHER INFORMATION: Forward PCR primer

<400> SEQUENCE: 2
tgtcacagtc cccaacacca                                          20

<210> SEQ ID NO 3
<211> LENGTH: 19
<212> TYPE: DNA
<213> ORGANISM: Artificial Sequence
<220> FEATURE:
<223> OTHER INFORMATION: Reverse PCR primer

```
<400> SEQUENCE: 3
ccgaagcatg tggaaagca                                          19

<210> SEQ ID NO 4
<211> LENGTH: 19
<212> TYPE: DNA
<213> ORGANISM: Artificial Sequence
<220> FEATURE:
<223> OTHER INFORMATION: DNA probe

<400> SEQUENCE: 4
tgtcacctcc cacggcccg                                          19
```